US009856217B2

(12) United States Patent
McKinney et al.

(10) Patent No.: US 9,856,217 B2
(45) Date of Patent: Jan. 2, 2018

(54) CRYSTALLINE COMPOUNDS

(71) Applicant: NEUROVANCE, INC., Princeton, NJ (US)

(72) Inventors: Anthony Alexander McKinney, Newton Center, MA (US); Franklin Bymaster, Brownsburg, IN (US); Walter Piskorski, Nashua, NH (US); Fred J. Fleitz, Germantown, WI (US); Yonglai Yang, Hockessin, DE (US); David A. Engers, West Lafayette, IN (US); Valeriya Smolenskaya, West Lafayette, IN (US); Venkat Kusukuntla, Germantown, WI (US)

(73) Assignee: NEUROVANCE, INC., Princeton, NJ (US)

(*) Notice: Subject to any disclaimer, the term of this patent is extended or adjusted under 35 U.S.C. 154(b) by 0 days.

(21) Appl. No.: 15/611,580

(22) Filed: Jun. 1, 2017

(65) Prior Publication Data
US 2017/0334850 A1 Nov. 23, 2017

Related U.S. Application Data

(63) Continuation of application No. 15/186,415, filed on Jun. 17, 2016, now Pat. No. 9,708,261.

(60) Provisional application No. 62/181,174, filed on Jun. 17, 2015.

(51) Int. Cl.
C07D 209/52 (2006.01)
C07C 211/17 (2006.01)

(52) U.S. Cl.
CPC .......... C07D 209/52 (2013.01); C07C 211/17 (2013.01)

(58) Field of Classification Search
CPC .......................... C07D 209/52; C07C 211/17
See application file for complete search history.

(56) References Cited

U.S. PATENT DOCUMENTS

| 7,094,799 | B2 | 8/2006 | Russell et al. |
| 8,461,196 | B2 | 6/2013 | Skolnick et al. |
| 8,877,798 | B2 | 11/2014 | Skolnick et al. |
| 9,205,074 | B2 | 12/2015 | Skolnick et al. |
| 9,708,261 | B2 | 7/2017 | Mckinney et al. |
| 2007/0043100 | A1 | 2/2007 | Hagen et al. |
| 2007/0082940 | A1 | 4/2007 | Skolnick et al. |
| 2008/0058535 | A1 | 3/2008 | Chen et al. |
| 2014/0206740 | A1 | 7/2014 | Mckinney et al. |
| 2014/0228421 | A1 | 8/2014 | Mckinney et al. |
| 2015/0148399 | A1 | 5/2015 | Skolnick et al. |
| 2016/0158197 | A1 | 6/2016 | Skolnick et al. |

FOREIGN PATENT DOCUMENTS

| WO | WO 2004/043920 A1 | 5/2004 |
| WO | WO 2006/023659 A2 | 3/2006 |
| WO | WO 2007/016155 A2 | 2/2007 |

(Continued)

OTHER PUBLICATIONS

U.S. Appl. No. 15/102,871, filed Jun. 9, 2016, Neurovance, Inc.

(Continued)

Primary Examiner — San-Ming Hui
(74) Attorney, Agent, or Firm — Hoxie & Associates LLC

(57) ABSTRACT

The present invention relates to crystalline forms of (1R, 5S)-1-(naphthalen-2-yl)-3-azabicyclo[3.1.0]hexane hydrochloride and compositions comprising the same and methods of making and using the same.

14 Claims, 56 Drawing Sheets

(56) References Cited

FOREIGN PATENT DOCUMENTS

| WO | WO 2008/013856 A2 | 1/2008 |
| WO | WO 2013/019271 A1 | 2/2013 |
| WO | WO 2015/089111 A1 | 6/2015 |
| WO | WO 2015/102826 A1 | 7/2015 |

OTHER PUBLICATIONS

U.S. Appl. No. 15/102,949, filed Jun. 9, 2016, Neurovance, Inc.
Bymaster, F. et al., "Pharmacological Characterization of the Norepinephrine and Dopamine Reuptake Inhibitor EB-1020: Implications for Treatment of Attention-Deficit Hyperactivity Disorder," Synapse, 2012, 66, 522-532.
Micheli, F. et al., "1-(Aryl)-6-[alkoxyalkyl]-3-azabicyclo[3.1.0]hexanes and 6-(Aryl)-6-[alkoxyalkyl]-3-azabicyclo[3.1.0]hexanes: A New Series of Potent and Selective Triple Reuptake Inhibitors," Journal of Medicinal Chemistry, 2010, 53 (6), 2534-2551.
Zhang, M. et al., "Studies on the Structure-Activity Relationship of Bicifadine Analogs as Monoamine Transporter Inhibitors," Biorganic & Medicinal Chemistry Letters, 2008, 18, 3682-3686.

CRYSTALLINE COMPOUNDS

This application is a continuation of U.S. patent application Ser. No. 15/186,415 filed Jun. 17, 2016, which claims priority to U.S. Provisional Application No. 62/181,174 filed Jun. 17, 2015, the contents of each of which are hereby incorporated by reference.

FIELD OF THE INVENTION

The present invention relates to crystalline forms of (1R,5S)-1-(naphthalen-2-yl)-3-azabicyclo[3.1.0]hexane hydrochloride and compositions comprising the same and methods of making and using the same.

BACKGROUND OF THE INVENTION (1R,5S)-1-(naphthalen-2-yl)-3-azabicyclo[3.1.0]hexane, also known as (+)-1-(naphthalen-2-yl)-3-azabicyclo[3.1.0]hexane, is a compound useful as an unbalanced triple reuptake inhibitor (TRI), most potent towards norepinephrine reuptake (NE), one-sixth as potent towards dopamine reuptake (DA), and one-fourteenth as much towards serotonin reuptake (5-HT). This compound and its utility are disclosed in more detail in U.S. Patent Publication No. 2007/0082940, the contents of which are hereby incorporated by reference in their entirety.

Active pharmaceutical ingredients can exist in different physical forms (e.g., liquid or solid in different crystalline, amorphous, hydrate, or solvate forms), which can vary the processability, stability, solubility, bioavailability, pharmacokinetics (absorption, distribution, metabolism, excretion, or the like), and/or bioequivalency of the active pharmaceutical ingredient and pharmaceutical compositions comprising it. Whether a compound will exist in a particular polymorph form is unpredictable. It is important in pharmaceutical development to generate and identify advantageous physical forms (e.g., free base or salt in solid, liquid, crystalline, hydrate, solvate, or amorphous forms) of active pharmaceutical ingredients. Therefore, there remains a need for particular polymorph forms of (1R,5S)-1-(naphthalen-2-yl)-3-azabicyclo[3.1.0]hexane.

SUMMARY OF THE INVENTION (1R,5S)-1-(naphthalen-2-yl)-3-azabicyclo[3.1.0]hexane, also known as (+)-1-(naphthalen-2-yl)-3-azabicyclo[3.1.0]hexane ("the Compound") is shown as Formula I below:

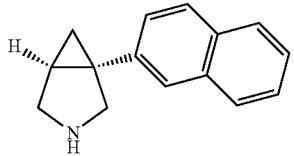

Formula I

The inventors have found particular polymorphs of the Compound in hydrochloric acid addition salt form. These particular polymorphs have different stability and dissolution profiles and are especially advantageous in the preparation of galenic formulations of various and diverse kind, especially Crystalline Form A as described below. Therefore, in the first aspect, the invention provides crystalline forms of (1R,5S)-1-(naphthalen-2-yl)-3-azabicyclo[3.1.0]hexane hydrochloride, e.g.:

1.1 Crystalline Form A of the Compound in hydrochloric acid addition salt form ((1R,5S)-1-(naphthalen-2-yl)-3-azabicyclo[3.1.0]hexane hydrochloride) ("Crystalline Form A").

1.2 Formula 1.1 wherein the Crystalline Form A belongs to the $P2_12_12_1$ space group and has the following unit cell parameters:
a=5.7779(2) Å, b=8.6633(2) Å, c=25.7280(8) Å, $\alpha=\beta=\gamma=90°$.

1.3 Formula 1.1 wherein the Crystalline Form A belongs to the $P2_12_12_1$ space group and has any combination of the following unit cell parameters:
a=5-7 Å, e.g., 6 Å, e.g., 5.6-5.9 Å, e.g., 5.7-5.8 Å, e.g., 5.8 Å, e.g., 5.78, e.g., 5.778 Å;
b=8-10 Å, e.g., 9 Å, e.g., 8.5-8.8 Å, e.g., 8.6-8.7 Å, e.g., 8.7 Å, e.g., 8.66 Å, e.g., 8.663 Å;
c=25-27 Å, e.g., 26 Å, e.g., 25.6-25.9 Å, e.g., 25.7-25.8 Å, e.g., 25.7-25.8 Å, e.g., 25.73 Å, e.g., 25.728 Å; and
$\alpha=\beta=\gamma=90°$.

1.4 Any of formulae 1.1-1.3 wherein the Crystalline Form A has a calculated volume of V=1287.83(7) Å$^3$.

1.5 Any of formulae 1.1-1.4 wherein the crystal structure of the Crystalline Form A is obtained with a crystal having approximate dimensions of 0.38 mm×0.30 mm×0.18 mm, e.g., a colorless plate having approximate dimensions of 0.38 mm×0.30 mm×0.18 mm.

1.6 Any of formulae 1.1-1.5 wherein the crystal structure of the Crystalline Form A is obtained with Mo Kα radiation, e.g., Mo Kα radiation having λ=0.71073 Å.

1.7 Any of formulae 1.1-1.6 wherein the crystal structure of the Crystalline Form A is obtained at 150 K.

1.8 Any of formulae 1.1-1.7 wherein the Crystalline Form A has a single crystal structure represented by the ORTEP drawing of FIG. 18.

1.9 Any of formulae 1.1-1.8 wherein the Crystalline Form A has a calculated XRPD pattern as show in FIG. 23.

1.10 Any of formulae 1.1-1.9 wherein the Crystalline Form A exhibits an XRPD pattern comprising at least three, e.g., at least five, 2-theta (°) values selected from the group consisting of 15.4, 16.6, 17.2, 18.5, 19.5, 20.5, 20.7, 22.9, and 25.7, wherein the XRPD is measured using an incident beam of Cu radiation, e.g., Cu Kα radiation, e.g., wherein the XRPD is measured using radiation of wavelength 1.54059 Å.

1.11 Any of formulae 1.1-1.10 wherein the Crystalline Form A exhibits an XRPD pattern comprising 2-theta (°) values of 15.4, 16.6, 17.2, 18.5, 19.5, 20.5, 20.7, 22.9, and 25.7, wherein the XRPD is measured using an incident beam of Cu radiation, e.g., Cu Kα radiation, e.g., wherein the XRPD is measured using radiation of wavelength 1.54059 Å.

1.12 Any of formulae 1.1-1.11 wherein the Crystalline Form A exhibits an XRPD pattern having characteristic 2-theta (°) values of 15.4, 16.6, 17.2, 18.5, 19.5, 20.5, 20.7, 22.9, and 25.7, wherein the XRPD is measured using an incident beam of Cu radiation, e.g., Cu Kα radiation, e.g., wherein the XRPD is measured using radiation of wavelength 1.54059 Å.

1.13 Any of formulae 1.1-1.12 wherein the Crystalline Form A exhibits an XRPD pattern comprising at least three, e.g., at least five, 2-theta (°) values selected from the group consisting 15.42, 16.55, 17.15, 18.50, 19.45, 20.46, 20.68, 22.90, and 25.69, wherein the XRPD is measured using an incident beam of Cu radiation, e.g., Cu Kα radiation, e.g., wherein the XRPD is measured using radiation of wavelength 1.54059 Å.

1.14 Any of formulae 1.1-1.13 wherein the Crystalline Form A exhibits an XPRD pattern comprising 2-theta (°) values of 15.42, 16.55, 17.15, 18.50, 19.45, 20.46, 20.68, 22.90, and 25.69, wherein the XRPD is measured using an incident beam of Cu radiation, e.g., Cu Kα radiation.

1.15 Any of formulae 1.1-1.14 wherein the Crystalline Form A exhibits an XRPD pattern having characteristic 2-theta (°) values of 15.42, 16.55, 17.15, 18.50, 19.45, 20.46, 20.68, 22.90, and 25.69, wherein the XRPD is measured using an incident beam of Cu radiation, e.g., Cu Kα radiation, e.g., wherein the XRPD is measured using radiation of wavelength 1.54059 Å.

1.16 Any of formulae 1.1-1.15 wherein the Crystalline Form A exhibits an XRPD pattern comprising at least three, e.g., at least five, 2-theta (°) values selected from those set forth in Table A below:

TABLE A

| °2θ | d space (Å) | Intensity (%) |
|---|---|---|
| 15.42 ± 0.20 | 5.741 ± 0.074 | 26 |
| 16.55 ± 0.20 | 5.352 ± 0.064 | 40 |
| 17.15 ± 0.20 | 5.167 ± 0.060 | 29 |
| 18.50 ± 0.20 | 4.792 ± 0.051 | 100 |
| 19.45 ± 0.20 | 4.560 ± 0.046 | 38 |
| 20.46 ± 0.20 | 4.338 ± 0.042 | 43 |
| 20.68 ± 0.20 | 4.291 ± 0.041 | 80 |
| 22.90 ± 0.20 | 3.880 ± 0.033 | 22 |
| 25.69 ± 0.20 | 3.466 ± 0.027 | 70 | wherein the XRPD is measured using an incident beam of Cu radiation, e.g., Cu Kα radiation, e.g., wherein the XRPD is measured using radiation of wavelength 1.54059 Å.

1.17 Any of formulae 1.1-1.16 wherein the Crystalline Form A exhibits an XPRD pattern comprising the 2-theta (°) values set forth in Table A of formula 1.16, wherein the XRPD is measured using an incident beam of Cu radiation, e.g., Cu Kα radiation, e.g., wherein the XRPD is measured using radiation of wavelength 1.54059 Å.

1.18 Any of formulae 1.1-1.17 wherein the Crystalline Form A exhibits an XPRD pattern having characteristic 2-theta (°) values as set forth in Table A of formula 1.16, wherein the XRPD is measured using an incident beam of Cu radiation, e.g., Cu Kα radiation, e.g., wherein the XRPD is measured using radiation of wavelength 1.54059 Å.

1.19 Any of formulae 1.1-1.18 wherein the Crystalline Form A exhibits an XPRD pattern comprising at least three, e.g., at least five, e.g. at least ten, 2-theta)(° values selected from the group consisting of 12.3, 13.8, 15.4, 16.6, 17.2, 18.2, 18.5, 19.5, 20.5, 20.7, 22.9, and 25.7, wherein the XRPD is measured using an incident beam of Cu radiation, e.g., Cu Kα radiation, e.g., wherein the XRPD is measured using radiation of wavelength 1.54059 Å.

1.20 Any of formulae 1.1-1.19 wherein the Crystalline Form A exhibits an XPRD pattern comprising 2-theta (°) values of 12.3, 13.8, 15.4, 16.6, 17.2, 18.2, 18.5, 19.5, 20.5, 20.7, 22.9, and 25.7, wherein the XRPD is measured using an incident beam of Cu radiation, e.g., Cu Kα radiation, e.g., wherein the XRPD is measured using radiation of wavelength 1.54059 Å.

1.21 Any of formulae 1.1-1.20 wherein the Crystalline Form A exhibits an XPRD pattern having representative 2-theta (°) values of 12.3, 13.8, 15.4, 16.6, 17.2, 18.2, 18.5, 19.5, 20.5, 20.7, 22.9, and 25.7, wherein the XRPD is measured using an incident beam of Cu radiation, e.g., Cu Kα radiation, e.g., wherein the XRPD is measured using radiation of wavelength 1.54059 Å.

1.22 Any of formulae 1.1-1.21 wherein the Crystalline Form A exhibits an XPRD pattern comprising at least three, e.g., at least five, e.g. at least ten, 2-theta)(° values selected from the group consisting of 12.26, 13.78, 15.42, 16.55, 17.15, 18.19, 18.50, 19.45, 20.46, 20.68, 22.90, and 25.69, wherein the XRPD is measured using an incident beam of Cu radiation, e.g., Cu Kα radiation, e.g., wherein the XRPD is measured using radiation of wavelength 1.54059 Å.

1.23 Any of formulae 1.1-1.22 wherein the Crystalline Form A exhibits an XPRD pattern comprising 2-theta (°) values of 12.26, 13.78, 15.42, 16.55, 17.15, 18.19, 18.50, 19.45, 20.46, 20.68, 22.90, and 25.69, wherein the XRPD is measured using an incident beam of Cu radiation, e.g., Cu Kα radiation, e.g., wherein the XRPD is measured using radiation of wavelength 1.54059 Å.

1.24 Any of formulae 1.1-1.23 wherein the Crystalline Form A exhibits an XPRD pattern having representative 2-theta (°) values of 12.26, 13.78, 15.42, 16.55, 17.15, 18.19, 18.50, 19.45, 20.46, 20.68, 22.90, and 25.69, wherein the XRPD is measured using an incident beam of Cu radiation, e.g., Cu Kα radiation, e.g., wherein the XRPD is measured using radiation of wavelength 1.54059 Å.

1.25 Any of formulae 1.1-1.24 wherein the Crystalline Form A exhibits an XPRD pattern comprising at least three, e.g., at least five, e.g., at least ten, 2-theta)(° values selected from those set forth in Table B below:

TABLE B

| °2θ | d space (Å) | Intensity (%) |
|---|---|---|
| 12.26 ± 0.20 | 7.211 ± 0.117 | 22 |
| 13.78 ± 0.20 | 6.421 ± 0.093 | 36 |
| 15.42 ± 0.20 | 5.741 ± 0.074 | 26 |
| 16.55 ± 0.20 | 5.352 ± 0.064 | 40 |
| 17.15 ± 0.20 | 5.167 ± 0.060 | 29 |
| 18.19 ± 0.20 | 4.873 ± 0.053 | 100 |
| 18.50 ± 0.20 | 4.792 ± 0.051 | 100 |
| 19.45 ± 0.20 | 4.560 ± 0.046 | 38 |
| 20.46 ± 0.20 | 4.338 ± 0.042 | 43 |
| 20.68 ± 0.20 | 4.291 ± 0.041 | 80 |
| 22.90 ± 0.20 | 3.880 ± 0.033 | 22 |
| 25.69 ± 0.20 | 3.466 ± 0.027 | 70 | wherein the XRPD is measured using an incident beam of Cu radiation, e.g., Cu Kα radiation, e.g., wherein the XRPD is measured using radiation of wavelength 1.54059 Å.

1.26 Any of formulae 1.1-1.25 wherein the Crystalline Form A exhibits an XPRD pattern comprising the 2-theta (°) values set forth in Table B of formula 1.25, wherein the XRPD is measured using an incident beam of Cu radiation, e.g., Cu Kα radiation, e.g., wherein the XRPD is measured using radiation of wavelength 1.54059 Å.

1.27 Any of formulae 1.1-1.26 wherein the Crystalline Form A exhibits an XPRD pattern having representative 2-theta (°) values as set forth in Table B of formula 1.25, wherein the XRPD is measured using an incident beam of Cu radiation, e.g., Cu Kα radiation, e.g., wherein the XRPD is measured using radiation of wavelength 1.54059 Å.

1.28 Any of formulae 1.1-1.27 wherein the Crystalline Form A exhibits an XRPD pattern comprising at least three, e.g., at least five, e.g., at least nine, e.g., at least ten, e.g., at least twelve, e.g., at least fifteen, e.g., at least twenty, 2-theta)(° values selected from the group consisting of 6.9, 12.3, 13.8, 14.5, 15.4, 16.6, 17.2, 18.2, 18.5, 19.5, 20.1, 20.5, 20.7, 21.0, 21.5, 22.9, 24.7, 25.2, 25.4, 25.7, 26.4, 27.5, and 27.8, wherein the XRPD is measured using an incident beam of Cu radiation, e.g., Cu Kα radiation, e.g., wherein the XRPD is measured using radiation of wavelength 1.54059 Å.

1.29 Any of formulae 1.1-1.28 wherein the Crystalline Form A exhibits an XPRD pattern comprising the following 2-theta (°) values:
6.9, 12.3, 13.8, 14.5, 15.4, 16.6, 17.2, 18.2, 18.5, 19.5, 20.1, 20.5, 20.7, 21.0, 21.5, 22.9, 24.7, 25.2, 25.4, 25.7, 26.4, 27.5, and 27.8, wherein the XRPD is measured using an incident beam of Cu radiation, e.g., Cu Kα radiation, e.g., wherein the XRPD is measured using radiation of wavelength 1.54059 Å.

1.30 Any of formulae 1.1-1.29 wherein the Crystalline Form A exhibits an XRPD pattern comprising at least three, e.g., at least five, e.g., at least nine, e.g., at least ten, e.g., at least twelve, e.g., at least fifteen, e.g., at least twenty, 2-theta)(° values selected from the group consisting of 6.87, 12.26, 13.78, 14.49, 15.42, 16.55, 17.15, 18.19, 18.50, 19.45, 20.06, 20.46, 20.68, 20.96, 21.54, 22.90, 24.69, 25.17, 25.44, 25.69, 26.36, 27.52, and 27.76, wherein the XRPD is measured using an incident beam of Cu radiation, e.g., Cu Kα radiation, e.g., wherein the XRPD is measured using radiation of wavelength 1.54059 Å.

1.31 Any of formulae 1.1-1.30 wherein the Crystalline Form A exhibits an XPRD pattern comprising the following 2-theta (°) values:
6.87, 12.26, 13.78, 14.49, 15.42, 16.55, 17.15, 18.19, 18.50, 19.45, 20.06, 20.46, 20.68, 20.96, 21.54, 22.90, 24.69, 25.17, 25.44, 25.69, 26.36, 27.52, and 27.76, wherein the XRPD is measured using an incident beam of Cu radiation, e.g., Cu Kα radiation, e.g., wherein the XRPD is measured using radiation of wavelength 1.54059 Å.

1.32 Any of formulae 1.1-1.31 wherein the Crystalline Form A exhibits an XRPD pattern comprising at least three, e.g., at least five, e.g., at least nine, e.g., at least ten, e.g., at least twelve, e.g., at least fifteen, e.g., at least twenty, 2-theta)(° values selected from those set forth in Table C below:

TABLE C

| °2θ | d space (Å) | Intensity (%) |
|---|---|---|
| 6.87 ± 0.20 | 12.859 ± 0.374 | 6 |
| 12.26 ± 0.20 | 7.211 ± 0.117 | 22 |
| 13.78 ± 0.20 | 6.421 ± 0.093 | 36 |
| 14.49 ± 0.20 | 6.106 ± 0.084 | 6 |
| 15.42 ± 0.20 | 5.741 ± 0.074 | 26 |
| 16.55 ± 0.20 | 5.352 ± 0.064 | 40 |
| 17.15 ± 0.20 | 5.167 ± 0.060 | 29 |
| 18.19 ± 0.20 | 4.873 ± 0.053 | 100 |
| 18.50 ± 0.20 | 4.792 ± 0.051 | 100 |
| 19.45 ± 0.20 | 4.560 ± 0.046 | 38 |
| 20.06 ± 0.20 | 4.422 ± 0.044 | 9 |
| 20.46 ± 0.20 | 4.338 ± 0.042 | 43 |
| 20.68 ± 0.20 | 4.291 ± 0.041 | 80 |
| 20.96 ± 0.20 | 4.236 ± 0.040 | 11 |
| 21.54 ± 0.20 | 4.123 ± 0.038 | 10 |

TABLE C-continued

| °2θ | d space (Å) | Intensity (%) |
|---|---|---|
| 22.90 ± 0.20 | 3.880 ± 0.033 | 22 |
| 24.69 ± 0.20 | 3.602 ± 0.029 | 3 |
| 25.17 ± 0.20 | 3.535 ± 0.028 | 14 |
| 25.44 ± 0.20 | 3.499 ± 0.027 | 13 |
| 25.69 ± 0.20 | 3.466 ± 0.027 | 70 |
| 26.36 ± 0.20 | 3.378 ± 0.025 | 13 |
| 27.52 ± 0.20 | 3.239 ± 0.023 | 23 |
| 27.76 ± 0.20 | 3.211 ± 0.023 | 7 | wherein the XRPD is measured using an incident beam of Cu radiation, e.g., Cu Kα radiation, e.g., wherein the XRPD is measured using radiation of wavelength 1.54059 Å.

1.33 Any of formulae 1.1-1.32 wherein the Crystalline Form A exhibits an XPRD pattern comprising the 2-theta (°) values set forth in Table C of formula 1.32, wherein the XRPD is measured using an incident beam of Cu radiation, e.g., Cu Kα radiation, e.g., wherein the XRPD is measured using radiation of wavelength 1.54059 Å.

1.34 Any of formulae 1.1-1.33 wherein the Crystalline Form A exhibits an XRPD pattern comprising at least three, e.g., at least five, d-spacing (Å) values selected from the group consisting of 5.7, 5.4, 5.2, 4.8, 4.6, 4.3, 3.9, and 3.5.

1.35 Any of formulae 1.1-1.34 wherein the Crystalline Form A exhibits an XRPD pattern comprising d-spacing (Å) values of 5.7, 5.4, 5.2, 4.8, 4.6, 4.3, 3.9, and 3.5.

1.36 Any of formulae 1.1-1.35 wherein the Crystalline Form A exhibits an XRPD pattern comprising at least three, e.g., at least five, d-spacing (Å) values selected from the group consisting of 5.74, 5.35, 5.17, 4.79, 4.56, 4.34, 4.29, 3.88, and 3.47.

1.37 Any of formulae 1.1-1.36 wherein the Crystalline Form A exhibits an XRPD pattern comprising d-spacing (Å) values of 5.74, 5.35, 5.17, 4.79, 4.56, 4.34, 4.29, 3.88, and 3.47.

1.38 Any of formulae 1.1-1.37 wherein the Crystalline Form A exhibits an XRPD pattern comprising at least three, e.g., at least five, d-spacing (Å) values selected from the group consisting of 5.741, 5.352, 5.167, 4.792, 4.560, 4.338, 4.291, 3.880, and 3.466.

1.39 Any of formulae 1.1-1.38 wherein the Crystalline Form A exhibits an XRPD pattern comprising d-spacing (Å) values of 5.741, 5.352, 5.167, 4.792, 4.560, 4.338, 4.291, 3.880, and 3.466.

1.40 Any of formulae 1.1-1.39 wherein the Crystalline Form A exhibits an XRPD pattern comprising at least three, e.g., at least five, d-spacing (Å) values selected from those set forth in Table A of formula 1.16.

1.41 Any of formulae 1.1-1.40 wherein the Crystalline Form A exhibits an XRPD pattern comprising the d-spacing (Å) values set forth in Table A of formula 1.16.

1.42 Any of formulae 1.1-1.41 wherein the Crystalline Form A exhibits an XRPD pattern comprising at least three, e.g., at least five, e.g., at least ten, d-spacing (Å) values selected from the group consisting of 7.2, 6.4, 5.7, 5.4, 5.2, 4.9, 4.8, 4.6, 4.3, 3.9, and 3.5.

1.43 Any of formulae 1.1-1.42 wherein the Crystalline Form A exhibits an XRPD pattern comprising d-spacing (Å) values of 7.2, 6.4, 5.7, 5.4, 5.2, 4.9, 4.8, 4.6, 4.3, 3.9, and 3.5.

1.44 Any of formulae 1.1-1.43 wherein the Crystalline Form A exhibits an XRPD pattern comprising at least three, e.g., at least five, e.g., at least ten, d-spacing (Å) values selected from the group consisting of 7.21, 6.42, 5.74, 5.35, 5.17, 4.87, 4.79, 4.56, 4.34, 4.29, 3.88, and 3.47.

1.45 Any of formulae 1.1-1.44 wherein the Crystalline Form A exhibits an XRPD pattern comprising d-spacing (Å) values of 7.21, 6.42, 5.74, 5.35, 5.17, 4.87, 4.79, 4.56, 4.34, 4.29, 3.88, and 3.47.

1.46 Any of formulae 1.1-1.45 wherein the Crystalline Form A exhibits an XRPD pattern comprising at least three, e.g., at least five, e.g., at least ten, d-spacing (Å) values selected from the group consisting of 7.211, 6.421, 5.741, 5.352, 5.167, 4.873, 4.792, 4.560, 4.338, 4.291, 3.880, and 3.466.

1.47 Any of formulae 1.1-1.46 wherein the Crystalline Form A exhibits an XRPD pattern comprising d-spacing (Å) values of 7.211, 6.421, 5.741, 5.352, 5.167, 4.873, 4.792, 4.560, 4.338, 4.291, 3.880, and 3.466.

1.48 Any of formulae 1.1-1.47 wherein the Crystalline Form A exhibits an XRPD pattern comprising at least three, e.g., at least five, e.g., at least ten, d-spacing (Å) values selected from those set forth in Table B of formula 1.25.

1.49 Any of formulae 1.1-1.48 wherein the Crystalline Form A exhibits an XRPD pattern comprising the d-spacing (Å) values set forth in Table B of formula 1.25.

1.50 Any of formulae 1.1-1.49 wherein the Crystalline Form A exhibits an XRPD pattern comprising at least three, e.g., at least five, e.g., at least nine, e.g., at least ten, e.g., at least twelve, e.g., at least fifteen, d-spacing (Å) values selected from the group consisting of 12.9, 7.2, 6.4, 6.1, 5.7, 5.4, 5.2, 4.9, 4.8, 4.6, 4.4, 4.3, 4.2, 4.1, 3.9, 3.6, 3.5, 3.4, and 3.2.

1.51 Any of formulae 1.1-1.50 wherein the Crystalline Form A exhibits an XRPD pattern comprising d-spacing (Å) values of 12.9, 7.2, 6.4, 6.1, 5.7, 5.4, 5.2, 4.9, 4.8, 4.6, 4.4, 4.3, 4.2, 4.1, 3.9, 3.6, 3.5, 3.4, and 3.2.

1.52 Any of formulae 1.1-1.51 wherein the Crystalline Form A exhibits an XRPD pattern comprising at least three, e.g., at least five, e.g., at least nine, e.g., at least ten, e.g., at least twelve, e.g., at least fifteen, e.g., at least twenty, d-spacing (Å) values selected from the group consisting of 12.86, 7.21, 6.42, 6.11, 5.74, 5.35, 5.17, 4.87, 4.79, 4.56, 4.42, 4.34, 4.29, 4.24, 4.12, 3.88, 3.60, 3.54, 3.50, 3.47, 3.38, 3.24, and 3.21.

1.53 Any of formulae 1.1-1.52 wherein the Crystalline Form A exhibits an XRPD pattern comprising d-spacing (Å) values of 12.86, 7.21, 6.42, 6.11, 5.74, 5.35, 5.17, 4.87, 4.79, 4.56, 4.42, 4.34, 4.29, 4.24, 4.12, 3.88, 3.60, 3.54, 3.50, 3.47, 3.38, 3.24, and 3.21.

1.54 Any of formulae 1.1-1.53 wherein the Crystalline Form A exhibits an XRPD pattern comprising at least three, e.g., at least five, e.g., at least nine, e.g., at least ten, e.g., at least twelve, e.g., at least fifteen, e.g., at least twenty, d-spacing (Å) values selected from the group consisting of 12.859, 7.211, 6.421, 6.106, 5.741, 5.352, 5.167, 4.873, 4.792, 4.560, 4.422, 4.338, 4.291, 4.236, 4.123, 3.880, 3.602, 3.535, 3.499, 3.466, 3.378, 3.239, and 3.211.

1.55 Any of formulae 1.1-1.54 wherein the Crystalline Form A exhibits an XRPD pattern comprising d-spacing (Å) values of 12.859, 7.211, 6.421, 6.106, 5.741, 5.352, 5.167, 4.873, 4.792, 4.560, 4.422, 4.338, 4.291, 4.236, 4.123, 3.880, 3.602, 3.535, 3.499, 3.466, 3.378, 3.239, and 3.211.

1.56 Any of formulae 1.1-1.55 wherein the Crystalline Form A exhibits an XRPD pattern comprising at least three, e.g., at least five, e.g., at least nine, e.g., at least ten, e.g., at least twelve, e.g., at least fifteen, e.g., at least twenty, d-spacing (Å) values selected from those set forth in Table C of formula 1.32.

1.57 Any of formulae 1.1-1.56 wherein the Crystalline Form A exhibits an XRPD pattern comprising the d-spacing (Å) values set forth in Table C of formula 1.32.

1.58 Any of formulae 1.1-1.57 wherein the Crystalline Form A exhibits an XRPD pattern comprising characteristic peaks of the XPRD pattern shown in FIG. 1, wherein the XRPD is measured using Cu radiation, e.g., Cu Kα radiation, e.g., wherein the XRPD is measured using radiation of wavelength 1.54059 Å.

1.59 Any of formulae 1.1-1.58 wherein the Crystalline Form A exhibits an XRPD pattern comprising representative peaks of the XPRD pattern shown in FIG. 1, wherein the XRPD is measured using Cu radiation, e.g., Cu Kα radiation, e.g., wherein the XRPD is measured using radiation of wavelength 1.54059 Å.

1.60 Any of formulae 1.1-1.59 wherein the Crystalline Form A exhibits an X-ray powder diffraction (XRPD) pattern, e.g., an X-ray powder diffraction pattern measured using an incident beam of Cu radiation, e.g., Cu Kα radiation, e.g., a high-resolution X-ray powder diffraction pattern measured using an incident beam of Cu Kα radiation, e.g., wherein the XRPD is measured using radiation of wavelength 1.54059 Å, comprising three peaks, in some embodiments, five peaks, selected from those shown in FIG. 1.

1.61 Any of formulae 1.1-1.60 wherein the Crystalline Form A exhibits an XRPD pattern, e.g., an XRPD pattern measured using an incident beam of Cu radiation, e.g., Cu Kα radiation, e.g., a high-resolution XRPD pattern measured using an incident beam of Cu Kα radiation, e.g., wherein the XRPD is measured using radiation of wavelength 1.54059 Å, comprising at least nine peaks, e.g., at least ten peaks, e.g., at least twelve peaks, e.g., at least fifteen peaks, e.g., at least twenty peaks, selected from those shown in FIG. 1.

1.62 Any of formulae 1.1-1.61 wherein the Crystalline Form A exhibits an X-ray powder diffraction (XRPD) pattern, e.g., an X-ray powder diffraction pattern measured using an incident beam of Cu radiation, e.g., Cu Kα radiation, e.g., wherein the XRPD is measured using radiation of wavelength 1.54059 Å, substantially as shown in FIG. 1.

1.63 Any of formulae 1.1-1.62 wherein the Crystalline Form A exhibits an X-ray powder diffraction (XRPD) pattern, e.g., an X-ray powder diffraction pattern measured using an incident beam of Cu radiation, e.g., Cu Kα radiation, e.g., wherein the XRPD is measured using radiation of wavelength 1.54059 Å, as shown in FIG. 1.

1.64 Any of formulae 1.1-1.63 wherein the Crystalline Form A exhibits an XRPD pattern comprising characteristic peaks of the XPRD pattern shown in any of FIGS. 1, 35, 37, and 47, e.g., FIG. 1, e.g., FIG. 35, e.g., FIG. 37, e.g., FIG. 47, wherein the XRPD is measured using Cu radiation, e.g., Cu Kα radiation, e.g., wherein the XRPD is measured using radiation of wavelength 1.54059 Å.

1.65 Any of formulae 1.1-1.64 wherein the Crystalline Form A exhibits an XRPD pattern comprising representative peaks of the XPRD pattern shown in any of FIGS. 1, 35, 37, and 47, e.g., FIG. 1, e.g., FIG. 35, e.g., FIG. 37, e.g., FIG. 47, wherein the XRPD is measured using Cu radiation, e.g., Cu Kα radiation, e.g., wherein the XRPD is measured using radiation of wavelength 1.54059 Å.

1.66 Any of formulae 1.1-1.65 wherein the Crystalline Form A exhibits an XRPD pattern, e.g., an XPRD pattern measured using an incident beam of Cu radiation, e.g., Cu Kα radiation, e.g., a high-resolution XRPD pattern measured using an incident beam of Cu Kα radiation, e.g., wherein the XRPD is measured using radiation of wavelength 1.54059 Å, comprising three peaks, in some embodiments, five peaks, selected from those shown in any of FIGS. 1, 35, 37, and 47, e.g., FIG. 1, e.g., FIG. 35, e.g., FIG. 37, e.g., FIG. 47.

1.67 Any of formulae 1.1-1.66 wherein the Crystalline Form A exhibits an XRPD pattern, e.g., an XRPD pattern measured using an incident beam of Cu radiation, e.g., Cu Kα radiation, e.g., a high-resolution XRPD pattern measured using an incident beam of Cu Kα radiation, e.g., wherein the XRPD is measured using radiation of wavelength 1.54059 Å, comprising at least nine peaks, e.g., at least ten peaks, e.g., at least twelve peaks, e.g., at least fifteen peaks, e.g., at least twenty peaks, selected from those shown in any of FIGS. 1, 35, 37, and 47, e.g., FIG. 1, e.g., FIG. 35, e.g., FIG. 37, e.g., FIG. 47.

1.68 Any of formulae 1.1-1.67 wherein the Crystalline Form A exhibits an XRPD pattern, e.g., an XRPD pattern measured using an incident beam of Cu radiation, e.g., Cu Kα radiation, e.g., wherein the XRPD is measured using radiation of wavelength 1.54059 Å, substantially as shown in any of FIGS. 1, 35, 37, and 47, e.g., FIG. 1, e.g., FIG. 35, e.g., FIG. 37, e.g., FIG. 47.

1.69 Any of formulae 1.1-1.68 wherein the Crystalline Form A exhibits an XRPD pattern, e.g., an XRPD pattern measured using an incident beam of Cu radiation, e.g., Cu Kα radiation, e.g., wherein the XRPD is measured using radiation of wavelength 1.54059 Å, as shown in any of FIGS. 1, 35, 37, and 47, e.g., FIG. 1, e.g., FIG. 35, e.g., FIG. 37, e.g., FIG. 47.

1.70 Any of formulae 1.1-1.69 wherein the Crystalline Form A exhibits a differential scanning calorimetry (DSC) thermogram comprising an endothermic peak between 245° C. and 249° C., e.g., between 245° C. and 248° C., e.g., wherein the Crystalline Form A exhibits a differential scanning calorimetry (DSC) thermogram comprising multiple, e.g., three, endotherms between 245° C. and 249° C., e.g., between 245° C. and 248° C., e.g., wherein the Crystalline Form A exhibits a differential scanning calorimetry (DSC) thermogram comprising an endothermic peak at 247° C. with an onset at 245° C., an endothermic shoulder at 248° C., and an endothermic peak at 248° C.

1.71 Any of formulae 1.1-1.70 wherein the Crystalline Form A exhibits a differential scanning calorimetry (DSC) thermogram comprising an endothermic peak at 247° C., e.g., an endothermic peak at 247° C. with an onset at 245° C.

1.72 Any of formulae 1.1-1.71 wherein the Crystalline Form A exhibits a differential scanning calorimetry (DSC) thermogram comprising an endothermic peak at 248° C.

1.73 Any of formulae 1.1-1.72 wherein the Crystalline Form A exhibits a differential scanning calorimetry (DSC) thermogram as shown in FIG. 2.

1.74 Any of formulae 1.1-1.73 wherein the Crystalline Form A exhibits a thermogravimetric analysis (TGA) thermogram comprising 0.4% weight loss up to 200° C.

1.75 Any of formulae 1.1-1.74 having a thermogravimetric analysis (TGA) thermogram comprising an onset decomposition temperature at 276° C.

1.76 Any of formulae 1.1-1.75 wherein the Crystalline Form A exhibits a thermogravimetric analysis (TGA) thermogram as shown in FIG. 2.

1.77 Any of formulae 1.1-1.76 wherein the Crystalline Form A exhibits a dynamic vapor sorption/desorption isotherm as shown in FIG. 3, e.g., a dynamic vapor sorption/desorption isotherm wherein Crystalline Form A shows:
a weight loss of 0.03% upon equilibration at 5% RH;
a weight gain of 0.10% from 5% to 95% RH; and
a 0.10% weight loss from 95% to 5% RH.

1.78 Crystalline Form B of the Compound in hydrochloric acid addition salt form ((1R,5S)-1-(naphthalen-2-yl)-3-azabicyclo[3.1.0]hexane hydrochloride) ("Crystalline Form B").

1.79 Formula 1.78 wherein the Crystalline Form B belongs to the $P2_12_12_1$ space group and has the following unit cell parameters:
a=5.9055(2) Å, b=7.4645(3) Å, c=29.1139(13) Å, α=β=γ=90°.

1.80 Formula 1.78 wherein the Crystalline Form B belongs to the $P2_12_12_1$ space group and has any combination of the following unit cell parameters:
a=5-7 Å, e.g., 6 Å, e.g., 5.7-6.1 Å, e.g., 5.8-6.0 Å, e.g., 5.9 Å, e.g., 5.91, e.g., 5.906 Å;
b=6-8 Å, e.g., 7 Å, e.g., 7.3-7.7 Å, e.g., 7.4-7.6 Å, e.g., 7.5 Å, e.g., 7.46 Å, e.g., 7.465 Å;
c=28-30 Å, e.g., 29 Å, e.g., 28.9-29.3 Å, e.g., 29.0-29.2 Å, e.g., 29.1 Å, e.g., 29.11 Å, e.g., 29.114 Å; and
α=β=γ=90°.

1.81 Any of formulae 1.78-1.80 wherein the Crystalline Form B has a calculated volume of V=1283.39(9) Å$^3$.

1.82 Any of formulae 1.78-1.81 wherein the crystal structure of the Crystalline Form B is obtained with a crystal having approximate dimensions of 0.31 mm×0.21 mm×0.09 mm, e.g., a colorless plate having approximate dimensions of 0.31 mm×0.21 mm×0.09 mm.

1.83 Any of formulae 1.78-1.82 wherein the crystal structure of the Crystalline Form B is obtained with Cu Kα radiation, e.g., Cu Kα having λ=1.54178 Å.

1.84 Any of formulae 1.78-1.83 wherein the crystal structure of the Crystalline Form B is obtained at 100(2) K.

1.85 Any of formulae 1.78-1.84 wherein the Crystalline Form B has a single crystal structure represented by the atomic displacement ellipsoid drawing of FIG. 24.

1.86 Any of formulae 1.78-1.85 wherein the Crystalline Form B has a calculated XPRD pattern as shown in FIG. 32.

1.87 Any of formulae 1.78-1.86 wherein the Crystalline Form B exhibits an XRPD pattern comprising at least three 2-theta (°) values selected from the group consisting of 6.0, 17.4, 18.9, 19.2, and 24.4, wherein the XRPD is measured using an incident beam of Cu radiation, e.g., Cu Kα radiation, e.g., wherein the XRPD is measured using radiation of wavelength 1.54059 Å.

1.88 Any of formulae 1.78-1.87 wherein the Crystalline Form B exhibits an XRPD pattern comprising 2- theta (°) values of 6.0, 17.4, 18.9, 19.2, and 24.4, wherein the XRPD is measured using an incident beam of Cu radiation, e.g., Cu Kα radiation, e.g., wherein the XRPD is measured using radiation of wavelength 1.54059 Å.

1.89 Any of formulae 1.78-1.88 wherein the Crystalline Form B exhibits an XRPD pattern having characteristic 2-theta (°) values of 6.0, 17.4, 18.9, 19.2, and 24.4, wherein the XRPD is measured using an incident beam of Cu radiation, e.g., Cu Kα radiation, e.g., wherein the XRPD is measured using radiation of wavelength 1.54059 Å.

1.90 Any of formulae 1.78-1.89 wherein the Crystalline Form B exhibits an XRPD pattern comprising at least three 2-theta (°) values selected from the group consisting of 6.04, 17.41, 18.94, 19.19, and 24.39, wherein the XRPD is measured using an incident beam of Cu radiation, e.g., Cu Kα radiation, e.g., wherein the XRPD is measured using radiation of wavelength 1.54059 Å.

1.91 Any of formulae 1.78-1.90 wherein the Crystalline Form B exhibits an XRPD pattern comprising 2-theta (°) values of 6.04, 17.41, 18.94, 19.19, and 24.39, wherein the XRPD is measured using an incident beam of Cu radiation, e.g., Cu Kα radiation, e.g., wherein the XRPD is measured using radiation of wavelength 1.54059 Å.

1.92 Any of formulae 1.78-1.91 wherein the Crystalline Form B exhibits an XRPD pattern having characteristic 2-theta (°) values of 6.04, 17.41, 18.94, 19.19, and 24.39, wherein the XRPD is measured using an incident beam of Cu radiation, e.g., Cu Kα radiation, e.g., wherein the XRPD is measured using radiation of wavelength 1.54059 Å.

1.93 Any of formulae 1.78-1.92 wherein the Crystalline Form B exhibits an XRPD pattern comprising at least three 2-theta (°) values selected from those set forth in Table D below:

TABLE D

| °2θ | d space (Å) | Intensity (%) |
| --- | --- | --- |
| 6.04 ± 0.20 | 14.620 ± 0.484 | 13 |
| 17.41 ± 0.20 | 5.089 ± 0.058 | 14 |
| 18.94 ± 0.20 | 4.681 ± 0.049 | 79 |
| 19.19 ± 0.20 | 4.622 ± 0.048 | 100 |
| 24.39 ± 0.20 | 3.646 ± 0.029 | 23 | wherein the XRPD is measured using an incident beam of Cu radiation, e.g., Cu Kα radiation, e.g., wherein the XRPD is measured using radiation of wavelength 1.54059 Å.

1.94 Any of formulae 1.78-1.93 wherein the Crystalline Form B exhibits an XRPD pattern comprising the 2-theta (°) values set forth in Table D of formula 1.93, wherein the XRPD is measured using an incident beam of Cu radiation, e.g., Cu Kα radiation, e.g., wherein the XRPD is measured using radiation of wavelength 1.54059 Å.

1.95 Any of formulae 1.78-1.94 wherein the Crystalline Form B exhibits an XRPD pattern having characteristic 2-theta (°) values as set forth in Table D of formula 1.93, wherein the XRPD is measured using an incident beam of Cu radiation, e.g., Cu Kα radiation, e.g., wherein the XRPD is measured using radiation of wavelength 1.54059 Å.

1.96 Any of formulae 1.78-1.95 wherein the Crystalline Form B exhibits an XRPD pattern comprising at least three, e.g., at least five, 2-theta (°) values selected from the group consisting of 6.0, 13.2, 17.4, 18.9, 19.2, 23.6, 23.8, 24.4, and 28.2, wherein the XRPD is measured using an incident beam of Cu radiation, e.g., Cu Kα radiation, e.g., wherein the XRPD is measured using radiation of wavelength 1.54059 Å.

1.97 Any of formulae 1.78-1.96 wherein the Crystalline Form B exhibits an XRPD pattern comprising 2-theta (°) values of 6.0, 13.2, 17.4, 18.9, 19.2, 23.6, 23.8, 24.4, and 28.2, wherein the XRPD is measured using an incident beam of Cu radiation, e.g., Cu Kα radiation, e.g., wherein the XRPD is measured using radiation of wavelength 1.54059 Å. 1.98 Any of formulae 1.78-1.97 wherein the Crystalline Form B exhibits an XRPD pattern having representative 2-theta (°) values of 6.0, 13.2, 17.4, 18.9, 19.2, 23.6, 23.8, 24.4, and 28.2, wherein the XRPD is measured using an incident beam of Cu radiation, e.g., Cu Kα radiation, e.g., wherein the XRPD is measured using radiation of wavelength 1.54059 Å.

1.99 Any of formulae 1.78-1.98 wherein the Crystalline Form B exhibits an XRPD pattern comprising at least three, e.g., at least five, 2-theta (°) values selected from the group consisting of 6.04, 13.21, 17.41, 18.94, 19.19, 23.59, 23.79, 24.39, and 28.15, wherein the XRPD is measured using an incident beam of Cu radiation, e.g., Cu Kα radiation, e.g., wherein the XRPD is measured using radiation of wavelength 1.54059 Å.

1.100 Any of formulae 1.78-1.99 wherein the Crystalline Form B exhibits an XRPD pattern comprising 2-theta (°) values of 6.04, 13.21, 17.41, 18.94, 19.19, 23.59, 23.79, 24.39, and 28.15, wherein the XRPD is measured using an incident beam of Cu radiation, e.g., Cu Kα radiation, e.g., wherein the XRPD is measured using radiation of wavelength 1.54059 Å.

1.101 Any of formulae 1.78-1.100 wherein the Crystalline Form B exhibits an XRPD pattern having representative 2-theta (°) values of 6.04, 13.21, 17.41, 18.94, 19.19, 23.59, 23.79, 24.39, and 28.15, wherein the XRPD is measured using an incident beam of Cu radiation, e.g., Cu Kα radiation, e.g., wherein the XRPD is measured using radiation of wavelength 1.54059 Å.

1.102 Any of formulae 1.78-1.101 wherein the Crystalline Form B exhibits an XRPD pattern comprising at least three, e.g., at least five, 2-theta (°) values selected from those set forth in Table E below:

TABLE E

| °2θ | d space (Å) | Intensity (%) |
| --- | --- | --- |
| 6.04 ± 0.20 | 14.620 ± 0.484 | 13 |
| 13.21 ± 0.20 | 6.699 ± 0.101 | 21 |
| 17.41 ± 0.20 | 5.089 ± 0.058 | 14 |
| 18.94 ± 0.20 | 4.681 ± 0.049 | 79 |
| 19.19 ± 0.20 | 4.622 ± 0.048 | 100 |
| 23.59 ± 0.20 | 3.769 ± 0.032 | 16 |
| 23.79 ± 0.20 | 3.737 ± 0.031 | 43 |
| 24.39 ± 0.20 | 3.646 ± 0.029 | 23 |
| 28.15 ± 0.20 | 3.168 ± 0.022 | 24 | wherein the XRPD is measured using an incident beam of Cu radiation, e.g., Cu Kα radiation, e.g., wherein the XRPD is measured using radiation of wavelength 1.54059 Å.

1.103 Any of formulae 1.78-1.102 wherein the Crystalline Form B exhibits an XRPD pattern comprising the 2-theta (°) values set forth in Table E of formula 1.102, wherein the XRPD is measured using an incident beam of Cu radiation, e.g., Cu Kα radiation, e.g., wherein the XRPD is measured using radiation of wavelength 1.54059 Å.

1.104 Any of formulae 1.78-1.103 wherein the Crystalline Form B exhibits an XRPD pattern having representative 2-theta (°) values as set forth in Table E of formula 1.102, wherein the XRPD is measured using an incident beam of Cu radiation, e.g., Cu Kα radiation, e.g., wherein the XRPD is measured using radiation of wavelength 1.54059 Å.

1.105 Any of formulae 1.78-1.104 wherein the Crystalline Form B exhibits an XRPD pattern comprising at least three, e.g., at least five, e.g., at least nine, e.g., at least ten, e.g., at least fifteen, e.g., at least twenty, e.g., at least twenty-five, 2-theta)(° values selected from the group consisting of 6.0, 12.1, 13.2, 14.9, 15.1, 16.0, 16.9, 17.4, 18.2, 18.9, 19.2, 19.9, 21.1, 21.3, 21.7, 22.6, 23.6, 23.8, 24.4, 25.3, 26.1, 26.6, 27.2, 28.2, 28.7, and 29.5, wherein the XRPD is measured using an incident beam of Cu radiation, e.g., Cu Kα radiation, e.g., wherein the XRPD is measured using radiation of wavelength 1.54059 Å.

1.106 Any of formulae 1.78-1.105 wherein the Crystalline Form B exhibits an XRPD pattern comprising the following 2-theta (°) values: 6.0, 12.1, 13.2, 14.9, 15.1, 16.0, 16.9, 17.4, 18.2, 18.9, 19.2, 19.9, 21.1, 21.3, 21.7, 22.6, 23.6, 23.8, 24.4, 25.3, 26.1, 26.6, 27.2, 28.2, 28.7, and 29.5, wherein the XRPD is measured using an incident beam of Cu radiation, e.g., Cu Kα radiation, e.g., wherein the XRPD is measured using radiation of wavelength 1.54059 Å.

1.107 Any of formulae 1.78-1.106 wherein the Crystalline Form B exhibits an XRPD pattern comprising at least three, e.g., at least five, e.g., at least nine, e.g., at least ten, e.g., at least fifteen, e.g., at least twenty, e.g., at least twenty-five, 2-theta)(° values selected from the group consisting of 6.04, 12.12, 13.21, 14.86, 15.13, 16.02, 16.90, 17.41, 18.23, 18.94, 19.19, 19.91, 21.05, 21.27, 21.74, 22.55, 23.59, 23.79, 24.39, 25.34, 26.06, 26.61, 27.15, 28.15, 28.66, and 29.47, wherein the XRPD is measured using an incident beam of Cu radiation, e.g., Cu Kα radiation, e.g., wherein the XRPD is measured using radiation of wavelength 1.54059 Å.

1.108 Any of formulae 1.78-1.107 wherein the Crystalline Form B exhibits an XRPD pattern comprising the following 2-theta (°) values:
6.04, 12.12, 13.21, 14.86, 15.13, 16.02, 16.90, 17.41, 18.23, 18.94, 19.19, 19.91, 21.05, 21.27, 21.74, 22.55, 23.59, 23.79, 24.39, 25.34, 26.06, 26.61, 27.15, 28.15, 28.66, and 29.47, wherein the XRPD is measured using an incident beam of Cu radiation, e.g., Cu Kα radiation, e.g., wherein the XRPD is measured using radiation of wavelength 1.54059 Å.

1.109 Any of formulae 1.78-1.108 wherein the Crystalline Form B exhibits an XRPD pattern comprising at least three, e.g., at least five, e.g., at least nine, e.g., at least ten, e.g., at least fifteen, e.g., at least twenty, e.g., at least twenty-five, e.g., at least five, 2-theta (°) values selected from those set forth in Table F below:

TABLE F

| °2θ | d space (Å) | Intensity (%) |
|---|---|---|
| 6.04 ± 0.20 | 14.620 ± 0.484 | 13 |
| 12.12 ± 0.20 | 7.296 ± 0.120 | 6 |
| 13.21 ± 0.20 | 6.699 ± 0.101 | 21 |
| 14.86 ± 0.20 | 5.958 ± 0.080 | 8 |
| 15.13 ± 0.20 | 5.853 ± 0.077 | 5 |
| 16.02 ± 0.20 | 5.529 ± 0.069 | 1 |
| 16.90 ± 0.20 | 5.242 ± 0.062 | 4 |
| 17.41 ± 0.20 | 5.089 ± 0.058 | 14 |
| 18.23 ± 0.20 | 4.861 ± 0.053 | 10 |
| 18.94 ± 0.20 | 4.681 ± 0.049 | 79 |
| 19.19 ± 0.20 | 4.622 ± 0.048 | 100 |
| 19.91 ± 0.20 | 4.457 ± 0.044 | 4 |
| 21.05 ± 0.20 | 4.217 ± 0.040 | 11 |
| 21.27 ± 0.20 | 4.173 ± 0.039 | 2 |
| 21.74 ± 0.20 | 4.085 ± 0.037 | 4 |
| 22.55 ± 0.20 | 3.939 ± 0.034 | 6 |
| 23.59 ± 0.20 | 3.769 ± 0.032 | 16 |
| 23.79 ± 0.20 | 3.737 ± 0.031 | 43 |
| 24.39 ± 0.20 | 3.646 ± 0.029 | 23 |
| 25.34 ± 0.20 | 3.512 ± 0.027 | 1 |
| 26.06 ± 0.20 | 3.416 ± 0.026 | 2 |
| 26.61 ± 0.20 | 3.347 ± 0.025 | 1 |
| 27.15 ± 0.20 | 3.282 ± 0.024 | 2 |
| 28.15 ± 0.20 | 3.168 ± 0.022 | 24 |
| 28.66 ± 0.20 | 3.112 ± 0.021 | 13 |
| 29.47 ± 0.20 | 3.028 ± 0.020 | 13 | wherein the XRPD is measured using an incident beam of Cu radiation, e.g., Cu Kα radiation, e.g., wherein the XRPD is measured using radiation of wavelength 1.54059 Å.

1.110 Any of formulae 1.78-1.109 wherein the Crystalline Form B exhibits an XRPD pattern comprising the 2-theta (°) values set forth in Table F of formula 1.109, wherein the XRPD is measured using an incident beam of Cu radiation, e.g., Cu Kα radiation, e.g., wherein the XRPD is measured using radiation of wavelength 1.54059 Å.

1.111 Any of formulae 1.78-1.110 wherein the Crystalline Form B exhibits an XRPD pattern comprising at least three d-spacing (Å) values selected from the group consisting of 14.6, 5.1, 4.7, 4.6, and 3.6.

1.112 Any of formulae 1.78-1.111 wherein the Crystalline Form B exhibits an XRPD pattern comprising d-spacing (Å) values of 14.6, 5.1, 4.7, 4.6, and 3.6.

1.113 Any of formulae 1.78-1.112 wherein the Crystalline Form B exhibits an XRPD pattern comprising at least three d-spacing (Å) values selected from the group consisting of 14.62, 5.09, 4.68, 4.62, and 3.65.

1.114 Any of formulae 1.78-1.113 wherein the Crystalline Form B exhibits an XRPD pattern comprising d-spacing (Å) values of 14.62, 5.09, 4.68, 4.62, and 3.65.

1.115 Any of formulae 1.78-1.114 wherein the Crystalline Form B exhibits an XRPD pattern comprising at least three d-spacing (Å) values selected from the group consisting of 14.620, 5.089, 4.681, 4.622, and 3.646.

1.116 Any of formulae 1.78-1.115 wherein the Crystalline Form B exhibits an XRPD pattern comprising d-spacing (Å) values of 14.620, 5.089, 4.681, 4.622, and 3.646.

1.117 Any of formulae 1.78-1.116 wherein the Crystalline Form B exhibits an XRPD pattern comprising at least three d-spacing (Å) values selected from those set forth in Table D of formula 1.93.

1.118 Any of formulae 1.78-1.117 wherein the Crystalline Form B exhibits an XRPD pattern comprising the d-spacing (Å) values set forth in Table D of formula 1.93.

1.119 Any of formulae 1.78-1.118 wherein the Crystalline Form B exhibits an XRPD pattern comprising at least three, e.g., at least five, d-spacing (Å) values selected from the group consisting of 14.6, 6.7, 5.1, 4.7, 4.6, 3.8, 3.7, 3.6, and 3.2.

1.120 Any of formulae 1.78-1.119 wherein the Crystalline Form B exhibits an XRPD pattern comprising d-spacing (Å) values of 14.6, 6.7, 5.1, 4.7, 4.6, 3.8, 3.7, 3.6, and 3.2.

1.121 Any of formulae 1.78-1.120 wherein the Crystalline Form B exhibits an XRPD pattern comprising at least three, e.g., at least five, d-spacing (Å) values selected from the group consisting of 14.62, 6.70, 5.09, 4.68, 4.62, 3.77, 3.74, 3.65, and 3.17.

1.122 Any of formulae 1.78-1.121 wherein the Crystalline Form B exhibits an XRPD pattern comprising d-spacing (Å) values of 14.62, 6.70, 5.09, 4.68, 4.62, 3.77, 3.74, 3.65, and 3.17.

1.123 Any of formulae 1.78-1.122 wherein the Crystalline Form B exhibits an XRPD pattern comprising at least three, e.g., at least five, d-spacing (Å) values selected from the group consisting of 14.620, 6.699, 5.089, 4.681, 4.622, 3.769, 3.737, 3.646, and 3.168.

1.124 Any of formulae 1.78-1.123 wherein the Crystalline Form B exhibits an XRPD pattern comprising d-spacing (Å) values of 14.620, 6.699, 5.089, 4.681, 4.622, 3.769, 3.737, 3.646, and 3.168.

1.125 Any of formulae 1.78-1.124 wherein the Crystalline Form B exhibits an XRPD pattern comprising at least three, e.g., at least five, d-spacing (Å) values selected from those set forth in Table E of formula 1.102.

1.126 Any of formulae 1.78-1.125 wherein the Crystalline Form B exhibits an XRPD pattern comprising the d-spacing (Å) values set forth in Table E of formula 1.102.

1.127 Any of formulae 1.78-1.126 wherein the Crystalline Form B exhibits an XRPD pattern comprising at least three, e.g., at least five, e.g., at least nine, e.g., at least ten, e.g., at least fifteen, e.g., at least twenty, d-spacing (Å) values selected from the group consisting of 14.6, 7.3, 6.7, 6.0, 5.9, 5.5, 5.2, 5.1, 4.9, 4.7, 4.6, 4.5, 4.2, 4.1, 3.9, 3.8, 3.7, 3.6, 3.5, 3.4, 3.3, 3.2, 3.1, and 3.0.

1.128 Any of formulae 1.78-1.127 wherein the Crystalline Form B exhibits an XRPD pattern comprising d-spacing (Å) values of 14.6, 7.3, 6.7, 6.0, 5.9, 5.5, 5.2, 5.1, 4.9, 4.7, 4.6, 4.5, 4.2, 4.1, 3.9, 3.8, 3.7, 3.6, 3.5, 3.4, 3.3, 3.2, 3.1, and 3.0.

1.129 Any of formulae 1.78-1.128 wherein the Crystalline Form B exhibits an XRPD pattern comprising at least three, e.g., at least five, e.g., at least nine, e.g., at least ten, e.g., at least fifteen, e.g., at least twenty, e.g., at least twenty-five, d-spacing (Å) values selected from the group consisting of 14.62, 7.30, 6.70, 5.96, 5.85, 5.53, 5.24, 5.09, 4.86, 4.68, 4.62, 4.46, 4.22, 4.17, 4.09, 3.94, 3.77, 3.74, 3.65, 3.51, 3.42, 3.35, 3.28, 3.17, 3.11, and 3.03.

1.130 Any of formulae 1.78-1.129 wherein the Crystalline Form B exhibits an XRPD pattern comprising d-spacing (Å) values of 14.62, 7.30, 6.70, 5.96, 5.85, 5.53, 5.24, 5.09, 4.86, 4.68, 4.62, 4.46, 4.22, 4.17, 4.09, 3.94, 3.77, 3.74, 3.65, 3.51, 3.42, 3.35, 3.28, 3.17, 3.11, and 3.03.

1.131 Any of formulae 1.78-1.130 wherein the Crystalline Form B exhibits an XRPD pattern comprising at least three, e.g., at least five, e.g., at least nine, e.g., at least ten, e.g., at least fifteen, e.g., at least twenty, e.g., at least twenty-five, d-spacing (Å) values selected from the group consisting of 14.620, 7.296, 6.699, 5.958, 5.853, 5.529, 5.242, 5.089, 4.861, 4.681, 4.622, 4.457, 4.217, 4.173, 4.085, 3.939, 3.769, 3.737, 3.646, 3.512, 3.416, 3.347, 3.282, 3.168, 3.112, and 3.028.

1.132 Any of formulae 1.78-1.131 wherein the Crystalline Form B exhibits an XRPD pattern comprising d-spacing (Å) values of 14.620, 7.296, 6.699, 5.958, 5.853, 5.529, 5.242, 5.089, 4.861, 4.681, 4.622, 4.457, 4.217, 4.173, 4.085, 3.939, 3.769, 3.737, 3.646, 3.512, 3.416, 3.347, 3.282, 3.168, 3.112, and 3.028.

1.133 Any of formulae 1.78-1.132 wherein the Crystalline Form B exhibits an XRPD pattern comprising at least three, e.g., at least five, e.g., at least nine, e.g., at least ten, e.g., at least fifteen, e.g., at least twenty, e.g., at least twenty-five, d-spacing (Å) values selected from those set forth in Table F of formula 1.109.

1.134 Any of formulae 1.78-1.133 wherein the Crystalline Form B exhibits an XRPD pattern comprising the d-spacing (Å) values set forth in Table F of formula 1.109.

1.135 Any of formulae 1.78-1.134 wherein the Crystalline Form B exhibits an X-ray powder diffraction pattern comprising characteristic peaks of the XRPD pattern shown in FIG. 5, wherein the XRPD is measured using Cu radiation, e.g., Cu Kα radiation, e.g., wherein the XRPD is measured using radiation of wavelength 1.541871 Å.

1.136 Any of formulae 1.78-1.135 wherein the Crystalline Form B exhibits an X-ray powder diffraction pattern comprising representative peaks of the XRPD pattern shown in FIG. 5, wherein the XRPD is measured using Cu radiation, e.g., Cu Kα radiation, e.g., wherein the XRPD is measured using radiation of wavelength 1.541871 Å.

1.137 Any of formulae 1.78-1.136 wherein the Crystalline Form B exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, comprising three peaks, in some embodiments, five peaks, selected from those shown in FIG. 5.

1.138 Any of formulae 1.78-1.137 wherein the Crystalline Form B exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, comprising at least five peaks, e.g., at least nine peaks, e.g., at least ten peaks, e.g., at least fifteen peaks, e.g., at least twenty peaks, e.g., at least twenty-five peaks, selected from those shown in FIG. 5.

1.139 Any of formulae 1.78-1.138 wherein the Crystalline Form B exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, substantially as shown in FIG. 5.

1.140 Any of formulae 1.78-1.139 wherein the Crystalline Form B exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, as shown in FIG. 5.

1.141 Any of formulae 1.78-1.140 wherein the Crystalline Form B exhibits an X-ray powder diffraction pattern comprising characteristic peaks of the XRPD pattern shown in FIG. 7, wherein the XRPD is measured using Cu radiation, e.g., Cu Kα radiation, e.g., wherein the XRPD is measured using radiation of wavelength 1.54059 Å, e.g., wherein XPRD pattern also comprises peaks of Crystalline Form A (e.g., a mixture of Crystalline Forms A and B).

1.142 Any of formulae 1.78-1.141 wherein the Crystalline Form B exhibits an X-ray powder diffraction pattern comprising representative peaks of the XRPD pattern shown in FIG. 7, wherein the XRPD is measured using Cu radiation, e.g., Cu Kα radiation, e.g., wherein the XRPD is measured using radiation of wavelength 1.54059 Å, e.g., wherein XPRD pattern also comprises peaks of Crystalline Form A (e.g., a mixture of Crystalline Forms A and B).

1.143 Any of formulae 1.78-1.142 wherein the Crystalline Form B exhibits an X-ray powder diffraction pattern, e.g., an X-ray powder diffraction pattern measured using an incident beam of Cu radiation, e.g., Cu Kα radiation, e.g., a high-resolution X-ray powder diffraction pattern measured using an incident beam of Cu Kα radiation, e.g., wherein the XRPD is measured using radiation of wavelength 1.54059 Å, comprising three peaks, in some embodiments, five peaks, selected from those shown in FIG. 7, e.g., wherein XPRD pattern also comprises peaks of Crystalline Form A (e.g., a mixture of Crystalline Forms A and B).

1.144 Any of formulae 1.78-1.143 wherein the Crystalline Form B exhibits an X-ray powder diffraction pattern, e.g., an X-ray powder diffraction pattern measured using an incident beam of Cu radiation, e.g., Cu Kα radiation, e.g., a high-resolution X-ray powder diffraction pattern measured using an incident beam of Cu Kα radiation, e.g., wherein the XRPD is measured using radiation of wavelength 1.54059 Å, comprising at least five peaks, e.g., at least nine peaks, e.g., at least ten peaks, e.g., at least fifteen peaks, e.g., at least twenty peaks, e.g., at least twenty-five peaks, selected from those shown in FIG. 7, e.g., wherein XPRD pattern comprises peaks of Crystalline Form A (e.g., a mixture of Crystalline Forms A and B).

1.145 Any of formulae 1.78-1.144 wherein the Crystalline Form B exhibits an X-ray powder diffraction pattern, e.g., an X-ray powder diffraction pattern measured using an incident beam of Cu radiation, e.g., Cu Kα radiation, e.g., a high-resolution X-ray powder diffraction pattern measured using an incident beam of Cu Kα radiation, e.g., wherein the XRPD is measured using radiation of wavelength 1.54059 Å, substantially as shown in FIG. 7, e.g., wherein XPRD pattern comprises peaks of Crystalline Form A (e.g., a mixture of Crystalline Forms A and B).

1.146 Any of formulae 1.78-1.145 wherein the Crystalline Form B exhibits an X-ray powder diffraction pattern, e.g., an X-ray powder diffraction pattern measured using an incident beam of Cu radiation, e.g., Cu Kα radiation, e.g., a high-resolution X-ray powder diffraction pattern measured using an incident beam of Cu Kα radiation, e.g., wherein the XRPD is measured using radiation of wavelength 1.54059 Å, as shown in FIG. 7, e.g., wherein XPRD pattern comprises peaks of Crystalline Form A (e.g., a mixture of Crystalline Forms A and B).

1.147 Any of formulae 1.78-1.146 wherein the Crystalline Form B exhibits an XRPD pattern comprising characteristic peaks of the XPRD pattern shown in any of FIGS. 7, 40, and 48, e.g., FIG. 7, e.g., FIG. 40, e.g., FIG. 48, wherein the XRPD is measured using Cu radiation, e.g., Cu Kα radiation, e.g., wherein the XRPD is measured using radiation of wavelength 1.54059 Å.

1.148 Any of formulae 1.78-1.147 wherein the Crystalline Form B exhibits an XRPD pattern comprising representative peaks of the XPRD pattern shown in any of FIGS. 7, 40, and 48, e.g., FIG. 7, e.g., FIG. 40, e.g., FIG. 48, wherein the XRPD is measured using Cu radiation, e.g., Kα radiation, e.g., wherein the XRPD is measured using radiation of wavelength 1.54059 Å.

1.149 Any of formulae 1.78-1.148 wherein the Crystalline Form B exhibits an XRPD pattern, e.g., an X-ray powder diffraction pattern measured using an incident beam of Cu radiation, e.g., Cu Kα radiation, e.g., a high-resolution X-ray powder diffraction pattern measured using an incident beam of Cu Kα radiation, e.g., wherein the XRPD is measured using radiation of wavelength 1.54059 Å, comprising three peaks, in some embodiments, five peaks, selected from those shown in any of FIGS. 7, 40, and 48, e.g., FIG. 7, e.g., FIG. 40, e.g., FIG. 48.

1.150 Any of formulae 1.78-1.149 wherein the Crystalline Form B exhibits an XRPD pattern, e.g., an X-ray powder diffraction pattern measured using an incident beam of Cu radiation, e.g., Cu Kα radiation, e.g., a high-resolution X-ray powder diffraction pattern measured using an incident beam of Cu Kα radiation, e.g., wherein the XRPD is measured using radiation of wavelength 1.54059 Å, comprising at least five, e.g., at least nine, e.g., at least ten, e.g., at least fifteen, e.g., at least twenty, e.g., at least twenty-five, selected from those shown in any of FIGS. 7, 40, and 48, e.g., FIG. 7, e.g., FIG. 40, e.g., FIG. 48.

1.151 Any of formulae 1.78-1.150 wherein the Crystalline Form B exhibits an XRPD pattern, e.g., an X-ray powder diffraction pattern measured using an incident beam of Cu radiation, e.g., Cu Kα radiation, e.g., wherein the XRPD is measured using radiation of wavelength 1.54059 Å, substantially as shown in any of FIGS. 7, 40, and 48, e.g., FIG. 7, e.g., FIG. 40, e.g., FIG. 48.

1.152 Any of formulae 1.1-1.151 wherein the Crystalline Form B exhibits an X-ray powder diffraction (XRPD) pattern, e.g., an X-ray powder diffraction pattern measured using an incident beam of Cu radiation, e.g., Cu Kα radiation, e.g., wherein the XRPD is measured using radiation of wavelength 1.54059 Å, as shown in any of FIGS. 7, 40, and 48, e.g., FIG. 7, e.g., FIG. 40, e.g., FIG. 48.

1.153 Any of formulae 1.78-1.152 wherein the Crystalline Form B exhibits a differential scanning calorimetry (DSC) thermogram comprising an endothermic peak between 247° C. and 248° C.

1.154 Any of formulae 1.78-1.153 wherein the Crystalline Form B exhibits a differential scanning calorimetry (DSC) thermogram comprising an endothermic peak at 247° C.

1.155 Any of formulae 1.78-1.154 wherein the Crystalline Form B exhibits a differential scanning calorimetry (DSC) thermogram comprising an endothermic peak at 248° C., e.g., an endothermic peak at 248° C. with an onset at 246° C.

1.156 Any of formulae 1.78-1.155 wherein the Crystalline Form B exhibits a differential scanning calorimetry (DSC) thermogram comprising an endothermic peak at 251° C.
1.157 Any of formulae 1.78-1.156 wherein the Crystalline Form B exhibits a differential scanning calorimetry (DSC) thermogram comprising an endothermic peak at 264° C.
1.158 Any of formulae 1.78-1.157 wherein the Crystalline Form B exhibits a differential scanning calorimetry (DSC) thermogram comprising an endothermic peak at 141° C., e.g., an endothermic peak at 141° C. with an onset between 137° C. and 138° C., e.g., an endothermic peak at 141° C. with an onset at 137° C., e.g., an endothermic peak at 141° C. with an onset at 138° C.
1.159 Any of formulae 1.78-1.158 wherein the Crystalline Form B exhibits a differential scanning calorimetry (DSC) thermogram as shown in FIG. 8.
1.160 Any of formulae 1.78-1.159 wherein the Crystalline Form B exhibits a thermogravimetric analysis (TGA) thermogram comprising 0.2% weight loss up to 200° C.
1.161 Any of formulae 1.78-1.160 wherein the Crystalline Form B exhibits a thermogravimetric analysis (TGA) thermogram comprising an onset decomposition temperature at 281° C.
1.162 Any of formulae 1.78-1.161 wherein the Crystalline Form B exhibits a thermogravimetric analysis (TGA) thermogram as shown in FIG. 8.
1.163 Crystalline Form C of the Compound in hydrochloric acid addition salt form ((1R,5S)-1-(naphthalen-2-yl)-3-azabicyclo[3.1.0]hexane hydrochloride) ("Crystalline Form C").
1.164 Formula 1.163 wherein the Crystalline Form C exhibits an XRPD pattern comprising a 2-theta value (°) of 17.7, wherein the XRPD is measured using an incident beam of Cu radiation, e.g., Cu Kα radiation, e.g., wherein the XRPD is measured using radiation of wavelength 1.54059 Å.
1.165 Formula 1.163 or 1.164 wherein the Crystalline Form C exhibits an XRPD pattern having a characteristic 2-theta (°) value of 17.7, wherein the XRPD is measured using an incident beam of Cu radiation, e.g., Cu Kα radiation, e.g., wherein the XRPD is measured using radiation of wavelength 1.54059 Å.
1.166 Any of formulae 1.163-1.165 wherein the Crystalline Form C exhibits an XRPD pattern comprising a 2-theta (°) value of 17.74, wherein the XRPD is measured using an incident beam of Cu radiation, e.g., Cu Kα radiation, e.g., wherein the XRPD is measured using radiation of wavelength 1.54059 Å.
1.167 Any of formulae 1.163-1.166 wherein the Crystalline Form C exhibits an XRPD pattern having a characteristic 2-theta (°) value of 17.74, wherein the XRPD is measured using an incident beam of Cu radiation, e.g., Cu Kα radiation, e.g., wherein the XRPD is measured using radiation of wavelength 1.54059 Å.
1.168 Any of formulae 1.163-1.167 wherein the Crystalline Form C exhibits an XRPD pattern comprising a 2-theta (°) value in Table G below:

TABLE G

| °2θ | d space (Å) | Intensity (%) |
|---|---|---|
| 17.74 ± 0.20 | 4.994 ± 0.056 | 100 | wherein the XRPD is measured using an incident beam of Cu radiation, e.g., Cu Kα radiation, e.g., wherein the XRPD is measured using radiation of wavelength 1.54059 Å.
1.169 Any of formulae 1.163-1.168 wherein the Crystalline Form C exhibits an XRPD pattern having characteristic 2-theta (°) value as set forth in Table G of formula 1.168, wherein the XRPD is measured using an incident beam of Cu radiation, e.g., Cu Kα radiation, e.g., wherein the XRPD is measured using radiation of wavelength 1.54059 Å.
1.170 Any of formulae 1.163-1.169 wherein the Crystalline Form C exhibits an XRPD pattern comprising at least one, e.g., at least three, e.g., at least five, 2-theta)(° values selected from the group consisting of 7.0, 13.2, 14.4, 17.7, 18.0, 19.9, 21.3, 22.6, 23.7, and 26.5, wherein the XRPD is measured using an incident beam of Cu radiation, e.g., Cu Kα radiation, e.g., wherein the XRPD is measured using radiation of wavelength 1.54059 Å.
1.171 Any of formulae 1.163-1.170 wherein the Crystalline Form C exhibits an XRPD pattern comprising 2-theta (°) values of 7.0, 13.2, 14.4, 17.7, 18.0, 19.9, 21.3, 22.6, 23.7, and 26.5, wherein the XRPD is measured using an incident beam of Cu radiation, e.g., Cu Kα radiation, e.g., wherein the XRPD is measured using radiation of wavelength 1.54059 Å.
1.172 Any of formulae 1.163-1.171 wherein the Crystalline Form C exhibits an XRPD pattern having representative 2-theta (°) values of 7.0, 13.2, 14.4, 17.7, 18.0, 19.9, 21.3, 22.6, 23.7, and 26.5, wherein the XRPD is measured using an incident beam of Cu radiation, e.g., Cu Kα radiation, e.g., wherein the XRPD is measured using radiation of wavelength 1.54059 Å.
1.173 Any of formulae 1.163-1.172 wherein the Crystalline Form C exhibits an XRPD pattern comprising at least one, e.g., at least three, e.g., at least five, e.g., at least ten, 2-theta (°) values selected from the group consisting of 6.97, 13.24, 14.39, 17.74, 17.98, 18.03, 19.85, 21.32, 22.60, 23.68, and 26.52, wherein the XRPD is measured using an incident beam of Cu radiation, e.g., Cu Kα radiation, e.g., wherein the XRPD is measured using radiation of wavelength 1.54059 Å.
1.174 Any of formulae 1.163-1.173 wherein the Crystalline Form C exhibits an XRPD pattern comprising 2-theta (°) values of 6.97, 13.24, 14.39, 17.74, 17.98, 18.03, 19.85, 21.32, 22.60, 23.68, and 26.52, wherein the XRPD is measured using an incident beam of Cu radiation, e.g., Cu Kα radiation, e.g., wherein the XRPD is measured using radiation of wavelength 1.54059 Å.
1.175 Any of formulae 1.163-1.174 wherein the Crystalline Form C exhibits an XRPD pattern having representative 2-theta (°) values of 6.97, 13.24, 14.39, 17.74, 17.98, 18.03, 19.85, 21.32, 22.60, 23.68, and 26.52, wherein the XRPD is measured using an incident beam of Cu radiation, e.g., Cu Kα radiation, e.g., wherein the XRPD is measured using radiation of wavelength 1.54059 Å.
1.176 Any of formulae 1.163-1.175 wherein the Crystalline Form C exhibits an XRPD pattern comprising at least one, e.g., at least three, e.g., at least five, e.g., at least ten, 2-theta (°) values selected from those set forth in Table H below:

TABLE H

| °2θ | d space (Å) | Intensity (%) |
|---|---|---|
| 6.97 ± 0.20 | 12.677 ± 0.363 | 15 |
| 13.24 ± 0.20 | 6.683 ± 0.101 | 13 |
| 14.39 ± 0.20 | 6.150 ± 0.085 | 21 |
| 17.74 ± 0.20 | 4.994 ± 0.056 | 100 |
| 17.98 ± 0.20 | 4.929 ± 0.054 | 27 |
| 18.03 ± 0.20 | 4.915 ± 0.054 | 24 |
| 19.85 ± 0.20 | 4.470 ± 0.045 | 47 |
| 21.32 ± 0.20 | 4.164 ± 0.039 | 23 |
| 22.60 ± 0.20 | 3.931 ± 0.034 | 95 |
| 23.68 ± 0.20 | 3.754 ± 0.031 | 25 |
| 26.52 ± 0.20 | 3.359 ± 0.025 | 34 | wherein the XRPD is measured using an incident beam of Cu radiation, e.g., Cu Kα radiation, e.g., wherein the XRPD is measured using radiation of wavelength 1.54059 Å.

1.177 Any of formulae 1.163-1.176 wherein the Crystalline Form C exhibits an XRPD pattern comprising the 2-theta (°) values set forth in Table H of formula 1.176, wherein the XRPD is measured using an incident beam of Cu radiation, e.g., Cu Kα radiation, e.g., wherein the XRPD is measured using radiation of wavelength 1.54059 Å.

1.178 Any of formulae 1.163-1.177 wherein the Crystalline Form C exhibits an XRPD pattern having representative 2-theta (°) values as set forth in Table H of formula 1.176, wherein the XRPD is measured using an incident beam of Cu radiation, e.g., Cu Kα radiation, e.g., wherein the XRPD is measured using radiation of wavelength 1.54059 Å.

1.179 Any of formulae 1.163-1.178 wherein the Crystalline Form C exhibits an XRPD pattern comprising at least one, e.g., at least three, e.g., at least five, e.g., at least ten, e.g., at least eleven, e.g., at least fifteen, e.g., at least twenty, 2-theta)(° values selected from the group consisting of 7.0, 13.2, 13.7, 14.0, 14.4, 16.3, 17.7, 18.0, 18.3, 19.9, 21.1, 21.3, 22.6, 23.4, 23.7, 23.9, 26.0, 26.5, 26.7, 26.9, 27.4, 28.0, 28.2, 29.1, and 29.5, wherein the XRPD is measured using an incident beam of Cu radiation, e.g., Cu Kα radiation, e.g., wherein the XRPD is measured using radiation of wavelength 1.54059 Å.

1.180 Any of formulae 1.163-1.179 wherein the Crystalline Form C exhibits an XRPD pattern comprising the following 2-theta (°) values:
7.0, 13.2, 13.7, 14.0, 14.4, 16.3, 17.7, 18.0, 18.3, 19.9, 21.1, 21.3, 22.6, 23.4, 23.7, 23.9, 26.0, 26.5, 26.7, 26.9, 27.4, 28.0, 28.2, 29.1, and 29.5, wherein the XRPD is measured using an incident beam of Cu radiation, e.g., Cu Kα radiation, e.g., wherein the XRPD is measured using radiation of wavelength 1.54059 Å.

1.181 Any of formulae 1.163-1.180 wherein the Crystalline Form C exhibits an XRPD pattern comprising at least one, e.g., at least three, e.g., at least five, e.g., at least ten, e.g., at least eleven, e.g., at least fifteen, e.g., at least twenty, e.g., at least twenty-five, 2-theta (°) values selected from the group consisting of 6.97, 13.24, 13.68, 13.97, 14.39, 16.29, 17.74, 17.98, 18.03, 18.30, 19.85, 21.06, 21.32, 22.60, 23.35, 23.68, 23.94, 25.99, 26.52, 26.66, 26.90, 27.40, 27.99, 28.19, 29.06, and 29.52, wherein the XRPD is measured using an incident beam of Cu radiation, e.g., Cu Kα radiation, e.g., wherein the XRPD is measured using radiation of wavelength 1.54059 Å.

1.182 Any of formulae 1.163-1.181 wherein the Crystalline Form C exhibits an XRPD pattern comprising the following 2-theta (°) values:
6.97, 13.24, 13.68, 13.97, 14.39, 16.29, 17.74, 17.98, 18.03, 18.30, 19.85, 21.06, 21.32, 22.60, 23.35, 23.68, 23.94, 25.99, 26.52, 26.66, 26.90, 27.40, 27.99, 28.19, 29.06, and 29.52,
wherein the XRPD is measured using an incident beam of Cu radiation, e.g., Cu Kα radiation, e.g., wherein the XRPD is measured using radiation of wavelength 1.54059 Å.

1.183 Any of formulae 1.163-1.182 wherein the Crystalline Form C exhibits an XRPD pattern comprising at least one, e.g., at least three, e.g., at least five, e.g., at least ten, e.g., at least eleven, e.g., at least fifteen, e.g., at least twenty, e.g., at least twenty-five, 2-theta (°) values selected from those set forth in Table I below:

TABLE I

| °2θ | d space (Å) | Intensity (%) |
|---|---|---|
| 6.97 ± 0.20 | 12.677 ± 0.363 | 15 |
| 13.24 ± 0.20 | 6.683 ± 0.101 | 13 |
| 13.68 ± 0.20 | 6.469 ± 0.094 | 2 |
| 13.97 ± 0.20 | 6.333 ± 0.090 | 3 |
| 14.39 ± 0.20 | 6.150 ± 0.085 | 21 |
| 16.29 ± 0.20 | 5.435 ± 0.066 | 6 |
| 17.74 ± 0.20 | 4.994 ± 0.056 | 100 |
| 17.98 ± 0.20 | 4.929 ± 0.054 | 27 |
| 18.03 ± 0.20 | 4.915 ± 0.054 | 24 |
| 18.30 ± 0.20 | 4.843 ± 0.052 | 13 |
| 19.85 ± 0.20 | 4.470 ± 0.045 | 47 |
| 21.06 ± 0.20 | 4.214 ± 0.040 | 6 |
| 21.32 ± 0.20 | 4.164 ± 0.039 | 23 |
| 22.60 ± 0.20 | 3.931 ± 0.034 | 95 |
| 23.35 ± 0.20 | 3.806 ± 0.032 | 14 |
| 23.68 ± 0.20 | 3.754 ± 0.031 | 25 |
| 23.94 ± 0.20 | 3.714 ± 0.031 | 13 |
| 25.99 ± 0.20 | 3.426 ± 0.026 | 14 |
| 26.52 ± 0.20 | 3.359 ± 0.025 | 34 |
| 26.66 ± 0.20 | 3.340 ± 0.025 | 16 |
| 26.90 ± 0.20 | 3.311 ± 0.024 | 14 |
| 27.40 ± 0.20 | 3.252 ± 0.023 | 6 |
| 27.99 ± 0.20 | 3.185 ± 0.022 | 6 |
| 28.19 ± 0.20 | 3.163 ± 0.022 | 3 |
| 29.06 ± 0.20 | 3.070 ± 0.021 | 5 |
| 29.52 ± 0.20 | 3.024 ± 0.020 | 7 | wherein the XRPD is measured using an incident beam of Cu radiation, e.g., Cu Kα radiation, e.g., wherein the XRPD is measured using radiation of wavelength 1.54059 Å.

1.184 Any of formulae 1.163-1.183 wherein the Crystalline Form C exhibits an XRPD pattern comprising the 2-theta (°) values set forth in Table I of formula 1.183, wherein the XRPD is measured using an incident beam of Cu radiation, e.g., Cu Kα radiation, e.g., wherein the XRPD is measured using radiation of wavelength 1.54059 Å.

1.185 Any of formulae 1.163-1.184 wherein the Crystalline Form C exhibits an XRPD pattern comprising a d-spacing (Å) value of 5.0.

1.186 Any of formulae 1.163-1.185 wherein the Crystalline Form C exhibits an XRPD pattern comprising a d-spacing (Å) value of 4.99.

1.187 Any of formulae 1.163-1.186 wherein the Crystalline Form C exhibits an XRPD pattern comprising a d-spacing (Å) value of 4.994.

1.188 Any of formulae 1.163-1.187 wherein the Crystalline Form C exhibits an XRPD pattern comprising a d-spacing (Å) value in Table G of formula 1.168.

1.189 Any of formulae 1.163-1.188 wherein the Crystalline Form C exhibits an XRPD pattern comprising at least one, e.g., at least three, e.g., at least five, d-spacing (Å) values selected from the group consisting of 12.7, 6.7, 6.2, 5.0, 4.9, 4.5, 4.2, 3.9, 3.8, and 3.4.

1.190 Any of formulae 1.163-1.189 wherein the Crystalline Form C exhibits an XRPD pattern comprising d-spacing (Å) values of 12.7, 6.7, 6.2, 5.0, 4.9, 4.5, 4.2, 3.9, 3.8, and 3.4.

1.191 Any of formulae 1.163-1.190 wherein the Crystalline Form C exhibits an XRPD pattern comprising at least one, e.g., at least three, e.g., at least five, e.g., at least ten, d-spacing (Å) values selected from the group consisting of 12.68, 6.68, 6.15, 4.99, 4.93, 4.92, 4.47, 4.16, 3.93, 3.75, and 3.36.

1.192 Any of formulae 1.163-1.191 wherein the Crystalline Form C exhibits an XRPD pattern comprising d-spacing (Å) values of 12.68, 6.68, 6.15, 4.99, 4.93, 4.92, 4.47, 4.16, 3.93, 3.75, and 3.36.

1.193 Any of formulae 1.163-1.192 wherein the Crystalline Form C exhibits an XRPD pattern comprising at least one, e.g., at least three, e.g., at least five, e.g., at least ten, d-spacing (Å) values selected from the group consisting of 12.677, 6.683, 6.150, 4.994, 4.929, 4.915, 4.470, 4.164, 3.931, 3.754, and 3.359.

1.194 Any of formulae 1.163-1.193 wherein the Crystalline Form C exhibits an XRPD pattern comprising d-spacing (Å) values of 12.677, 6.683, 6.150, 4.994, 4.929, 4.915, 4.470, 4.164, 3.931, 3.754, and 3.359.

1.195 Any of formulae 1.163-1.194 wherein the Crystalline Form C exhibits an XRPD pattern comprising at least one, e.g., at least three, e.g., at least five, e.g., at least ten, d-spacing (Å) values selected from those set forth in Table H of formula 1.176.

1.196 Any of formulae 1.163-1.195 wherein the Crystalline Form C exhibits an XRPD pattern comprising the d-spacing (Å) values set forth in Table H of formula 1.176.

1.197 Any of formulae 1.163-1.196 wherein the Crystalline Form C exhibits an XRPD pattern comprising at least one, e.g., at least three, e.g., at least five, e.g., at least ten, e.g., at least eleven, e.g., at least fifteen, d-spacing (Å) values selected from the group consisting of 12.7, 6.7, 6.5, 6.3, 6.2, 5.4, 5.0, 4.9, 4.8, 4.5, 4.2, 3.9, 3.8, 3.7, 3.4, 3.3, 3.2, 3.1, and 3.0.

1.198 Any of formulae 1.163-1.197 wherein the Crystalline Form C exhibits an XRPD pattern comprising d-spacing (Å) values of 12.7, 6.7, 6.5, 6.3, 6.2, 5.4, 5.0, 4.9, 4.8, 4.5, 4.2, 3.9, 3.8, 3.7, 3.4, 3.3, 3.2, 3.1, and 3.0.

1.199 Any of formulae 1.163-1.198 wherein the Crystalline Form C exhibits an XRPD pattern comprising at least one, e.g., at least three, e.g., at least five, e.g., at least ten, e.g., at least eleven, e.g., at least fifteen, e.g., at least twenty, e.g., at least twenty-five, d-spacing (Å) values selected from the group consisting of 12.68, 6.68, 6.47, 6.33, 6.15, 5.44, 4.99, 4.93, 4.92, 4.84, 4.47, 4.21, 4.16, 3.93, 3.81, 3.75, 3.71, 3.43, 3.36, 3.34, 3.31, 3.25, 3.19, 3.16, 3.07, and 3.02.

1.200 Any of formulae 1.163-1.199 wherein the Crystalline Form C exhibits an XRPD pattern comprising d-spacing (Å) values of 12.68, 6.68, 6.47, 6.33, 6.15, 5.44, 4.99, 4.93, 4.92, 4.84, 4.47, 4.21, 4.16, 3.93, 3.81, 3.75, 3.71, 3.43, 3.36, 3.34, 3.31, 3.25, 3.19, 3.16, 3.07, and 3.02.

1.201 Any of formulae 1.163-1.200 wherein the Crystalline Form C exhibits an XRPD pattern comprising at least one, e.g., at least three, e.g., at least five, e.g., at least ten, e.g., at least eleven, e.g., at least fifteen, e.g., at least twenty, e.g., at least twenty-five, d-spacing (Å) values selected from the group consisting of 12.677, 6.683, 6.469, 6.333, 6.150, 5.435, 4.994, 4.929, 4.915, 4.843, 4.470, 4.214, 4.164, 3.931, 3.806, 3.754, 3.714, 3.426, 3.359, 3.340, 3.311, 3.252, 3.185, 3.163, 3.070, and 3.024.

1.202 Any of formulae 1.163-1.201 wherein the Crystalline Form C exhibits an XRPD pattern comprising d-spacing (Å) values of 12.677, 6.683, 6.469, 6.333, 6.150, 5.435, 4.994, 4.929, 4.915, 4.843, 4.470, 4.214, 4.164, 3.931, 3.806, 3.754, 3.714, 3.426, 3.359, 3.340, 3.311, 3.252, 3.185, 3.163, 3.070, and 3.024.

1.203 Any of formulae 1.163-1.202 wherein the Crystalline Form C exhibits an XRPD pattern comprising at least one, e.g., at least three, e.g., at least five, e.g., at least ten, e.g., at least eleven, e.g., at least fifteen, e.g., at least twenty, e.g., at least twenty-five, d-spacing (Å) values selected from those set forth in Table I of formula 1.183.

1.204 Any of formulae 1.163-1.203 having an XRPD pattern comprising the d-spacing (Å) values set forth in Table I of formula 1.183.

1.205 Any of formulae 1.163-1.204 wherein the Crystalline Form C exhibits an X-ray powder diffraction pattern comprising characteristic peaks of the XRPD pattern shown in FIG. 9, wherein the XRPD is measured using Cu radiation, e.g., Cu Kα radiation, e.g., wherein the XRPD is measured using radiation of wavelength 1.541871 Å.

1.206 Any of formulae 1.163-1.205 wherein the Crystalline Form C exhibits an X-ray powder diffraction pattern comprising representative peaks of the XRPD pattern shown in FIG. 9, wherein the XRPD is measured using Cu radiation, e.g., Cu Kα radiation, e.g., wherein the XRPD is measured using radiation of wavelength 1.541871 Å.

1.207 Any of formulae 1.163-1.206 wherein the Crystalline Form C exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, comprising three peaks, in some embodiments, five peaks, selected from those shown in FIG. 9.

1.208 Any of formulae 1.163-1.207 wherein the Crystalline Form C exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, comprising at least one peak, e.g., at least five peaks, e.g., at least eleven peaks, e.g., least fifteen peaks, e.g., at least twenty peaks, e.g., at least twenty-five peaks, selected from those shown in FIG. 9.

1.209 Any of formulae 1.163-1.208 wherein the Crystalline Form C exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, substantially as shown in FIG. 9.

1.210 Any of formulae 1.163-1.209 wherein the Crystalline Form C exhibits an X-ray powder diffraction pattern, e.g., an X-ray powder diffraction pattern measured using an incident beam of Cu radiation, e.g., Cu 1.211 Any of formulae 1.163-1.210 wherein the Crystalline Form C exhibits an X-ray powder diffraction pattern comprising characteristic peaks of the XRPD pattern shown in FIG. 11, wherein the XRPD is measured using Cu radiation, e.g., Cu Kα radiation, e.g., wherein the XRPD is measured using radiation of wavelength 1.54059 Å, e.g., wherein XPRD pattern also comprises peaks of Crystalline Form A (e.g., a mixture of Crystalline Forms A and C).

1.212 Any of formulae 1.163-1.211 wherein the Crystalline Form C exhibits an X-ray powder diffraction pattern comprising representative peaks of the XRPD pattern shown in FIG. 11, wherein the XRPD is measured using Cu radiation, e.g., Cu Kα radiation, e.g., wherein the XRPD is measured using radiation of wavelength 1.54059 Å, e.g., wherein XPRD pattern also comprises peaks of Crystalline Form A (e.g., a mixture of Crystalline Forms A and C).

1.213 Any of formulae 1.163-1.212 wherein the Crystalline Form C exhibits an X-ray powder diffraction pattern, e.g., an X-ray powder diffraction pattern measured using an incident beam of Cu radiation, e.g., Cu Kα radiation, e.g., a high-resolution X-ray powder diffraction pattern measured using an incident beam of Cu Kα radiation, e.g., wherein the XRPD is measured using radiation of wavelength 1.54059 Å, comprising three peaks, in some embodiments, five peaks, selected from those shown in FIG. 11, e.g., wherein XPRD pattern also comprises peaks of Crystalline Form A (e.g., a mixture of Crystalline Forms A and C).

1.214 Any of formulae 1.163-1.213 wherein the Crystalline Form C exhibits an X-ray powder diffraction pattern, e.g., an X-ray powder diffraction pattern measured using an incident beam of Cu radiation, e.g., Cu Kα radiation, e.g., a high-resolution X-ray powder diffraction pattern measured using an incident beam of Cu Kα radiation, e.g., wherein the XRPD is measured using radiation of wavelength 1.54059 Å, comprising at least one peak, e.g., at least five peaks, e.g., at least eleven peaks, e.g., least fifteen peaks, e.g., at least twenty peaks, e.g., at least twenty-five peaks, selected from those shown in FIG. 11, e.g., wherein XPRD pattern also comprises peaks of Crystalline Form A (e.g., a mixture of Crystalline Forms A and C).

1.215 Any of formulae 1.163-1.214 wherein the Crystalline Form C exhibits an X-ray powder diffraction pattern, e.g., an X-ray powder diffraction pattern measured using an incident beam of Cu radiation, e.g., Cu Kα radiation, e.g., a high-resolution X-ray powder diffraction pattern measured using an incident beam of Cu Kα radiation, e.g., wherein the XRPD is measured using radiation of wavelength 1.54059 Å, substantially as shown in FIG. 11, e.g., wherein XPRD pattern also comprises peaks of Crystalline Forms A and C (e.g., a mixture of Crystalline Forms A and C).

1.216 Any of formulae 1.163-1.215 wherein the Crystalline Form C exhibits an X-ray powder diffraction pattern, e.g., an X-ray powder diffraction pattern measured using an incident beam of Cu radiation, e.g., Cu Kα radiation, e.g., a high-resolution X-ray powder diffraction pattern measured using an incident beam of Cu Kα radiation, e.g., wherein the XRPD is measured using radiation of wavelength 1.54059 Å, as shown in FIG. 11, e.g., wherein XPRD pattern also comprises peaks of Crystalline Form A (e.g., a mixture of Crystalline Forms A and C).

1.217 Any of formulae 1.163-1.216 wherein the Crystalline Form C exhibits an XRPD pattern comprising characteristic peaks of the XPRD pattern as shown in any of FIGS. 11 and 43, e.g., FIG. 11, e.g., FIG. 43, wherein the XRPD is measured using Cu radiation, e.g., Cu Kα radiation, e.g., wherein the XRPD is measured using radiation of wavelength 1.54059 Å.

1.218 Any of formulae 1.163-1.217 wherein the Crystalline Form C exhibits an XRPD pattern comprising representative peaks of the XPRD pattern as shown in any of FIGS. 11 and 43, e.g., FIG. 11, e.g., FIG. 43, wherein the XRPD is measured using Cu radiation, e.g., Kα radiation, e.g., wherein the XRPD is measured using radiation of wavelength 1.54059 Å.

1.219 Any of formulae 1.163-1.218 wherein the Crystalline Form C exhibits an XRPD pattern, e.g., an X-ray powder diffraction pattern measured using an incident beam of Cu radiation, e.g., Cu Kα radiation, e.g., a high-resolution X-ray powder diffraction pattern measured using an incident beam of Cu Kα radiation, e.g., wherein the XRPD is measured using radiation of wavelength 1.54059 Å, comprising three peaks, in some embodiments, five peaks, selected from those shown in any of FIGS. 11 and 43, e.g., FIG. 11, e.g., FIG. 43.

1.220 Any of formulae 1.163-1.219 wherein the Crystalline Form C exhibits an XRPD pattern, e.g., an X-ray powder diffraction pattern measured using an incident beam of Cu radiation, e.g., Cu Kα radiation, e.g., a high-resolution X-ray powder diffraction pattern measured using an incident beam of Cu Kα radiation, e.g., wherein the XRPD is measured using radiation of wavelength 1.54059 Å, comprising at least one peak, e.g., at least five peaks, e.g., at least ten peaks, e.g., at least eleven peaks, e.g., at least fifteen peaks, e.g., at least twenty peaks, e.g., at least twenty-five peaks, selected from those shown in any of FIGS. 11 and 43, e.g., FIG. 11, e.g., FIG. 43.

1.221 Any of formulae 1.163-1.220 wherein the Crystalline Form C exhibits an XRPD pattern, e.g., an X-ray powder diffraction pattern measured using an incident beam of Cu radiation, e.g., Cu Kα radiation, e.g., wherein the XRPD is measured using radiation of wavelength 1.54059 Å, substantially as shown in any of FIGS. 11 and 43, e.g., FIG. 11, e.g., FIG. 43.

1.222 Any of formulae 1.163-1.221 wherein the Crystalline Form C exhibits an XRPD pattern, e.g., an X-ray powder diffraction pattern measured using an incident beam of Cu radiation, e.g., Cu Kα radiation, e.g., wherein the XRPD is measured using radiation of wavelength 1.54059 Å, as shown in any of FIGS. 11 and 43, e.g., FIG. 11, e.g., FIG. 43.

1.223 Any of formulae 1.163-1.222 wherein the Crystalline Form C exhibits a differential scanning calorimetry (DSC) thermogram comprising an endothermic peak between 247° C. and 248° C., e.g., between 247° C. and 248° C. with an onset at 246° C.

1.224 Any of formulae 1.163-1.223 wherein the Crystalline Form C exhibits a differential scanning calorimetry (DSC) thermogram comprising an endothermic peak at 247° C., e.g., an endothermic peak at 247° C. with an onset at 246° C.

1.225 Any of formulae 1.163-1.224 wherein the Crystalline Form C exhibits a differential scanning calorimetry (DSC) thermogram comprising an endothermic peak at 248° C., e.g., an endothermic peak at 248° C. with an onset at 246° C.

1.226 Any of formulae 1.163-1.225 wherein the Crystalline Form C exhibits a differential scanning calorimetry (DSC) thermogram comprising an endothermic peak at 122° C., e.g, an endothermic peak at 122° C. with an onset at 112° C.

1.227 Any of formulae 1.163-1.226 wherein the Crystalline Form C exhibits a differential scanning calorimetry (DSC) thermogram comprising an endothermic peak at 271° C.

1.228 Any of formulae 1.163-1.227 wherein the Crystalline Form C exhibits a differential scanning calorimetry (DSC) thermogram as shown in FIG. 12.

1.229 Any of formulae 1.163-1.228 wherein the Crystalline Form C exhibits a thermogravimetric analysis (TGA) comprising 1.3% weight loss up to 200° C.

1.230 Any of formulae 1.163-1.229 wherein the Crystalline Form C exhibits a thermogravimetric analysis (TGA) thermogram comprising an onset decomposition temperature at 266° C.

1.231 Any of formulae 1.163-1.230 wherein the Crystalline Form C exhibits a thermogravimetric analysis (TGA) thermogram as shown in FIG. 12.

1.232 A Crystalline Form of (1R,5S)-1-(naphthalen-2-yl)-3-azabicyclo[3.1.0]hexane hydrochloride as described and/or made as in any of the examples.

1.233 A Crystalline Form of (1R,5S)-1-(naphthalen-2-yl)-3-azabicyclo[3.1.0]hexane hydrochloride having an X-ray powder diffraction and/or X-ray crystal structure as depicted in any of the Figures.

1.234 The Crystalline Form of any of formulae 1.1-1.233 wherein the XRPD pattern is measured using a copper source, e.g., a copper anode.

1.235 A combination of any of the Crystalline Forms A through F, e.g., any of formulae 1.1-1.234 and any of formulae 2.1-2.25, e.g., a combination of Crystalline Form A and Crystalline Form B; a combination of Crystalline Form A and Crystalline Form C; a combination of Crystalline Form A, Crystalline Form B, and Crystalline Form C; a combination of Crystalline Form B and Crystalline Form C; a combination of Crystalline Form B and Crystalline Form D; a combination of Crystalline Form E and Crystalline Form F.

1.236 The Crystalline Form according to any of formulae 1.1-1.234, e.g., Crystalline Form A, e.g., any of formulae 1.1-1.77, e.g., Crystalline Form B, e.g., any of formulae 1.78-1.162, wherein said Crystalline Form is free or substantially free of any other form, e.g., less than 20 wt. %, e.g., less than 15 wt. %, e.g., less than 10 wt. %, preferably less than 5 wt. %, preferably less than 3 wt. %, more preferably less than 2 wt. %, still preferably less than 1 wt. %, still preferably less than 0.1 wt. %, most preferably less than 0.01 wt. %, of the amorphous form.

1.237 The Crystalline Form according to any of formulae 1.1-1.234, e.g., Crystalline Form A, e.g., any of formulae 1.1-1.77, e.g., Crystalline Form B, e.g., any of formulae 1.78-1.162, wherein said Crystalline Form is free or substantially free of any other form, e.g., less than 20 wt. %, e.g., less than 10 wt. %, preferably less than 5 wt. %, preferably less than 3 wt. %, more preferably less than 2 wt. %, still preferably less than 1 wt. %, still preferably less than 0.1 wt. %, most preferably less than 0.01 wt. %, of any other crystalline form.

1.238 The Crystalline Form according to any of formulae 1.1-1.234, e.g., Crystalline Form A, e.g., any of formulae 1.1-1.77, e.g., Crystalline Form B, e.g., any of formulae 1.78-1.162, wherein said Crystalline Form is free or substantially free of any other form, e.g., less than 20 wt. %, e.g., less than 10 wt. %, preferably less than 5 wt. %, preferably less than 3 wt. %, more preferably less than 2 wt. %, still preferably less than 1 wt. %, still preferably less than 0.1 wt. %, most preferably less than 0.01 wt. %, of the amorphous form and any other crystalline form.

1.239 The Crystalline Form according to any of formulae 1.1-1.238 when made by any of processes described in formula 4.1-4.20 or similarly described in any of the examples or having an X-ray powder diffraction or X-ray crystal structure as depicted in any of the Figures.

In the second aspect, the invention provides a citrate salt of (1R,5S)-1-(naphthalen-2-yl)-3-azabicyclo[3.1.0]hexane.

In the third aspect, the invention provides a phosphate salt of (1R,5S)-1-(naphthalen-2-yl)-3-azabicyclo[3.1.0]hexane.

In the fourth aspect, the invention provides a crystalline form as made or described in any of the examples or having an X-ray powder diffraction as depicted in any of the Figures, e.g.:

2.1 Crystalline Form D.

2.2 Formula 2.1 wherein the Crystalline Form D exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, comprising characteristic peaks of the XPRD pattern shown in FIG. 15.

2.3 Formula 2.1 or 2.2 wherein the Crystalline Form D exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, comprising representative peaks of the XPRD pattern shown in FIG. 15.

2.4 Any of formula 2.1-2.3 wherein the Crystalline Form D exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, comprising three peaks, in some embodiments, five peaks, selected from those shown in FIG. 15.

2.5 Any of formula 2.1-2.4 wherein the Crystalline Form D exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, comprising ten peaks, in some embodiments twenty peaks, in some embodiments twenty-five peaks, selected from those shown in FIG. 15.

2.6 Any of formula 2.1-2.5 wherein the Crystalline Form D exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, substantially as shown in FIG. 15.

2.7 Any of formulae 2.1-2.6 wherein the Crystalline Form D exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, as shown in FIG. 15.

2.8 Any of formulae 2.1-2.7 wherein the Crystalline Form D is a citrate salt of (1R,5S)-1-(naphthalen-2-yl)-3-azabicyclo[3.1.0]hexane.

2.9 Crystalline Form E.

2.10 Formula 2.9 wherein the Crystalline Form E exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, comprising characteristic peaks of the XPRD pattern shown in FIG. 16.

2.11 Formula 2.9 or 2.10 wherein the Crystalline Form E exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, comprising representative peaks of the XPRD pattern shown in FIG. 16.

2.12 Any of formula 2.9-2.11 wherein the Crystalline Form E exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, comprising three peaks, in some embodiments, five peaks, selected from those shown in FIG. 16.

2.13 Any of formula 2.9-2.12 wherein the Crystalline Form E exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, comprising ten peaks, in some embodiments twenty peaks, in some embodiments twenty-five peaks, selected from those shown in FIG. 16.

2.14 Any of formula 2.9-2.13 wherein the Crystalline Form E exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, substantially as shown in FIG. 16.

2.15 Any of formulae 2.9-2.14 wherein the Crystalline Form E exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, as shown in FIG. 16.

2.16 Any of formulae 2.9-2.15 wherein the Crystalline Form E is a phosphate salt of (1R,5S)-1-(naphthalen-2-yl)-3-azabicyclo[3.1.0]hexane.

2.17 Crystalline Form F.

2.18 Formula 2.17 wherein the Crystalline Form F exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, comprising characteristic peaks of the XPRD pattern shown in FIG. 17.

2.19 Formula 2.17 or 2.18 wherein the Crystalline Form F exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, comprising representative peaks of the XPRD pattern shown in FIG. 17.

2.20 Any of formula 2.17-2.19 wherein the Crystalline Form F exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, comprising three peaks, in some embodiments, five peaks, selected from those shown in FIG. 17.

2.21 Any of formula 2.17-2.20 wherein the Crystalline Form F exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, comprising ten peaks, in some embodiments twenty peaks, in some embodiments twenty-five peaks, selected from those shown in FIG. 17.

2.22 Any of formula 2.17-2.21 wherein the Crystalline Form F exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, substantially as shown in FIG. 17.

2.23 Any of formulae 2.17-2.22 wherein the Crystalline Form F exhibits an X-ray powder diffraction pattern, e.g., an X-ray powder diffraction pattern measured using an incident beam of Cu radiation, e.g., Cu Kα radiation, e.g., wherein the XRPD is measured using radiation of wavelength 1.541871 Å, as shown in FIG. 17.

2.24 Any of formulae 2.17-2.23 wherein the Crystalline Form F is a phosphate salt of (1R,5S)-1-(naphthalen-2-yl)-3-azabicyclo[3.1.0]hexane.

2.25 The Crystalline Form of any of formulae 2.1-2.24 wherein the XRPD pattern is measured using a copper source, e.g., a copper anode.

2.26 A combination of any of the Crystalline Forms A through F, e.g., any of formulae 1.1-1.234 and any of formulae 2.1-2.25, e.g., a combination of Crystalline Form A and Crystalline Form B; a combination of Crystalline Form A and Crystalline Form C; a combination of Crystalline Form A, Crystalline Form B, and Crystalline Form C; a combination of Crystalline Form B and Crystalline Form C; a combination of Crystalline Form B and Crystalline Form D; a combination of Crystalline Form E and Crystalline Form F.

2.27 The Crystalline Form according to any of formulae 2.1-2.25, wherein said Crystalline Form is free or substantially free of any other form, e.g., less than 20 wt. %, e.g., less than 15 wt. %, e.g., less than 10 wt. %, preferably less than 5 wt. %, preferably less than 3 wt. %, more preferably less than 2 wt. %, still preferably less than 1 wt. %, still preferably less than 0.1 wt. %, most preferably less than 0.01 wt. %, of the amorphous form.

2.28 The Crystalline Form according to any of formulae 2.1-2.25, wherein said Crystalline Form is free or substantially free of any other form, e.g., less than 20 wt. %, e.g., less than 10 wt. %, preferably less than 5 wt. %, preferably less than 3 wt. %, more preferably less than 2 wt. %, still preferably less than 1 wt. %, still preferably less than 0.1 wt. %, most preferably less than 0.01 wt. %, of any other crystalline form.

2.29 The Crystalline Form according to any of formulae 2.1-2.25, wherein said Crystalline Form is free or substantially free of any other form, e.g., less than 20 wt. %, e.g., less than 10 wt. %, preferably less than 5 wt. %, preferably less than 3 wt. %, more preferably less than 2 wt. %, still preferably less than 1 wt. %, still preferably less than 0.1 wt. %, most preferably less than 0.01 wt. %, of the amorphous form and any other crystalline form.

2.30 The Crystalline Form according to any of formulae 2.1-2.29 when made by any of processes described in formula 4.1-4.20 or similarly described in any of the examples or having an X-ray powder diffraction or X-ray crystal structure as depicted in any of the Figures.

Phase transitions of solids can be thermodynamically reversible or irreversible. Crystalline forms that transform reversibly at a specific transition temperature ($T_t$) are enantiotropic polymorphs. If the crystalline forms are not interconvertible under these conditions, the system is monotropic (one thermodynamically stable form).

Crystalline Forms A, B, and C are anhydrous enantiotropes of (1R,5S)-1-(naphthalen-2-yl)-3-azabicyclo[3.1.0]hexane hydrochloride. Crystalline Form C is the stable solid phase below the transition temperature $T_{t,C \to B}$, Crystalline Form B is the stable solid phase between $T_{t,C \to B}$ and $T_{t,B \to A}$, and Crystalline Form A is the stable solid phase above $T_{t,B \to A}$. $T_{t,C \to B}$ is expected below 2° C. $T_{t,C \to A}$ will be between 2° C. and ambient temperature, and $T_{t,B \to A}$ is between 37 and 54° C.

Owing to kinetic constraints, the thermodynamic transformation of Crystalline Form A to Crystalline Form B is hindered. Therefore, surprisingly, Crystalline Form A appears to be sufficiently kinetically stable so as to persist in the solid state under temperature conditions where it is thermodynamically metastable.

Agitating Crystalline Form A as a slurry for 16 days in dichloromethane at ambient temperature (see Example 6a) does not cause a solvent mediated form conversion to Crystalline Form B, the more stable form at that temperature. This indicates that the critical free energy barrier for nucleation is not overcome in the absence of seeds of the more stable polymorph within the time frame evaluated.

Under exposure to accelerated stress conditions for two weeks, Crystalline Forms A and B remain unchanged at 30° C./56% RH or 40° C./75% RH (Example 11). In contrast, Crystalline Form C converts to a mixture of Crystalline Forms A and B within two weeks at 40° C./75% RH (Example 11). Thus, unlike Crystalline Form A, Crystalline Form C converts under conditions in which it is metastable.

For Crystalline Form A, in the absence of seeds of the more stable polymorph, the critical free energy barrier for the nucleation of Crystalline Form B is not overcome in the solid state or in solvent mediated conversion experiments within the time evaluated.

Thus, Crystalline Form A may be synthesized on large scale easily, yet, also, surprisingly, persists in the solid state even under conditions in which it is thermodynamically metastable.

In the fifth aspect, the invention provides the following:

3.1. A pharmaceutical composition comprising any of the Crystalline Form A through F according to any of formulae 1.1-1.239 or 2.1-2.30, e.g., Crystalline Form A, e.g., any of formulae 1.1-1.77, e.g., Crystalline Form B, e.g., any of formulae 1.78-1.162, and a pharmaceutically acceptable diluent or carrier.

3.2. The pharmaceutical composition according to formula 3.1, wherein the composition is sustained release.

3.3. The pharmaceutical composition according to formula 3.1 or 3.2, comprising 1 mg to 1800 mg, e.g., 10 mg to 1800 mg, e.g., 25 mg to 1800 mg, e.g., 10 mg to 1600 mg, e.g., 10 mg to 1200 mg, e.g., 50 mg to 1200 mg, e.g., 50 mg to 1000 mg, e.g., 75 mg to 1000 mg, e.g., 75 mg to 800 mg, e.g., 75 mg to 500 mg, e.g., 100 mg to 750 mg, e.g., 100 mg to 500 mg, e.g., 100 mg to 400 mg, e.g., 100 mg to 300 mg, e.g., 100 mg to 200 mg, of any of the Crystalline Form A through F of the invention, e.g., any of formulae 1.1-1.239, e.g., Crystalline Form A, e.g., any of formulae 1.1-1.77, e.g., Crystalline Form B, e.g., any of formulae 1.78-1.162, e.g., any of formulae 2.1-2.30.

3.4. The composition of any one of formulae 3.1-3.3 comprising 75 mg to 1000 mg, e.g., 100 mg to 600 mg, e.g., 100 mg to 400 mg, e.g., 100 mg to 200 mg, of any of the Crystalline Form A through F of the invention, e.g., any of formulae 1.1-1.239, e.g., Crystalline Form A, e.g., any of formulae 1.1-1.77, e.g., Crystalline Form B, e.g., any of formulae 1.78-1.162, e.g., any of formulae 2.1-2.30.

3.5. The composition of any one of formulae 3.1-3.3 comprising 50 mg to 600 mg, e.g., 100 mg to 600 mg, e.g., 100 mg to 400 mg, e.g., 100 mg to 200 mg, of any of the Crystalline Form A through F of the invention, e.g., any of formulae 1.1-1.239, e.g., Crystalline Form A, e.g., any of formulae 1.1-1.77, e.g., Crystalline Form B, e.g., any of formulae 1.78-1.162, e.g., any of formulae 2.1-2.30.

3.6. The composition of any one of formulae 3.1-3.3 comprising 5 mg to 500 mg, e.g., 5 mg to 10 mg, e.g., 10 mg to 25 mg, e.g., 30 mg to 50 mg, e.g., 10 mg to 300 mg, e.g., 25 mg to 300 mg, e.g., 50 mg to 100 mg, e.g., 100 mg to 250 mg, e.g., 250 mg to 500 mg, of any one of Crystalline Forms A through F of the invention, e.g., e.g., any of formulae 1.1-1.239, e.g., Crystalline Form A, e.g., any of formulae 1.1-1.77, e.g., Crystalline Form B, e.g., any of formulae 1.78-1.162, e.g., any of formulae 2.1-2.30.

3.7. The composition of any one of formulae 3.1-3.3 for administration of 0.5 mg/kg to 20 mg/kg per day, e.g., 1 mg/kg to 15 mg/kg per day, e.g., 1 mg/kg to 10 mg/kg per day, e.g., 2 mg/kg to 20 mg/kg per day, e.g., 2 mg/kg to 10 mg/kg per day, e.g., 3 mg/kg to 15 mg/kg per day, of any of the Crystalline Form A through F of the invention, e.g., any of formulae 1.1-1.239, e.g., Crystalline Form A, e.g., any of formulae 1.1-1.77, e.g., Crystalline Form B, e.g., any of formulae 1.78-1.162, e.g., any of formulae 2.1-2.30.

3.8. The composition of any one of formulae 3.1-3.7 comprising less than 50% w/w of any one of Crystalline Forms A through F of the invention, e.g., less than 40% w/w, e.g., less than 30% w/w, less than 20% w/w, e.g., 1-40% w/w, e.g., 5-40% w/w, e.g., 10-30% w/w, e.g., 15-25% w/w, e.g., 15-20% w/w, e.g., 17% w/w, e.g., 25% w/w, e.g., any of formulae 1.1-1.239, e.g., Crystalline Form A, e.g., any of formulae 1.1-1.77, e.g., Crystalline Form B, e.g., any of formulae 1.78-1.162, e.g., any of formulae 2.1-2.30.

3.9. The composition of any one of formulae 3.1-3.8 wherein the pharmaceutically acceptable diluent or carrier comprises hydroxypropyl methylcellulose.

3.10. The composition of formula 3.9, wherein the composition comprises at least 10% w/w of the hydroxypropyl methylcellulose, e.g., 10-50% w/w, e.g., 10-40% w/w, e.g., 20-50% w/w, e.g., 20-40% w/w, e.g., 30-40% w/w, e.g., 37% w/w.
3.11. The composition of formula 3.9 or 3.10, wherein the degree of methoxy substitution of the hydroxypropyl methylcellulose is 19-24%.
3.12. The composition of any one of formulae 3.9-3.11, wherein the degree of hydroxypropoxy substitution of the hydroxypropyl methylcellulose is 4-12%.
3.13. The composition of any one of formulae 3.9-3.12, wherein the hydroxypropyl methylcellulose is hypromellose 2208.
3.14. The composition of any one of formulae 3.9-3.13, wherein the hydroxypropyl methylcellulose has a nominal viscosity of 4,000 mPA·σ.
3.15. The composition of any one of formulae 3.9-3.13, wherein the hydroxypropyl methylcellulose has a viscosity of 2,000-6,000 mPA·σ, e.g., 2,600 to 5,000 mPA·σ, e.g., 2,663 to 4,970 mPA·σ.
3.16. The composition of any one of formulae 3.9-3.15, wherein the pharmaceutically acceptable diluent or carrier comprises alpha-lactose monohydrate.
3.17. The composition of formula 3.16, wherein the composition comprises at least 10% w/w of the alpha-lactose monohydrate, e.g., 10-80% w/w, e.g., 20-70% w/w, e.g., 20-60% w/w, e.g., 20-50% w/w, e.g., 20-40% w/w, e.g., 20-30% w/w, e.g., 30-70% w/w, e.g., 30-60% w/w, e.g., 30-50% w/w, e.g., 30%-40% w/w, e.g., 37% w/w.
3.18. The composition of formula 3.16 or 3.17, wherein the composition comprises milled alpha-lactose monohydrate.
3.19. The composition of any one of formulae 3.1-3.18, wherein the composition comprises a co-processed mixture of hydroxpropyl methylcellulose and alpha-lactose monohydrate (e.g., Retalac®).
3.20. The composition of formula 3.19, wherein the mixture comprises equal parts of the hydroxpropyl methylcellulose and alpha-lactose monohydrate.
3.21. The composition of formula 3.19 or 3.20, wherein the mixture comprises particles of hydroxpropyl methylcellulose and alpha-lactose monohydrate with $d_{50}$ (median diameter) in the range of 100 μm to 200 μm, e.g., 125 μm.
3.22. The composition of any one of formulae 3.19-3.21, wherein the mixture comprises particles of hydroxpropyl methylcellulose and alpha-lactose monohydrate wherein the particle size distribution is as follows:
<63 μm≤25%
<100 μm: 35%
<250 μm≥80%.
3.23. The composition of any one of formulae 3.19-3.22, wherein the composition comprises at least 20% w/w of the mixture, e.g., at least 30% w/w, e.g., at least 40% w/w, e.g., at least 50% w/w, e.g., at least 60% w/w, e.g., at least 70% w/w, e.g, at least 80% w/w, e.g., 20-90% w/w, e.g., 30-80% w/w, e.g., 40-80% w/w, e.g., 50-80% w/w, e.g., 60-80% w/w, e.g., 70-80% w/w, e.g., 75% w/w.
3.24. The composition of any one of formulae 3.1-3.23, wherein the pharmaceutically acceptable diluent or carrier comprises a lubricant, e.g., magnesium stearate.
3.25. The composition of formula 3.24, wherein the lubricant is one or more of glyceryl behenate, magnesium stearate, talc, and sodium stearyl fumarate, e.g, magnesium stearate.
3.26. The composition of formula 3.24 or 3.25, wherein the composition comprises less than 10% w/w of the lubricant, e.g., less than 5% w/w, less than 3% w/w, less than 1% w/w, e.g., 0.1 to 1% w/w, e.g., 0.1 to 0.8% w/w, e.g., 0.5% w/w.
3.27. The composition of any one of formulae 3.24-3.26, wherein the composition comprises less than 10% w/w of magnesium stearate, e.g., less than 5% w/w, less than 3% w/w, less than 1%, e.g., 0.1 to 1% w/w, e.g., 0.1 to 0.8% w/w, e.g., 0.5% w/w.
3.28. The composition of any one of formulae 3.1-3.27, wherein the pharmaceutically acceptable diluent or carrier comprises one or more of a diluent, disintegrant, binder, and modified release agent.
3.29. The composition of formula 3.28, wherein the diluent is one or more of mannitol (e.g., Pearlitol 300 DC), micro-crystalline cellulose (e.g., Avicel pH 102), and pre-gelatinized starch (e.g., Starch 1500).
3.30. The composition of formula 3.29, wherein the disintegrant is one or both of crospovidone (e.g., Polyplasdone XL-10) and sodium starch glycolate (e.g., Explotab).
3.31. The composition of formula 3.28, wherein the binder is polyvinylpyrrolidone (e.g., Povidone K29/32).
3.32. The composition of formula 3.28, wherein the modified release agent is one or more of hydroxypropyl cellulose (e.g., Klucel EXF, Klucel MXF, and/or Klucel HXF) and hydroxypropyl methylcellulose (e.g., Methocel K100M, Methocel K4M PREM, Methocel K15M PREM CR).
3.33. The composition of formula 3.28 or 3.32, wherein the composition comprises at least 5% w/w of the modified release agent, e.g., 5-60% w/w, e.g., 10-50% w/w, e.g., 10-40% w/w.
3.34. The composition of formula 3.32 or 3.33, wherein the modified release agent is hydroxypropyl methylcellulose.
3.35. A method for the prophylaxis or treatment of a disorder and/or alleviation of associated symptoms of any disorder treatable by inhibiting reuptake of multiple biogenic amines causally linked to the targeted CNS disorder, wherein the biogenic amines targeted for reuptake inhibition are selected from norepinephrine, and/or serotonin, and/or dopamine, in a particular embodiment, a method for the prophylaxis or treatment of any of the following disorders:
(i) attention deficit hyperactivity disorder (ADHD, both pediatric and adult) and related behavioral disorders, as well as forms and symptoms of alcohol abuse, drug abuse, obsessive compulsive disorder, learning disorders, reading problems, gambling addiction, manic symptoms, phobias, panic attacks, oppositional defiant disorder, conduct disorder, disruptive behavior disorder, academic problems in school, smoking, abnormal sexual behaviors, schizoid behaviors, somatization, depression (including but not limited to major depressive disorder, recurrent; dysthymic disorder; depressive disorder not otherwise specified (NOS); major depressive disorder, single episode; depression associated with bipolar disorder, Alzheimers, psychosis or Parkinson's disease; postnatal depression; and seasonal affected disorder), sleep disorders, generalized anxiety, stuttering, and tic disorders (such as Tourette's syndrome);
(ii) ADHD, substance abuse, depression, anxiety disorders (including but not limited to panic disorder, generalized anxiety, obsessive compulsive disorder, post-traumatic stress disorder, and social anxiety disorder), autism, traumatic brain injury, cognitive impairment, schizophrenia (particularly for cognition), obesity, chronic pain disorders, personality disorder, and mild cognitive impairment;

(iii) anxiety, panic disorder, posttraumatic stress disorder, obsessive compulsive disorder, schizophrenia and allied disorders, obesity, tic disorders, addiction, Parkinson's disease, and chronic pain;

(iv) substance abuse disorders (including but not limited to alcohol-related disorders, nicotine-related disorders, amphetamine-related disorders, *cannabis*-related disorders, cocaine-related disorders, hallucinogen-use disorders, inhalant-related disorders, and opioid-related disorders);

(v) cognitive disorders, bipolar disorder, anorexia nervosa, bulimia nervosa, cyclothymic disorder, chronic fatigue syndrome, chronic or acute stress, fibromyalgia and other somatoform disorders (including somatization disorder, conversion disorder, pain disorder, hypochondriasis, body dysmorphic disorder, undifferentiated somatoform disorder, somatoform NOS), incontinence (i.e., stress incontinence, genuine stress incontinence, and mixed incontinence), inhalation disorders, mania, migraine headaches, peripheral neuropathy;

(vi) addictive disorders (including but not limited to eating disorders, impulse control disorders, alcohol-related disorders, nicotine-related disorders, amphetamine-related disorders, *cannabis*-related disorders, cocaine-related disorders, hallucinogen use disorders, inhalant-related disorders, opioid-related disorders)

(vii) fragile X-associated disorder;

(viii) autism spectrum disorder (ASD), e.g., in a patient with a fragile X-associated disorder;

(ix) ADHD in a patient with a fragile X-associated disorder;

(x) co-morbid ADHD and depression;

(xi) co-morbid ADHD and substance abuse;

(xii) co-morbid ADHD and anxiety;

comprising administering to a patient in need thereof a therapeutically effective amount of any of Crystalline Form A through F according to any of formulae 1.1-1.239, e.g., Crystalline Form A, e.g., any of formulae 1.1-1.77, e.g., Crystalline Form B, e.g., any of formulae 1.78-1.162, e.g., any of formulae 2.1-2.30, or a pharmaceutical composition according to any of formulae 3.1-3.34.

3.36. A pharmaceutical composition according to any of formulae 3.1-3.34 for use as a medicament, e.g., for use in the manufacture of a medicament for the treatment or prophylaxis of any of the disorders described in formula 3.35.

3.37. Crystalline Form A through F according to any of formulae 1.1-1.239, e.g., Crystalline Form A, e.g., any of formulae 1.1-1.77, e.g., Crystalline Form B, e.g., any of formulae 1.78-1.162, e.g., any of formulae 2.1-2.30, for use in the prophylaxis or treatment of any of the disorders described in formula 3.35, or for use in the manufacture of a medicament for the treatment or prophylaxis of any of the disorders described in formula 3.35.

In the sixth aspect, the invention provides the Crystalline Form according to any of formulae 1.1-1.239 or any of formulae 2.1-2.30 when made by any of the processes described or similarly described as follows:

4.1 Adding water to the Compound in hydrochloric acid addition salt form ((1R,5S)-1-(naphthalen-2-yl)-3-azabicyclo[3.1.0]hexane hydrochloride);

heating to dissolve all solids, e.g., heating to an internal temperature between 30-40° C., e.g., 34° C.;

adding an organic solvent, e.g., tetrahydrofuran and/or isopropylacetate; separating aqueous layer;

adding base, e.g., aqueous ammonia, to the aqueous layer;

adding an organic solvent, e.g., isopropylacetate;

agitating, e.g., for a minimum of 15 minutes;

allowing layers to settle, e.g., for a minimum of 30 minutes;

separating organic layer;

drying organic layer, e.g., with magnesium sulphate;

filtering;

washing filtercake with an organic solvent, e.g., isopropylacetate;

concentrating filtrate and washes;

adding isopropyl alcohol;

stirring at room temperature to dissolve all solids;

adding hydrochloric acid, e.g., HCl in isopropanol, to form solids, e.g., adding HCl over 10 minutes, e.g., adding HCl in isopropanol over 10 minutes;

adding additional hydrochloric acid, e.g., HCl in isopropanol, e.g., adding additional HCl over 55 minutes, e.g., adding HCl in isopropanol over 55 minutes;

stirring slurry, e.g., stirring slurry for 35 minutes;

adding additional hydrochloric acid, e.g., HCl in isopropanol, e.g., adding additional HCl over 10 minutes, e.g., adding HCl in isopropanol over 10 minutes;

stirring slurry, e.g., stirring slurry for 30 minutes;

filtering;

washing filtercake with an organic solvent, e.g., isopropyl alcohol; and drying filtercake.

4.2 Storing Crystalline Form A at 40° C./75% RH, e.g., storing Crystalline Form A at 40° C./75% RH for 7 days; and isolating crystals.

4.3 Preparing a solution of (1R,5S)-1-(naphthalen-2-yl)-3-azabicyclo[3.1.0]hexane hydrochloride, e.g., Crystalline Form A, e.g., in chloroform, dichloromethane, hexafluoroisopropylalcohol, methanol, and/or 2,2,2,-trifluoroethanol (TFE);

sonicating;

achieving complete dissolution as judged by visual observation;

filtering;

evaporating at ambient conditions, e.g., in a vial covered with aluminium foil perforated with pinholes; and isolating crystals.

4.4 Preparing a solution of (1R,5S)-1-(naphthalen-2-yl)-3-azabicyclo[3.1.0]hexane hydrochloride, e.g., Crystalline Form A, e.g., in chloroform, dichloromethane, ethanol, and/or methanol;

filtering;

admixing with antisolvent, e.g., toluene, heptane, acetonitrile, methyl ethyl ketone, acetone, hexanes, tetrahydrofuran, dioxane, ethyl acetate, and/or isopropyl ether; and isolating crystals.

4.5 Exposing (1R,5S)-1-(naphthalen-2-yl)-3-azabicyclo [3.1.0]hexane hydrochloride, e.g., Crystalline Form A, to vapor, e.g., organic solvent vapor, e.g., dichloromethane and/or ethanol vapor; and
isolating crystals.
4.6 Preparing a suspension of (1R,5S)-1-(naphthalen-2-yl)-3-azabicyclo[3.1.0]hexane hydrochloride, e.g., Crystalline Form A, e.g., in dichloromethane, ethanol, isopropyl alcohol, 1-propanol, and/or water;
agitating at ambient temperature or elevated temperature; and
isolating crystals, e.g., by vacuum filtration.
4.7 Preparing a solution of (1R,5S)-1-(naphthalen-2-yl)-3-azabicyclo[3.1.0]hexane hydrochloride, e.g., Crystalline Form A, at elevated temperature in an organic solvent, e.g., dichloromethane, ethanol, isopropyl alcohol, and/or 1-propanol;
filtering, e.g., through 0.2 μm nylon filter, into a warm vial;
cooling;
optionally further cooling by placing in a refrigerator and/or freezer; and
isolating crystals.
4.8 Preparing a solution of (1R,5S)-1-(naphthalen-2-yl)-3-azabicyclo[3.1.0]hexane hydrochloride, e.g., Crystalline Form A, at elevated temperature in an organic solvent, e.g., dichloromethane, ethanol, isopropyl alcohol, and/or 1-propanol;
filtering, e.g., through 0.2 μm nylon filter, into a cooled vial;
cooling below 0° C., e.g., placing in −78° C. bath, e.g., an isopropyl alcohol/dry ice bath;
optionally further cooling by placing in a freezer; and
isolating crystals.
4.9 Preparing a solution of (1R,5S)-1-(naphthalen-2-yl)-3-azabicyclo[3.1.0]hexane hydrochloride, e.g., Crystalline Form A in an organic solvent, e.g., ethanol, isopropyl alcohol, methanol, acetone, toluene, 1-propanol, water, and/or dioxane; sonicating;
achieving complete dissolution as judged by visual observation;
filtering, e.g., through 0.2 μm nylon filter;
evaporating at ambient temperature; and
isolating crystals.
4.10 Preparing a solution or suspension of (1R,5S)-1-(naphthalen-2-yl)-3-azabicyclo[3.1.0]hexane hydrochloride, e.g., Crystalline Form A in an organic solvent, e.g., dichloromethane, ethanol, isopropyl alcohol, and/or 1-propanol; cooling, e.g, in a freezer; and isolating crystals.
4.11 Preparing a solution or suspension of (1R,5S)-1-(naphthalen-2-yl)-3-azabicyclo[3.1.0]hexane hydrochloride, e.g., Crystalline Form A in an organic solvent, e.g., hexafluoroisopropyl alcohol and/or 2,2,2-trifluoroethanol;
filtering, e.g., through 0.2 μm nylon filter;
adding anti-solvent, e.g., an organic anti-solvent, e.g., isopropyl ether, tetrahydrofuran, acetonitrile, ethyl acetate, and/or methyl ethyl ketone, until precipitation; and
isolating crystals, e.g., by vacuum filtration.
4.12 Dissolving (1R,5S)-1-(naphthalen-2-yl)-3-azabicyclo[3.1.0]hexane in an organic solvent, e.g., isopropanol;
adding HCl, e.g., HCl in isopropanol; and
optionally filtering.

4.13 Seeding a solution or slurry with crystals of the desired form, e.g., seeding a solution or slurry with Crystalline Form A, e.g., seeding while the temperature of the solution or slurry is above room temperature, e.g., 65° C.
4.14 Dissolving a solution of (1R,5S)-1-(naphthalen-2-yl)-3-azabicyclo[3.1.0]hexane hydrochloride in an organic solvent, e.g., ethanol, while heating, e.g., to 70° C.;
optionally filtering, e.g., via an encapsulated carbon filter;
optionally concentrating, e.g., to 5 total volumes (relative to (1R,5S)-1-(naphthalen-2-yl)-3-azabicyclo [3.1.0]hexane hydrochloride input);
optionally reheating to redissolve any solids;
optionally cooling, e.g., cooling to 65° C.;
seeding the solution;
optionally stirring to develop the seed bed;
optionally cooling; and
optionally filtering.
4.15 Dissolving (1R,5S)-1-(naphthalen-2-yl)-3-azabicyclo[3.1.0]hexane hydrochloride in water, e.g., with heat, e.g., heating to an internal temperature between 30-40° C., e.g., 34° C.;
washing the aqueous solution;
adding a base, e.g., ammonia;
extracting (1R,5S)-1-(naphthalen-2-yl)-3-azabicyclo [3.1.0]hexane with an organic solvent, e.g., isopropyl acetate;
optionally drying, e.g., over magnesium sulphate;
optionally concentrating to yield a solid;
optionally adding an organic solvent to dissolve the solid, e.g., isopropanol; and
adding HCl, e.g., HCl in isopropanol;
optionally filtering; and
optionally washing with an organic solvent, e.g., isopropanol.
4.16 Dissolving a solution of (1R,5S)-1-(naphthalen-2-yl)-3-azabicyclo[3.1.0]hexane hydrochloride in an organic solvent, e.g., ethanol, while heating, e.g., to 70° C.; optionally filtering, e.g., via an encapsulated carbon filter;
concentrating, e.g., to 5 total volumes (relative to (1R,5S)-1-(naphthalen-2-yl)-3-azabicyclo[3.1.0] hexane hydrochloride input);
optionally seeding before or after concentrating; and
optionally filtering.
4.17 Dissolving (1R,5S)-1-(naphthalen-2-yl)-3-azabicyclo[3.1.0]hexane in an organic solvent;
adding HCl, e.g., HCl in isopropanol; and
optionally filtering.
4.18 Any of processes 4.1-4.17 further comprising isolating the Crystalline Form, e.g., any of formulae 1.1-1.239 or 2.1-2.30, e.g., Crystalline Form A, e.g., any of formulae 1.1-1.77, e.g. Crystalline Form B, e.g., any of formulae 1.78-1.162.
4.19 A Crystalline Form according to any of formulae 1.1-1.239 or 2.1-2.30 when made by any of Examples 1-3, e.g., Example 1.
4.20 A Crystalline Form according to any of formulae 1.1-1.239 or 2.1-2.30 when made by any of the syntheses described in the Examples, e.g., Example 1, e.g., e.g., Example 3, e.g., any of Examples 6-13, e.g., Example 17, e.g., Example 18.

In the seventh aspect, the invention provides a process for making Crystalline Form A through F according to any of formulae 1.1-1.239 or 2.1-2.30, e.g., Crystalline Form A, e.g., any of formulae 1.1-1.77, e.g., Crystalline Form B, e.g., any of formulae 1.78-1.162, by any process described in any of formula 4.1-4.20 or described in any of the Examples.

In the eight aspect, the invention provides a process for making a pharmaceutical composition comprising any of the Crystalline Form A through F according to any of formulae 1.1-1.239 or 2.1-2.30, e.g., Crystalline Form A, e.g., any of formulae 1.1-1.77, e.g., Crystalline Form B, e.g., any of formulae 1.78-1.162, e.g., a pharmaceutical composition according to any of formula 3.1-3.34, wherein the process comprises:

isolating any of the Crystalline Form A through F according to any of formulae 1.1-1.239 or 2.1-2.30, e.g., Crystalline Form A, e.g., any of formulae 1.1-1.77, e.g., Crystalline Form B, e.g., any of formulae 1.78-1.162, and admixing the isolated Crystalline Form with a pharmaceutically acceptable diluent or carrier.

BRIEF DESCRIPTION OF THE DRAWINGS

FIG. 4A depicts a high resolution X-ray powder diffraction pattern of Crystalline Form A;

FIG. 4B depicts an X-ray powder diffraction pattern of Crystalline Form B; and

FIG. 4C depicts an X-ray powder diffraction pattern of Crystalline Form C.

FIG. 13A depicts an X-ray powder diffraction pattern of Crystalline Form B (slow cooling in IPA, solids precipitate in refrigerator);

FIG. 13B depicts an X-ray powder diffraction pattern of Crystalline Form C+Crystalline Form B (slow crystalline cooling in IPA, with seeds, solids precipitate in freezer);

FIG. 13C depicts an X-ray powder diffraction pattern of Crystalline Form C+Crystalline Form A (slow cooling in IPA, solids precipitate in freezer);

FIG. 13D depicts an X-ray powder diffraction pattern of Crystalline Form B (slow cooling in IPA, solids precipitate in freezer);

FIG. 13E depicts an X-ray powder diffraction pattern of Crystalline Form B+Crystalline Form A (crash cooling in IPA, solids precipitate in dry ice/IPA);

FIG. 13F depicts an X-ray powder diffraction pattern of Crystalline Form A+Crystalline Form C (slow cooling in IPA, solids precipitate in freezer); and FIG. 13G depicts an X-ray powder diffraction pattern Crystalline Form C, slow cooling in IPA.

FIG. 14D depicts an X-ray powder diffraction pattern of Crystalline Form D (30-min stir at 70° C. in pH 4.4 buffer);

FIG. 14E depicts an X-ray powder diffraction pattern of Crystalline Form E (contains peaks of Crystalline Form F, slurry at 50° C. in pH 6.0 buffer); and FIG. 14F depicts an X-ray powder diffraction pattern Crystalline Form F (30-min stir at 70° C. in pH 8.1 buffer).

DETAILED DESCRIPTION OF THE INVENTION

Figure 1:
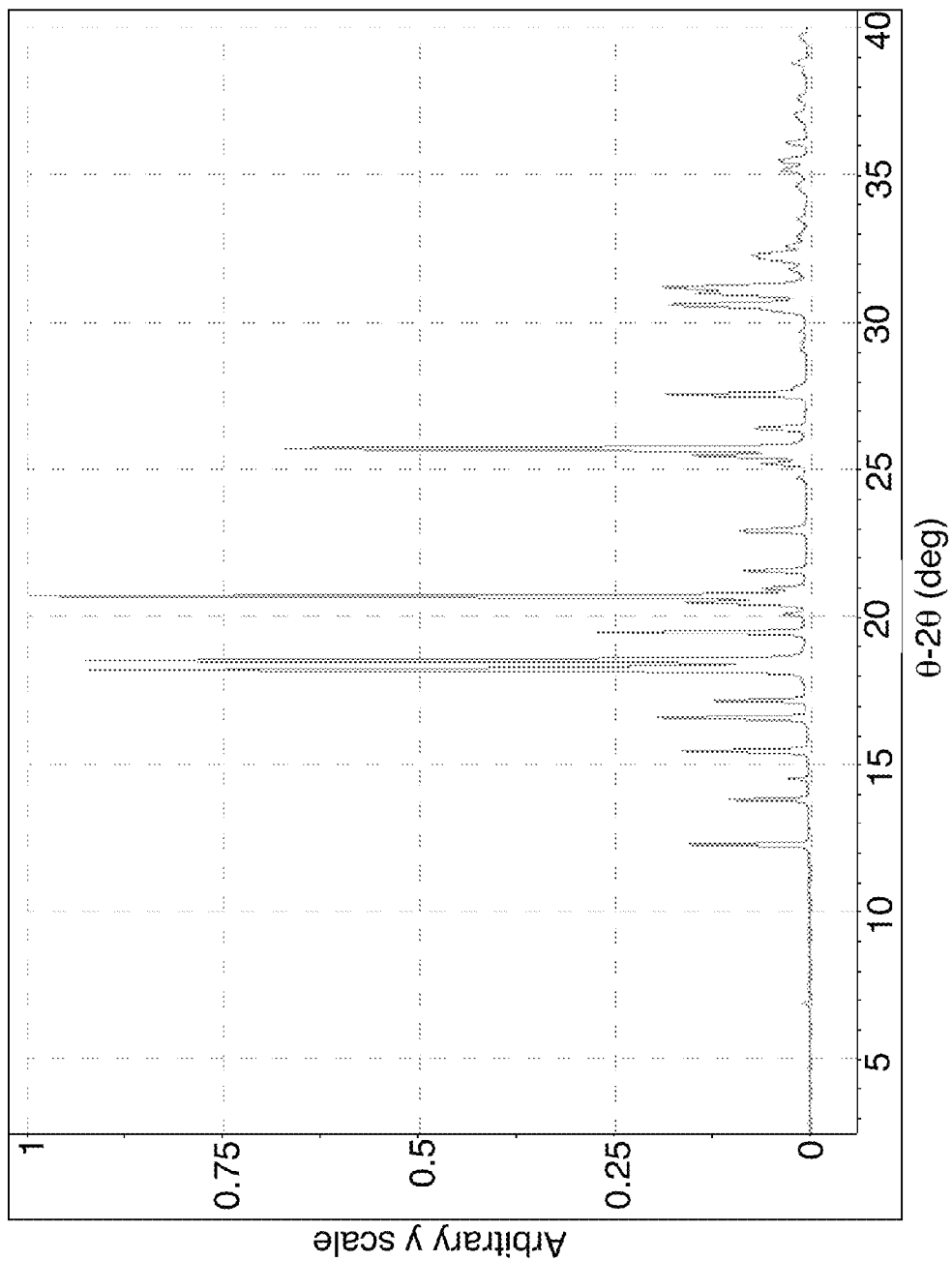
FIG. 1 depicts a high-resolution X-ray powder diffraction (XRPD) pattern of Crystalline Form A.

As used herein, the term "the Compound" refers to (1R,5S)-1-(naphthalen-2-yl)-3-azabicyclo[3.1.0]hexane, also known as (+)-1-(naphthalen-2-yl)-3-azabicyclo[3.1.0]hexane. The term "the Compound in hydrochloric acid addition salt form" refers to (1R,5S)-1-(naphthalen-2-yl)-3-azabicyclo[3.1.0]hexane hydrochloride or (+)-1-(naphthalen-2-yl)-3-azabicyclo[3.1.0]hexane hydrochloride having the following structure:

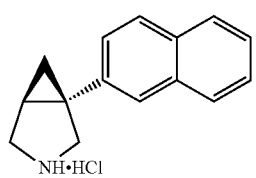

This compound is free or substantially free of the corresponding (−)-enantiomer, e.g., containing no more than 20% w/w (weight/weight) of the corresponding (−) enantiomer, in free or pharmaceutically acceptable salt form, e.g., no more than 10% w/w of the corresponding (−) enantiomer, in free or pharmaceutically acceptable salt form, e.g., no more than 5% w/w of the corresponding (−) enantiomer, in free or pharmaceutically acceptable salt form, e.g., no more than 2% w/w of the corresponding (−) enantiomer, in free or pharmaceutically acceptable salt form, e.g., no more than 1% w/w of the corresponding (−) enantiomer, in free or pharmaceutically acceptable salt form.

"Crystalline Form A" refers to a crystalline form of the Compound in hydrochloric acid addition salt form as described in any of formulae 1.1-1.77 or as characterized in relevant sections of the Examples below.

"Crystalline Form B" refers to a crystalline form of the Compound in hydrochloric acid addition salt form as described in any of formulae 1.78-1.162 or as characterized in relevant sections of the Examples below.

"Crystalline Form C" refers to a crystalline form of the Compound in hydrochloric acid addition salt form as described in any of formulae 1.163-1.231 or as characterized in relevant sections of the Examples below.

"Crystalline Form D" refers to a crystalline form as described in any of formulae 2.1-2.8 or as characterized in relevant sections of the Examples below.

"Crystalline Form E" refers to a crystalline form as described in any of formulae 2.9-2.16 or as characterized in relevant sections of the Examples below.

"Crystalline Form F" refers to a crystalline form as described in any of formulae 2.17-2.24 or as characterized in relevant sections of the Examples below.

The invention claims Crystalline Form A through F and combinations thereof as described herein, for example in any of formulae 1.1-1.239 or in any of formulae 2.1-2.30. These Crystalline Forms can be made and characterized as set forth in the Example section below. Therefore, the invention provides any of Crystalline Form A through F as set forth in any of formulae 1.1-1.239 or in any of formulae 2.1-2.30 or as characterized in the Example section below.

The term "substantially free" of other crystalline forms refer to less than 10 wt. %, in some embodiments less than 5 wt. %, in some embodiments less than 2 wt. %, still in some embodiments less than 1 wt. %, still in some embodiments less than 0.1%, yet in some embodiments less than 0.01 wt. % of other forms or other crystal forms, e.g., amorphous or other crystal forms.

The term "solvate" refers to crystalline solid adducts containing either stoichiometric or nonstoichiometric amounts of a solvent incorporated within the crystal structure. Therefore, the term "non-solvate" form herein refers to crystalline forms that are free or substantially free of solvent molecules within the crystal structures of the invention. Similarly, the term "non-hydrate" form herein refers to salt crystals that are free or substantially free of water molecules within the crystal structures of the invention.

The term "amorphous" form refers to solids of disordered arrangements of molecules and do not possess a distinguishable crystal lattice.

The term "patient" includes human and non-human. In one embodiment, the patient is a human. In another embodiment, the patient is a non-human.

The term "anti-solvent" means a solvent in which the Compound and/or the Compound in hydrochloric acid addition salt form ((1R,5S)-1-(naphthalen-2-yl)-3-azabicyclo[3.1.0]hexane hydrochloride) has low solubility or is insoluble. For instance, an anti-solvent includes a solvent in which the Compound and/or the Compound in hydrochloric acid addition salt form has a solubility of less than 35 mg/ml, e.g., a solubility of 10-30 mg/ml, e.g., a solubility of 1-10 mg/ml, e.g., a solubility of less than 1 mg/ml.

The term "XRPD" means X-ray powder diffraction.

It is to be understood that an X-ray powder diffraction pattern of a given sample may vary (standard deviation) depending on the instrument used, the time and temperature of the sample when measured, and standard experimental errors. Therefore, the 2-theta values, d-spacing values, heights and relative intensity of the peaks will have an acceptable level of deviation. For example, the values may have an acceptable deviation of e.g., about 20%, 15%, 10%, 5%, 3%, 2% or 1%. In a particular embodiment, the 2-theta values (°) or the d-spacing values (Å) of the XRPD pattern of the crystalline forms of the current invention may have an acceptable deviation of ±0.2 degrees and/or ±0.2 Å. Further, the XRPD pattern of the Crystalline Forms of the invention may be identified by the characteristic peaks as recognized by one skilled in the art. For example, the Crystalline Forms of the invention may be identified by, e.g., two characteristic peaks, in some instances, three characteristic peaks, in another instance, five characteristic peaks. Therefore, the term "substantially as" set forth in a particular table or depicted or shown in a particular figure refers to any crystal which has an XRPD having the major or characteristic peaks as set forth in the tables/figures as recognized by one skilled in the art.

It is also to be understood that the differential scanning calorimetry or thermogravimetric analysis thermograms of a given sample may vary (standard deviation) depending on the instrument used, the time and temperature of the sample when measured, and standard experimental errors. The temperature value itself may deviate by ±10° C., preferably ±5° C., preferably ±3° C. of the reference temperature.

Under most circumstances for XRPDs, peaks within the range of up to about 30° 2θ are selected. Rounding algorithms are used to round each peak to the nearest 0.1° or 0.01° 2θ, depending upon the instrument used to collect the data and/or the inherent peak resolution. Peak position variabilities are given to within ±0.2° 2θ.

The wavelength used to calculate d-spacings (Å) values herein is 1.5405929 Å, the Cu-$K_{\alpha 1}$ wavelength (*Phys. Rev.*, A56 (6), 4554-4568 (1997)).

Per USP guidelines, variable hydrates and solvates may display peak variances greater than ±0.2° 2θ.

"Prominent peaks" are a subset of the entire observed peak list and are selected from observed peaks by identifying preferably non-overlapping, low-angle peaks, with strong intensity.

If multiple diffraction patterns are available, then assessments of particle statistics (PS) and/or preferred orientation (PO) are possible. Reproducibility among XRPD patterns from multiple samples analyzed on a single diffractometer indicates that the particle statistics are adequate. Consistency of relative intensity among XRPD patterns from multiple diffractometers indicates good orientation statistics. Alternatively, the observed XRPD pattern may be compared with a calculated XRPD pattern based upon a single crystal structure, if available. Two-dimensional scattering patterns using area detectors can also be used to evaluate PS/PO. If the effects of both PS and PO are determined to be negligible, then the XRPD pattern is representative of the powder average intensity for the sample and prominent peaks may be identified as "representative peaks." In general, the more data collected to determine representative peaks, the more confident one can be of the classification of those peaks.

"Characteristic peaks," to the extent they exist, are a subset of representative peaks and are used to differentiate one crystalline polymorph from another crystalline polymorph (polymorphs being crystalline forms having the same chemical composition). Characteristic peaks are determined by evaluating which representative peaks, if any, are present in one crystalline polymorph of a compound against all other known crystalline polymorphs of that compound to within ±0.2° 2θ. Not all crystalline polymorphs of a compound necessarily have at least one characteristic peak.

It has been observed that in reactions to make Crystalline Form A, Crystalline Form B may also form. However, synthesis of products may be controlled by, for example, seeding with Crystalline Form A.

The Crystalline Form A through F, e.g., formulae 1.1-1.239, e.g., formulae 2.1-2.30, and combinations thereof as described herein are useful as an unbalanced triple reuptake Inhibitor™, most potent towards norepinephrine reuptake (NE), one-sixth as potent towards dopamine reuptake (DA) and one-fourteenth as much towards serotonin reuptake (5-HT). Therefore, the Crystalline Form A through F, e.g., formulae 1.1-1.239, e.g., formulae 2.1-2.30, and combinations thereof as described herein are useful for the prophylaxis or treatment of a disorder and/or alleviation of associated symptoms of any disorder treatable by inhibiting reuptake of multiple biogenic amines causally linked to the targeted CNS disorder, wherein the biogenic amines targeted for reuptake inhibition are selected from norepinephrine, and/or serotonin, and/or dopamine. Therefore, the invention provides a method for the prophylaxis or treatment of any of the following disorders:

attention deficit hyperactivity disorder (ADHD) and related behavioral disorders, as well as forms and symptoms of substance abuse (alcohol abuse, drug abuse), obsessive compulsive behaviors, learning disorders, reading problems, gambling addiction, manic symptoms, phobias, panic attacks, oppositional defiant behavior, conduct disorder, academic problems in school, smoking, abnormal sexual behaviors, schizoid behaviors, somatization, depression, sleep disorders, generalized anxiety, stuttering, and tic disorders. Further disorders are disclosed in U.S. Publication No. 2007/0082940, the contents of which are hereby incorporated by reference in their entirety;

depression, anxiety disorders, autism, traumatic brain injury, cognitive impairment, and schizophrenia (particularly for cognition), obesity, chronic pain disorders, personality disorder, and mild cognitive impairment;

panic disorder, posttraumatic stress disorder, obsessive compulsive disorder, schizophrenia and allied disorders, obesity, tic disorders, Parkinson's disease;

disorders disclosed in WO 2013/019271, the contents of which are hereby incorporated by reference in their entirety;

fragile X-associated disorder;

fragile X-associated disorder wherein the patient was refractory to a prior course of treatment for the fragile X-associated disorder;

attention-deficit/hyperactivity disorder (ADHD) wherein the ADHD is co-morbid with one or both of anxiety and depression (e.g., depression), e.g., in a patient with a fragile X-associated disorder;

autism spectrum disorder (ASD);

disorders disclosed in International Application No. PCT/US2014/069401, the contents of which are hereby incorporated by reference in their entirety, comprising administering to a patient in need thereof a therapeutically effective amount of any of Crystalline Form A through F according to any of formulae 1.1-1.239, e.g., Crystalline Form A, e.g., any of formulae 1.1-1.77, e.g., Crystalline Form B, e.g., any of formulae 1.78-1.162, e.g., any of formulae 2.1-2.30.

Disorders contemplated for treatment employing the Crystalline Forms of the invention as described herein include disorders in the Quick Reference to the Diagnostic Criteria From DSM-IV (Diagnostic and Statistical Manual of Mental Disorders, Fourth Edition), The American Psychiatric Association, Washington, D.C., 1994. These target disorders, include, but are not limited to, Attention-Deficit/Hyperactivity Disorder, Predominately Inattentive Type; Attention-Deficit/Hyperactivity Disorder, Predominately Hyperactivity-Impulsive Type; Attention-Deficit/Hyperactivity Disorder, Combined Type; Attention-Deficit/Hyperactivity Disorder not otherwise specified (NOS); Conduct Disorder; Oppositional Defiant Disorder; and Disruptive Behavior Disorder not otherwise specified (NOS).

Depressive disorders amenable for treatment and/or prevention according to the invention include, but are not limited to, Major Depressive Disorder, Recurrent; Dysthymic Disorder; Depressive Disorder not otherwise specified (NOS); and Major Depressive Disorder, Single Episode.

Addictive disorders amenable for treatment and/or prevention employing the methods and compositions of the invention include, but are not limited to, eating disorders, impulse control disorders, alcohol-related disorders, nicotine-related disorders, amphetamine-related disorders, *cannabis*-related disorders, cocaine-related disorders, hallucinogen use disorders, inhalant-related disorders, and opioid-related disorders.

Preferably, the Crystalline Form of the invention is Crystalline Form A.

As used herein, "therapeutically effective amount" refers to an amount effective, when administered to a human or non-human patient, to provide a therapeutic benefit such as amelioration of symptoms. The specific dose of substance administered to obtain a therapeutic benefit will, of course, be determined by the particular circumstances surrounding the case, including, for example, the specific substance administered, the route of administration, the condition being treated, and the individual being treated.

A dose or method of administration of the dose of the present disclosure is not particularly limited. Dosages employed in practicing the present disclosure will of course vary depending, e.g. on the mode of administration and the therapy desired. In general, satisfactory results, are indicated to be obtained on oral administration at dosages of the order from about 0.01 to 2.0 mg/kg. An indicated daily dosage for oral administration may be in the range of from about 0.75 mg to 200 mg, conveniently administered once, or in divided doses 2 to 4 times, daily or in sustained release form. Unit dosage forms for oral administration thus for example may comprise from about 0.2 mg to 75 mg or 150 mg, e.g. from about 0.2 mg or 2.0 mg or 50 mg or 75 mg or 100 mg to 200 mg or 500 mg of any of Crystalline Forms A through F or combinations thereof, preferably Crystalline Form A, e.g., any of formulae 1.1-1.77, together with a pharmaceutically acceptable diluent or carrier therefor.

The Crystalline Forms of the invention may be administered by any suitable route, including orally, parenterally, transdermally, or by inhalation, including by sustained release, although various other known delivery routes, devices and methods can likewise be employed. In some embodiments, provided is a sustained release pharmaceutical composition, e.g., an oral sustained release pharmaceutical composition, comprising any of the Crystalline Forms of the invention, e.g., Crystalline Form A, e.g., any of formulae 1.1-1.77, over a sustained delivery period of approximately 6 hours or longer, e.g., 8 hours or longer, e.g., 12 hours or longer, e.g., 18 hours or longer, e.g., 24 hours or longer. In some embodiments, provided is an immediate release pharmaceutical composition, e.g., an oral immediate release pharmaceutical composition, comprising any of the Crystalline Forms of the invention, e.g., Crystalline Form A, e.g., any of formulae 1.1-1.77.

Further dosage and formulation are provided in International Application No. PCT/US2014/069401 and International Application No. PCT/US2014/069416, the contents of each of which are hereby incorporated by reference in their entirety.

(1R,5S)-1-(naphthalen-2-yl)-3-azabicyclo[3.1.0]hexane in hydrochloric acid addition salt form may be prepared as described in U.S. Patent Publication No. 2007/0082940 or International Publication No. WO 2013/019271, both of which are incorporated herein by reference in their entirety.

While both U.S. Patent Publication No. 2007/0082940 and International Publication No. WO 2013/019271 describe synthesis of (1R,5S)-1-(naphthalen-2-yl)-3-azabicyclo[3.1.0]hexane hydrochloride, neither discuss any particular crystal form of (1R,5S)-1-(naphthalen-2-yl)-3-azabicyclo[3.1.0]hexane hydrochloride.

The following section illustrates methods of making and characterizing Crystalline Forms A through F of the invention. Both thermodynamic and kinetic crystallization techniques are employed. These techniques are described in more detail below.

Antisolvent Precipitation: Solutions are prepared in various solvents and filtered through a 0.2-μm nylon filter into a vial. Antisolvent is then added until precipitation is observed. The resulting solids are isolated by vacuum filtration and analyzed.

Crash Cool (CC): Solutions are prepared in various solvents at an elevated temperature and filtered warm through a 0.2-μm nylon filter into a pre-cooled vial. The vial is placed in a (dry ice+isopropanol) cooling bath. Samples are placed into a freezer if no solids are observed to immediately precipitate. The resulting solids are isolated by vacuum filtration and analyzed.

Fast Evaporation (FE): Solutions are prepared in various solvents and sonicated between aliquot additions to assist in dissolution. Once a mixture reaches complete dissolution, as judged by visual observation, the solution is filtered through a 0.2-μm nylon filter. The filtered solution is allowed to evaporate at ambient in an uncapped vial. Solutions are evaporated to dryness unless designated as partial evaporations. The solids that formed are isolated and analyzed.

Freeze-Drying (Lyophilization): Solutions are prepared in 1:1 dioxane: water or water, filtered through a 0.2-μm nylon filter, and frozen in a vial or flask immersed in a bath of dry ice and isopropanol. The vial or flask containing the frozen sample is attached to a Flexi-Dry lyophilizer and dried for a measured time period. After drying, the solids are isolated and stored in the freezer over desiccant until use.

Milling: A solid sample is placed into a stainless steel grinding jar with a grinding ball. The sample is then ground at 30 Hz on a ball mill (Retsch Mixer Mill model MM200) for a set amount of time. The solids are collected and analyzed.

Relative Humidity Stress: Solids are stored at approximately 40° C./75% RH condition for a measured time period by placing the solids into a vial inside a sealed temperature/humidity chamber at the controlled condition. Samples are analyzed after removal from the stress environment.

Rotary Evaporation: Solutions of the Compound in hydrochloric acid addition salt form ((1R,5S)-1-(naphthalen-2-yl)-3-azabicyclo[3.1.0]hexane hydrochloride) in HFIPA are prepared. Solids are obtained by rotary evaporation of the solvent under vacuum, with the sample vial immersed in a heated water bath at approximately 40° C. Solids are then dried for an additional approximate 10 minutes under vacuum at ambient temperature. After evaporation, the solids are stored in the freezer over desiccant until use.

Slow Cooling (SC): Solutions are prepared in various solvents at an elevated temperature. The solutions are filtered warm through a 0.2-μm nylon filter into a warm vial. The vial is capped and left on the hot plate, and the hot plate is turned off to allow the sample to cool slowly to ambient temperature. If no solids are present after cooling to ambient temperature, the sample is placed in a refrigerator and/or freezer for further cooling. Solids are collected by vacuum filtration and analyzed.

Slow Evaporation (SE): Solutions are prepared in various solvents and sonicated to assist in dissolution. Once a mixture reaches complete dissolution, as judged by visual observation, the solution is filtered through a 0.2-μm nylon filter. The filtered solution is allowed to evaporate at ambient conditions in a vial covered with aluminum foil perforated with pinholes. Solutions are evaporated to dryness unless designated as partial evaporations. The solids that form are isolated and analyzed.

Slurry Experiments: Suspensions are prepared by adding enough solids to a given solvent so that excess solids are present. The mixture is then agitated in a sealed vial at ambient temperature or an elevated temperature. After a given period of time, the solids are isolated by vacuum filtration and analyzed.

Vapor Diffusion (VD): Solutions are prepared in various solvents and filtered through a 0.2-μm nylon filter. The filtered solution is dispensed into a 1-dram vial, which is then placed inside a 20-mL vial containing antisolvent. The 1-dram vial is left uncapped and the 20-mL vial is capped to allow vapor diffusion to occur. The resulting solids are isolated and analyzed.

Vapor Stress (VS): A solid sample is placed into a 1-dram vial. The 1-dram vial is then placed into a 20-mL vial containing solvent. The 20-mL vial is capped and left at ambient for a measured time period. Samples are analyzed after removal from the stress environment.

XRPD Overlays: The overlays of XRPD patterns are generated using Pattern Match 2.3.6.

XRPD Indexing: The high-resolution XRPD patterns of Crystalline Forms of the invention are indexed using X'Pert High Score Plus (X'Pert High Score Plus 2.2a (2.2.1)) or proprietary software. Indexing and structure refinement are computational studies.

Instrumental Techniques: The test materials in this study are analyzed using the instrumental techniques described below.

Differential Scanning calorimetry (DSC): DSC is performed using a TA Instruments differential scanning calorimeter. Temperature calibration is performed using NIST traceable indium metal. The sample is placed into an aluminum DSC pan, covered with a lid, and the weight is accurately recorded. A weighed aluminum pan configured as the sample pan is placed on the reference side of the cell. The data acquisition parameters and pan configuration are displayed in the image of each thermogram. The method code on the thermogram is an abbreviation for the start and end temperature as well as the heating rate; e.g., −30-250-10 means "from −30° C. to 250° C., at 10° C./min". The following table summarizes the abbreviations used in each image for pan configurations:

| Abbreviation | Meaning |
| --- | --- |
| TOC | Tzero crimped pan |
| HS | Lid hermetically sealed |
| HSLP | Lid hermetically sealed and perforated with a laser pinhole |
| C | Lid crimped |
| NC | Lid not crimped |

Thermogravimetric Analysis (TGA): TG analyses are performed using a TA Instruments thermogravimetric analyzer. Temperature calibration is performed using nickel and Alumel™. Each sample is placed in an aluminum pan. The sample is hermetically sealed, the lid pierced, then inserted into the TG furnace. The furnace is heated under nitrogen. The data acquisition parameters are displayed in the image of each thermogram. The method code on the thermogram is an abbreviation for the start and end temperature as well as the heating rate; e.g., 25-350-10 means "from 25° C. to 350° C., at 10° C./min".

X-ray Powder Diffraction (XRPD): Inel XRG-300. X-ray powder diffraction analyses are performed on an Inel XRG-3000 diffractometer, equipped with a curved position-sensitive detector with a 2θ range of 120°. Real time data is collected using Cu Kα radiation at a resolution of 0.03 °2θ. The tube voltage and amperage are set to 40 kV and 30 mA, respectively. Patterns are displayed from 2.5 to 40 °2θ to facilitate direct pattern comparisons. Samples are prepared for analysis by packing them into thin-walled glass capillaries. Each capillary is mounted onto a goniometer head that is motorized to permit spinning of the capillary during data acquisition. Instrument calibration is performed daily using a silicon reference standard. The data acquisition and processing parameters are displayed on each pattern found in the data section.

X-ray Powder Diffraction (XRPD): Bruker D-8 Discover Diffractometer. XRPD patterns are collected with a Bruker D-8 Discover diffractometer and Bruker's General Area Diffraction Detection System (GADDS, v. 4.1.20). An incident beam of Cu Kα radiation is produced using a fine-focus tube (40 kV, 40 mA), a Gobel mirror, and a 0.5 mm double-pinhole collimator. The sample is packed between 3-micron thick films to form a portable disc-shaped specimen. The prepared specimen is loaded in a holder secured to a translation stage and analyzed in transmission geometry. The incident beam is scanned and rastered to optimize orientation statistics. A beam-stop is used to minimize air scatter from the incident beam at low angles. Diffraction patterns are collected using a Hi-Star area detector located 15 cm from the sample and processed using GADDS. Prior to the analysis a silicon standard is analyzed to verify the Si 111 peak position. The data acquisition and processing parameters are displayed on each pattern found in the data section.

X-ray Powder Diffraction (XRPD): PANalytical X'Pert Pro Diffractometer.

XRPD patterns are collected using a PANalytical X'Pert Pro diffractometer. The specimen is analyzed using Cu radiation produced using an Optix long fine-focus source. An elliptically graded multilayer mirror is used to focus the Cu Kα X-rays of the source through the specimen and onto the detector. The specimen is sandwiched between 3-micron thick films, analyzed in transmission geometry, and rotated parallel to the diffraction vector to optimize orientation statistics. A beam-stop, short antiscatter extension, antiscatter knife edge, and helium purge are used to minimize the background generated by air scattering. Soller slits are used for the incident and diffracted beams to minimize axial divergence. Diffraction patterns are collected using a scanning position-sensitive detector (X'Celerator) located 240 mm from the specimen. The data-acquisition parameters of each diffraction pattern are displayed above the image of each pattern in the data section. Prior to the analysis, a silicon specimen (NIST standard reference material 640d) is analyzed to verify the position of the silicon 111 peak.

For indexing, agreement between the allowed peak positions, marked with bars, and the observed peaks indicates a consistent unit cell determination. Successful indexing of the pattern indicates that the sample is composed primarily of a single crystalline phase. Space groups consistent with the assigned extinction symbol, unit cell parameters, and derived quantities are tabulated below the figure. To confirm the tentative indexing solution, the molecular packing motifs within the crystallographic unit cells must be determined. No attempts at molecular packing are performed.

ABBREVIATIONS acetonitrile (ACN)
birefringence (B)
brine (saturated aqueous solution of sodium chloride)
density (d)
dichloromethane (DCM)
equivalents (eq)
ethanol (EtOH)
ethyl acetate (EtOAc)
extinction (E)
formula weight (FW)
gram (g)
hour or hours (h, hrs)
hexafluoroisopropanol (HFIPA)
high performance (pressure) liquid chromatography (HPLC)
isopropanol (IPA)
isopropyl acetate (IPAc)
isopropyl ether (IPE)
kilogram (kg)
liters (L)
methanol (MeOH)
methyl ethyl ketone (MEK)
minute(s) (min)
milliliters (mL)
molarity of a solution (mol/L) (M)
molecular weight (MW)
moles (mol)
room temperature (RT)
saturated (sat)
sodium hexamethyldisilylazane (NaHMDS)
starting material (SM)
tetrahydrofuran (THF)
2,2,2,-trifluoroethanol (TFE)
versus (vs)
weight (wt)

Example 1—Preparation of Crystalline Form A

| Compound | MW (g/mol) | d (g/mL) | Equivalents | Amt/mol |
|---|---|---|---|---|
| Reaction | | | | |
| 2-naphthylacetonitrile | 167.21 | NA | 1.0 mol eq (SM) | 1500 g/8.97 mol |
| (S)-(+)-epichlorohydrin | 92.52 | 3.12 | 1.30 mol eq | 1081 g/11.67 mol |
| tetrahydrofuran | 72.11 | 0.889 | 6.0 ml/g SM | 9.0 L |
| 2M sodium bis(trimethyl-silyl) amide in THF | 2.0M | 0.916 | 2 mol eq | 9.0 L/18.6 mol |
| 2M sodium bis(trimethyl-silyl) amide in THF | 2.0M | 0.916 | 0.067 mol eq | 0.30 L/0.60 mol |
| borane-dimethylsulfide | 10.0M | 0.80 | 2.5 mol eq | 2.25 L |
| borane-dimethylsulfide | 10.0M | 0.80 | 0.39 mol eq | 0.35 L |
| Isolation | | | | |
| 2M HCl (aqueous) | 2M | NA | 11.5 mL/g SM | 17.3 L |
| isopropyl acetate | 102.13 | 0.872 | 4 mL/g SM | 6.0 L |
| water | 18.02 | 1.00 | 5 mL/g SM | 7.5 L |
| ammonia (aqueous) | NA | 0.889 | 1.5 mL/g SM | 2.25 L |
| isopropyl acetate | 102.13 | 0.872 | 5 mL/g SM | 7.5 L |
| isopropyl acetate | 102.13 | 0.872 | 5 mL/g SM | 7.5 L |
| 5% aqueous dibasic sodium phosphate | NA | NA | 4 mL/g SM | 6.0 L |
| brine saturated | NA | NA | 4 mL/g SM | 6.0 L |
| isopropyl acetate | 102.13 | 0.872 | 10 mL/g SM | 15 L |
| para-toluenesulfonic acid-monohydrate | 190.22 | NA | 0.93 mol eq | 1586 g/8.34 mol |
| isopropyl acetate | 102.13 | 0.872 | 2 mL/g SM | 3.0 L |
| isopropyl acetate | 102.13 | 0.872 | 2 mL/g SM | 3.0 L |

Charge 2-naphthylacetonitrile (1500 g, 8.97 mol, SM) to a 3-neck, 50 L round bottom flask equipped with an overhead stirrer, addition funnel, thermocouple, cooling bath, nitrogen inlet and drying tube. Charge tetrahydrofuran (6.0 L, 4 mL/g, SM) to the reaction vessel. Stir at room temperature until all of the 2-naphthylacetonitrile is dissolved. Charge (S)-(+)-epichlorohydrin (1081 g, 11.67 mol, 1.30 eq) to the reaction vessel. Cool the reaction mixture to an internal temperature of −28° C. Use dry ice/acetone bath to cool. Dry ice added to bath intermittently to keep cooling bath between −35 and −25° C. during sodium bis(trimethylsilyl)amide addition. Charge a solution of sodium bis(trimethylsilyl)amide in THF (9.0 L, 18.0 mol, 2 mol eq) to the addition funnel and slowly add to the chilled reaction mixture at a rate such that the internal temperature remains at less than −14° C. Addition requires 1 hr 40 minutes. During the addition the internal temperature is generally between −20 and −17° C. After completion of the addition, the resulting solution is stirred at between −21 and −16° C. for 2 hours 30 minutes. Monitor the reaction by HPLC. Maintain −20 to −15° C. temperature of the reaction mixture while analyzing sample by HPLC.

HPLC assay at 2 hr 30 minutes shows reaction is not complete. Add additional sodium bis(trimethylsilyl)amide in THF (0.30 L, 0.60 mol, 0.067 mole eq) over 10 minutes via addition funnel, keeping the internal temperature of the reaction mixture less than −15° C. Stir 15 minutes at which point HPLC assay shows reaction is complete. Charge borane-dimethylsulfide (2.25 L, 22.5 mol, 2.5 mole eq) complex via addition funnel at a rate such that the internal temperature of the reaction mixture remains below 0° C. Addition requires 40 minutes. After completion of the borane addition slowly heat the reaction mixture to 40° C.

Once an internal temperature of 40° C. is obtained discontinue heating. A slow steady exotherm over approximately two hours is observed which results in a maximum internal temperature of 49° C. Upon completion of the exotherm increase the internal temperature to 60° C. Stir reaction mixture overnight at 60° C. Monitor the reaction by HPLC. Maintain 60° C. temperature of the reaction mixture while analyzing sample by HPLC.

Charge additional borane-dimethylsulfide (0.35 L, 0.70 mol, 0.39 mole eq) to reaction mixture via addition funnel. Stir the reaction mixture 3 hours 30 minutes at 60° C. Cool reaction mixture to room temperature.

To a second 3-neck, 50 L round bottom flask equipped with an overhead stirrer, thermocouple, cooling bath, and nitrogen inlet charge 2M HCl in water (17.3 L, 11.5 mL/g SM, prepared from 2.9 L concentrated HCl and 14.4 L water). Cool HCl/water solution to 3° C. Slowly transfer room temperature reaction mixture containing the cyclopropyl amine to the chilled HCl solution at a rate such that the maximum internal temperature of the quench mixture is 23° C. Quench requires 2 hr 50 minutes. When the reaction quench is complete, heat the two phase mixture to 50° C. Stir for one hour at 50° C. Cool to room temperature. Add isopropylacetate (6.0 L, 4 mL/g SM). Add water (7.5 L, 5 mL/g SM). Agitate mixture for a minimum of 15 minutes. Discontinue agitation and allow layers to settle for a minimum of 30 minutes. Discard the organic (upper) layer. Add aqueous ammonia (2.25 L, 1.5 mL/g SM) to the aqueous layer. Add isopropylacetate (7.5 L, 5 mL/g). Agitate mixture for a minimum of 15 minutes. Discontinue agitation and allow layers to settle for a minimum of 30 minutes. Separate layers. Product is in the organic (upper) layer. Add isopropylacetate (7.5 L, 5 mL/g SM) to aqueous layer. Agitate mixture for a minimum of 15 minutes. Discontinue agitation and allow layers to settle for a minimum of 30 minutes. Separate layers. Product is in the organic (upper) layer. Combine the two isopropylacetate extracts. Add 5% dibasic sodium phosphate in water (6.0 L, 4 mL/g SM) to combined extracts. Agitate mixture for a minimum of 15 minutes. Discontinue agitation and allow layers to settle for a minimum of 30 minutes. Separate layers and discard aqueous (lower) layer. Add saturated brine (6.0 L, 4 mL/g SM) to combined extracts. Agitate mixture for a minimum of 15 minutes. Discontinue agitation and allow layers to settle for a minimum of 30 minutes. Separate layers and discard aqueous (lower) layer. Concentrate the final organic layer in a tared 20 L Buchi flask in vacuo. Obtain a total of 1967.6 g of a light orange waxy solid. Transfer solids to a 50 L 3-neck round bottom flask equipped with an overhead stirrer, thermocouple, heating mantel, nitrogen inlet and drying tube. Add isopropyl acetate (15 L, 10 mL/g SM). Heat the mixture to 50° C. Add p-toluene sulfonic acid monohydrate (1586 g, 8.34 mol, 0.93 mole eq) in portions over 30 minutes keeping the temperature less than 60° C. Upon completion of the addition discontinue heating and allow the mixture to cool to room temperature. Collect the solids by filtration. Wash the filtercake with isopropyl acetate (3 L, 2 mL/g SM). Wash the filtercake a second time with isopropyl acetate (3 L, 2 mL/g SM). Dry filtercake to a constant weight in the filter funnel by pulling air through the cake using vacuum. After an initial drying period the filtercake is broken up with a spatula and the cake agitated at intervals to promote drying. Obtain 2049 g of a white solid. HPLC assay: 98.2% for the main peak and a cis:trans ratio of 98.5:1.5.

| Compound | MW (g/mol) | d (g/mL) | Equivalents | Amt/mol |
|---|---|---|---|---|
| Reaction | | | | |
| naphthylcyclopropylamine-tosylate salt | 399.51 | NA | 1.0 mole eq | 2037.9 g/5.10 mol |
| isopropylacetate | 102.13 | 0.872 | 6.5 mL/g SM | 13.2 L |
| thionyl chloride | 118.97 | 1.638 | 1.2 eq | 445 mL/6.13 mol |
| 5M NaOH | 5.0M | NA | 6.0 mol eq | 6.1 L/30.5 mol |
| Isolation | | | | |
| 1M NaOH | 1.0M | NA | 1 mL/g SM | 2.1 L |
| isopropyl acetate (back extraction) | 102.13 | 0.872 | 3.75 mL/g SM | 7.6 L |
| saturated brine | NA | NA | 2 mL/g SM | 4.1 L |
| magnesium sulfate | NA | NA | NA | NA |
| isopropylacetate (wash) | 102.13 | 0.872 | 0.5 mL/g SM | 1.0 L |
| isopropylacetate (dilution) | 102.13 | 0.872 | 3.5 mL/g SM | 7.2 L |
| hydrogen chloride in isopropyl alcohol | 5.7M | NA | 1.0 eq | 0.90 L |
| isopropylacetate (wash) | 102.13 | 0.872 | 1.13 mL/g SM | 2.3 L |
| isopropylacetate (wash) | 102.13 | 0.872 | 1.13 mL/g SM | 2.3 L |
| isopropyl alcohol | 60.1 | 0.786 | 7.45 mL/g SM | 34.6 L |
| isopropyl alcohol | 60.1 | 0.786 | 1.5 mL/g SM | 6.9 L |
| isopropyl alcohol | 60.1 | 0.786 | 1.5 mL/g SM | 6.9 L |

Note: Addition of 5 M NaOH to the reaction mixture is exothermic and requires active cooling.

Charge 2039.7 g (5.10 mol, 1.0 mol eq) of the naphthyl-cyclopropylamine-tosylate salt obtained above to a 50 L 3-neck round bottom flask equipped with an overhead stirrer, thermocouple, addition funnel, nitrogen inlet, drying tube and room temperature water bath. Charge 13.2 L of isopropyl acetate (IPAc, 13.2 L, 6.5 mL/g SM) to the reaction flask and stir at room temperature to give an white slurry. Add 445 mL of thionyl chloride (6.13 mol, 1.2 mol eq) via the addition funnel keeping the temperature less than 25° C. Addition requires 1 hr 5 minutes. Stir the thick slurry at ambient temperature for a minimum of two hours. Monitor the reaction by HPLC. Maintain the reaction mixture at ambient temperature while analyzing sample by HPLC. Add 5M NaOH (6.1 L, 30.5 mol, 6.0 mol eq) via addition funnel using an ice/water bath to keep less than 30° C. Addition requires 1 hr 40 min. Monitor the reaction by HPLC. Maintain the reaction mixture at ambient temperature while analyzing sample by HPLC. Stir reaction mixture at 25° C. for 1 hr 5 min then allow layers to settle. Separate the layers. Wash the organic (upper) layer with 1M NaOH (2.1 L, 1 mL/g SM). Combine the two aqueous layers. Back extract the combined aqueous layers with isopropylacetate (7.6 L, 3.75 mL/g SM). Combine the washed organic layer and the back extract. Wash the combined organic layers with saturated brine (4.1 L, 2 mL/g SM). Dry organic layers over granular magnesium sulfate. Filter to remove solids. Wash filtercake with isopropylacetate (1 L, 0.5 mL/g SM). Concentrate combined filtrate and wash in a 20 L Buchi Rotavap flask to a total volume of 4.2 L. Transfer to a 22 L 3-neck round bottom flask equipped with overhead stirrer, addition funnel, thermocouple, cooling bath, nitrogen inlet, and drying tube. Dilute with isopropylacetate (7.2 L, total volume of solution=11.4 L, 5.6 mL/g SM). Add hydrogen chloride in isopropyl alcohol (5.7 M, 0.90 L, 5.13 mol, 1.0 mol eq) via addition funnel over 50 minutes at a rate such that the internal temperature remains below 30° C. Stir the slurry for 45 minutes at room temperature. Filter to collect solids. Wash filtercake with isopropylacetate (2.3 L, 1.13 mL/g SM). Wash filtercake a second time with isopropylacetate (2.3 L, 1.13 mL/g SM). Partially dry filtercake by pulling air through the cake with vacuum. HPLC assay of the wet cake shows 96.3 area percent purity and an EE of 89.5%.

Combine wet cakes from this experiment and from another batch in a 50 L 3-neck round bottom flask equipped with overhead stirrer, heating mantel, thermocouple, reflux condenser, nitrogen inlet, and drying tube. Add isopropyl alcohol (34.6 L, 7.45 mL/g SM). Heat the slurry to reflux. Maintain reflux for three hours. Discontinue heating and allow to cool to room temperature. Filter to collect solids. Wash filtercake with isopropyl alcohol (6.9 L, 1.5 mL/g SM). Wash filtercake a second time with isopropyl alcohol (6.9 L, 1.5 mL/g SM). Dry filtercake to a constant weight by pulling air through the cake using vacuum. Obtain 2009 g of product as a tan solid. HPLC: >99.5%. Chiral HPLC: 95.4%.

| Compound | MW (g/mol) | d (g/mL) | Equivalents | Amt/mol |
|---|---|---|---|---|
| Reaction | | | | |
| (1R,5S)-1-(naphthalen-2-yl)-3-azabicyclo[3.1.0] hydrochloride | 245.74 | NA | 1.0 | 2009 g |
| ethanol (special industrial) | 46.07 | 0.789 | 10.7 mL/g | 21.5 L |
| Isolation | | | | |
| ethanol (SI), wash | 46.07 | 0.789 | 2.14 mL/g | 4.3 L |

Note: Minimal amount of ethanol necessary to completely dissolve the starting material should be used.

Charge (1R,5S)-1-(naphthalen-2-yl)-3-azabicyclo[3.1.0] hexane hydrochloride to a 50 L 3-neck round bottom flask equipped with an overhead stirrer, thermocouple, reflux condenser, heating mantel, nitrogen inlet and drying tube. Add ethanol (20 L, mL/g SM). Heat the stirred slurry to 77° C. Add additional ethanol in 0.5 L aliquots and return mixture to reflux until all solids dissolve. Complete dissolution after the addition of 1.5 L additional ethanol, 21.5 L total. Discontinue heating and allow solution to cool to room temperature. Filter to collect solids. Wash filtercake with ethanol (4.3 L, 2.14 mL/g SM). Dry filtercake to a constant weight by pulling air through the filtercake using vacuum. Obtain 1435 g of light tan solids. Yield=74%. HPLC: 99.5%. Chiral HPLC: 99.9%.

| Compound | MW (g/mol) | d (g/mL) | Equivalents | Amt/mol |
|---|---|---|---|---|
| Reaction | | | | |
| (1R, 5S)-1-(naphthalen-2-yl)-3-azabicyclo[3.1.0] hydrochloride (SM) | 245.74 | NA | 1.0 mol eq | 1406 g/5.72 mol |
| water | 18.02 | 1.0 | 10 mL/g SM | 14.0 |
| tetrahydrofuran | 72.11 | 0.889 | 2 mL/g SM | 2.8 L |
| isopropylacetate | 102.13 | 0.872 | 2 mL/g SM | 2.8 L |
| Isolation | | | | |
| ammonia (aqueous) | 15.0M | 0.90 | 3.0 mol eq | 1.14 L/17.1 mol |
| isopropyl acetate | 102.13 | 0.872 | 10 mL/g SM | 14.0 L |
| magnesium sulfate | NA | NA | NA | NA |
| isopropyl acetate (wash) | 102.13 | 0.872 | 42 mL/g SM | 2.0 L |
| isopropyl alcohol | 60.1 | 0.786 | 10 mL/g SM | 14.0 L |
| hydrogen chloride in isopropyl alcohol | 5.7M | NA | 0.84 mol eq | 845 mL |
| hydrogen chloride in isopropyl alcohol | 5.6M | NA | 0.11 mol eq | 110 mL |
| hydrogen chloride in isopropyl alcohol | 5.6M | NA | 0.06 mol eq | 60 mL |
| isopropyl alcohol (wash one) | 60.1 | 0.786 | 2.0 mL/g SM | 2.8 L |
| isopropyl alcohol (wash two) | 60.1 | 0.786 | 2.0 mL/g SM | 2.8 L |

Charge the Compound in hydrochloric acid addition salt form ((1R,5S)-1-(naphthalen-2-yl)-3-azabicyclo[3.1.0] hexane hydrochloride) (1406 g, 5.72 mol, 1.0 mol eq) (the compound obtained from the step above and another batch) to a 22 L, 3-neck round bottom flask equipped with an overhead stirrer, heating mantel, thermocouple, and nitrogen inlet. Add water (14 L, 10 mL/g SM). Heat the slurry to an internal temperature of 34° C. to dissolve all solids. Transfer to a large separatory funnel. Add tetrahydrofuran (2.8 L, 2 mL/g SM). Add isopropylacetate (2.8 L, 2 mL/g SM). Discontinue stirring and allow layers to separate. Discard the organic (upper) layer. Product is in the lower (aqueous) layer. To the aqueous (lower) layer add aqueous ammonia (1.14 L, 17.1 mol, 3.0 mol eq). Add isopropylacetate (14.0 L, 10 mL/g SM). Agitate mixture for a minimum of 15 minutes. Discontinue agitation and allow layers to settle for a minimum of 30 minutes. Separate the layers. Product is in the organic (upper) layer. Add granular magnesium sulfate to the organic layer. Filter to remove solids. Wash the filtercake with isopropylacetate (1 L). Wash the filtercake a second time with isopropylacetate (1 L). Concentrate combined filtrate and washes in a 20 L Buchi rotavap flask to give an off-white solid. Charge solid to a 22 L round bottom flask equipped with overhead stirrer, thermocouple, addition funnel, nitrogen inlet and drying tube. Add isopropyl alcohol (14 L, 10 mL/g SM). Stir at room temperature to dissolve all solids. Charge 5.7 N HCl in IPA (175 mL, 1.0 mol, 0.17 mol eq) via addition funnel over 10 minutes to form white solids. Stir the thin slurry at room temperature for 30 minutes. Charge 5.7 N HCl in IPA (670 mL, 3.82 mol, 0.67 mol eq) followed by 5.6 N HCl in IPA (110 mL, 0.62 mol, 0.11 mol eq) via addition funnel over 55 minutes. Stir the slurry for 35 minutes then assay the mother liquors for loss. Add 5.6 N HCl in IPA (60 mL, 0.34 mol, 0.06 mol eq) over 10 minutes via addition funnel. Stir the slurry for 30 minutes then assay the mother liquors for loss. Filter to collect solids. Wash filtercake with isopropyl alcohol (2.8 L, 2 mL/g SM). Wash filtercake a second time with isopropyl alcohol (2.8 L, 2 mL/g SM). Dry filtercake to a constant weight by pulling air through the filtercake using vacuum. Obtain 1277 g of product as an off-white solid. HPLC: 99.9%.

The resulting compound exhibits a crystalline XRPD pattern (FIG. 1), and is designated as Crystalline Form A. The XRPD pattern is collected with a PANalytical X'Pert PRO MPD diffractometer using an incident beam of Cu radiation produced using an Optix long, fine-focus source. An elliptically graded multilayer mirror is used to focus Cu Kα X-rays through the specimen and onto the detector. Prior to the analysis, a silicon specimen (NIST SRM 640d) is analyzed to verify the Si 111 peak position. A specimen of the sample is sandwiched between 3-μm-thick films and analyzed in transmission geometry. A beam-stop, short anti-scatter extension, and an anti-scatter knife edge are used to minimize the background generated by air. Soller slits for the incident and diffracted beams are used to minimize broadening from axial divergence. The diffraction pattern is collected using a scanning position-sensitive detector (X'Celerator) located 240 mm from the specimen and Data Collector software v. 2.2b. The experimental XRPD pattern is collected according to cGMP specifications. The XRPD pattern collected is shown in FIG. 1 (Panalytical X-Pert Pro MPD PW3040 Pro, X-ray Tube: Cu (1.54059 Å), Voltage: 45 kV, Amperage: 40 mA, Scan Range: 1.01-40.00 °2θ, Step Size: 0.017 °2θ, Collection Time: 1939 s, Scan Speed: 1.2°/min., Slit: DS: 1/2°, SS: null, Revolution Time: 1.0 s, Mode: Transmission).

Figure 2:
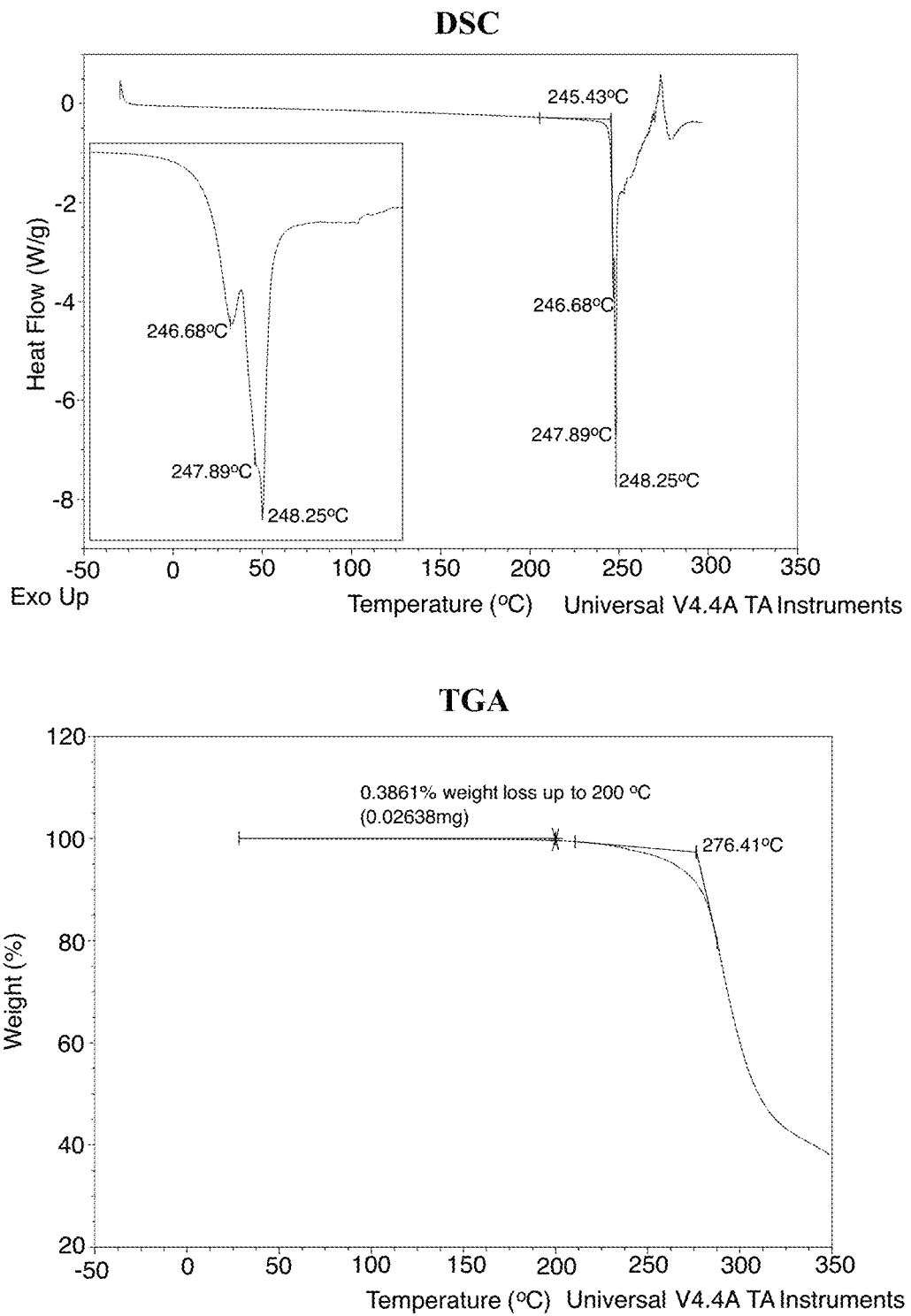
FIG. 2 depicts DSC and TGA thermograms of Crystalline Form A.

Thermal analysis results are shown in FIG. 2 (DSC, Size: 1.7800 mg, Method: (−30)-300-10, TOC; TGA, Size: 6.8320 mg, Method: 00-350-10). By TGA, Crystalline Form A exhibits approximately 0.4% weight loss up to 200° C. The dramatic weight change in the TGA at approximately 276° C. is consistent with decomposition. The DSC thermogram (FIG. 2) displays multiple endotherms between approximately 245 and 248° C. concurrent with the dramatic weight change by TGA, suggesting overlapping events are occurring during heating.

Characterization data for Crystalline Form 1 are summarized in Table 1 below:

TABLE 1

| Analysis | Result |
| --- | --- |
| DSC[a] | 247° C. (endo, peak; 245° C. onset); 248° C. (endo, shoulder); 248° C. (endo, peak) |
| TGA[a] | 0.4% weight loss up to 200° C. 276° C. (onset, decomposition) |

[a]Temperatures are rounded to the nearest ° C.;
weight loss values are rounded to one decimal place.

Figure 3:
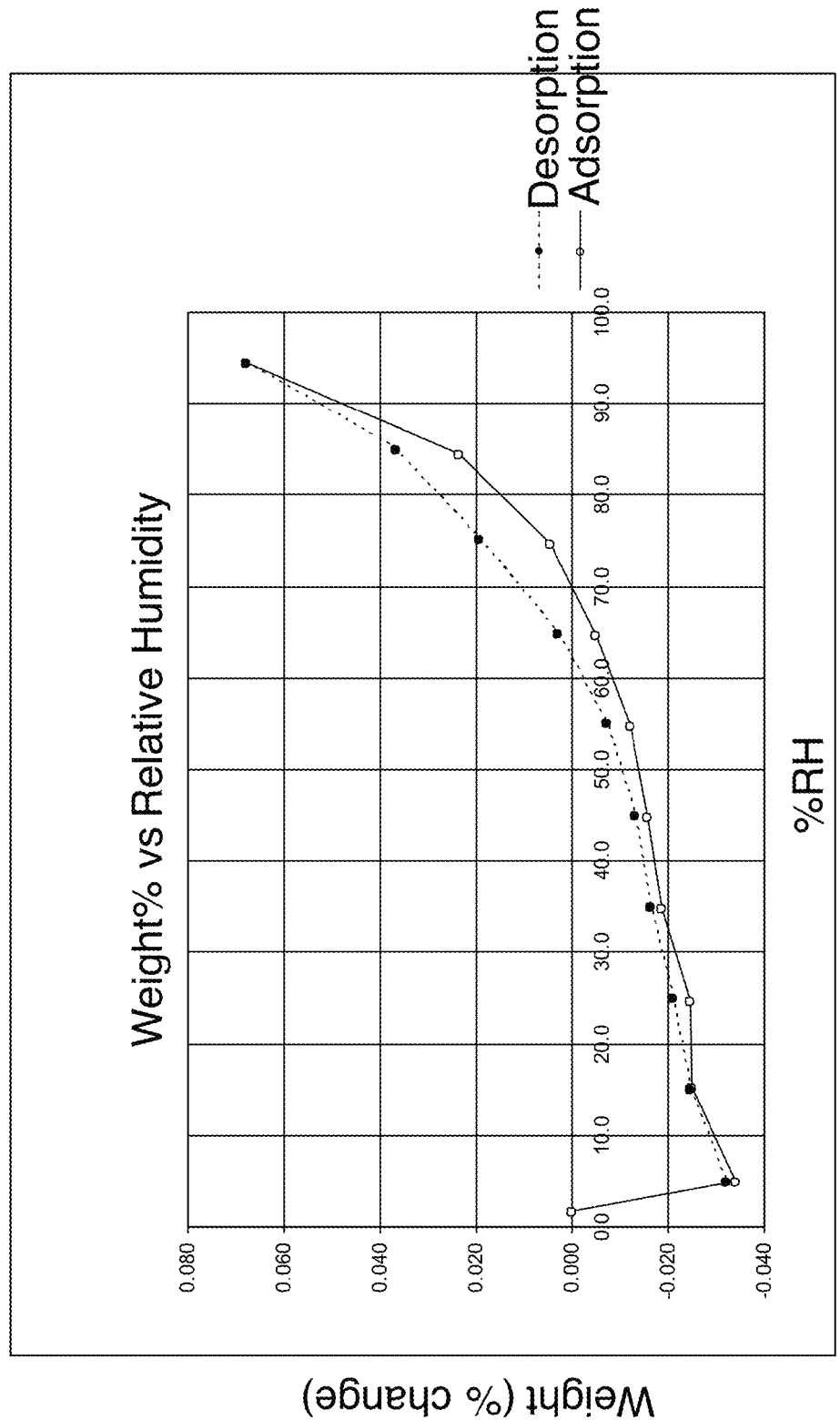
FIG. 3 depicts dynamic vapor sorption/desorption isotherm of Crystalline Form A.

Based on the dynamic vapor sorption/desorption data collected (FIG. 3), Crystalline Form A obtained is a non-hygroscopic material. Upon initial equilibration at 5% RH, Crystalline Form A shows a weight loss of 0.03%; a weight gain of 0.10% is observed from 5% to 95% RH. During the desorption step from 95% to 5% RH, Crystalline Form A exhibits approximately 0.10% weight loss.

Figure 50:
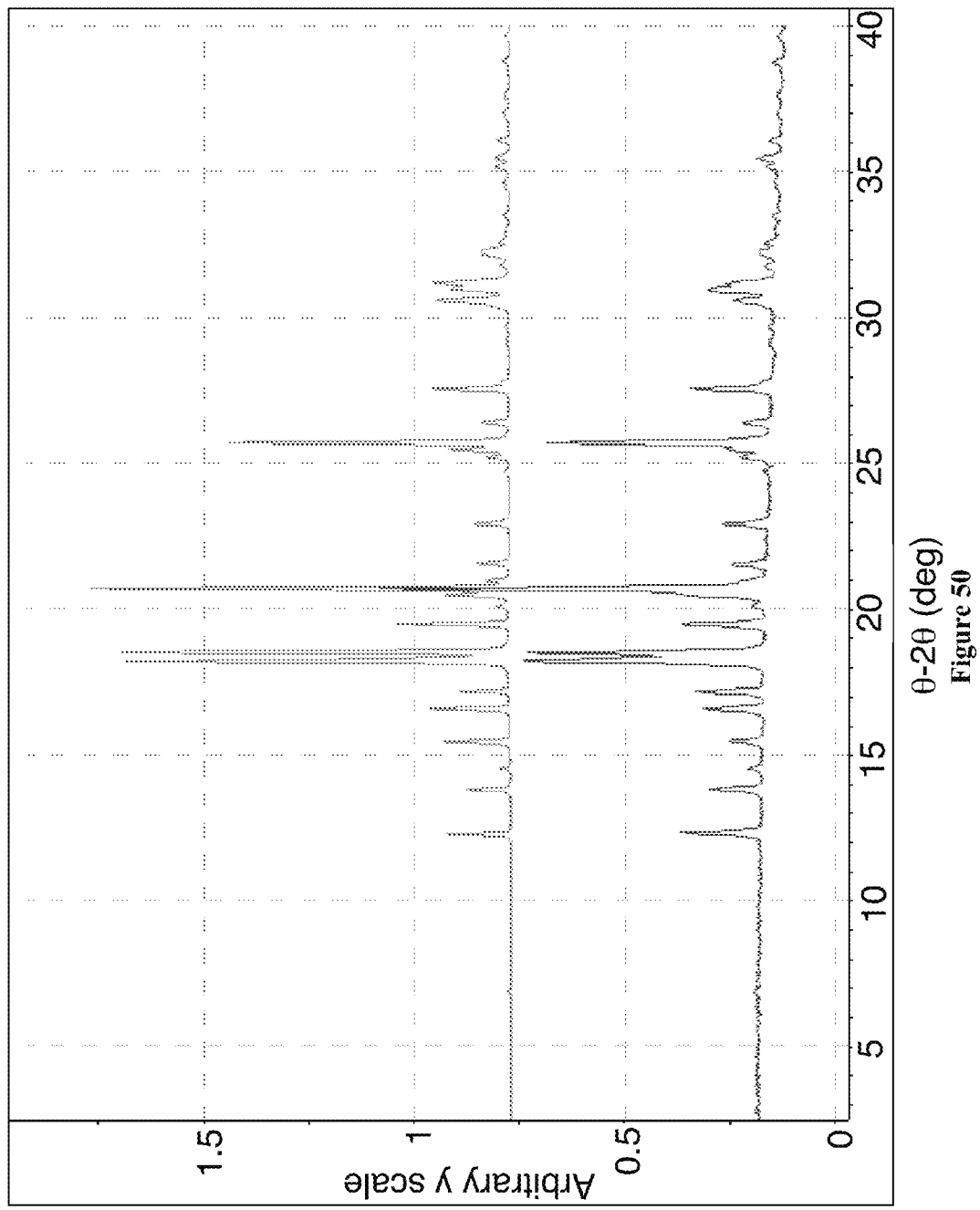
FIG. 50 depicts XRPD patterns of Crystalline Form A before and after DVS analysis (top: before, bottom: after).

Post-moisture balance material is similar to starting material by XRPD (FIG. 50).

Data acquisition parameters for dynamic vapor sorption/desorption isotherm:

| Step Time min | Elap Time min | Weight mg | Weight % chg | Samp Temp deg C. | Samp RH % |
| --- | --- | --- | --- | --- | --- |
| n/a | 0.1 | 11.532 | 0.000 | 25.20 | 1.70 |
| 13.1 | 13.2 | 11.528 | −0.034 | 25.18 | 5.06 |
| 11.5 | 24.7 | 11.529 | −0.025 | 25.19 | 15.24 |
| 13.0 | 37.7 | 11.529 | −0.024 | 25.22 | 24.81 |
| 13.0 | 50.7 | 11.530 | −0.019 | 25.21 | 34.82 |
| 17.0 | 67.7 | 11.530 | −0.016 | 25.21 | 44.81 |
| 25.0 | 92.7 | 11.531 | −0.012 | 25.20 | 54.86 |
| 28.3 | 121.0 | 11.532 | −0.005 | 25.20 | 64.82 |
| 12.8 | 133.8 | 11.533 | 0.005 | 25.20 | 74.66 |
| 13.0 | 146.8 | 11.535 | 0.024 | 25.19 | 84.55 |
| 13.3 | 160.0 | 11.540 | 0.068 | 25.19 | 94.54 |
| 10.8 | 170.8 | 11.536 | 0.037 | 25.18 | 85.08 |
| 11.0 | 181.8 | 11.534 | 0.019 | 25.18 | 75.28 |
| 13.0 | 194.8 | 11.532 | 0.003 | 25.18 | 64.96 |
| 13.0 | 207.8 | 11.531 | −0.007 | 25.18 | 55.08 |
| 13.0 | 220.8 | 11.531 | −0.013 | 25.18 | 45.09 |
| 13.0 | 233.8 | 11.530 | −0.016 | 25.18 | 35.13 |
| 13.0 | 246.8 | 11.530 | −0.021 | 25.17 | 25.12 |
| 13.0 | 267.8 | 11.529 | −0.025 | 25.17 | 15.20 |
| 21.0 | 267.8 | 11.529 | −0.025 | 25.17 | 15.20 |
| 10.0 | 277.8 | 11.528 | −0.032 | 25.17 | 4.95 |

| Notes | Range 5% to 95% 25° C. at 10% increments |
| --- | --- |
| Drying | OFF |
| Max Equil Time | 180 min |
| Equil Crit | 0.0100 wt % in 5.00 min |
| T-RH Steps | 25, 5; 25, 15; 25, 25; 25, 35; 25, 45; 25, 55; 25, 65; 25, 75; 25, 85; 25, 95; 25, 85; 25, 75; 25, 65; 25, 55; 25, 45; 25, 35; 25, 25; 25, 15; 25, 5 |
| Data Logging Interval | 2.00 min or 0.0100 wt % |

Example 2—Preparation of Crystals of Form A

Solution of the Compound in hydrochloric acid addition salt form ((1R,5S)-1-(naphthalen-2-yl)-3-azabicyclo[3.1.0] hexane hydrochloride) is prepared using 98.5 mg of the Compound from Example 1 in 2 mL methanol and filtered through a 0.2-μm nylon filter. A 0.5 mL aliquot of the filtered solution is dispensed into a 1-dram open vial, which is then placed inside a 20-mL vial containing 3 mL antisolvent ethyl acetate. The 1-dram vial is left uncapped and the 20-mL vial is capped to allow vapor diffusion to occur. Single crystals are grown in the 1-dram vial after approximately 7 days.

Data Collection: A colorless plate of $C_{15}H_{16}ClN$ [Cl, $C_{15}H_{16}N$] having approximate dimensions of 0.38×0.30× 0.18 mm, is mounted on a fiber in random orientation. Preliminary examination and data collection are performed with Mo Kα radiation (λ=0.71073 Å) on a Nonius Kappa CCD diffractometer equipped with a graphite crystal, incident beam monochromator. Refinements are performed using SHELX97 (Sheldrick, G. M. *Acta Cryst.*, 2008, A64, 112). Cell constants and an orientation matrix for data collection are obtained from least-squares refinement using the setting angles of 5812 reflections in the range 1°<θ<27°. The refined mosaicity from DENZO/SCALEPACK is 0.38° indicating good crystal quality (Otwinowski, Z.; Minor, W. *Methods Enzymol.* 1997, 276, 307). The space group is determined by the program XPREP (Bruker, XPREP in SHELXTL v. 6.12., Bruker AXS Inc., Madison, Wis., USA, 2002). From the systematic presence of the following conditions: h00 h=2n; 0k0 k=2n; 00ll=2n, and from subsequent least-squares refinement, the space group is determined to be $P2_12_12_1$ (no. 19). The data are collected to a maximum 2θ value of 55.71°, at a temperature of 150±1 K.

Data Reduction: Frames are integrated with DENZO-SMN (Otwinowski, Z.; Minor, W. *Methods Enzymol.* 1997, 276, 307). A total of 5812 reflections are collected, of which 2930 are unique. Lorentz and polarization corrections are applied to the data. The linear absorption coefficient is 0.273 $mm^{-1}$ for Mo Kα radiation. An empirical absorption correction using SCALEPACK (Otwinowski, Z.; Minor, W. *Methods Enzymol.* 1997, 276, 307) is applied. Transmission coefficients range from 0.953 to 0.953. Intensities of equivalent reflections are averaged. The agreement factor for the averaging is 2.9% based on intensity.

Structure Solution and Refinement: The structure is solved by direct methods using SIR2004 (Burla, M. C., Caliandro, R., Camalli, M., Carrozzini, B., Cascarano, G. L., De Caro, L., Giacovazzo, C., Polidori, G., and Spagna, R., *J. Appl. Cryst.* 2005, 38, 381). The remaining atoms are located in succeeding difference Fourier syntheses. Hydrogen atoms are included in the refinement but restrained to ride on the atom to which they are bonded. The structure is refined in full-matrix least-squares by minimizing the function:

$$\Sigma w(|F_o|^2 - |F_c|^2)^2$$

The weight w is defined as $1/[\sigma^2(F_o^2)+(0.0384P)^2+(0.2436P)]$, where $P=(F_o^2+2F_c^2)/3$. Scattering factors are taken from the "International Tables for Crystallography" (International Tables for Crystallography, Vol. C, Kluwer Academic Publishers: Dordrecht, The Netherlands, 1992, Tables 4.2.6.8 and 6.1.1.4). Of the 2930 reflections used in the refinements, only the reflections with $F_o^2 > 2\sigma(F_o^2)$ are used in calculating R. A total of 2678 reflections are used in the calculation. The final cycle of refinement includes 162 variable parameters and converges (largest parameter shift is <0.01 times its estimated standard deviation) with unweighted and weighted agreement factors of:

$$R = \Sigma|F_o - F_c|/\Sigma F_o = 0.033$$

$$R_w = \sqrt{(\Sigma w(F_o^2 - F_c^2)^2/\Sigma w(F_o^2)^2)} = 0.080$$

The standard deviation of an observation of unit weight (goodness of fit) is 1.066. The highest peak in the final difference Fourier has a height of 0.19 e/Å$^3$. The minimum negative peak has a height of −0.24 e/Å$^3$. The Flack factor for the determination of the absolute structure (Flack, H. D. *Acta Cryst.* 1983, A39, 876) refines to −0.02(6).

Calculated X-Ray Powder Diffraction (XRPD) Pattern: A calculated XRPD pattern is generated for Cu radiation using PowderCell 2.3 (PowderCell for Windows Version 2.3 Kraus, W.; Nolze, G. Federal Institute for Materials Research and Testing, Berlin Germany, EU, 1999) and the atomic coordinates, space group, and unit cell parameters from the single crystal data. Because the single crystal data are collected at low temperatures (150 K), peak shifts may be evident between the pattern calculated from low temperature data and the room temperature experimental powder diffraction pattern, particularly at high diffraction angles.

ORTEP and Packing Diagrams: The ORTEP diagram is prepared using the ORTEP III (Johnson, C. K. ORTEPIII, Report ORNL-6895, Oak Ridge National Laboratory, TN, U.S.A. 1996. OPTEP-3 for Windows V1.05, Farrugia, L. J., *J. Appl. Cryst.* 1997, 30, 565) program within the PLATON (Spek, A. L. *PLATON. Molecular Graphics Program.* Utrecht University, Utrecht, The Netherlands, 2008. Spek, A. L, *J. Appl. Cryst.* 2003, 36, 7) software package. Atoms are represented by 50% probability anisotropic thermal ellipsoids. Packing diagrams are prepared using CAMERON (Watkin, D. J.; Prout, C. K.; Pearce, L. J. CAMERON, Chemical Crystallography Laboratory, University of Oxford, Oxford, 1996) modeling software. Assessment of chiral centers are performed with the PLATON (Spek, A. L. *PLATON. Molecular Graphics Program.* Utrecht University, Utrecht, The Netherlands, 2008. *Spek, A. L, J. Appl. Cryst.* 2003, 36, 7) software package. Absolute configuration is evaluated using the specification of molecular chirality rules (Cahn, R. S.; Ingold, C; Prelog, V. *Angew. Chem. Intern. Ed. Eng.*, 1966, 5, 385; Prelog, V. G. Helmchen *Angew. Chem. Intern. Ed. Eng.*, 1982, 21, 567). Additional figures are generated with the Mercury 2.4 (Macrae, C. F. Edgington, P. R. McCabe, P. Pidcock, E. Shields, G. P. Taylor, R. Towler M. and van de Streek, J.; *J. Appl. Cryst.*, 2006, 39, 453-457) visualization package. Hydrogen bonding is represented as dashed lines.

Results: The orthorhombic cell parameters and calculated volume are: a=5.7779(2) Å, b=8.6633(2) Å, c=25.7280(8) Å, α=β=γ=90°, V=1287.83(7) Å$^3$. The formula weight of the asymmetric unit in the crystal structure is 245.75 g mol$^{-1}$ with Z=4, resulting in a calculated density of 1.267 g cm$^{-3}$. The space group is determined to be P2$_1$2$_1$2$_1$. A summary of the crystal data and crystallographic data collection parameters are provided in Table 2 below.

The R-value is 0.033 (3.3%).

Figure 18:
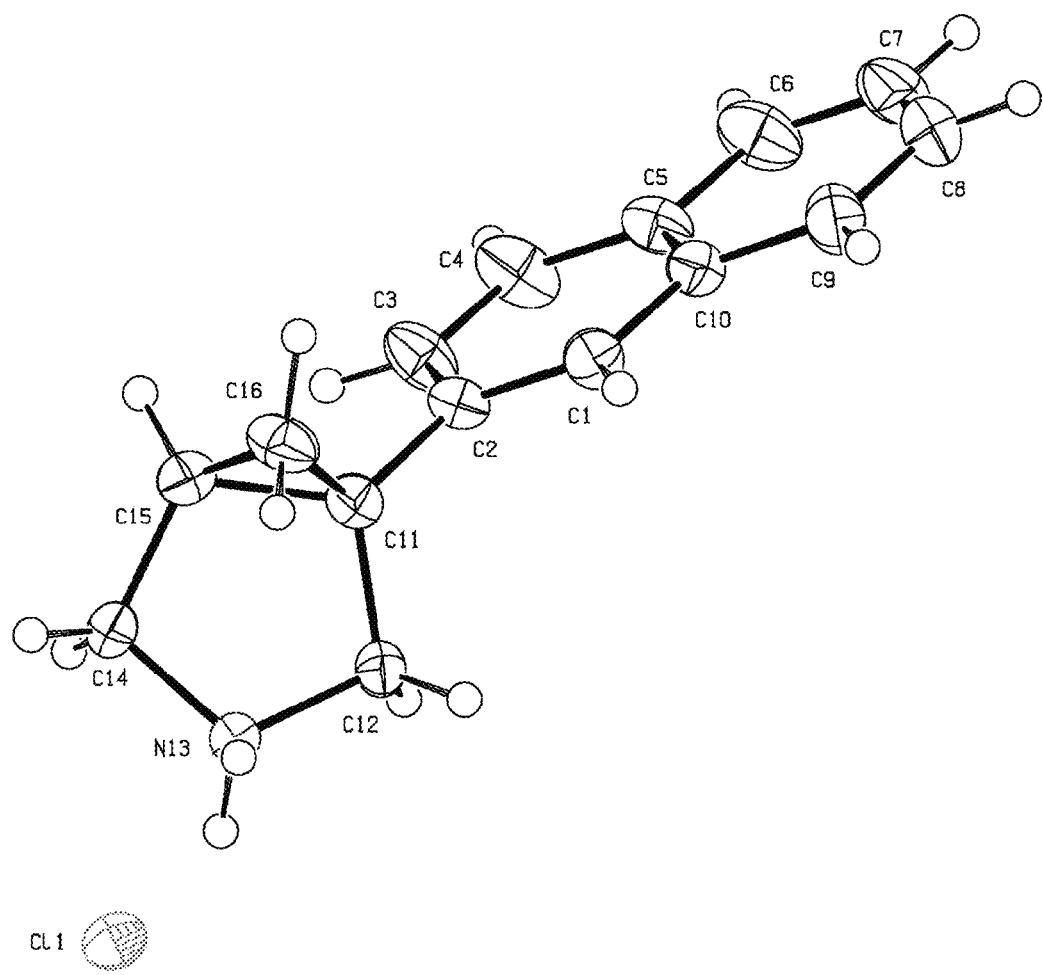
FIG. 18 depicts an ORTEP drawing of Crystalline Form A. Atoms are represented by 50% probability anisotropic thermal ellipsoids.

An ORTEP drawing of Crystalline Form A is shown in FIG. 18.

The asymmetric unit, shown in FIG. 18, contains a protonated (1R,5S)-1-(naphthalen-2-yl)-3-azabicyclo[3.1.0] hexane molecule and a chloride counter ion. The proton is located in the difference map and allowed to refine freely on the nitrogen, indicating salt formation.

Figure 19:
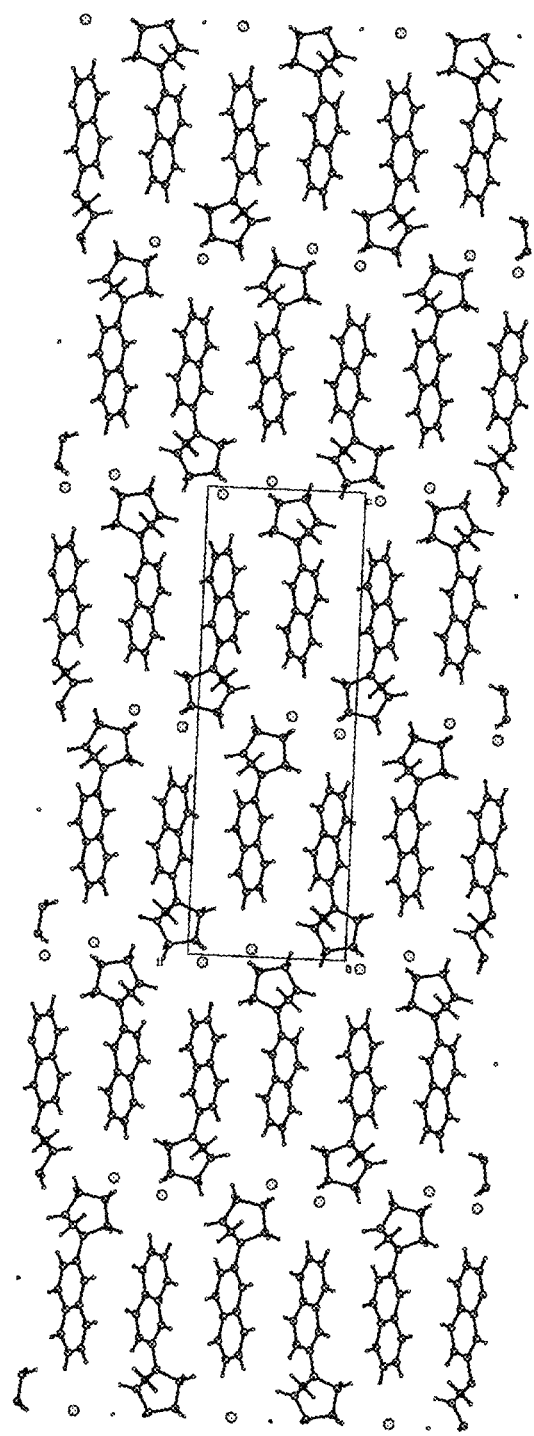
FIG. 19 depicts a packing diagram of Crystalline Form A viewed down the crystallographic a axis.
Figure 20:
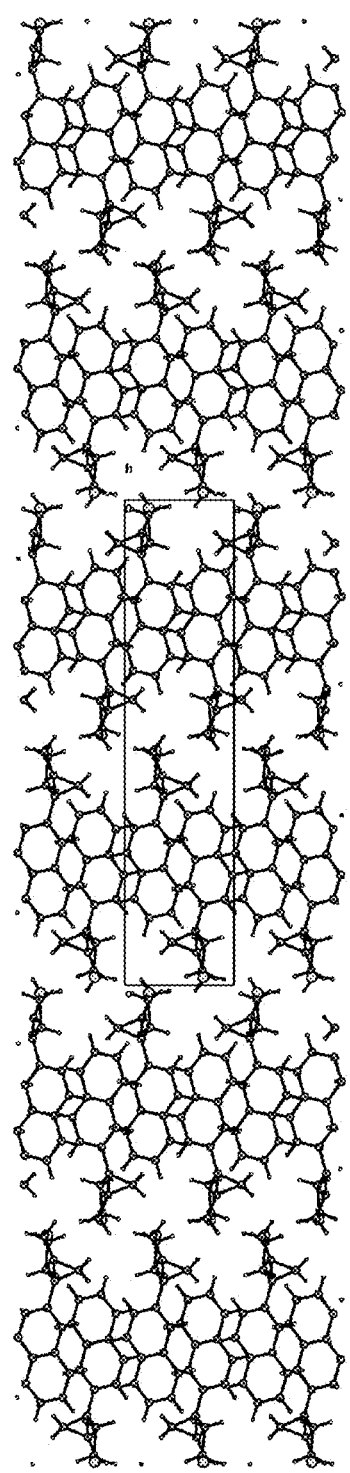
FIG. 20 depicts a packing diagram of Crystalline Form A viewed down the crystallographic b axis.
Figure 21:
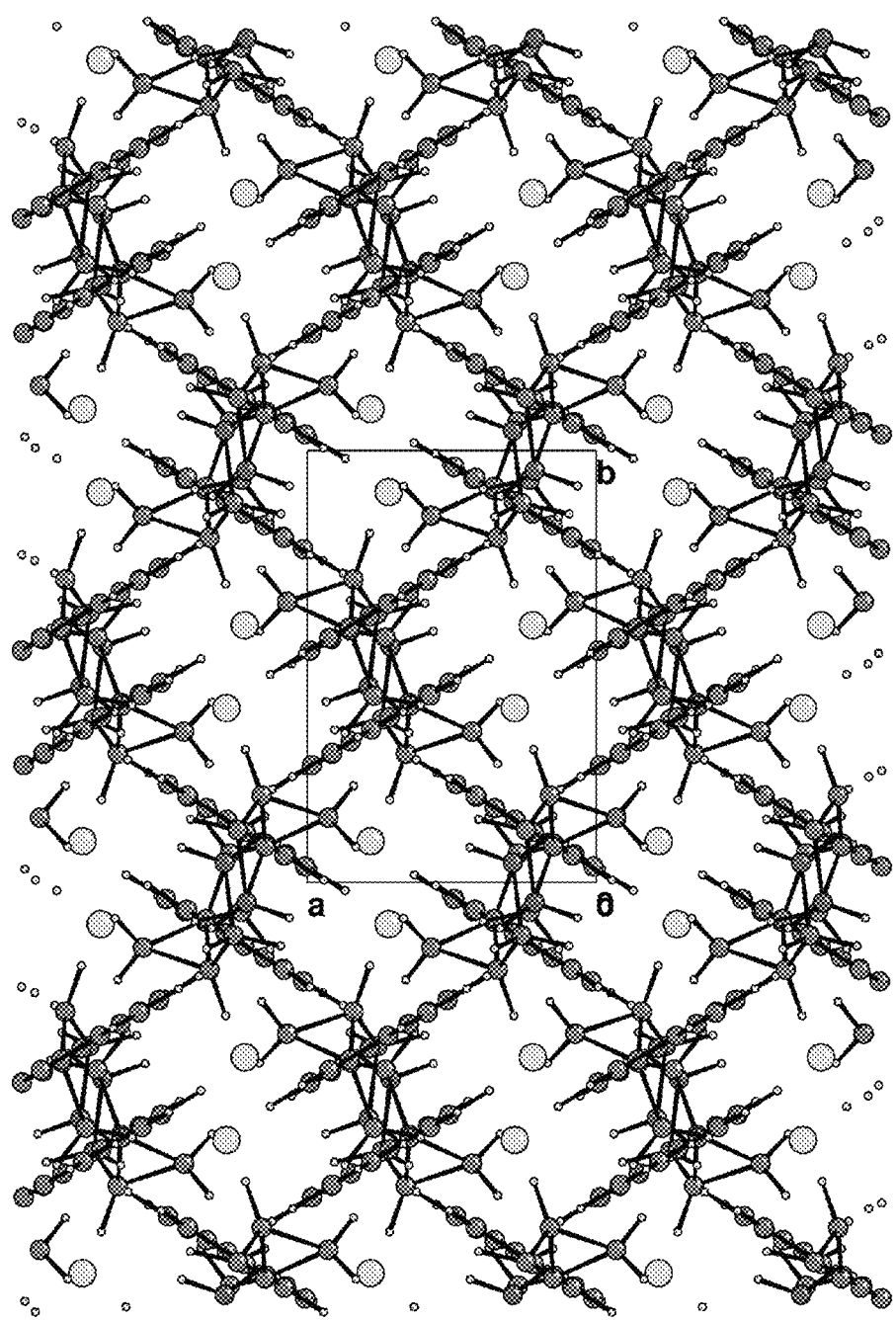
FIG. 21 depicts a packing diagram of Crystalline Form A viewed down the crystallographic c axis.
Figure 22:
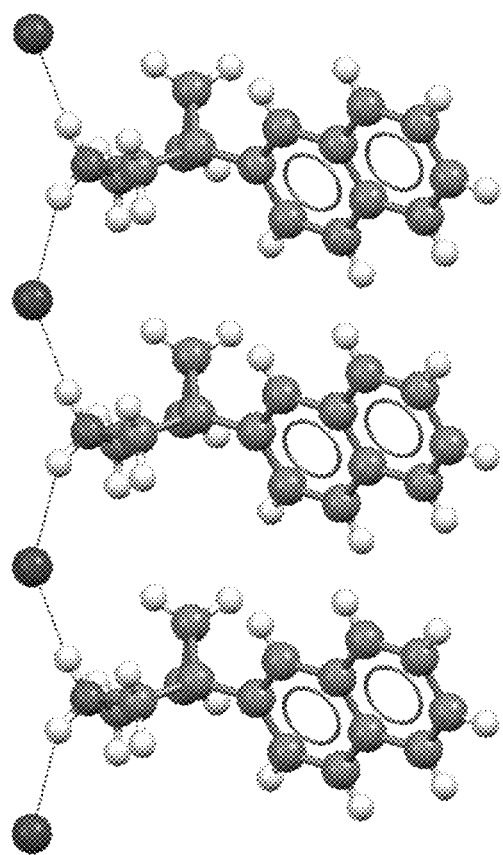
FIG. 22 depicts hydrogen bonding in Crystalline Form A.

Packing diagrams viewed along the a, b, and c crystallographic axes are shown in FIGS. 19-21, respectively. Hydrogen bonding occurs between the chlorine and nitrogen atoms, and the structure consists of infinite one-dimensional hydrogen bonded chains along the crystallographic a axis, shown in FIG. 22.

The absolute structure can be determined through an analysis of anomalous X-ray scattering by the crystal. A refined parameter x, known as the Flack parameter (Flack, H. D.; Bernardinelli, G., *Acta Cryst.*, 1999, A55, 908; Flack, H. D.; Bernardinelli, G., *J. Appl. Cryst.*, 2000, 33, 1143), encodes the relative abundance of the two components in an inversion twin. The structure contains a fraction 1−x of the model being refined, and x of its inverse. Provided that a low standard uncertainty is obtained, the Flack parameter should be close to 0 if the solved structure is correct, and close to 1 if the inverse model is correct. The measured Flack parameter for the structure of Crystalline Form A shown in FIG. 18 is −0.02 with a standard uncertainty of 0.06.

After a structure is solved the quality of the data may be assessed for its inversion-distinguishing power, which is done by an examination of the standard uncertainty of the Flack parameter. For Crystalline Form A, the standard uncertainty, (u), equals 0.06, which indicates strong inversion-distinguishing power. The compound is enantiopure and absolute structure can be assigned directly from the crystal structure.

Refinement of the Flack parameter (x) (Flack, H. D. *Acta Cryst.* 1983, A39, 876) does not result in a quantitative statement about the absolute structure assignment. However, an approach applying Bayesian statistics to Bijvoet differences can provide a series of probabilities for different hypotheses of the absolute structure (Hooft, R. W., *J. Appl. Cryst.*, 2008, 41, 96-103; Bijvoet, J. M.; Peederman, A. F.; van Bommel, A. J., *Nature* 1951, 168, 271). This analysis provides a Flack equivalent (Hooft) parameter in addition to probabilities that the absolute structure is either correct, incorrect or a racemic twin. For the current data set the Flack equivalent (Hooft) parameter is determined to be −0.01(3), the probability that the structure is correct is 1.000, the probability that the structure is incorrect is 0.000 and the probability that the material is a racemic twin is $0.4^{-59}$.

The structure contains two chiral centers located at C11 and C15 (see FIG. 18, ORTEP drawing), which are assigned as R and S configuration, respectively.

Figure 23:
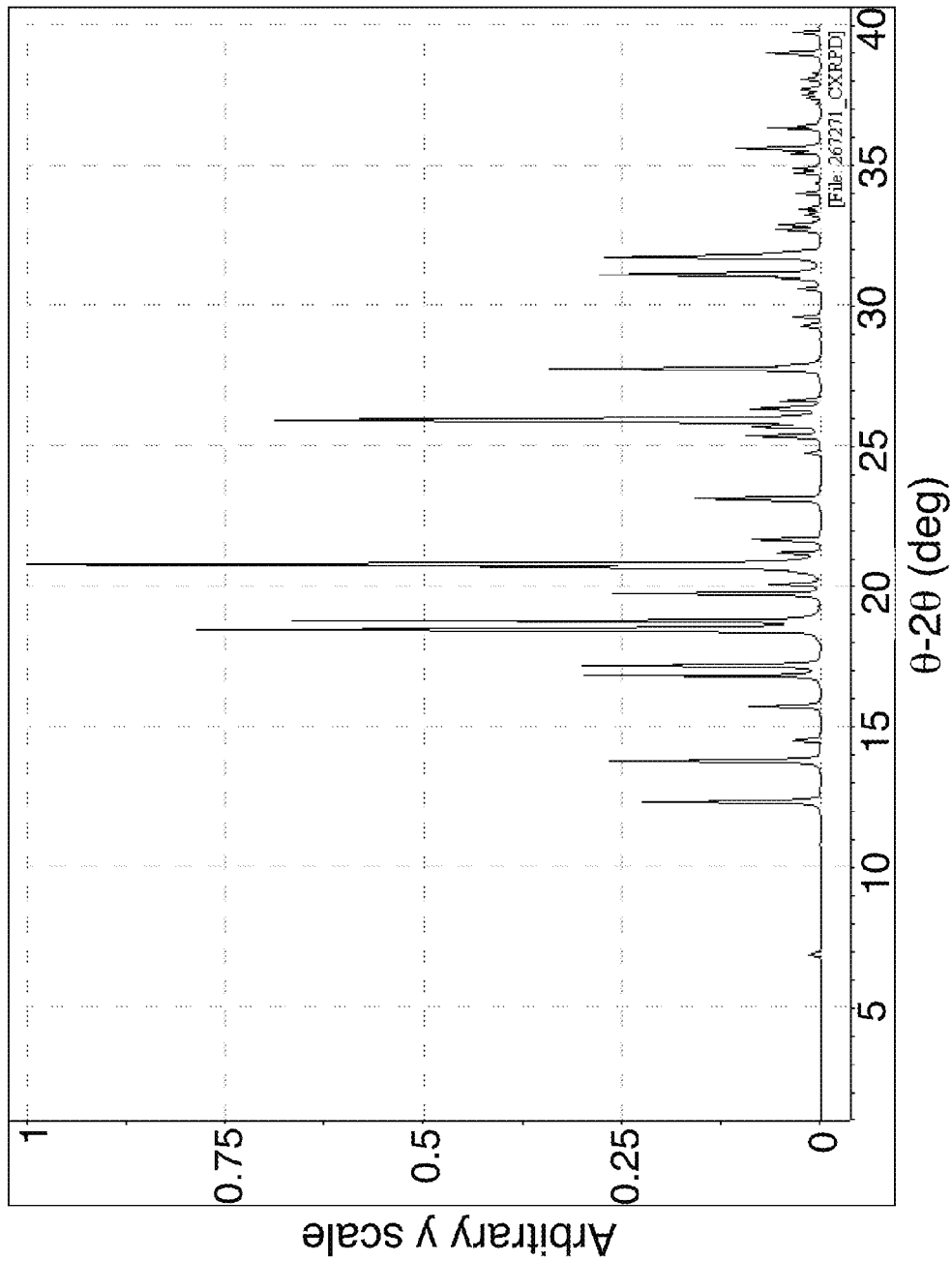
FIG. 23 depicts a calculated X-ray powder diffraction (XRPD) pattern of Crystalline Form A.

FIG. 23 shows a calculated X-ray powder diffraction pattern of Crystalline Form A, generated from the single crystal data.

The experimental X-ray powder diffraction pattern of Crystalline Form A is shown FIG. 1.

Figure 34:
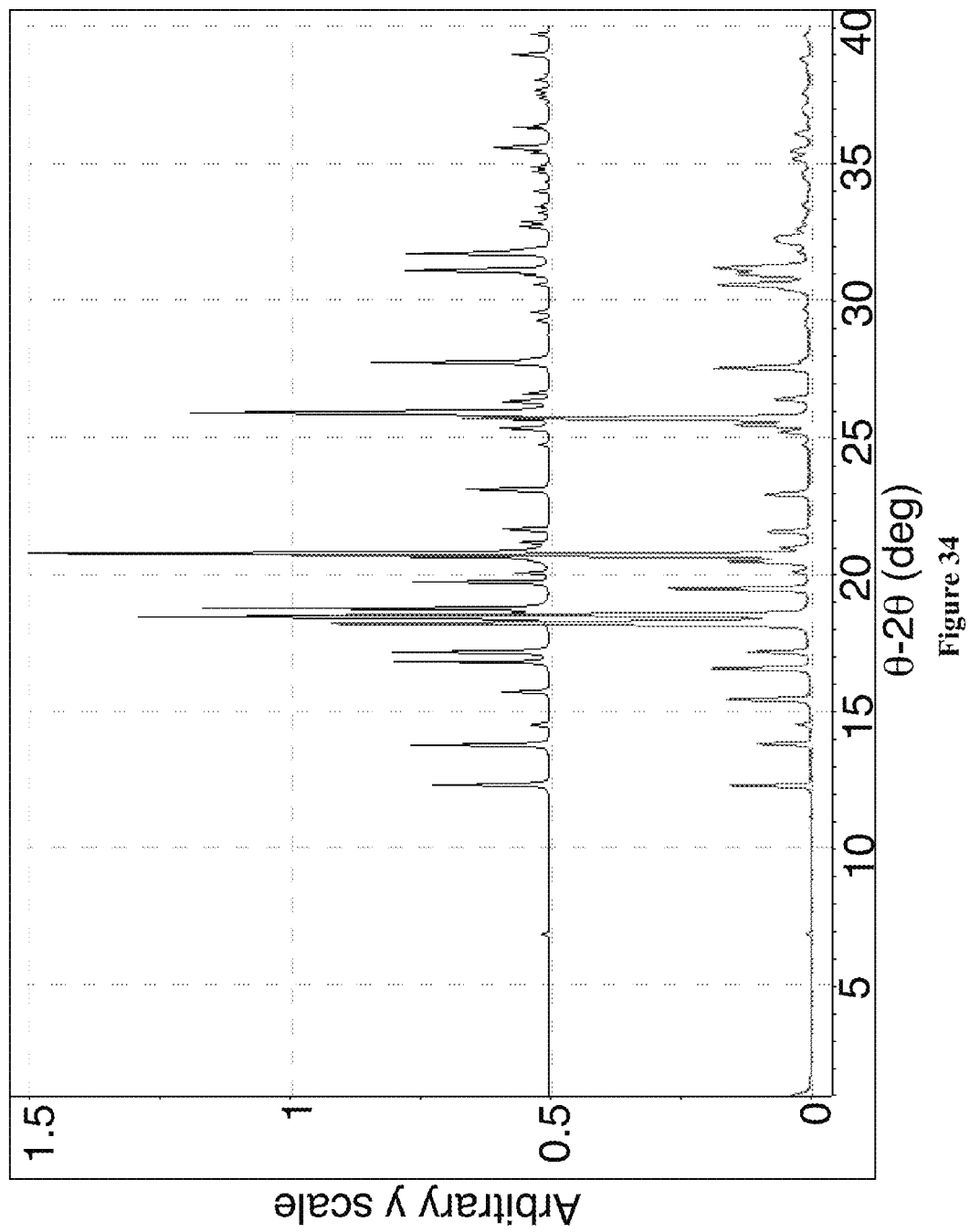
FIG. 34 depicts experimental and calculated XRPD patterns of Crystalline Form A (top: calculated XRPD pattern; bottom: experimental XRPD pattern at room temperature).

The experimental XRPD of Crystalline Form A from FIG. 1 is overlaid with the calculated pattern in FIG. 34.

Differences in intensities between the calculated and experimental x-ray powder diffraction patterns often are due to preferred orientation. Preferred orientation is the tendency for crystals to align themselves with some degree of order. This preferred orientation of the sample can significantly affect peak intensities, but not peak positions, in the experimental powder diffraction pattern. Furthermore, some shift in peak position between the calculated and experimental powder diffraction patterns may be expected because the experimental powder pattern is collected at ambient temperature and the single crystal data is collected at 150 K. Low temperatures are used in single crystal analysis to improve the quality of the structure but can contract the crystal resulting in a change in the unit cell parameters, which is reflected in the calculated powder diffraction pattern. These shifts are particularly evident at high diffraction angles.

Tables of positional parameters and their estimated standard deviations (Table 3), anisotropic temperature factor coefficients (Table 4), bond distances (Table 5), bond angles (Table 6), hydrogen bonds and angles (Table 7) and torsion angles (Table 8) are provided below.

TABLE 2

Crystal Data and Data Collection Parameters for (1R,5S)-1-(naphthalen-2-yl)-3-azabicyclo [3.1.0] hexane hydrochloride Form A (Crystalline Form A)

| | |
|---|---|
| formula | $C_{15}H_{16}ClN$ |
| formula weight | 245.75 |
| space group | $P2_12_12_1$ (No. 19) |
| a, Å | 5.7779(2) |
| b, Å | 8.6633(2) |
| c, Å | 25.7280(8) |
| V, Å$^3$ | 1287.83(7) |
| Z | 4 |
| $d_{calc}$, g cm$^{-3}$ | 1.267 |
| crystal dimensions, mm | 0.38 ×0.30 ×0.18 |
| temperature, K | 150 |
| radiation (wavelength, Å) | Mo K$_\alpha$ (0.71073) |
| monochromator | graphite |
| linear abs coef, mm$^{-1}$ | 0.273 |
| absorption correction applied | empirical$^a$ |
| transmission factors: | 0.953, 0.953 |
| min, max diffractometer | Nonius Kappa CCD |
| h, k, l range | −7 to 7 −11 to 11 −33 to 33 |
| 2θ range, deg | 1.58-55.71 |
| mosaicity, deg | 0.38 |
| programs used | SHELXTL |
| F$_{000}$ | 520.0 |
| weighting $1/[\sigma^2(F_o^2)+(0.0384P)^2+0.2436P]$ where P = $(F_o^2 + 2F_c^2)/3$ | |

TABLE 2-continued

Crystal Data and Data Collection Parameters for (1R,5S)-1-(naphthalen-2-yl)-3-azabicyclo [3.1.0] hexane hydrochloride Form A (Crystalline Form A)

| | |
|---|---|
| data collected | 5812 |
| unique data | 2930 |
| $R_{int}$ | 0.029 |
| data used in refinement | 2930 |
| cutoff used in R-factor calculations | $F_o^2 > 2.0\sigma(F_o^2)$ |
| data with I > 2.0σ(I) | 2678 |
| number of variables | 162 |
| largest shift/esd in final cycle | 0.00 |
| R(F$_o$) | 0.033 |
| Rw(F$_o^2$) | 0.080 |
| goodness of fit | 1.066 |
| absolute structure determination | Flack parameter$^b$ (−0.02(6)) Hooft parameter$^c$ (−0.01(3)) Friedel Coverage 90% |

$^a$Otwinowski, Z.; Minor, W. *Methods Enzymol.* 1997, 276, 307.
$^b$Flack, H. D. *Acta Cryst.*, 1983 A39, 876.
$^c$Hooft, R.W.W., Straver, L.H., and Spek, A.L. *J. Appl. Cryst.*, 2008, 41, 96-103.

TABLE 3

Positional Parameters and Their Estimated Standard Deviations for Crystalline Form A

| Atom | x | y | z | U(Å$^2$) |
|---|---|---|---|---|
| C11 | −0.21843(7) | 1.09587(4) | 0.483829(15) | 0.02856(9) |
| N13 | 0.2878(3) | 1.04618(14) | 0.53004(5) | 0.0234(3) |
| C1 | 0.4183(3) | 0.93704(19) | 0.70605(6) | 0.0294(4) |
| C2 | 0.2847(3) | 0.88296(17) | 0.66572(6) | 0.0268(4) |
| C3 | 0.0828(3) | 0.7983(2) | 0.67700(7) | 0.0380(5) |
| C4 | 0.0151(3) | 0.7719(3) | 0.72723(8) | 0.0426(6) |
| C5 | 0.1497(3) | 0.8274(2) | 0.76923(7) | 0.0340(5) |
| C6 | 0.0855(4) | 0.8007(3) | 0.82173(8) | 0.0465(6) |
| C7 | 0.2208(4) | 0.8543(2) | 0.86149(7) | 0.0483(6) |
| C8 | 0.4249(4) | 0.9340(2) | 0.85125(7) | 0.0447(6) |
| C9 | 0.4915(4) | 0.9627(2) | 0.80087(7) | 0.0391(5) |
| C10 | 0.3549(3) | 0.9099(2) | 0.75855(6) | 0.0294(4) |
| C11 | 0.3521(3) | 0.91598(19) | 0.61066(6) | 0.0261(4) |
| C12 | 0.2704(3) | 1.06743(16) | 0.58785(5) | 0.0270(4) |
| C14 | 0.2577(3) | 0.87808(16) | 0.51906(6) | 0.0282(4) |
| C15 | 0.3409(3) | 0.7984(2) | 0.56741(7) | 0.0314(5) |
| C16 | 0.5712(3) | 0.8497(2) | 0.58846(7) | 0.0352(5) |
| H131 | 0.436(4) | 1.082(2) | 0.5177(8) | 0.036(5)* |
| H132 | 0.168(4) | 1.105(2) | 0.5138(7) | 0.039(5)* |
| H1 | 0.555 | 0.993 | 0.699 | 0.035 |
| H3 | −0.008 | 0.759 | 0.649 | 0.046 |
| H4 | −0.123 | 0.716 | 0.734 | 0.051 |
| H6 | −0.052 | 0.745 | 0.829 | 0.056 |
| H7 | 0.175 | 0.837 | 0.896 | 0.058 |
| H8 | 0.519 | 0.969 | 0.879 | 0.054 |
| H9 | 0.630 | 1.018 | 0.794 | 0.047 |
| H15 | 0.285 | 0.692 | 0.575 | 0.038 |
| H12A | 0.109 | 1.089 | 0.598 | 0.032 |
| H12B | 0.370 | 1.154 | 0.600 | 0.032 |
| H14A | 0.351 | 0.847 | 0.489 | 0.034 |
| H14B | 0.093 | 0.853 | 0.512 | 0.034 |
| H16A | 0.659 | 0.776 | 0.610 | 0.042 |
| H16B | 0.667 | 0.918 | 0.566 | 0.042 |

Starred atoms are refined isotropically
$U_{eq} = (1/3)\Sigma_i\Sigma_j U_{ij} a^*_i a^*_j a_i \cdot a_j$
Hydrogen atoms are included in calculation of structure factors but not refined

TABLE 4

Anisotropic Temperature Factor Coefficients - U's for Crystalline Form A

| Name | U(1,1) | U(2,2) | U(3,3) | U(1,2) | U(1,3) | U(2,3) |
|---|---|---|---|---|---|---|
| C11 | 0.02543(19) | 0.02561(17) | 0.03463(19) | 0.00075(15) | 0.00262(16) | 0.00196(16) |
| N13 | 0.0268(7) | 0.0213(6) | 0.0222(6) | 0.0008(6) | −0.0013(6) | −0.0002(5) |
| C1 | 0.0292(9) | 0.0301(9) | 0.0290(8) | −0.0056(7) | 0.0005(7) | 0.0014(7) |
| C2 | 0.0258(8) | 0.0290(8) | 0.0256(7) | 0.0017(7) | −0.0019(6) | 0.0053(6) |
| C3 | 0.0278(9) | 0.0550(12) | 0.0313(9) | −0.0099(9) | −0.0063(8) | 0.0089(8) |
| C4 | 0.0286(10) | 0.0605(13) | 0.0388(11) | −0.0118(10) | −0.0015(8) | 0.0154(10) |
| C5 | 0.0326(10) | 0.0394(10) | 0.0301(8) | 0.0019(8) | 0.0016(7) | 0.0094(8) |
| C6 | 0.0458(12) | 0.0584(13) | 0.0354(10) | −0.0020(11) | 0.0068(10) | 0.0160(9) |
| C7 | 0.0664(14) | 0.0518(11) | 0.0266(8) | 0.0055(12) | 0.0037(10) | 0.0084(8) |
| C8 | 0.0628(14) | 0.0437(12) | 0.0276(9) | 0.0012(10) | −0.0062(9) | −0.0020(8) |
| C9 | 0.0479(12) | 0.0386(10) | 0.0309(10) | −0.0053(9) | −0.0015(8) | −0.0037(8) |
| C10 | 0.0334(9) | 0.0282(8) | 0.0265(8) | 0.0020(7) | −0.0002(6) | 0.0017(7) |
| C11 | 0.0252(8) | 0.0282(8) | 0.0249(7) | −0.0008(7) | −0.0014(6) | 0.0018(7) |
| C12 | 0.0352(9) | 0.0244(7) | 0.0215(7) | −0.0015(7) | 0.0001(7) | −0.0019(5) |
| C14 | 0.0343(8) | 0.0221(7) | 0.0283(7) | 0.0013(6) | −0.0041(7) | −0.0040(6) |
| C15 | 0.0393(11) | 0.0245(8) | 0.0303(8) | 0.0047(7) | −0.0011(7) | 0.0004(7) |
| C16 | 0.0308(9) | 0.0452(10) | 0.0297(8) | 0.0105(8) | 0.0006(7) | 0.0081(8) |

The form of the anisotropic temperature factor is: $\exp[-2\pi\ h^2 a^{*2} U(1,1) + k^2 b^{*2} U(2,2) + l^2 c^{*2} U(3,3) + 2\ hka^* b^* U(1,2) + 2\ hla^* c^* U(1,3)+$

TABLE 5

Bond Distances in Angstroms for Crystalline Form A

| Atom 1 | Atom 2 | Distance | Atom 1 | Atom 2 | Distance |
|---|---|---|---|---|---|
| N13 | C14 | 1.4936(18) | C7 | H7 | 0.950 |
| N13 | C12 | 1.5023(18) | C8 | C9 | 1.375(3) |
| N13 | H131 | 0.96(2) | C8 | H8 | 0.950 |
| N13 | H132 | 0.96(2) | C9 | C10 | 1.420(3) |
| C1 | C2 | 1.376(2) | C9 | H9 | 0.950 |
| C1 | C10 | 1.419(2) | C11 | C16 | 1.503(2) |
| C1 | H1 | 0.950 | C11 | C15 | 1.510(2) |
| C2 | C3 | 1.408(2) | C11 | C12 | 1.513(2) |
| C2 | C11 | 1.497(2) | C12 | H12A | 0.990 |
| C3 | C4 | 1.370(3) | C12 | H12B | 0.990 |
| C3 | H3 | 0.950 | C14 | C15 | 1.501(2) |
| C4 | C5 | 1.415(3) | C14 | H14A | 0.990 |
| C4 | H4 | 0.950 | C14 | H14B | 0.990 |
| C5 | C10 | 1.412(3) | C15 | C16 | 1.504(3) |
| C5 | C6 | 1.420(3) | C15 | H15 | 1.000 |
| C6 | C7 | 1.369(3) | C16 | H16A | 0.990 |
| C6 | H6 | 0.950 | C16 | H16B | 0.990 |
| C7 | C8 | 1.391(3) | | | |

Numbers in parentheses are estimated standard deviations in the least significant digits.

TABLE 6

Bond Angles in Degrees for Crystalline Form A

| Atom 1 | Atom 2 | Atom 3 | Angle |
|---|---|---|---|
| C14 | N13 | C12 | 107.39(11) |
| C14 | N13 | H131 | 110.6(12) |
| C12 | N13 | H131 | 110.3(12) |
| C14 | N13 | H132 | 110.8(13) |
| C12 | N13 | H132 | 108.7(12) |
| H131 | N13 | H132 | 109.2(16) |
| C2 | C1 | C10 | 121.10(16) |
| C2 | C1 | H1 | 119.50 |
| C10 | C1 | H1 | 119.50 |
| C1 | C2 | C3 | 119.14(15) |
| C1 | C2 | C11 | 120.17(15) |
| C3 | C2 | C11 | 120.69(15) |
| C4 | C3 | C2 | 121.22(17) |
| C4 | C3 | H3 | 119.40 |
| C2 | C3 | H3 | 119.40 |
| C3 | C4 | C5 | 120.43(18) |
| C3 | C4 | H4 | 119.80 |
| C5 | C4 | H4 | 119.80 |
| C10 | C5 | C4 | 119.01(16) |
| C10 | C5 | C6 | 119.16(17) |
| C4 | C5 | C6 | 121.82(18) |
| C7 | C6 | C5 | 120.4(2) |
| C7 | C6 | H6 | 119.80 |
| C5 | C6 | H6 | 119.80 |
| C6 | C7 | C8 | 120.71(18) |
| C6 | C7 | H7 | 119.60 |
| C8 | C7 | H7 | 119.60 |
| C9 | C8 | C7 | 120.36(19) |
| C9 | C8 | H8 | 119.80 |
| C7 | C8 | H8 | 119.80 |
| C8 | C9 | C10 | 120.6(2) |
| C8 | C9 | H9 | 119.70 |
| C10 | C9 | H9 | 119.70 |
| C5 | C10 | C1 | 119.08(16) |
| C5 | C10 | C9 | 118.71(16) |
| C1 | C10 | C9 | 122.21(17) |
| C2 | C11 | C16 | 120.40(14) |
| C2 | C11 | C15 | 123.87(14) |
| C16 | C11 | C15 | 59.90(12) |
| C2 | C11 | C12 | 116.85(14) |
| C16 | C11 | C12 | 116.53(15) |
| C15 | C11 | C12 | 106.60(13) |
| N13 | C12 | C11 | 104.89(12) |
| N13 | C12 | H12A | 110.80 |
| C11 | C12 | H12A | 110.80 |
| N13 | C12 | H12B | 110.80 |
| C11 | C12 | H12B | 110.80 |
| H12A | C12 | H12B | 108.80 |
| N13 | C14 | C15 | 104.74(12) |
| N13 | C14 | H14A | 110.80 |
| C15 | C14 | H14A | 110.80 |
| N13 | C14 | H14B | 110.80 |
| C15 | C14 | H14B | 110.80 |
| H14A | C14 | H14B | 108.90 |
| C14 | C15 | C16 | 116.45(15) |
| C14 | C15 | C11 | 108.31(14) |
| C16 | C15 | C11 | 59.81(11) |
| C14 | C15 | H15 | 119.20 |
| C16 | C15 | H15 | 119.20 |
| C11 | C15 | H15 | 119.20 |
| C11 | C16 | C15 | 60.29(12) |
| C11 | C16 | H16A | 117.70 |
| C15 | C16 | H16A | 117.70 |
| C11 | C16 | H16B | 117.70 |
| C15 | C16 | H16B | 117.70 |
| H16A | C16 | H16B | 114.90 |

Numbers in parentheses are estimated standard deviations in the least significant digits.

TABLE 7

Hydrogen Bond Distances in Angstroms and Angles in Degrees for Crystalline Form A

| D | H | A | D-H | A-H | D-A | D-H-A |
|---|---|---|---|---|---|---|
| N13 | H131 | Cl1 | 0.96(2) | 2.18(2) | 3.121(2) | 164.1(15) |
| N13 | H132 | Cl1 | 0.96(2) | 2.36(2) | 3.187(2) | 144.0(15) |
| N13 | H132 | Cl1 | 0.96(2) | 2.674(18) | 3.1217(19) | 109.2(14) |

Numbers in parentheses are estimated standard deviations in the least significant digits

TABLE 8

Torsion Angles in Degrees for Crystalline Form A

| Atom 1 | Atom 2 | Atom 3 | Atom 4 | Angle |
|---|---|---|---|---|
| C14 | N13 | C12 | C11 | 28.20 (0.18) |
| C12 | N13 | C14 | C15 | -27.51 (0.18) |
| C10 | C1 | C2 | C3 | -0.50 (0.25) |
| C10 | C1 | C2 | C11 | 178.63 (0.15) |
| C2 | C1 | C10 | C5 | -0.71 (0.25) |
| C2 | C1 | C10 | C9 | 179.13 (0.16) |
| C1 | C2 | C3 | C4 | 1.39 (0.26) |
| C11 | C2 | C3 | C4 | -177.73 (0.18) |
| C1 | C2 | C11 | C12 | -85.92 (0.20) |
| C1 | C2 | C11 | C15 | 137.54 (0.17) |
| C1 | C2 | C11 | C16 | 65.41 (0.21) |
| C3 | C2 | C11 | C12 | 93.19 (0.19) |
| C3 | C2 | C11 | C15 | -43.34 (0.24) |
| C3 | C2 | C11 | C16 | -115.47 (0.18) |
| C2 | C3 | C4 | C5 | -1.05 (0.30) |
| C3 | C4 | C5 | C6 | -179.38 (0.20) |
| C3 | C4 | C5 | C10 | -0.18 (0.30) |
| C4 | C5 | C6 | C7 | 179.21 (0.21) |
| C10 | C5 | C6 | C7 | 0.02 (0.46) |
| C4 | C5 | C10 | C1 | 1.04 (0.26) |
| C4 | C5 | C10 | C9 | -178.80 (0.18) |
| C6 | C5 | C10 | C1 | -179.74 (0.18) |
| C6 | C5 | C10 | C9 | 0.42 (0.27) |
| C5 | C6 | C7 | C8 | -0.85 (0.33) |
| C6 | C7 | C8 | C9 | 1.25 (0.30) |
| C7 | C8 | C9 | C10 | -0.80 (0.29) |
| C8 | C9 | C10 | C1 | -179.87 (0.17) |
| C8 | C9 | C10 | C5 | -0.03 (0.25) |
| C2 | C11 | C12 | N13 | -160.97 (0.14) |
| C15 | C11 | C12 | N13 | -17.56 (0.17) |
| C16 | C11 | C12 | N13 | 46.58 (0.18) |
| C2 | C11 | C15 | C14 | 141.11 (0.16) |
| C2 | C11 | C15 | C16 | -108.36 (0.18) |
| C12 | C11 | C15 | C14 | 0.94 (0.18) |
| C12 | C11 | C15 | C16 | 111.47 (0.15) |
| C16 | C11 | C15 | C14 | -110.53 (0.16) |
| C2 | C11 | C16 | C15 | 114.01 (0.17) |
| C12 | C11 | C16 | C15 | -94.57 (0.15) |
| N13 | C14 | C15 | C11 | 16.15 (0.18) |
| N13 | C14 | C15 | C16 | -48.59 (0.19) |
| C14 | C15 | C16 | C11 | 96.68 (0.16) |

Numbers in parentheses are estimated standard deviations in the least significant digits.

Example 3—Preparation of Crystalline Forms A Through F

Crystalline Form A through Form F are prepared as follows by using Crystalline Form A obtained from Example 1 above. A variety of crystallization techniques are used, including evaporation, cooling, solvent/antisolvent precipitation, slurry, vapor stress, and vapor diffusion, as described above. The results are presented in Table 9 below:

TABLE 9

| Solvent | Method[a] | Observations | XRPD Result |
|---|---|---|---|
| — | 40° C./75% RH/7 d | off-white solids, irregular, B/E | A |
| chloroform | SE | off-white solids, needles, B/E | A |
| chloroform/heptane | VD/RT/7 d | off-white solids, needles, B/E | A |
| chloroform/toluene | VD/RT/7 d | off-white solids, irregular, B/E | A |
| DCM | SE | off-white solids, needles, B/E | A + B |
|  | VS/RT/7 d | off-white solids, irregular, B/E | A |
|  | slurry/RT/7 d | off-white solids, needles, B/E | B (for XRPD see FIGS. 4B, 5, 6, and 7; for DSC and TGA see FIG. 8) |
|  | SC (40° C. to RT, refrigerator/2 d, freezer/8 d) | off-white solids, needles, B/E | B |
|  | CC (40° C. to dry ice/IPA) | milky solution | B |
|  | freezer/9 d | off-white solids, needles, B/E |  |
| DCM/ACN | VD/RT/7 d | off-white solids, needles, B/E | A |
| DCM/MEK | VD/RT/7 | off-white solids, needles, B/E | A |
| EtOH | FE | off-white solids, irregular, B/E | A + B |
|  | VS/RT/7 | off-white solids, irregular, B/E | A |
|  | slurry/RT/7 d | off-white solids, irregular, B/E | A |
|  | SC (70° C. to RT, refrigerator/2 d, freezer/8 d) | off-white solids, irregular, B/E | A + weak C peaks |
|  | CC (70° C. to dry ice/IPA) | milky solution | C + weak A peaks (~18.5, 20.7, 25.7 °2θ) |
| EtOH/acetone | VD/RT/9 d | no solids | — |
|  | acetone addition | no solids |  |
| EtOH/hexanes | VD/RT/7 d | off-white solids, irregular, B/E | A |
| EtOH/THF | VD/RT/9 d | no solids | — |
| HFIPA | SE | off-white solids, irregular, B/E | A + weak B peaks |
| HFIPA/IPE | AS precipitation | off-white solids, irregular, B/E | A + weak peak (~18.9 °2θ) |
| HFIPA/THF | AS precipitation | off-white solids, irregular, B/E | A |
| IPA | FE | off-white solids, irregular, B/E | A |
|  | slurry/RT/7 d | off-white solids, irregular, B/E | A |
|  | SC (70° C. to RT, refrigerator/2 d, freezer/7 d) | off-white solids, needles, B/E | C (for XRPD see FIGS. 4C, 9, and 13G; for DSC and TGA see FIG. 12)[b] |
|  | CC (70° C. to dry ice/IPA) | milky solution | C + possible weak A peak (~25.7 °2θ) (after 22 days of ambient storage: C + possible weak |

TABLE 9-continued

| Solvent | Method[a] | Observations | XRPD Result |
|---|---|---|---|
| | freezer/2 d | off-white solids, irregular, B/E | A peaks (~12.3, 15.4, 16.6, 20.7, 25.7 °2θ, for XRPD see FIGS. 10 and 11)[c] |
| MeOH | SE | off-white solids, irregular, B/E | A |
| MeOH:acetone (1:5) | FE | off-white solids, irregular, B/E | A |
| MeOH/dioxane | VD/RT/7 d | off-white solids, needles, B/E | A |
| MeOH/EtOAc | VD/RT/7 d | plates, single crystal | — |
| MeOH/EtOAc | VD/RT/7 d | plates | — |
| MeOH/IPE | VD/RT/7 d | very thin plates, possible single crystal | A |
| MeOH: toluene (1:5) | FE | off-white solids, needles, B/E | A |
| 1-propanol | FE | off-white solids, irregular, B/E | A |
| | slurry/RT/7 d | off-white solids, irregular, B/E | A |
| 1-propanol | Sc (70° C. to RT, refrigerator/2 d) CC (70° C. to dry ice/IPA) | off-white solids, needles, B/E milky solution | B |
| | freezer/2 d | off-white solids, needles, B/E | B + weak A and C peaks (~17.8, 18.5, 20.7 °2θ) |
| TFE | SE | light-orange solids, irregular, B/E | A + weak B peaks |
| TFE/ACN | AS precipitation | off-white solids, needles, B/E | A |
| TFE/EtOAc | AS precipitation | off-white solids, needles, B/E | A |
| TFE/MEK | AS precipitation | off-white solids, needles, B/E | A |
| water | FE | off-white solids, irregular, B/E | B |
| | slurry/RT/7 d | off-white solids, irregular, B/E | B |
| dioxane:water (1:1) | FE | off-white solids, irregular, B/E | A |

[a]Reported temperatures, times, and RH value are approximate.
[b]About 25 mg scale. Concentration of IPA solution: 10 mg/mL.
[c]About 27 mg scale. Concentration of IPA solution: 10 mg/mL.

Crystalline Form B—

As summarized above, Crystalline Form B is obtained from evaporation and slurry in water, slurry, slow and crash cooling in DCM, as well as slow cooling in 1-propanol. In addition, materials exhibiting XRPD patterns of Crystalline Form A with Crystalline Form B peaks result from evaporation in DCM, ethanol, HFIPA, and TFE. Material exhibiting XRPD pattern of Crystalline Form B with weak Crystalline Form A and Crystalline Form C peaks is observed from a crash cooling experiment in 1-propanol.

Figure 6:
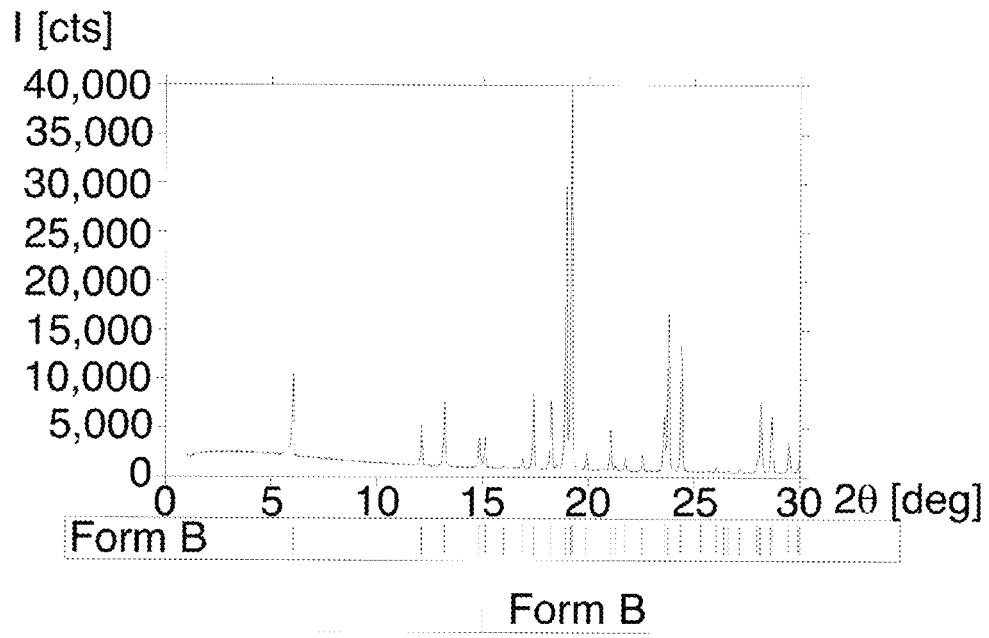
FIG. 6 depicts an indexing solution for Crystalline Form B.
Figure 7:
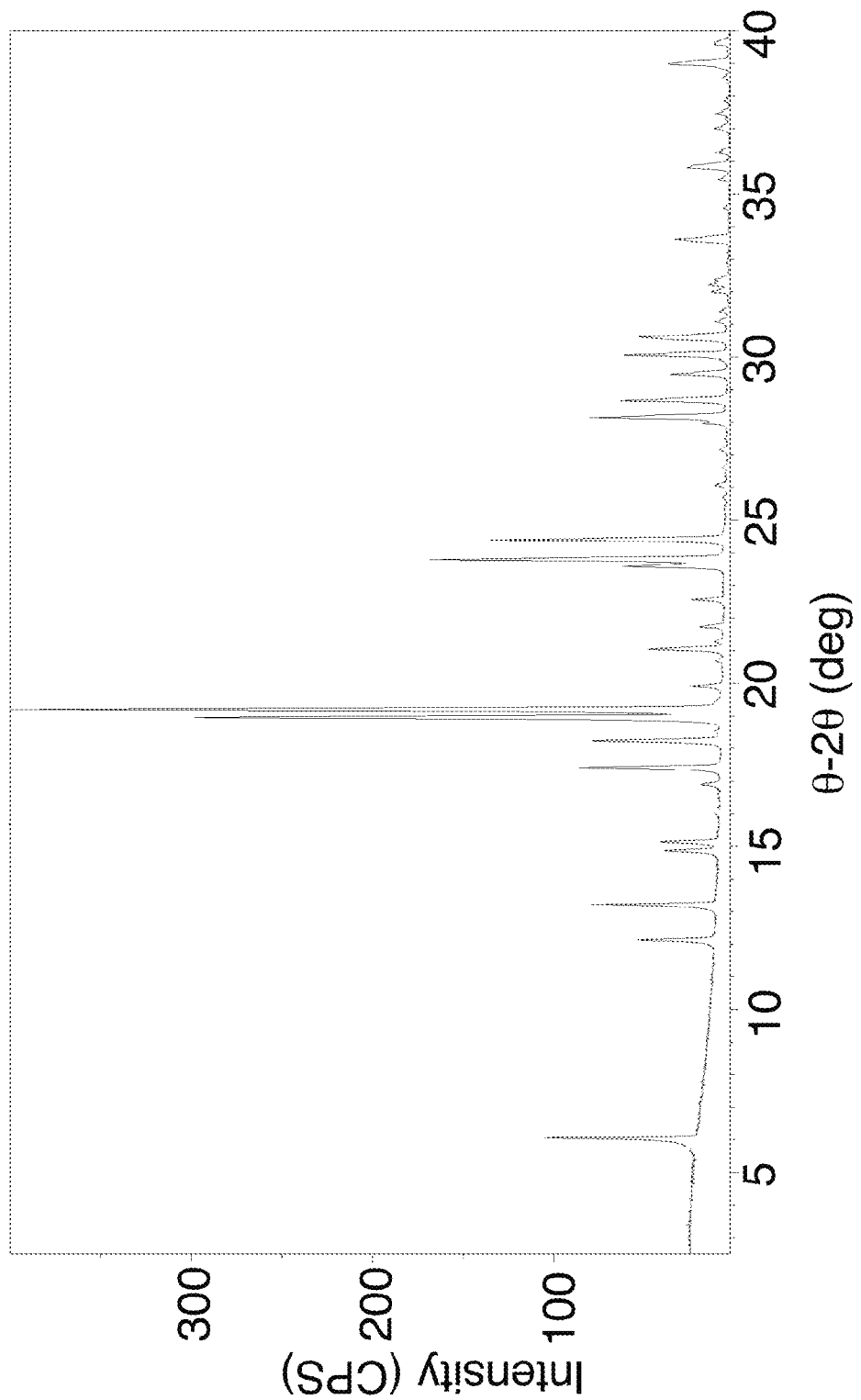
FIG. 7 depicts a high-resolution X-ray powder diffraction (XRPD) pattern of Crystalline Form B.

Crystalline Form B is indexed from a high-resolution XRPD pattern using X'Pert High Score Plus (X'Pert High Score Plus 2.2a (2.2.1)) (FIG. 6, high-resolution XRPD pattern also shown in FIG. 7). The pattern appears to represent a mixture of Crystalline Forms B and A. Agreement between the allowed peak positions, marked with bars for the current form and the observed peaks indicates a consistent unit cell determination. Peaks at 18.5°, 20.7°, 25.7°, and 27.5° two-theta are not consistent with the indexing solution of Crystalline Form B and are likely from Crystalline Form A. Space groups consistent with the assigned extinction symbol, unit cell parameters, and derived quantities are tabulated below the figure. To confirm the tentative indexing solution, the molecular packing motifs within the crystallographic unit cell must be determined. No attempts at molecular packing are performed. Crystalline Form B is indexed with a similar volume per formula unit compared to Crystalline Form A, suggesting Crystalline Form B is an unsolvated crystalline form.

Figure 4:
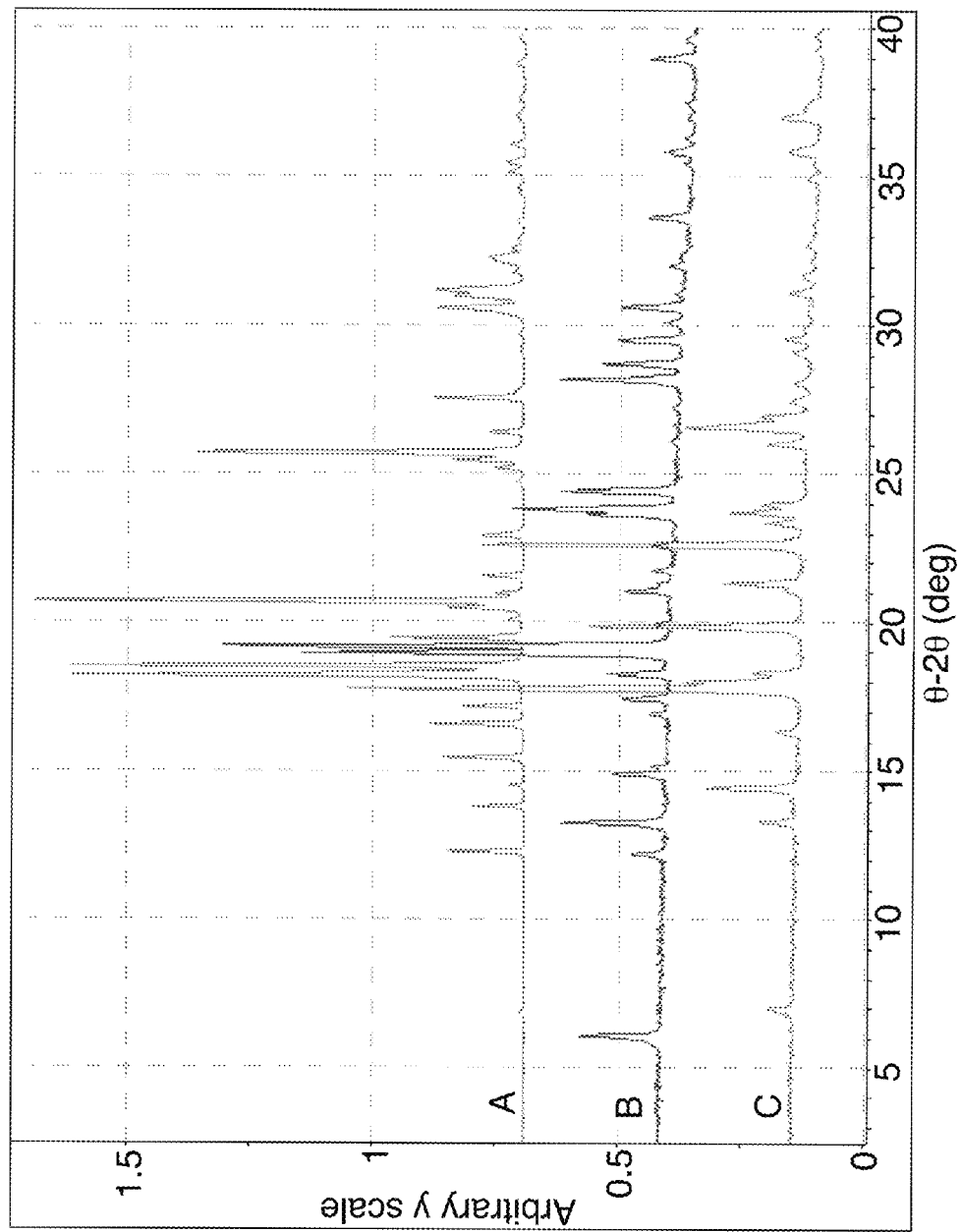
FIG. 4 depicts an overlay of X-ray powder diffraction (XRPD) patterns of Crystalline Form A, Form B, and Form C (from top to bottom)
Figure 5:
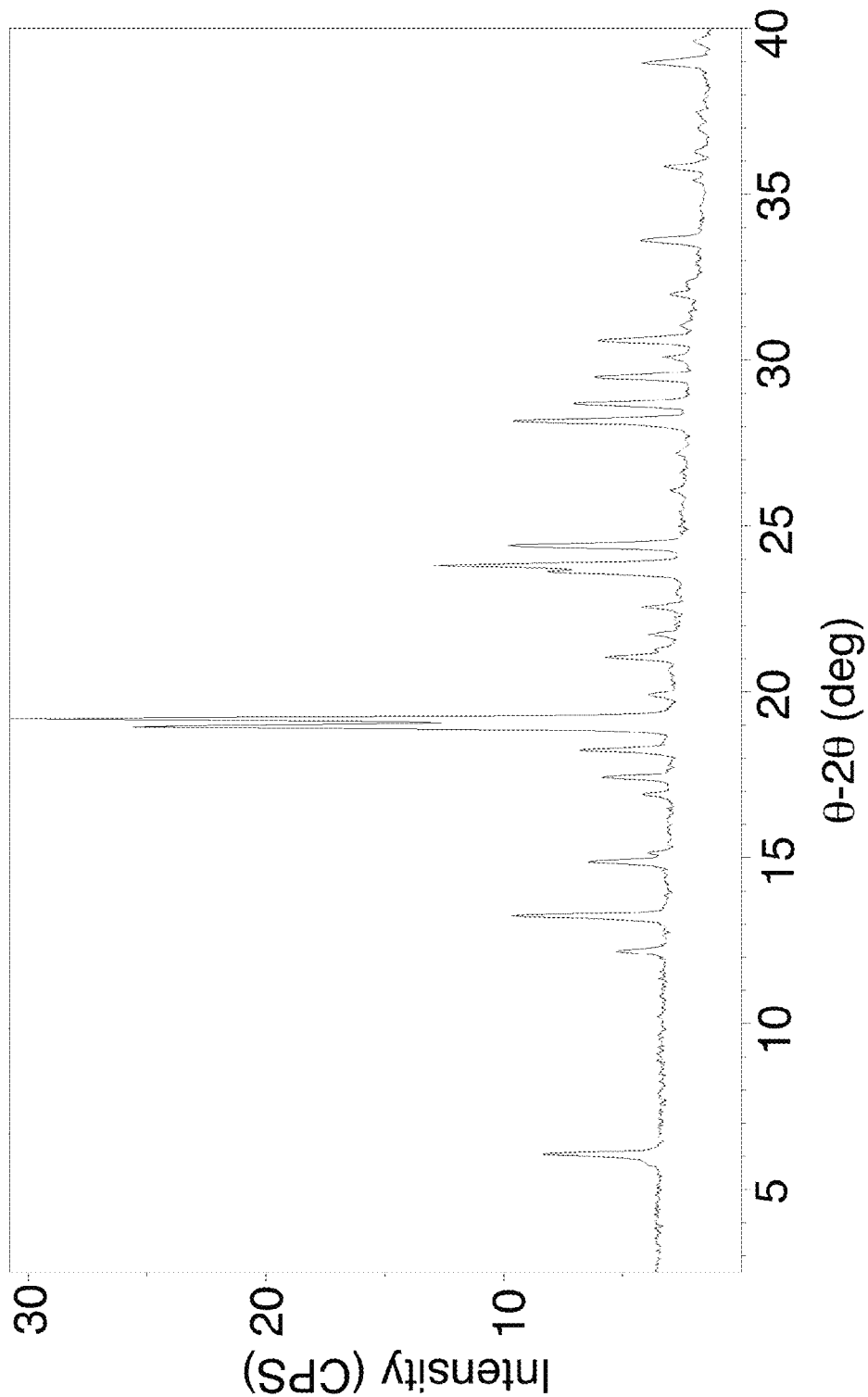
FIG. 5 depicts an X-ray powder diffraction (XRPD) pattern of Crystalline Form B.

XRPD Data acquisition parameters for FIGS. 4B and 5: INEL XRG-3000, X-ray Tube: 1.54187100 Å, Voltage: 40 (kV), Amperage: 30 (mA), Acquisition Time: 300 sec, Spinning capillary, Step size: approximately 0.03 °2θ.

XRPD Data acquisition parameters for FIGS. 6 and 7: Panalytical X-Pert Pro MPD PW3040 Pro, X-ray Tube: Cu (1.54059 Å), Voltage: 45 kV, Amperage: 40 mA, Scan Range: 1.00-39.99 °2θ, Step Size: 0.017 °2θ, Collection Time: 1939 s, Scan Speed: 1.2°/min., Slit: DS: 1/2°, SS: null, Revolution Time: 1.0 s, Mode: Transmission.

Characterization data for Crystalline Form B are summarized in Table 10 below:

TABLE 10

| Analysis | Result |
|---|---|
| XRPD | B (for XRPD see FIGS. 4B and 5) B + possible weak A peaks[b] (~ 18.5, 20.7, 25.7, 27.5 °2θ) (for XRPD see FIGS. 6 and 7) |
| DSC[a] | 141° C. (endo, peak; 137° C. onset); 248° C. (endo, peak; 246° C. onset); 251° C. (endo, peak); 264° C. (endo, peak) (for DSC see FIG. 8) |
| TGA[a] | 0.2% weight loss up to 200° C. 281° C. (onset, decomposition) (for TGA see FIG. 8) |

[a]Temperatures are rounded to the nearest ° C.; weight loss values are rounded to one decimal place.
[b]High-resolution XRPD.

Figure 8:
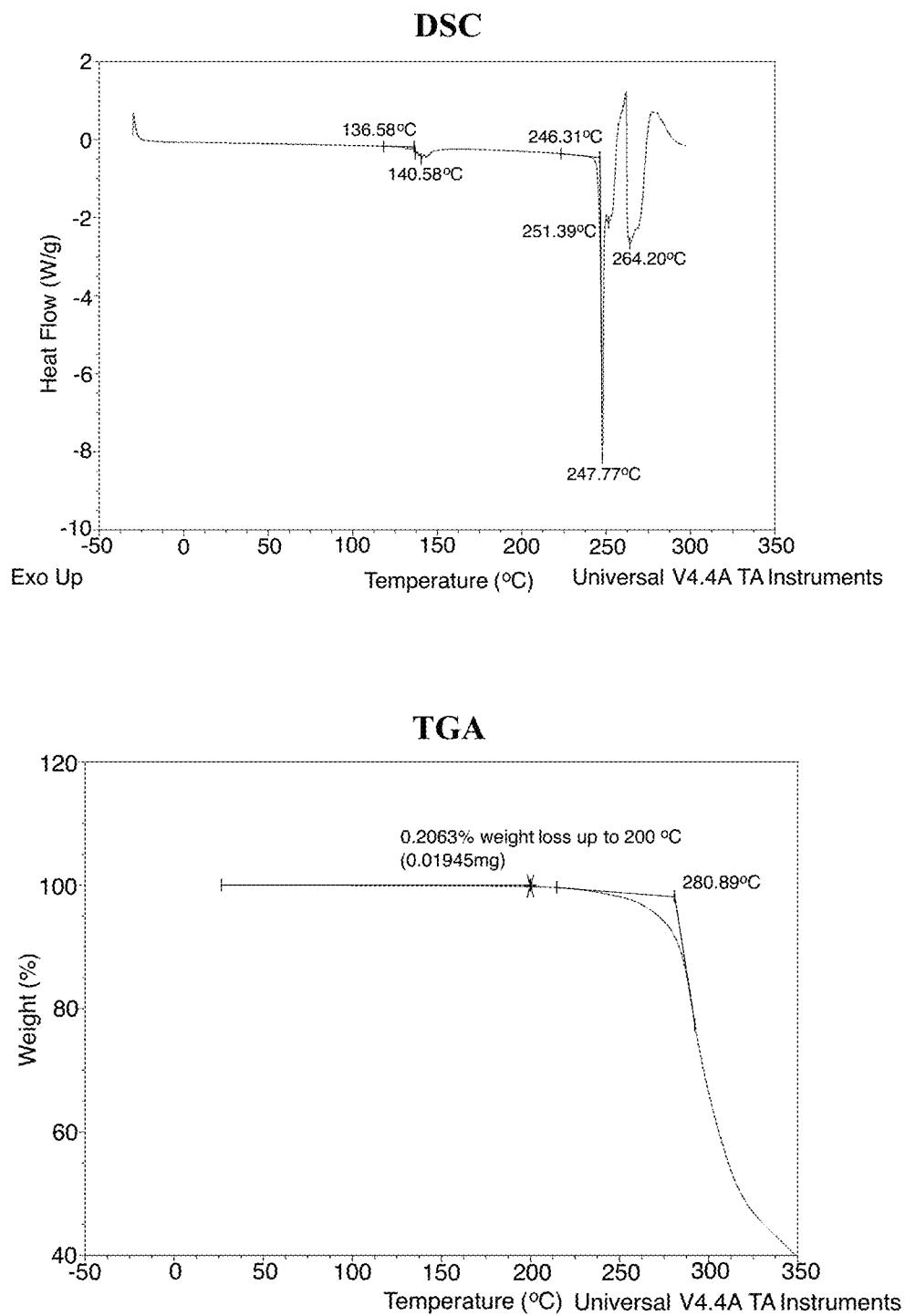
FIG. 8 depicts DSC and TGA thermograms of Crystalline Form B.

The thermal analysis results for Crystalline Form B are shown in FIG. 8 (DSC, Size: 1.2600 mg, Method: (−30)-300-10, TOC; TGA, Size: 9.4320 mg, Method: 00-350-10). By TGA, Crystalline Form B exhibits a small weight loss of approximately 0.2% from ambient to 200° C., possibly due to trace amounts of solvent. The dramatic change in the slope of the TGA thermogram at approximately 281° C. is consistent with decomposition. By DSC, a broad endotherm observed at approximately 141° C. (peak) is suspected to be attributed to either a solid form change or possibly a loss of volatiles on heating. Crystalline Form B displays an endotherm at approximately 248° C. (peak), similar to the thermal behavior observed for Crystalline Form A, followed by two broad endotherms at approximately 251 and 264° C. Based on the data obtained, Crystalline Form B is an unsolvated, crystalline material.

Crystalline Form C—

Crystalline Form C may be made by slow cooling in isopropanol. Material exhibiting XRPD pattern of Crystalline Form A with weak Crystalline Form C peaks results from a slow cooling experiment in ethanol; while the crash cooling experiments in ethanol and isopropanol afford XRPD pattern Crystalline Form C with weak Crystalline Form A peaks.

Six scale-up attempts are conducted to prepare Crystalline Form C by cooling in isopropanol on approximately 50-150 mg scale (Table 11) and the solids tested by XRPD. At refrigerator temperature, precipitated solids yield Form B. Seeding with Form C after cooling in the refrigerator (no solids observed) and before placing in the freezer yield XRPD pattern of Form C with B peaks. Precipitation at freezer temperature results in solids with an XRPD pattern of Form C with A peaks. For a solution placed in the freezer after cooling to room temperature with a lower concentration (7 mg/mL compared to 10 mg/mL) yield Form B. By crash cooling (ambient solution placed into dry ice/isopropanol), solids generated are a mixture of Forms B and A. The last attempt on an approximate 50-mg scale generates a mixture of Forms A and C. The different outcome of these experiments suggest possible factors affecting the crystallization of Form C on a larger scale (e.g., concentration, temperature, cooling time, and seeding), and competitive crystallization of Forms A and B that are possibly more stable under the experimental conditions used. Note that Form C remains unchanged by XRPD after 22 days of ambient storage.

Figure 13:
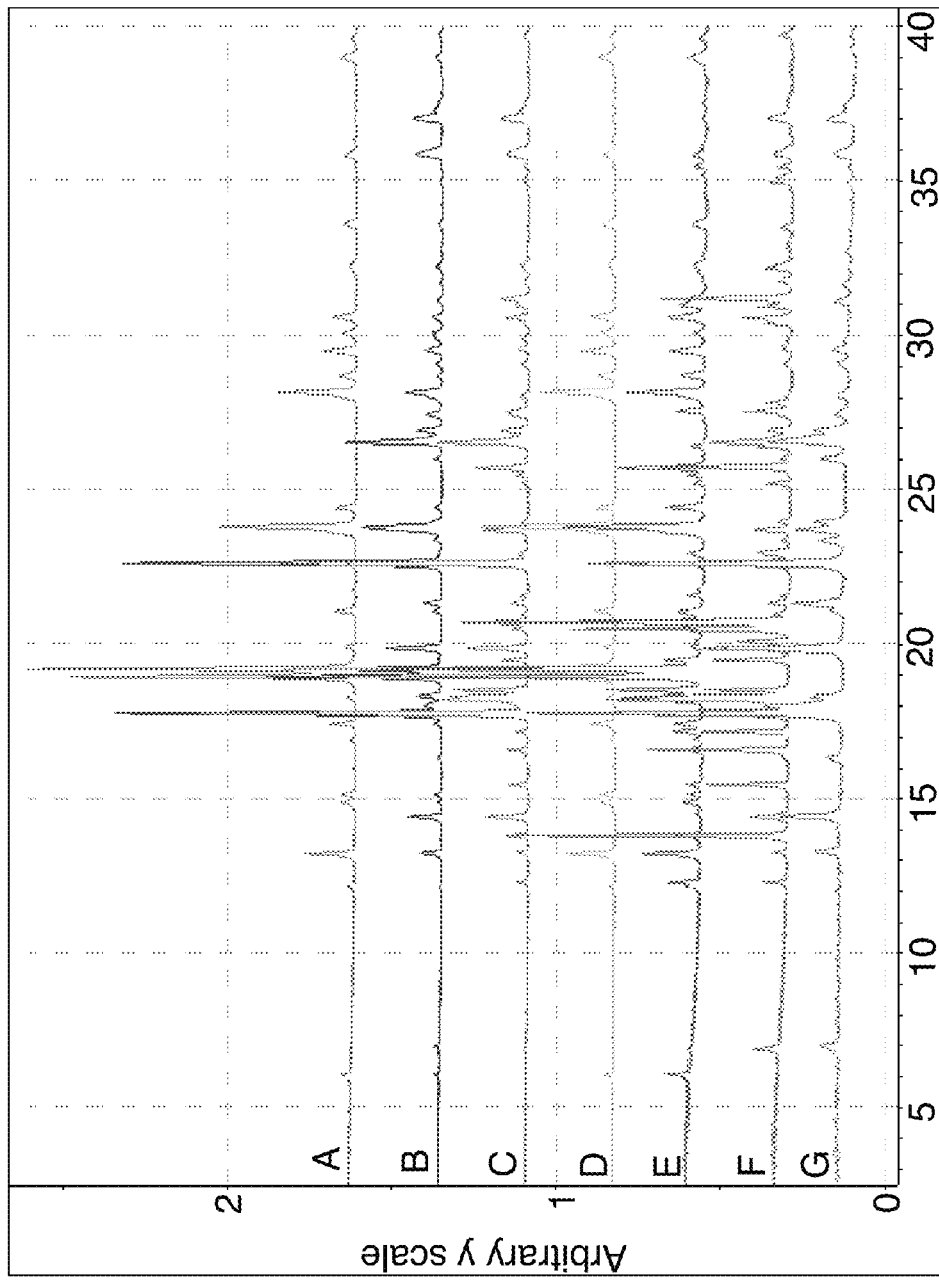
FIG. 13 depicts an overlay of X-ray powder diffraction (XRPD) patterns of Crystalline Form A, Form B, and Form C (from top to bottom)

XRPD Data acquisition parameters for FIGS. 13A, C, and F: Panalytical X-Pert Pro MPD PW3040 Pro, X-ray Tube: Cu (1.54059 Å), Voltage: 45 kV, Amperage: 40 mA, Scan Range: 1.00-39.99 °2θ, Step Size: 0.017 °2θ, Collection Time: 717 s, Scan Speed: 3.3°/min., Slit: DS: 1/2°, SS: null, Revolution Time: 1.0 s, Mode: Transmission.

XRPD Data acquisition parameters for FIG. 13B: Panalytical X-Pert Pro MPD PW3040 Pro, X-ray Tube: Cu (1.54059 Å), Voltage: 45 kV, Amperage: 40 mA, Scan Range: 1.00-39.99 °2θ, Step Size: 0.017 °2θ, Collection Time: 720 s, Scan Speed: 3.2°/min., Slit: DS: 1/2°, SS: null, Revolution Time: 1.0 s, Mode: Transmission.

XRPD Data acquisition parameters for FIG. 13D: Panalytical X-Pert Pro MPD PW3040 Pro, X-ray Tube: Cu (1.54059 Å), Voltage: 45 kV, Amperage: 40 mA, Scan Range: 1.00-39.99 °2θ, Step Size: 0.017 °2θ, Collection Time: 718 s, Scan Speed: 3.3°/min., Slit: DS: 1/2°, SS: null, Revolution Time: 1.0 s, Mode: Transmission.

XRPD Data acquisition parameters for FIG. 13E: Panalytical X-Pert Pro MPD PW3040 Pro, X-ray Tube: Cu (1.54060 Å), Voltage: 45 kV, Amperage: 40 mA, Scan Range: 1.00-39.99 °2θ, Step Size: 0.017 °2θ, Collection Time: 720 s, Scan Speed: 3.2°/min., Slit: DS: 1/2°, SS: null, Revolution Time: 1.0 s, Mode: Transmission.

TABLE 11

| Attempted material | Solvent | Method[a] | Observations | XRPD Result |
|---|---|---|---|---|
| C | IPA | SC (70° C. to RT, refrigerator/2 d) | off-white solids, needles, B/E[b] | B (for XRPD see FIG. 13A) |
| | | SC (70° C. to RT, refrigerator/4 h, freezer/3 d) | off-white solids, irregular & needles, B/E[c,d] | C + B (for XRPD see FIG. 13B) |
| | | SC (70° C. to RT, refrigerator/4 h, freezer/2 d) | off-white solids, irregular & needles, B/E[c] | C + A (for XRPD see FIG. 13C) |
| | | SC (70° C. to RT, freezer/7 d) | off-white solids, irregular, B/E[e] | B (for XRPD see FIG. 13D) |
| | | CC (70° C. to dry ice/IPA/4 h) | off-white solids, irregular, B/E[c] | B + A (for XRPD see FIG. 13E) |
| | | SC (70° C. to RT, refrigerator/4 h, freezer/3 d) | off-white solids, irregular, B/E[c] | A + C (for XRPD see FIG. 13F) |

[a]Reported temperatures and times are approximate.
[b]Concentration of IPA solution: 11 mg/mL.
[c]Concentration of IPA solution: 10 mg/mL.
[d]Seeded with Crystalline Form C (for XRPD of seeds see FIGS. 4C and 9) before moving into the freezer.
[e]Concentration of IPA solution: 7 mg/mL.

Form C is indexed from a high-resolution XRPD pattern (FIG. 10) using proprietary software. The pattern appears to represent a mixture of Forms C and A. Agreement between the allowed peak positions, marked with bars for the current form and the observed peaks indicates a consistent unit cell determination. Peaks at 12.3°, 15.4°, 16.6°, 20.7°, and 25.7° two-theta are not consistent with the indexing solution of Form C and are likely from Form A. Space groups consistent with the assigned extinction symbol, unit cell parameters, and derived quantities are tabulated below the figure. To confirm the tentative indexing solution, the molecular packing motifs within the crystallographic unit cell must be determined. No attempts at molecular packing are performed. Form C is indexed with a similar volume per formula unit compared to Form A, suggesting Form C is an unsolvated crystalline form.

Figure 9:
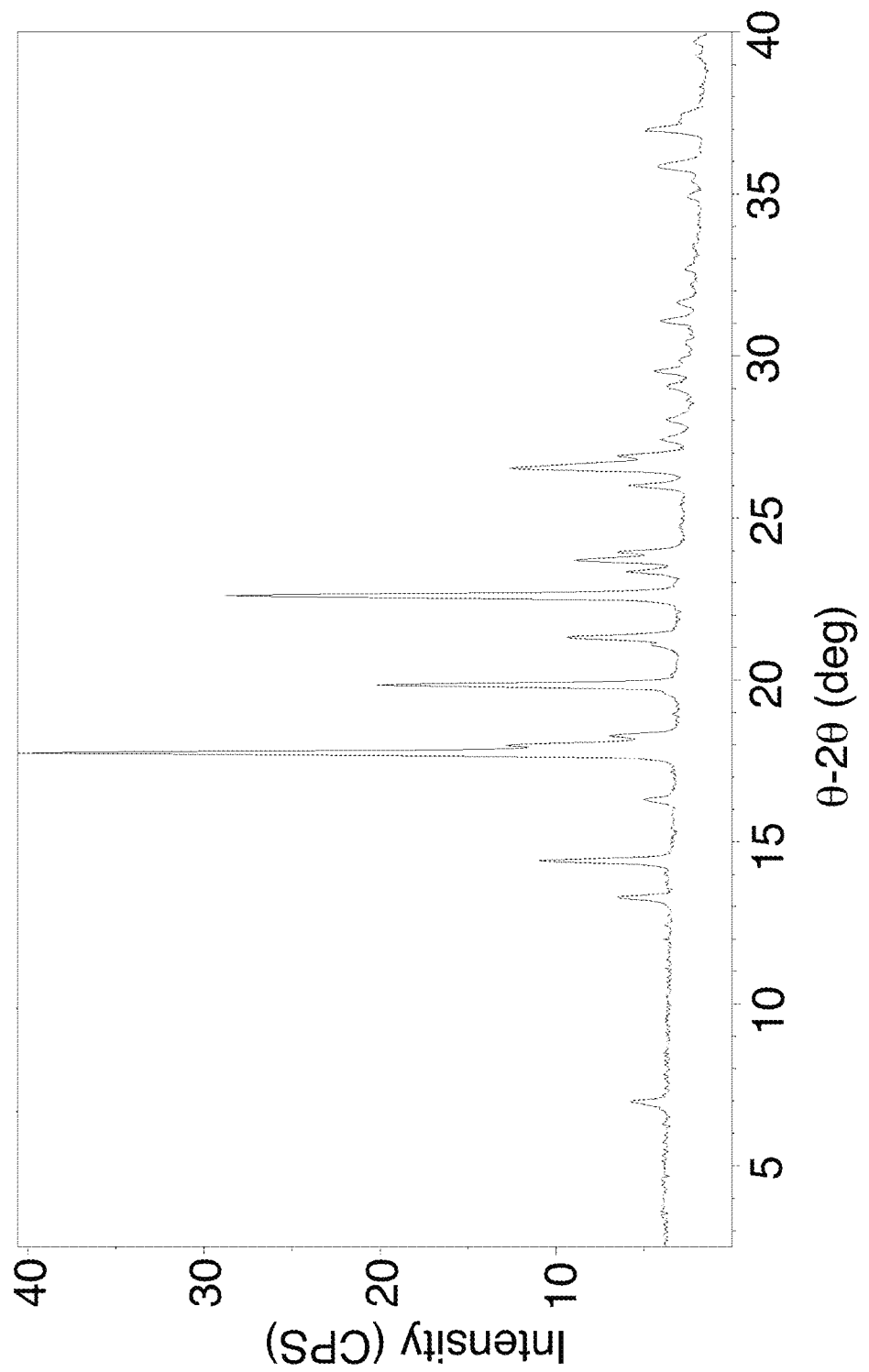
FIG. 9 depicts an X-ray powder diffraction (XRPD) pattern of Crystalline Form C.

XRPD acquisition parameters for FIGS. 4C, 9, and 13G: INEL XRG-3000, X-ray Tube: 1.54187100 Å, Voltage: 40 (kV), Amperage: 30 (mA), Acquisition Time: 300 sec, Spinning capillary, Step size: approximately 0.03 °2θ.

Figure 10:
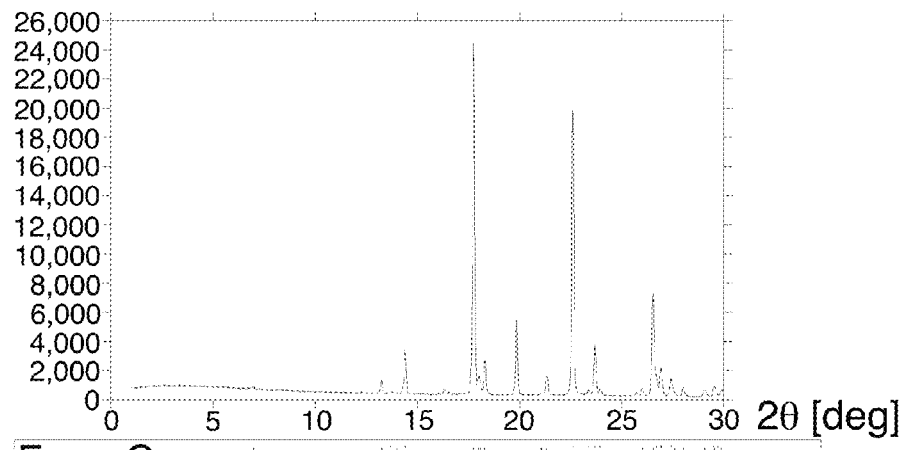
FIG. 10 depicts an indexing solution for Crystalline Form C.
Figure 11:
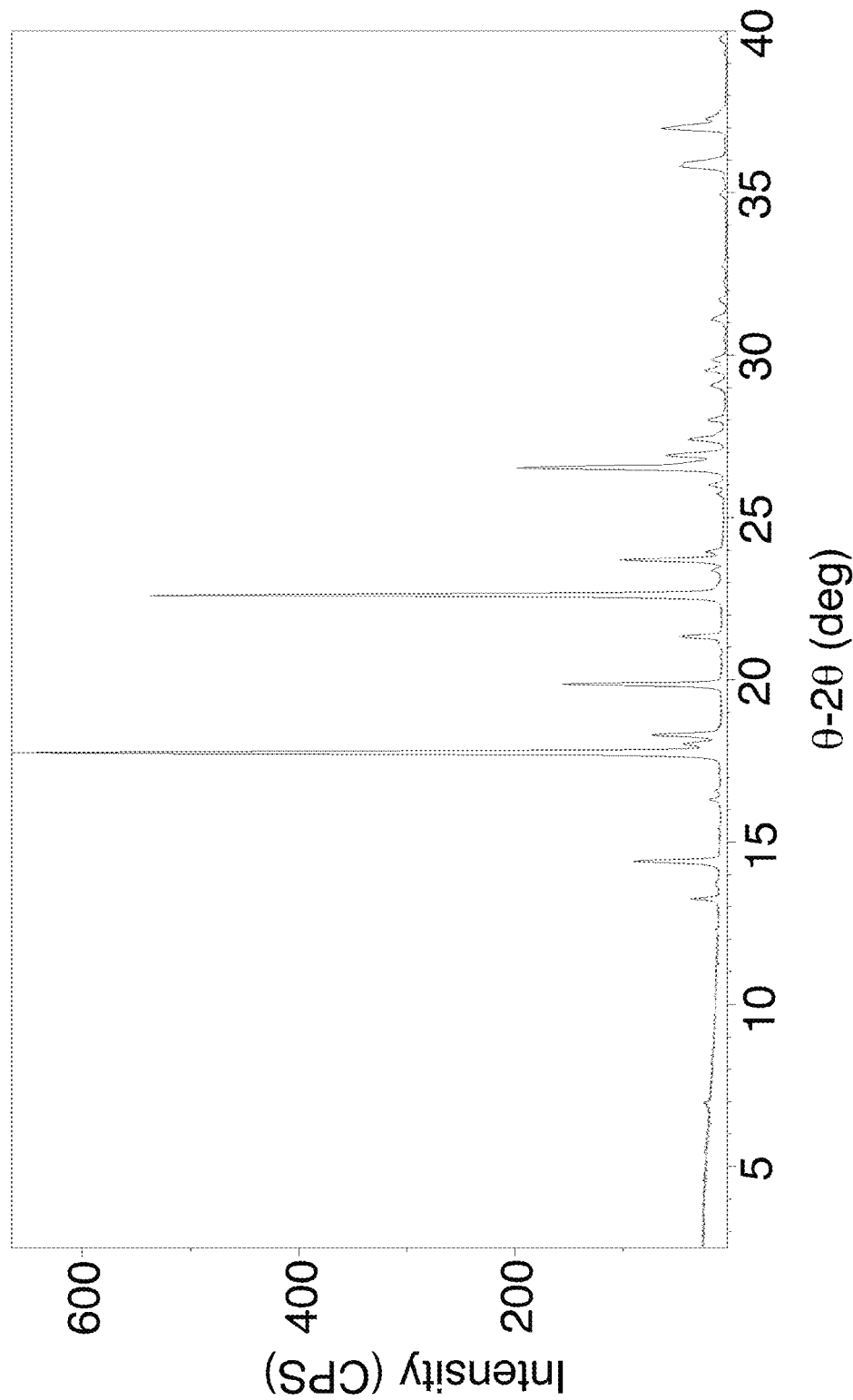
FIG. 11 depicts a high-resolution X-ray powder diffraction (XRPD) pattern of Crystalline Form C.

XRPD Data acquisition parameters for FIGS. 10 and 11: Panalytical X-Pert Pro MPD PW3040 Pro, X-ray Tube: Cu (1.54059 Å), Voltage: 45 kV, Amperage: 40 mA, Scan Range: 1.00-39.99 °2θ, Step Size: 0.017 °2θ, Collection Time: 720 s, Scan Speed: 3.2°/min., Slit: DS: 1/2°, SS: null, Revolution Time: 1.0 s, Mode: Transmission.

Characterization data for Form C are summarized in Table 12 below:

TABLE 12

| Analysis | Result |
|---|---|
| XRPD | C (for XRPD see FIGS. 4C, 9, and 13G) |
| DSC[a] | 122° C. (endo, peak; 112° C. onset); 248° C. (endo, peak; 246° C. onset; ΔH: 88 J/g); 271° C. (endo, peak) (for DSC see FIG. 12) |
| TGA[a] | 1.3% weight loss up to 200° C. 266° C. (onset, decomposition) (for TGA see FIG. 12) |
| XRPD | C + possible weak A peak (~25.7° 2θ) C + possible weak A peaks[b] (for XRPD see FIGS. 10 and 11) (~12.3, 15.4, 16.6, 20.7, 25.7° 2θ) |

[a]Temperatures are rounded to the nearest ° C.; weight loss values are rounded to one decimal place; reported ΔH values are rounded to the nearest whole number.
[b]High-resolution XRPD, reanalyzed after 22 days of ambient storage.

Figure 12:
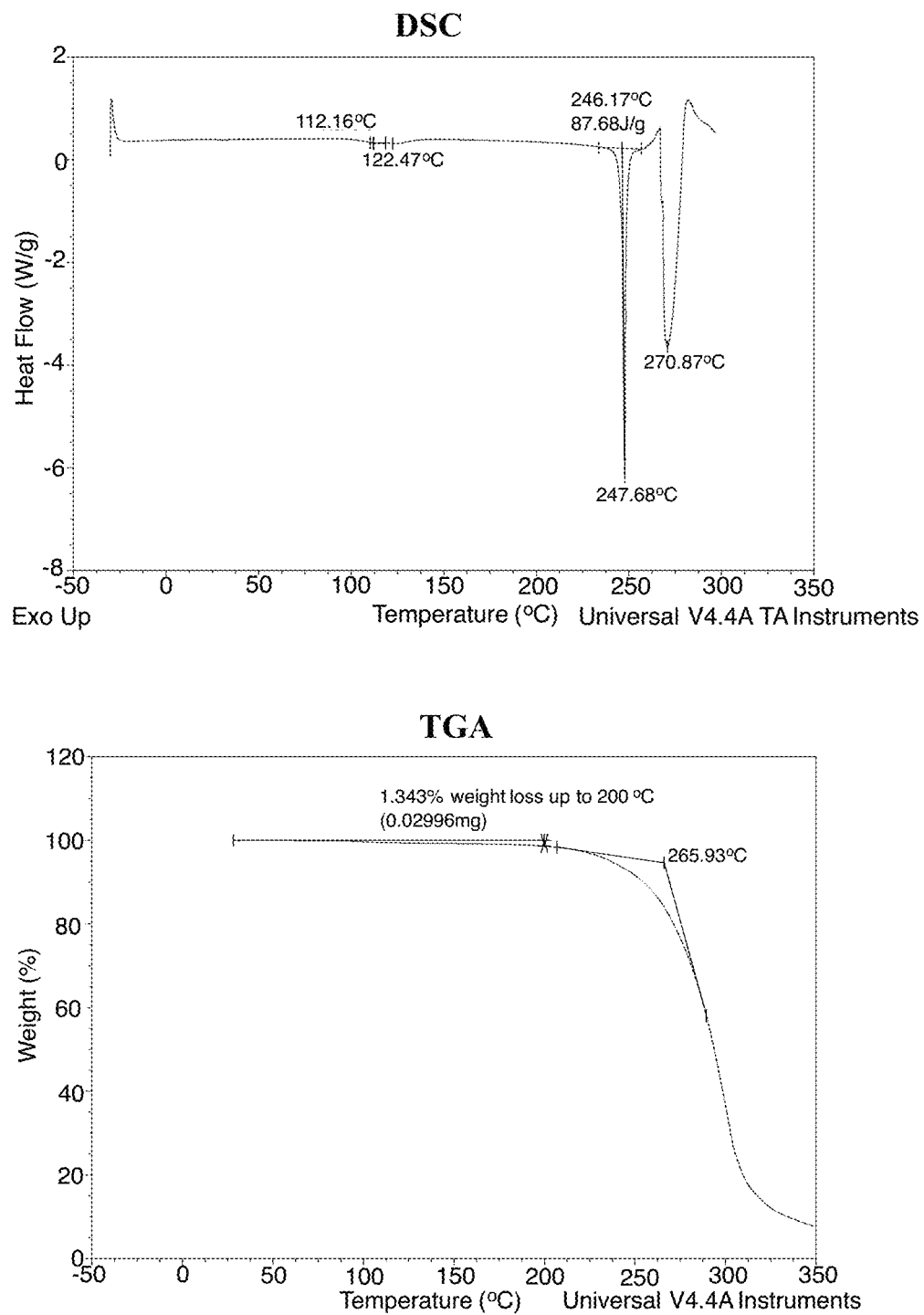
FIG. 12 depicts DSC and TGA thermograms of Crystalline Form C.

The thermal analysis results for Form C are shown in FIG. 12 (DSC, Size: 1.0100 mg, Method: (−30)-300-10, TOC;

TGA, Size: 2.2300 mg, Method: 00-350-10). By TGA, Form C exhibits a weight loss of approximately 1.3% from ambient to 200° C., possibly due to loss of volatiles upon heating. The dramatic change in the slope of the TGA thermogram at approximately 266° C. is consistent with decomposition. By DSC, a broad small endotherm observed at approximately 122° C. (peak) is suspected to be attributed to either a solid form change or possibly a loss of volatiles on heating. Form C displays an endotherm at approximately 248° C. (peak), similar to the thermal behavior observed for Form A, followed by a broad endotherm at approximately 271° C.

Based on the data obtained, Form C is an unsolvated, crystalline material.

Crystalline Forms D, E, and F—

Crystalline Form A is dissolved in pH adjusted buffered media. Undissolved solid or precipitate observed is analyzed by XRPD. Some experiments are conducted at elevated temperature to increase solubility, the undissolved solids are also analyzed by XRPD. The resulting Crystalline Forms D, E, and F are generated during these experiments as summarized in Table 13 below.

XRPD Data acquisition parameters for FIGS. 14D-F: INEL XRG-3000, X-ray Tube: 1.54187100 Å, Voltage: 40 (kV), Amperage: 30 (mA), Acquisition Time: 300 sec, Spinning capillary, Step size: approximately 0.03 °2θ.

TABLE 13

| pH Buffer | Method[a] | Observations | XRPD Result |
|---|---|---|---|
| pH 2.0 (50 mM KCl/HCl) | slurry/RT/7 d | off-white solids, irregular, B/E | A |
| | SC (70° C. to RT) | off-white solids, irregular, B/E | A |
| pH 4.4 (50 mM citric acid/sodium citrate) | spontaneous precipitation | off-white solids, irregular, B/E | D |
| | slurry/RT/7 d | off-white solids, irregular, B/E | B + weak D peaks |
| | stir at 70° C./30 min | off-white solids, irregular, B/E | D (for XRPD see FIG. 14D) |
| pH 6.0 (50 mM Na₂HPO₄/NaH₂PO₄) | slurry/50° C./3 d | off-white solids, irregular, B/E | E (contains peaks of F) (for XRPD see FIG. 14E) |
| pH 8.1 (50 mM Na₂HPO₄/NaH₂PO₄) | stir at 70° C./30 min | off-white solids, irregular, B/E | F (for XRPD see FIG. 14F) |

[a]Reported times and temperatures are approximate.

- pH 2.0 buffer (50 mM KCl/HCl): Crystalline Form A is recovered from slow cooling (approximately 70° C. to ambient) and slurry at room temperature.
- pH 4.4 buffer (50 mM citric acid/sodium citrate): Crystalline Form D results from spontaneous precipitation at room temperature and after stirring a suspension at approximately 70° C.; a room temperature slurry yields Crystalline Form B with weak Crystalline Form D peaks by XRPD.
- pH 6.0 buffer (50 mM Na₂HPO₄/NaH₂PO₄): Crystalline Form E with peaks also found in Crystalline Form F by XRPD is observed from slurry at approximately 50° C.
- pH 8.1 buffer (50 mM Na₂HPO₄/NaH₂PO₄): Crystalline Form F results from stirring a suspension at approximately 70° C.

Figure 14:
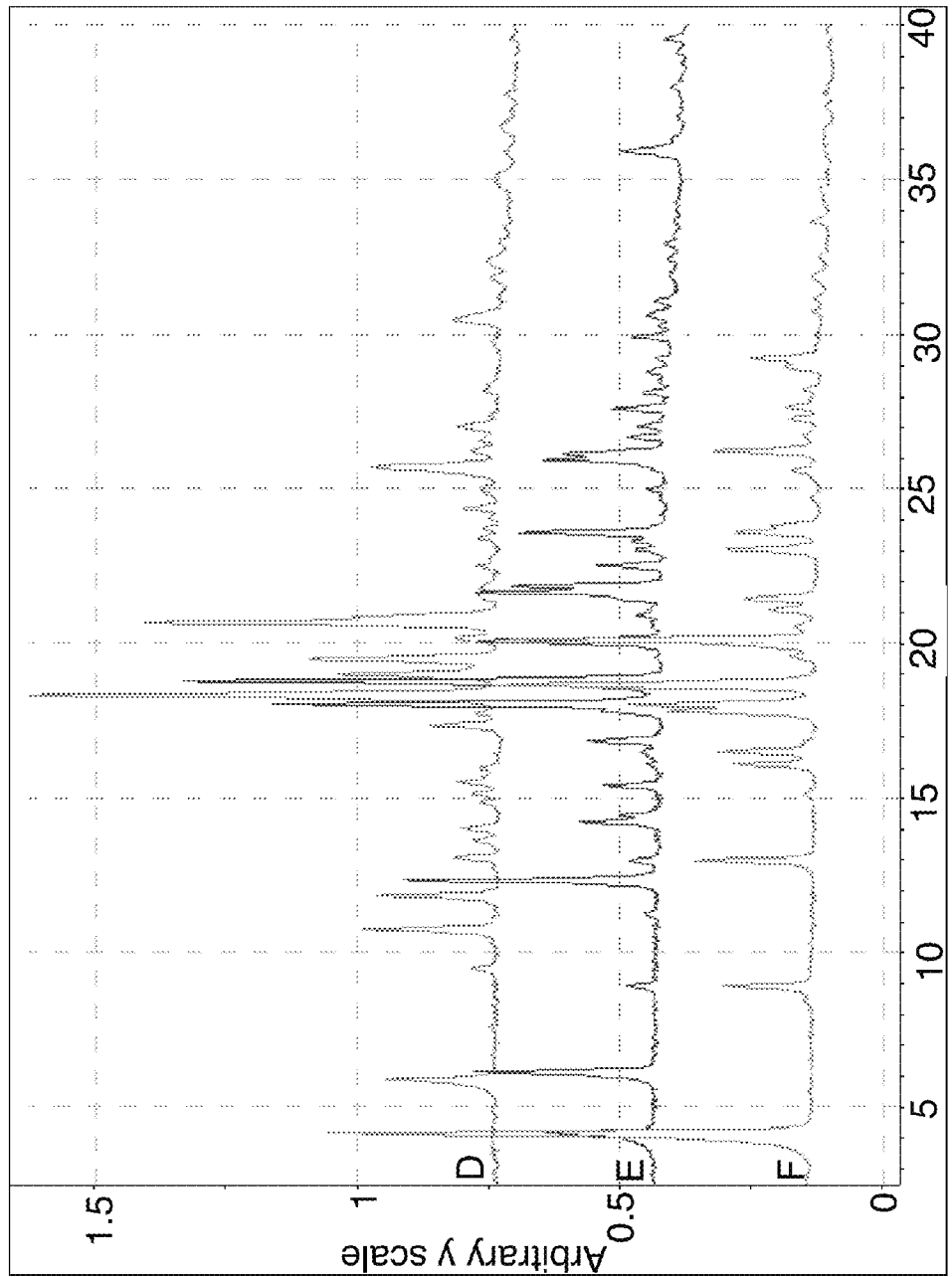
FIG. 14 depicts an overlay of X-ray powder diffraction (XRPD) patterns of Crystalline Form D, Form E, and Form F (from top to bottom)
Figure 15:
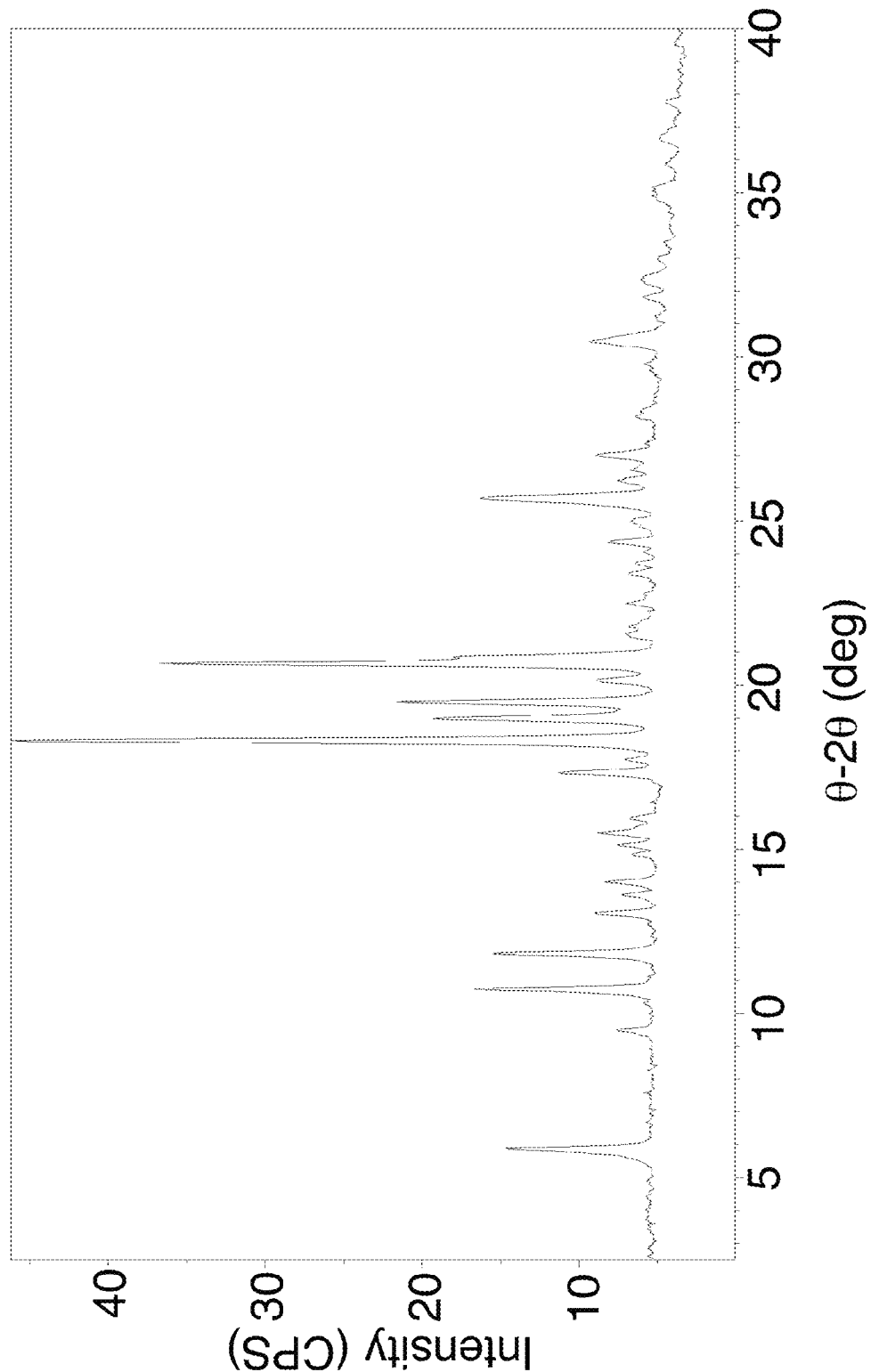
FIG. 15 depicts an X-ray powder diffraction (XRPD) pattern of Crystalline Form D.
Figure 16:
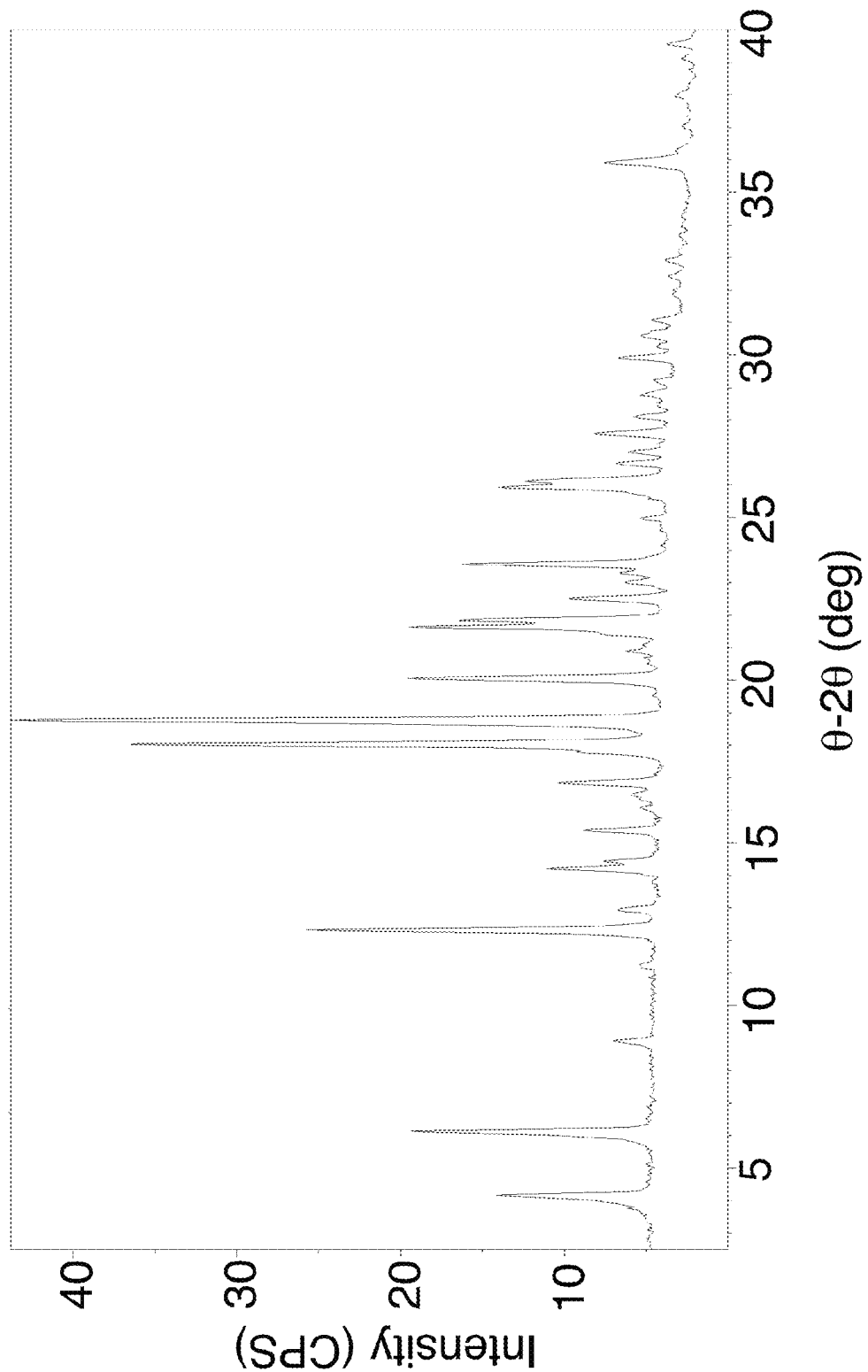
FIG. 16 depicts an X-ray powder diffraction (XRPD) pattern of Crystalline Form E (contains peaks of Crystalline Form F).
Figure 17:
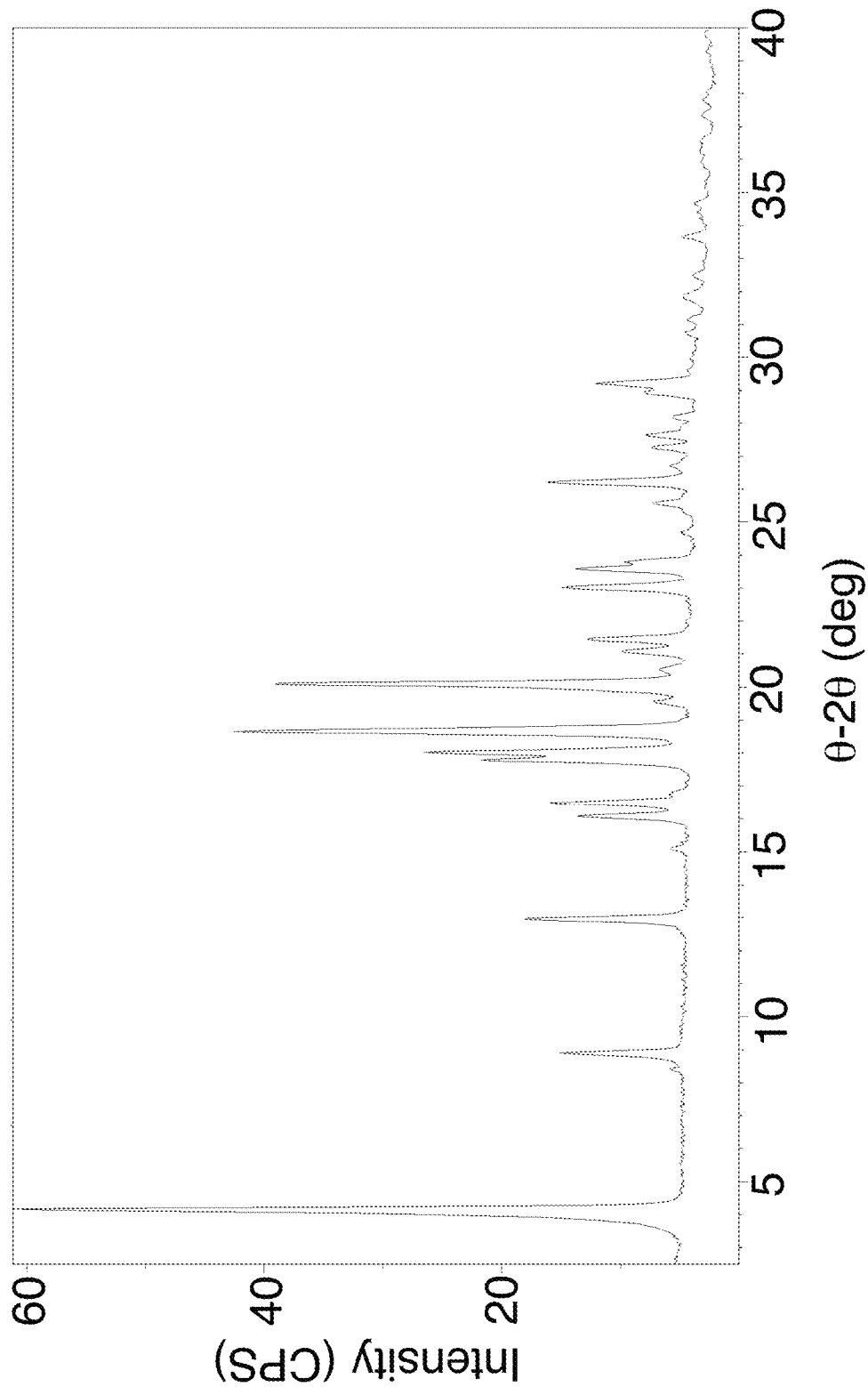
FIG. 17 depicts an X-ray powder diffraction (XRPD) pattern of Crystalline Form F.

Crystalline Forms D, E, and F are characterized by XRPD as shown in FIG. 14.

Example 4—Amorphous

Attempts to prepare amorphous (1R,5S)-1-(naphthalen-2-yl)-3-azabicyclo[3.1.0]hexane hydrochloride are performed by milling, lyophilization, and rotary evaporation (Table 14). Possible disordered Crystalline Form A materials are recovered from all attempts used in this study.

XRPD Data acquisition parameters for FIGS. 52-55: Bruker Discovery D8, X-ray Tube: Cu (1.54059 Å), Scan Range: 2.14-37.02 °2θ, Step Size: 0.04 °2θ, Acquisition Time: 900 s.

TABLE 14

Figure 51:
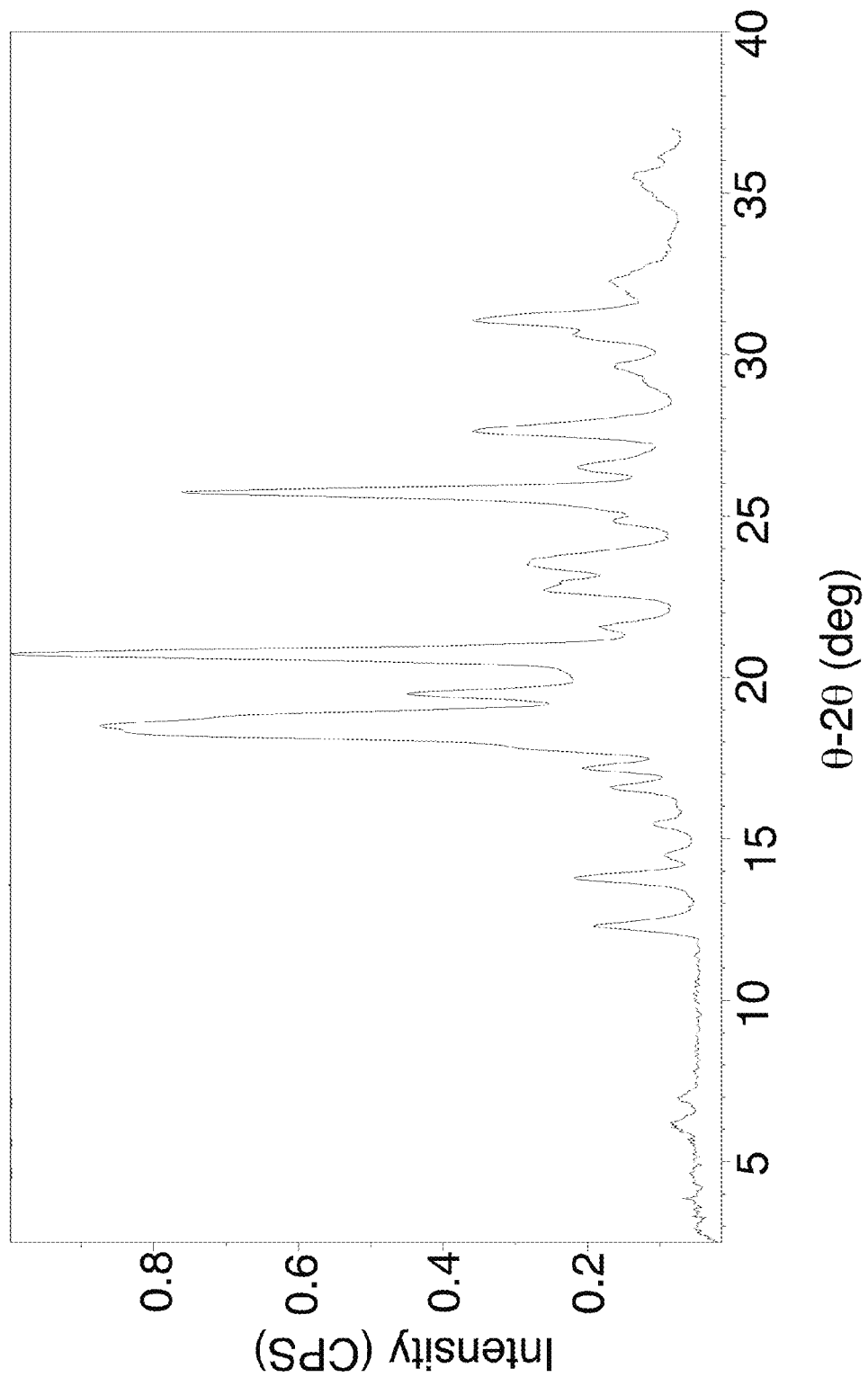
FIGS. 51-54 depict XRPD patterns of disordered Crystalline Form A.
Figure 52:
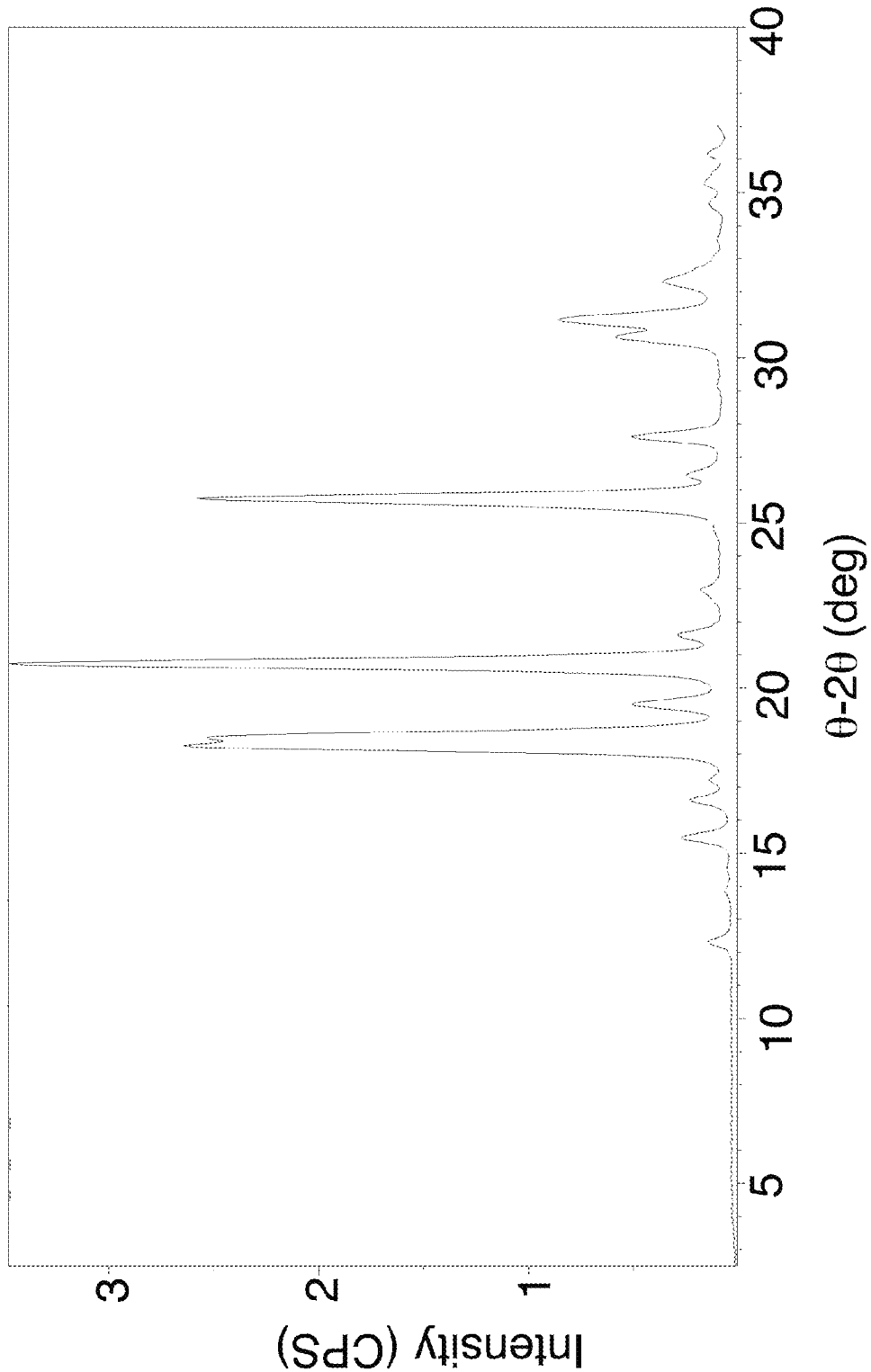
Figure 53:
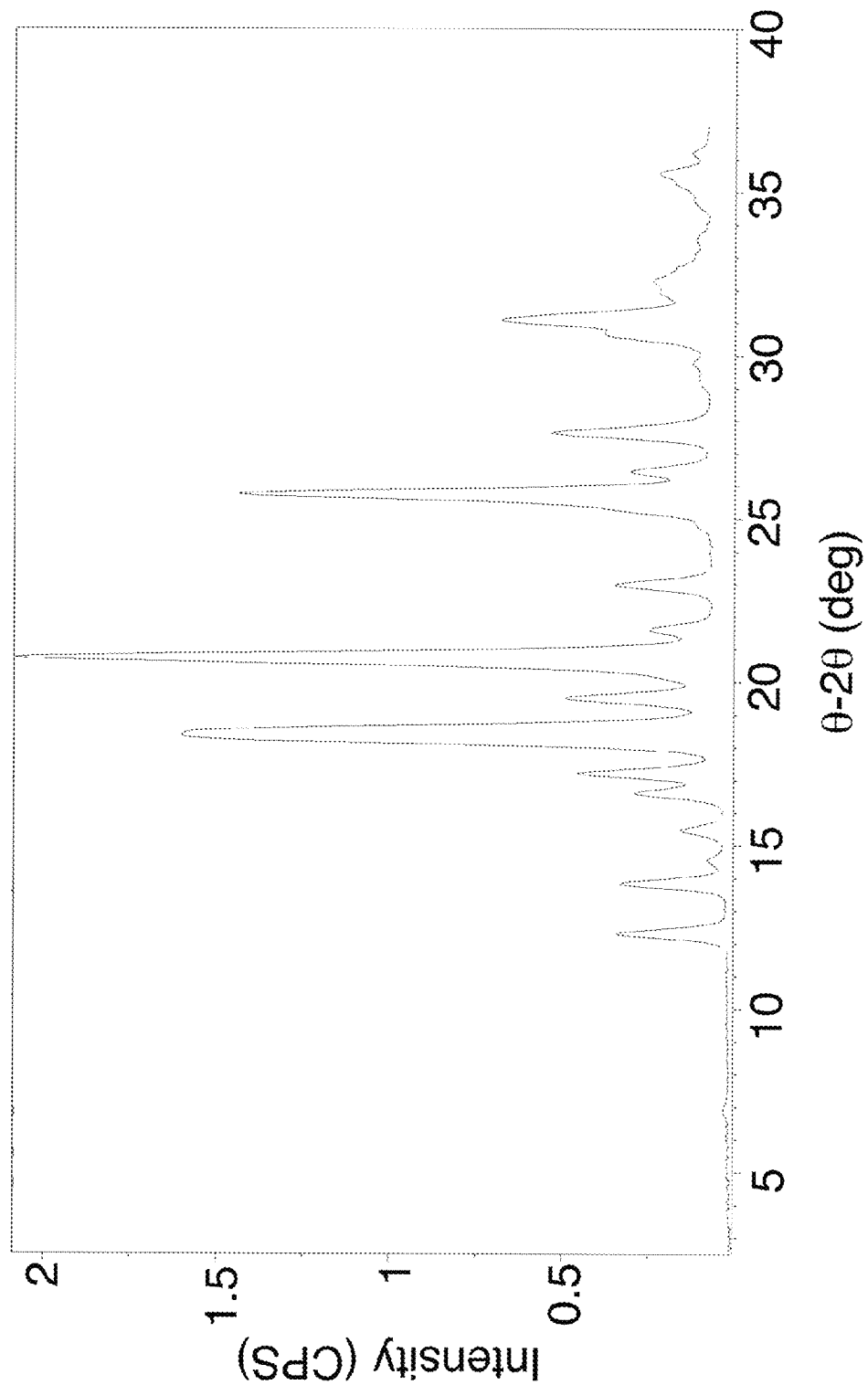
Figure 54:
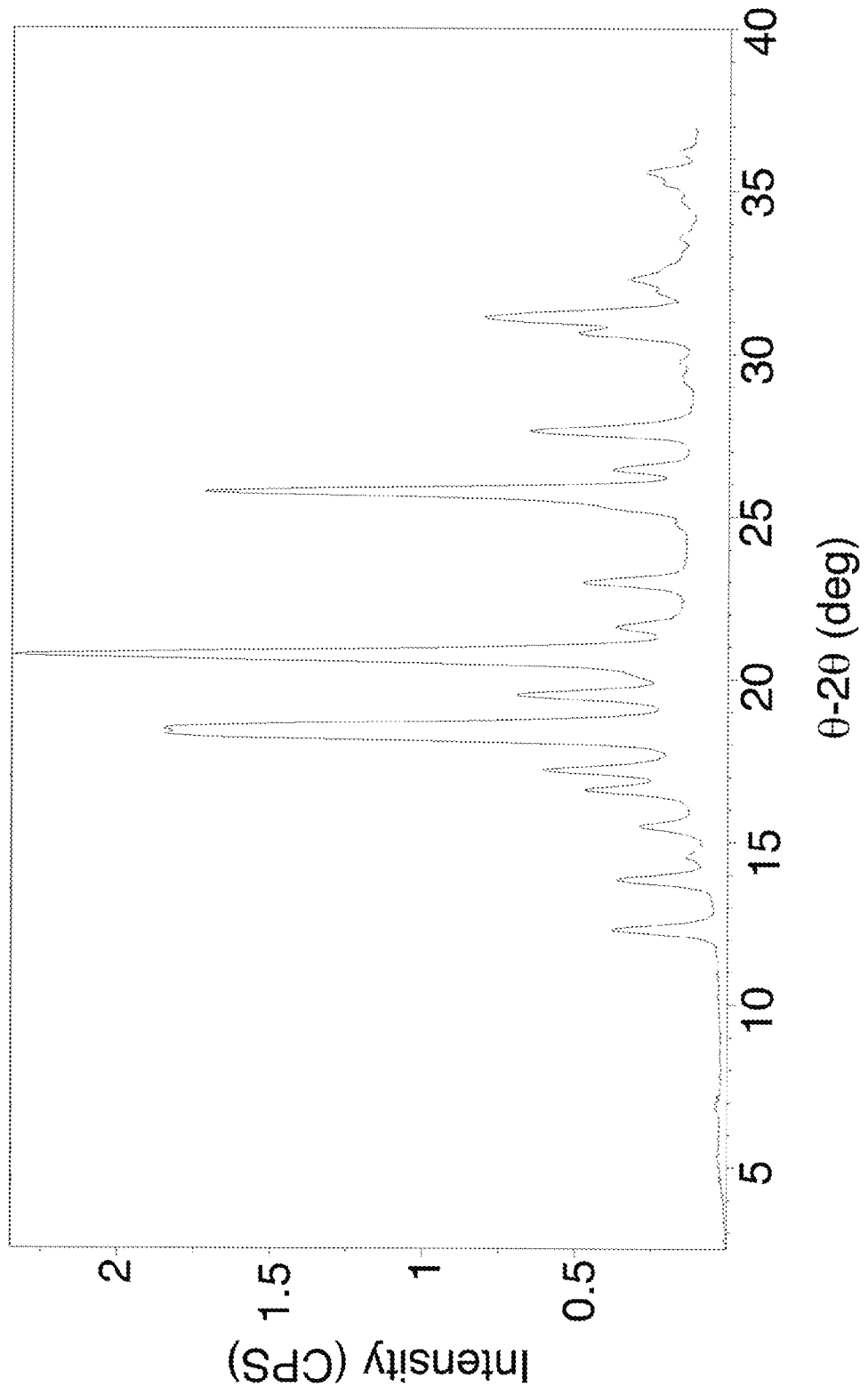
Figure 55:
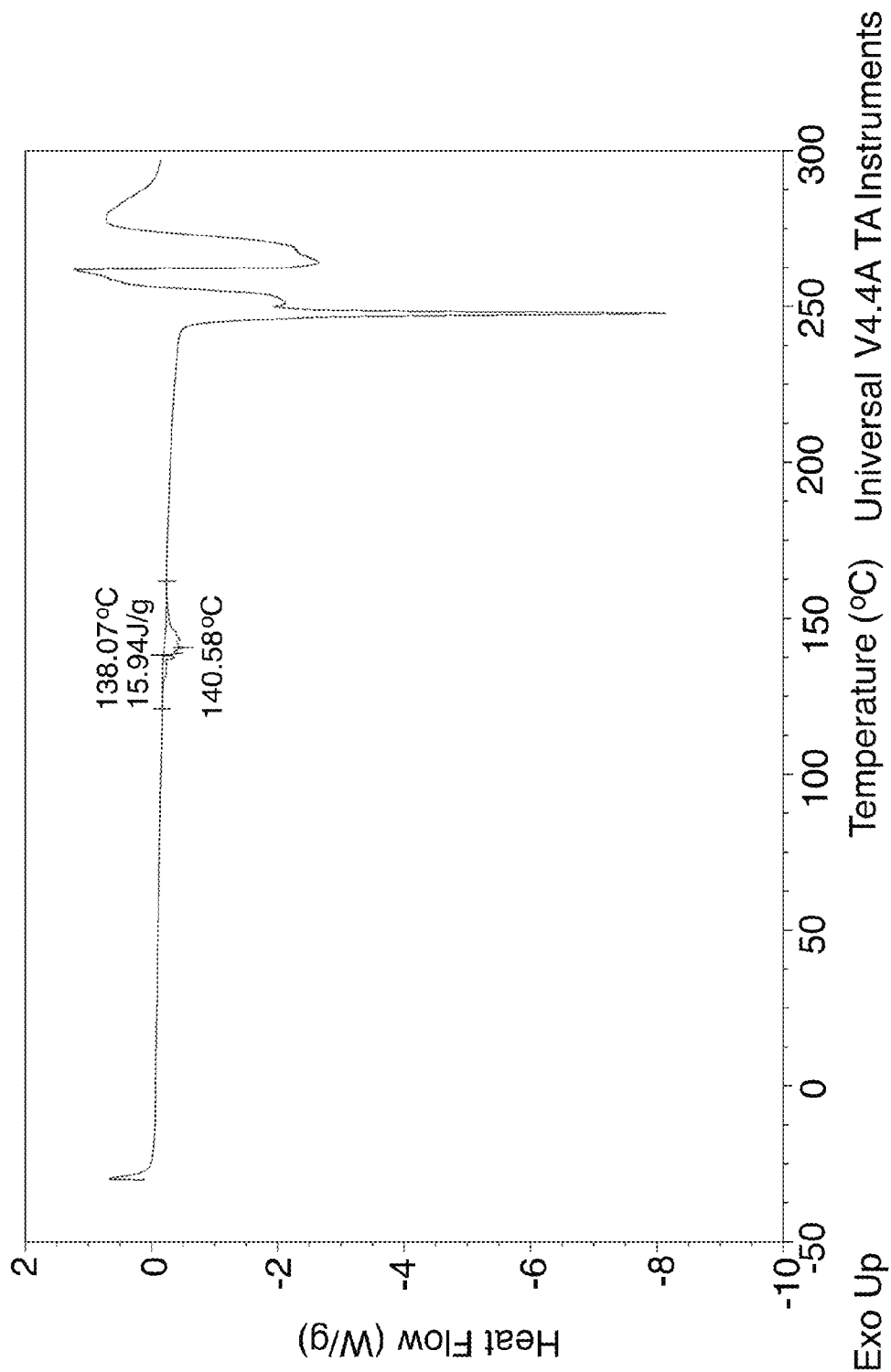
FIG. 55 depicts a DSC Thermogram of Crystalline Form B.

| Conditions[a] | Observations | Analysis | Results |
|---|---|---|---|
| freeze-drying in dioxane: water (1:1)/3d | off-white solids, aggregates, no B | XRPD | disordered A (for XRPD see FIG. 51) |
| freeze-drying in water/3 d | off-white solids, aggregates, no B | XRPD | disordered A (for XRPD see FIG. 52) |
| milling/30 Hz, 4 × 10 min | off-white solids, aggregates, no B | XRPD | disordered A (for XRPD see FIG. 53) |
| rotary evaporation in HFIPA | off-white solids, aggregates, no B | XRPD | disordered A (for XRPD see FIG. 54) |

[a]Reported times are approximate

Example 5—Preparation of Crystalline Form A

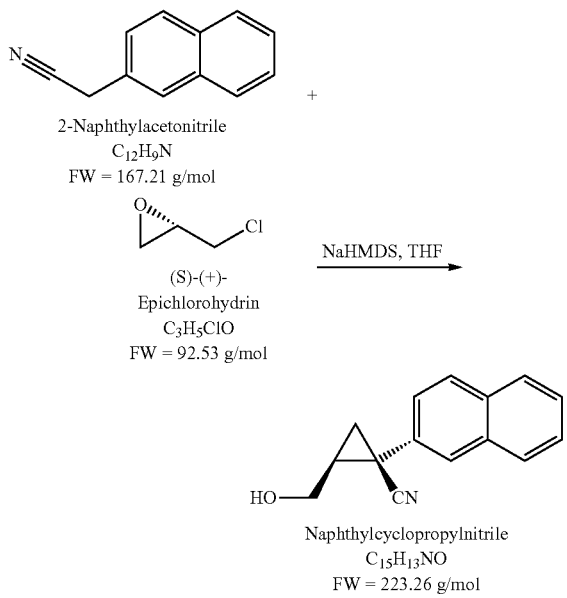

2-Naphthylacetonitrile
C₁₂H₉N
FW = 167.21 g/mol (S)-(+)-Epichlorohydrin
C₃H₅ClO
FW = 92.53 g/mol NaHMDS, THF Naphthylcyclopropylnitrile
C₁₅H₁₃NO
FW = 223.26 g/mol 1. BH₃—DMS, THF
2. TsOH, IPAc

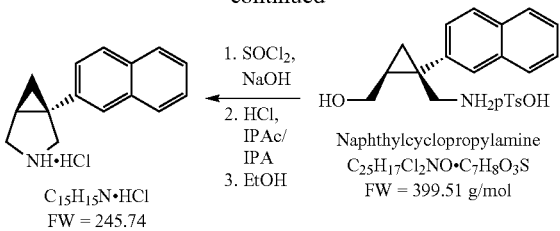

Commercially available reagents are used as received unless otherwise noted. Reactions requiring an inert atmosphere are run under nitrogen unless otherwise noted. Step 1 and 2:

| Compound | MW (g/mol) | d (g/mL) | Equivalents | Amt/mol |
|---|---|---|---|---|
| Reaction | | | | |
| 2-naphthylacetonitrile | 167.21 | NA | 1.0 mol eq (SM) | 4500 g/26.91 mol |
| (S)-(+)-epichlorohydrin | 92.52 | 3.12 | 1.30 mol eq | 3200 g/34.58 mol |
| tetrahydrofuran | 72.11 | 0.889 | 6.0 ml/g SM | 32 L |
| 2M sodium bis(trimethylsilyl)amide in THF | 2.0M | 0.916 | 2 mol eq | 24700 g/5308 mol |
| borane-dimethylsulfide | 10.0M | 0.80 | 2.5 mol eq | 6500 g/67 mol |
| Isolation | | | | |
| 2M HCl (aqueous) | 2M | NA | 11.5 ml/g SM | 57000 mL |
| isopropyl acetate | 102.13 | 0.872 | 4 mL/g SM | as required |
| water | 18.02 | 1.00 | 5 mL/g SM | as required |
| ammonia (aqueous) | NA | 0.889 | 1.5 mL/g SM | 6300 mL |
| 5% aqueous dibasic sodium phosphate | NA | NA | 4 mL/g SM | 18000 mL |
| para-toluenesulfonic acid monohydrate | 190.22 | NA | 0.93 mol eq. | 49000 g/8.34 mol |

2-naphthylacetonitrile (4500 g) is dissolved in THF (32 L), 3.2 kg of (S)-(+)-epichlorohydrin are added and the solution cooled to −16° C. A 2.0 M solution of sodium hexamethyldisilylazane in tetrahydrofuran (THF) (24.7 kg) is then added, keeping the internal temperature below −10° C. This addition requires 2 hr 45 minutes to complete. The reaction mixture is then stirred an additional six hours at approximately −15° C. after which a sample is analyzed by HPLC. While keeping the internal temperature less than 0° C., borane-dimethylsulfide (6.5 kg) is added over 36 minutes. After completion of the borane addition, the reaction mixture is slowly heated to 60° C. to reduce the nitrile to the amine. During this heat-up, an exotherm is noted which initiates at 45° C. After heating at 60° C. for two hours a sample of the reaction mixture is analyzed by HPLC. The reaction mixture is cooled to 24° C. and transferred to a solution of 2M HCl over 1 hr. The two-phase mixture is heated to 50° C. and stirred for 1 hour at this temperature followed by cooling to 29° C. The pH of the quenched reaction mixture is measured and found to be 5. Additional 2M HCl is added, the mixture heated to 50° C. and stirred for one hour, then cooled to 25° C. The pH is measured and found to be 1. Reaction workup continues by the addition of isopropyl acetate (IPAc), stirring, layer separation, and discard of the organic layer. Aqueous ammonia is added to the aqueous layer and the pH measured, which shows a pH of 8. Additional ammonia is added and the pH re-measured and found to be 8.5. Workup then continues by extraction with two extraction of the aqueous layer with IPAc. The combined organic extracts are then washed with 5% dibasic sodium phosphate in water followed by a brine wash. The resulting organic layer is partially concentrated to azeotropically dry followed by dilution with IPAc. p-Toluenesulfonic acid hydrate (4.9 kg) is then added in portions to precipitate the desired product as its pTsOH salt, which is isolated by filtration. The filtercake is washed with IPAc and then dried to a constant weight to give 5785 g of the desired product as a white solid. Yield: 54%. HPLC: 98.2%.

Step 3 and 4:

| Compound | MW (g/mol) | d (g/mL) | Equivalents | Amt/mol |
|---|---|---|---|---|
| Reaction | | | | |
| 2-naphthylcyclopropylamine-tosylate salt | 399.51 | NA | 1.0 mol eq | 5785 g/145.18 mol |
| isopropylacetate | 102.13 | 0.872 | as required | 176 L |
| thionyl chloride | 118.97 | 1.638 | 1.2 eq | 2.1 Kg/17.65 mol |
| 5M NaOH | 5.0M | NA | 6.0 mol eq. | 16.7 Kg |
| Isolation | | | | |
| magnesium sulfate | NA | NA | 0.5 g/g | 2.9 Kg |
| hydrogen chloride in isopropyl alcohol | 5.7M | NA | 1.0 mol eq. | 0.90 L |
| isopropyl alcohol | 60.1 | 0.786 | 1.5 mL/g | as required |
| Ethyl alcohol 200 (special industrial denatured) | 80.25 | 0.786 | 1.5 mL/g | as required |

Step 3:

The amine-pTsOH salt (5785 g) obtained from step 2 is suspended in IPAc (176 L) to give a slurry. Thionyl chloride (2.1 kg) is then added over one hour. Upon completion of the thionyl chloride addition the reaction mixture is stirred one additional hour and a sample is analysed by HPLC. Aqueous sodium hydroxide (5M, 6 mol equivalents) is added over one hour followed by four hours of additional stirring. The layers are allowed to settle and the pH of the aqueous layer is found to be 9. The layers are separated and the organic layer washed with 1M NaOH in water. The aqueous layers are combined and back extracted with IPAc and the initial organic layer and the back extract combined. These combined organic layers are washed with 0.5M HCl to extract (1R,5S)-1-(naphthalen-2-yl)-3-azabicyclo[3.1.0]hexane into the aqueous layer. The acidic aqueous layer is washed with a 1:1 mixture of IPAc and THF to remove color. The aqueous layer is basified with aqueous ammonia followed by extraction with IPAc. After layer separation the organic layer is washed with brine, dried over magnesium sulfate, and partially concentrated. After the concentration, hydrogen chloride in isopropyl alcohol (IPA) (1.0 mol equivalent of HCl, 0.90 L) is added to form the crude salt, which is isolated by filtration, washed with IPAc and then partially dried. The wet cake is refluxed in IPAc. The crude salt is refluxed in IPA and the solids isolated by filtration, washed with IPA, and then dried. >99.5 HPLC area percent and 97.7% chiral area percent purity. 1759 g of the desired product.

Step 4:

The crude (1R,5S)-1-(naphthalen-2-yl)-3-azabicyclo[3.1.0]hexane hydrochloride (1753 g) obtained from step 3 is dissolved in 20 volumes of hot ethanol (70° C.) and then filtered via an inline filter as a polish filtration. The dissolution vessel and the inline filter and transfer line are then rinsed with additional hot ethanol (61° C.) and the rinse combined with the filtrate. The combined filtrate and washes are partially concentrated in vacuo to approximately 11.5 total volumes (relative to crude (1R,5S)-1-(naphthalen-2-yl)-3-azabicyclo[3.1.0]hexane hydrochloride input) and then reheated to redissolve the solids. The solution is cooled to 65° C. and seed crystals added as slurry in ethanol. After stirring at approx. 65° C. to develop the seed bed, the slurry is cooled to room temperature. The resulting solids are isolated by filtration, the filtercake is washed with ethanol, and the washed solids dried. A total of 1064 g of tan product is obtained. >99.5% for both chiral and achiral HPLC.

Step 5:

The (1R,5S)-1-(naphthalen-2-yl)-3-azabicyclo[3.1.0]hexane hydrochloride (1064 g) obtained from step 4 is dissolved in 10.7 L of water while warming to 35° C. Once all solids dissolve, the aqueous solution is washed with 1:1 THF:IPAc to remove most of the color. After the wash, aqueous ammonia is added to the aqueous layer and (1R,5S)-1-(naphthalen-2-yl)-3-azabicyclo[3.1.0]hexane is extracted into IPAc. The organic layer is dried over magnesium sulfate and then concentrated in vacuo to give an off-white solid. The solid is dissolved in IPA and transferred to a 22 L 3-neck round bottom flask via inline filtration. Filtered hydrogen chloride in IPA is then added to reform the salt, which is isolated via filtration. The filtercake is washed with IPA and then dried to give 926 g of (1R,5S)-1-(naphthalen-2-yl)-3-azabicyclo[3.1.0]hexane hydrochloride as a slightly off-white solid.

Figure 35:
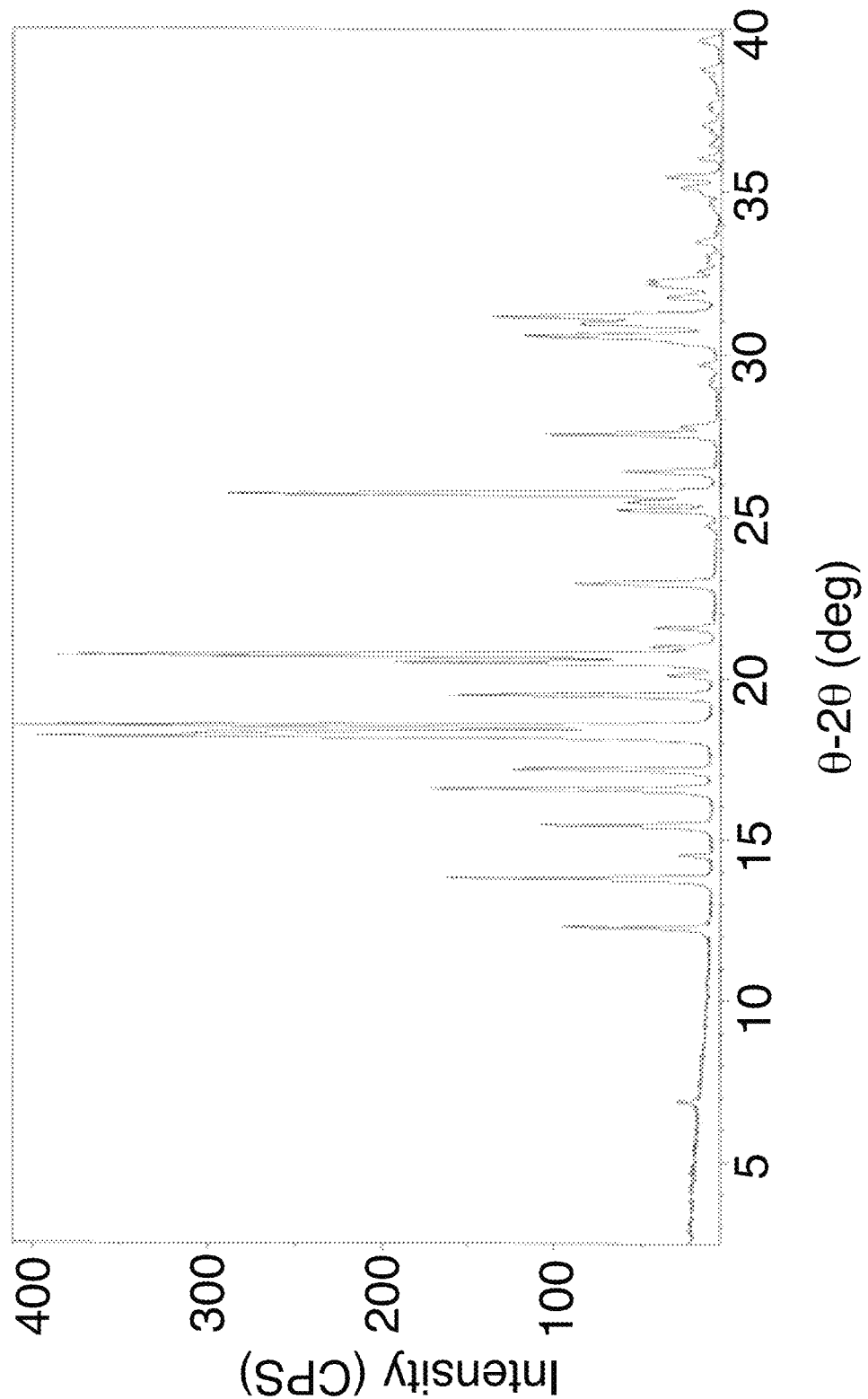
FIG. 35 depicts an XRPD pattern of Crystalline Form A.

An XRPD of the product is shown in FIG. 35 and is consistent with Crystalline Form A. The XRPD pattern is collected with a PANalytical X'Pert PRO MPD diffractometer using an incident beam of Cu radiation produced using an Optix long, fine-focus source. An elliptically graded multilayer mirror is used to focus Cu Kα X-rays through the specimen and onto the detector. Prior to the analysis, a silicon specimen (NIST SRM 640d) is analyzed to verify the observed position of the Si 111 peak is consistent with the NIST-certified position. A specimen of the sample is sandwiched between 3-μm-thick films and analyzed in transmission geometry. A beam-stop, short antiscatter extension, and an anti-scatter knife edge are used to minimize the background generated by air. Soller slits for the incident and diffracted beams are used to minimize broadening from axial divergence. The diffraction pattern is collected using a scanning position-sensitive detector (X'Celerator) located 240 mm from the specimen and Data Collector software v. 2.2b. Data acquisition parameters are: Panalytical X-Pert Pro MPD PW3040 Pro, X-ray Tube: Cu (1.54059 Å), Voltage: 45 kV, Amperage: 40 mA, Scan Range: 1.00-39.99 °2θ, Step Size: 0.017 °2θ, Collection Time: 717 s, Scan Speed: 3.3°/min., Slit: DS: 1/2°, SS: null, Revolution Time: 1.0 s, Mode: Transmission.

Figure 36:
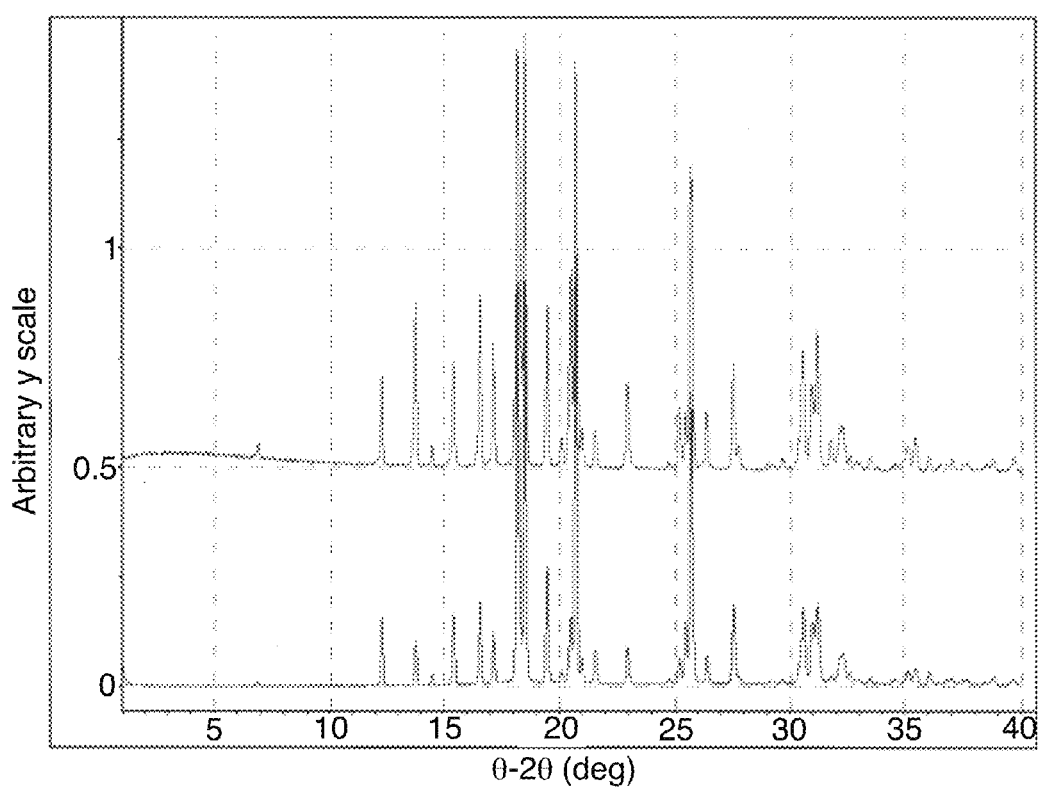
FIG. 36 depicts an XRPD pattern comparison of (1R,5S)-1-(naphthalen-2-yl)-3-azabicyclo[3.1.0]hexane hydrochloride from Examples 1 and 5 (top: Example 5; bottom: Example 1) (patterns are offset along the y-axis for comparison).

FIG. 36 overlays the XRPD patterns from FIG. 1 and FIG. 35. There are some differences in relative peak intensities that are likely due to preferred orientation (PO). PO is the tendency for crystals, usually plates or needles, to pack against each other with some degree of order. PO can affect peak intensities, but not peak positions, in XPRD patterns.

Figure 37:
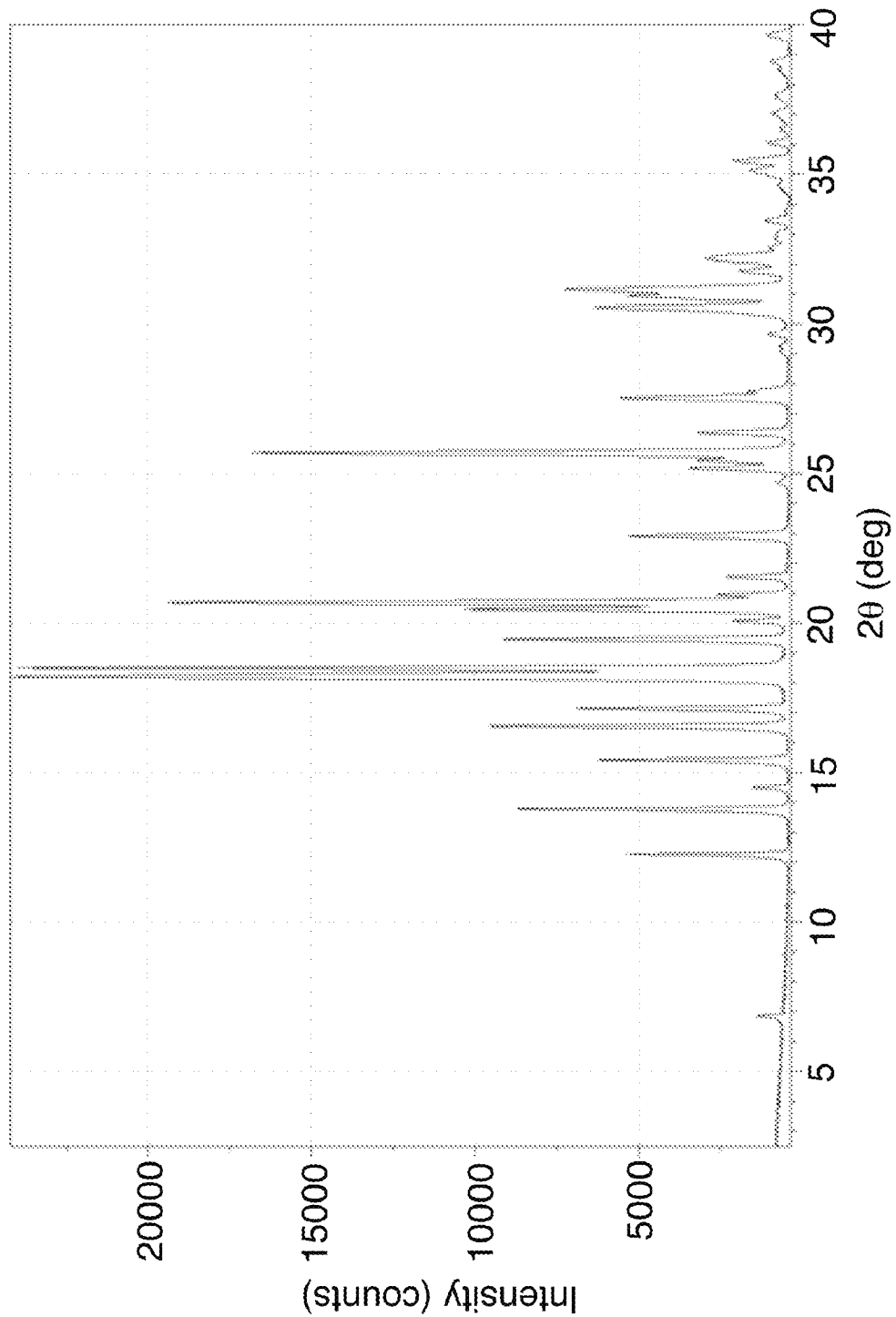
FIG. 37 depicts an XRPD pattern of Crystalline Form A collected with Cu Kα radiation.

An XRPD of the product after long-term storage is shown in FIG. 37 and is consistent with Crystalline Form A. The XRPD pattern is collected with a PANalytical X'Pert PRO MPD diffractometer using an incident beam of Cu radiation produced using an Optix long, fine-focus source. An elliptically graded multilayer mirror is used to focus Cu Kα X-rays through the specimen and onto the detector. Prior to the analysis, a silicon specimen (NIST SRM 640e) is analyzed to verify the observed position of the Si 111 peak is consistent with the NIST-certified position. A specimen of the sample is sandwiched between 3-μm-thick films and analyzed in transmission geometry. A beam-stop, short antiscatter extension, and antiscatter knife edge are used to minimize the background generated by air. Soller slits for the incident and diffracted beams are used to minimize broadening from axial divergence. The diffraction pattern is collected using a scanning position-sensitive detector (X'Celerator) located 240 mm from the specimen and Data Collector software v. 2.2b. Data acquisition parameters are: Panalytical X-Pert Pro MPD PW3040 Pro, X-ray Tube: Cu (1.54059 Å), Voltage: 45 kV, Amperage: 40 mA, Scan Range: 1.00-39.99 °2θ, Step Size: 0.017 °2θ, Collection Time: 719 s, Scan Speed: 3.3°/min., Slit: DS: 1/2°, SS: null, Revolution Time: 1.0 s, Mode: Transmission.

Figure 38:
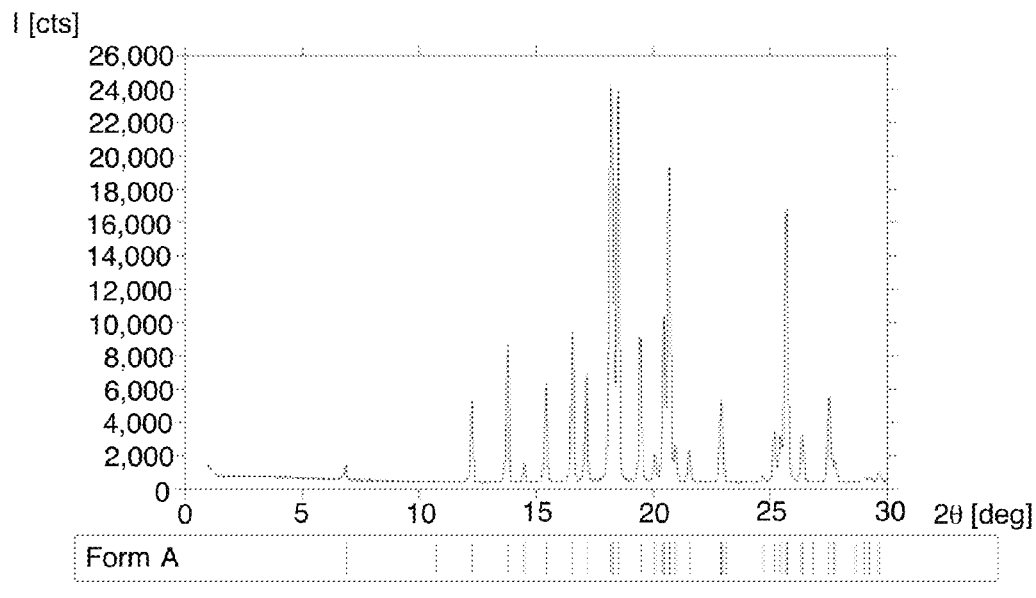
FIG. 38 depicts an indexing result for the XRPD pattern depicted in FIG. 37 collected with Cu Kα radiation.
Figure 39:
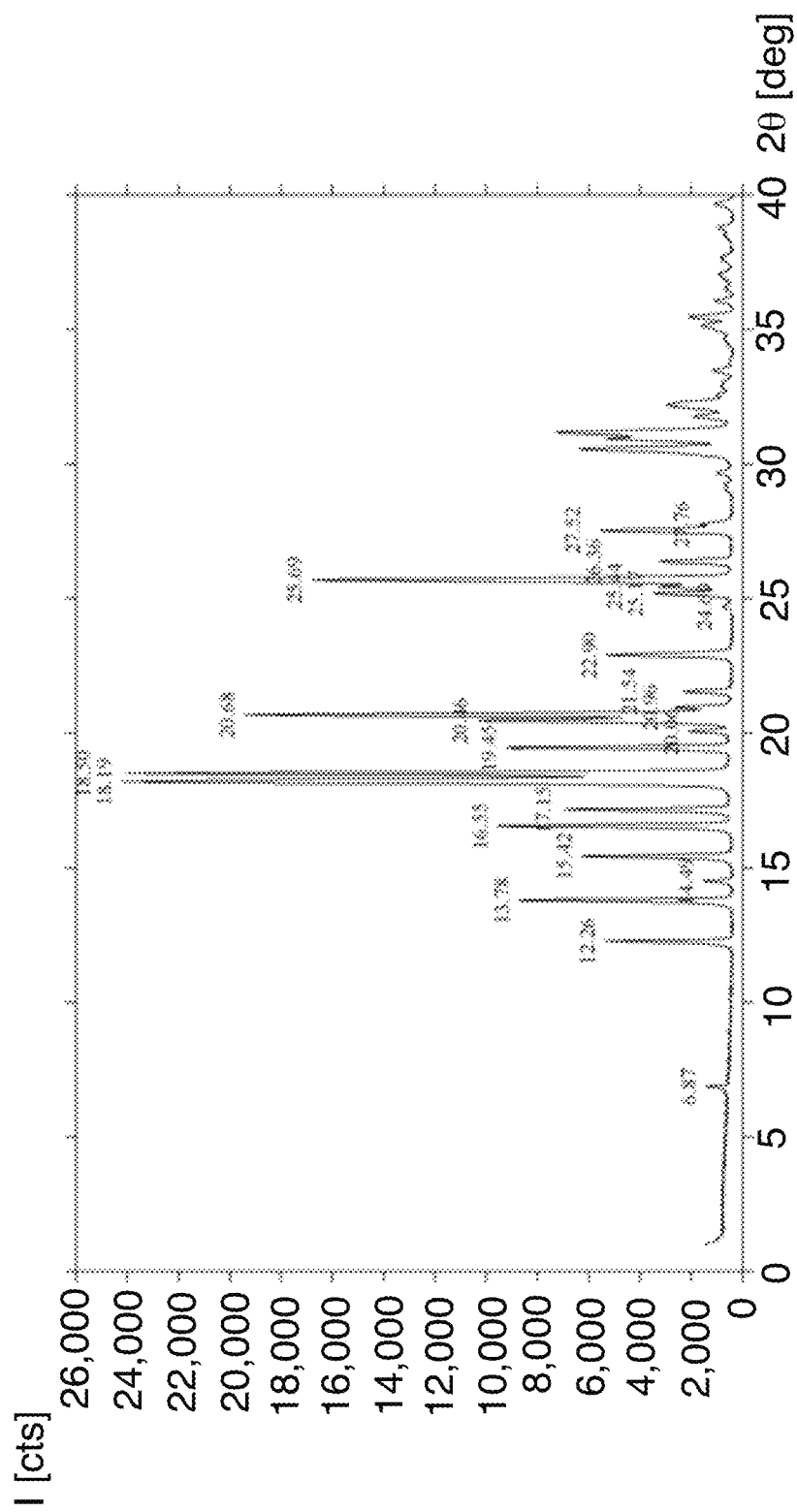
FIG. 39 depicts observed peaks for the XPRD pattern depicted in FIG. 37 collected with Cu Kα radiation.

One PANalytical pattern is analyzed for Crystalline Form A, and preferred orientation and particle statistic effects are assessed through comparison with additional XRPD patterns analyzed using alternate geometry in addition to a calculated XRPD pattern from single crystal analysis. An indexing result for the XRPD shown in FIG. 37 collected with Cu Kα radiation is shown in FIG. 38. The XRPD pattern is indexed using X'Pert High Score Plus 2.2a (2.2.1). Observed peaks are shown in FIG. 39 and listed in Table C in formula 1.32 above, representative peaks are listed in Table B in formula 1.25 above, and characteristic peaks are listed in Table A in formula 1.16 above.

Example 6—Preparation of Crystals of Form B

Figure 47:
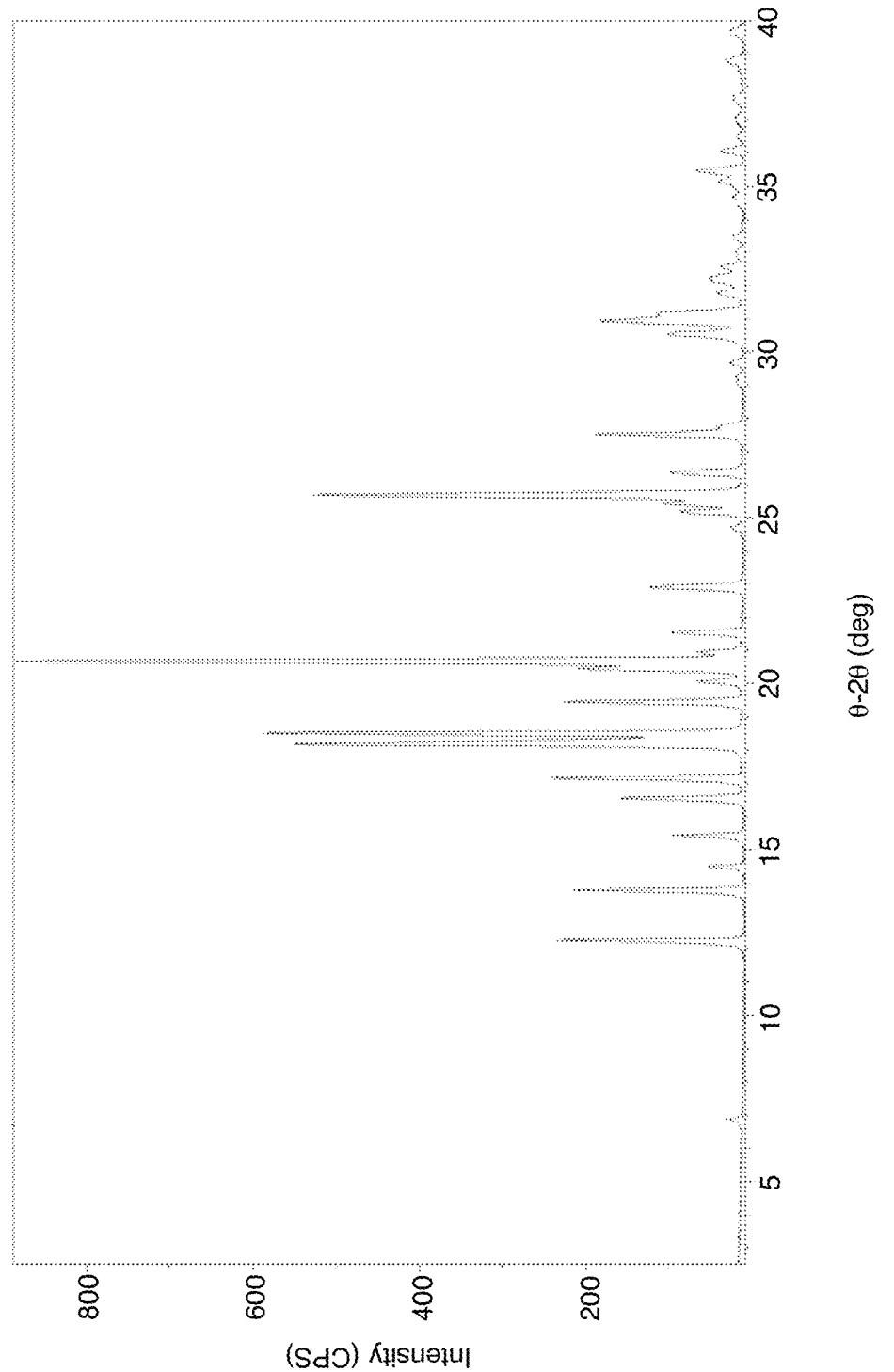
FIG. 47 depicts an XRPD pattern of Crystalline Form A.

Example 6a 558.9 mg of Crystalline Form A from Example 5 above is slurried in 5 mL dichloromethane. The preparation is stirred (300 RPM) in a sealed vial at ambient temperature for 16 days. White solids are isolated by vacuum filtration, rinsed with 1 mL of dichloromethane, and briefly dried under nitrogen. Product is Crystalline Form A. An XRPD pattern of the product is in FIG. 47. The XRPD pattern is collected with a PANalytical X'Pert PRO MPD diffractometer using an incident beam of Cu radiation produced using an Optix long, fine-focus source. An elliptically graded multilayer mirror is used to focus Cu Kα X-rays through the specimen and onto the detector. Prior to the analysis, a silicon specimen (NIST SRM 640e) is analyzed to verify the observed position of the Si 111 peak is consistent with the NIST-certified position. A specimen of the sample is sandwiched between 3-μm-thick films and analyzed in transmission geometry. A beam-stop, short antiscatter extension, and an antiscatter knife edge are used to minimize the background generated by air. Soller slits for the incident and diffracted beams are used to minimize broadening from axial divergence. Diffraction patterns are collected using a scanning position-sensitive detector (X'Celerator) located 240 mm from the specimen and Data Collector software v. 2.2b. Data acquisition parameters are: Panalytical X-Pert Pro MPD PW3040 Pro, X-ray Tube: Cu (1.54059 Å), Voltage: 45 kV, Amperage: 40 mA, Scan Range: 1.00-39.99 °2θ, Step Size: 0.017 °2θ, Collection Time: 720 s, Scan Speed: 3.2°/min., Slit: DS: 1/2°, SS: null, Revolution Time: 1.0 s, Mode: Transmission.

Example 6b 34.3 mg of Crystalline Form A from Example 6a is contacted with 1 mL of water. The sample is sonicated until solids dissolve. The sample is capped and left at ambient temperature until nucleation is observed, within one day. Singles are isolated from the bulk sample for analysis.

Data Collection: A colorless plate of $C_{15}H_{16}ClN$ [$C_{15}H_{16}N$, Cl], having approximate dimensions of 0.31× 0.21×0.09 mm, is mounted on a nylon loop in random orientation. Preliminary examination and data collection are performed with Cu Kα radiation (λ=1.54178 Å) on a Rigaku Rapid II diffractometer equipped with confocal optics. Refinements are performed using SHELX2014 (Sheldrick, G. M. *Acta Cryst.* 2015, C71, 3-8). Cell constants and an orientation matrix for data collection are obtained from least-squares refinement using the setting angles of 22958 reflections in the range 2°<θ<26°. From the systematic presence of the following conditions: h00 h=2n; 0k0 k=2n; 00ll=2n, and from subsequent least-squares refinement, the space group is determined to be $P2_12_12_1$ (no. 19). The data are collected to a maximum diffraction angle (2θ) of 144.79°, at a temperature of 100 K.

Data Reduction: Frames are integrated with HKL3000 (Otwinowski, Z.; Minor, W. *Methods Enzymol.* 1997, 276, 307). A total of 22958 reflections are collected, of which 2415 are unique. Lorentz and polarization corrections are applied to the data. The linear absorption coefficient is 2.422 mm$^{-1}$ for Cu Kα radiation. An empirical absorption correction using SCALEPACK (Otwinowski, Z.; Minor, W. *Methods Enzymol.* 1997, 276, 307) is applied. Transmission coefficients range from 0.753 to 0.976. A secondary extinction correction is applied (Sheldrick, G. M. *Acta Cryst.* 2015, C71, 3-8). The final coefficient, refined in least-squares, is 0.0055(8) (in absolute units). Intensities of equivalent reflections are averaged. The agreement factor for the averaging is 4.95% based on intensity.

Structure Solution and Refinement: The structure is solved by direct methods using SHELXS-97 (Sheldrick, G. M. *Acta Cryst.* 2015, C71, 3-8). The remaining atoms are located in succeeding difference Fourier syntheses. Hydrogen atoms are included in the refinement but restrained to ride on the atom to which they are bonded. The structure is refined in full-matrix least-squares by minimizing the function:

$$\Sigma w(|F_o|^2 - |F_c|^2)^2$$

The weight w is defined as $1/[\sigma^2(F_o^2) + (0.0437P)^2 + (2.1802P)]$, where $P=(F_o^2 + 2F_c^2)/3$. Scattering factors are taken from the "International Tables for Crystallography" (International Tables for Crystallography, Vol. C, Kluwer Academic Publishers: Dordrecht, the Netherlands, 1992, Tables 4.2.6.8 and 6.1.1.4). Of the 2415 reflections used in the refinements, only the reflections with $F_o^2 > 2\sigma(F_o^2)$ are used in calculating the fit residual, R. A total of 2372 reflections are used in the calculation. The final cycle of refinement includes 155 variable parameters and converges with unweighted and weighted agreement factors of:

$$R = \Sigma|F_o - F_c|/\Sigma F_o = 0.0453$$

$$R_w = \sqrt{(\Sigma w(F_o^2 - F_c^2)^2 / \Sigma w(F_o^2)^2)} = 0.1224$$

The standard deviation of an observation of unit weight (goodness of fit) is 1.150. The highest peak in the final difference Fourier has a height of 0.318 e/Å$^3$. The minimum negative peak has a height of −0.313 e/Å$^3$.

Calculated X-ray Powder Diffraction (XRPD) Pattern: A calculated XRPD pattern is generated for Cu radiation using Mercury (Macrae, C. F.; Edgington, P. R.; McCabe, P.; Pidcock, E.; Shields, G. P.; Taylor, R.; Towler, M.; and van de Streek, J., *J. Appl. Cryst.*, 2006, 39, 453-457) and the atomic coordinates, space group, and unit cell parameters from the single crystal structure. Because the single crystal data are collected at low temperatures (100 K), peak shifts may be evident between the pattern calculated from low temperature data and the room temperature experimental powder diffraction pattern, particularly at high diffraction angles. The calculated XRPD pattern is adjusted to room temperature using the previously obtained unit cell parameters from XRPD indexing.

Atomic Displacement Ellipsoid and Packing Diagrams: The atomic displacement ellipsoid diagram is prepared using Mercury (Macrae, C. F.; Edgington, P. R.; McCabe, P.; Pidcock, E.; Shields, G. P.; Taylor, R.; Towler, M.; and van de Streek, J., *J. Appl. Cryst.*, 2006, 39, 453-457). Atoms are represented by 50% probability anisotropic thermal ellipsoids. Packing diagrams and additional figures are prepared using Mercury. Hydrogen bonding is represented as dashed lines. Assessment of chiral centers is performed with PLATON (Spek, A. L. PLATON. Molecular Graphics Program. Utrecht University, Utrecht, The Netherlands, 2008. Spek, A. L., *J. Appl. Cryst.* 2003, 36, 7). Absolute configuration is evaluated using the specification of molecular chirality rules (Cahn, R. S.; Ingold, C; Prelog, V. *Angew. Chem. Intern. Ed. Eng.*, 1966, 5, 385 and Prelog, V., Helmchen, G. Angew. Chem. Intern. Ed. Eng., 1982, 21, 567).

Results: The orthorhombic cell parameters and calculated volume are: a=5.9055(2) Å, b=7.4645(3) Å, c=29.1139(13) A (α=β=γ=90°), V=1283.39(9) Å$^3$. The formula weight of the asymmetric unit in Crystalline Form B is 245.74 g mol$^{-1}$ with Z=4, resulting in a calculated density of 1.272 g cm$^{-3}$. The space group is determined to be $P2_12_12_1$ (no. 19). A summary of the crystal data and crystallographic data collection parameters are provided in Table 15 below. The space group and unit cell parameters are consistent with those obtained for Form B by XRPD indexing.

The R value is 0.0453 (4.53%).

Figure 24:
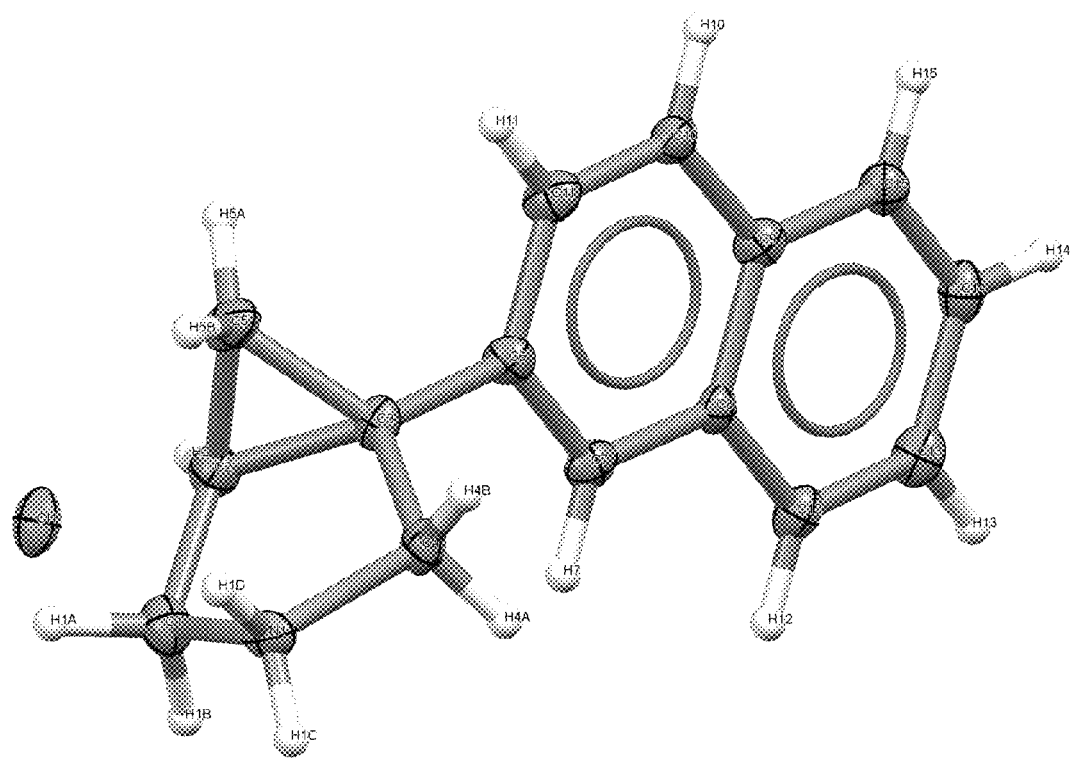
FIG. 24 depicts an atomic displacement ellipsoid drawing for Crystalline Form B (atoms are represented by 50% probability anisotropic thermal ellipsoids).

An atomic displacement ellipsoid drawing of Crystalline Form B is shown in FIG. 24.

The asymmetric unit shown in FIG. 24 contains one protonated (1R,5S)-1-(naphthalen-2-yl)-3-azabicyclo[3.1.0]hexane molecule and one chloride counter ion.

Figure 25:
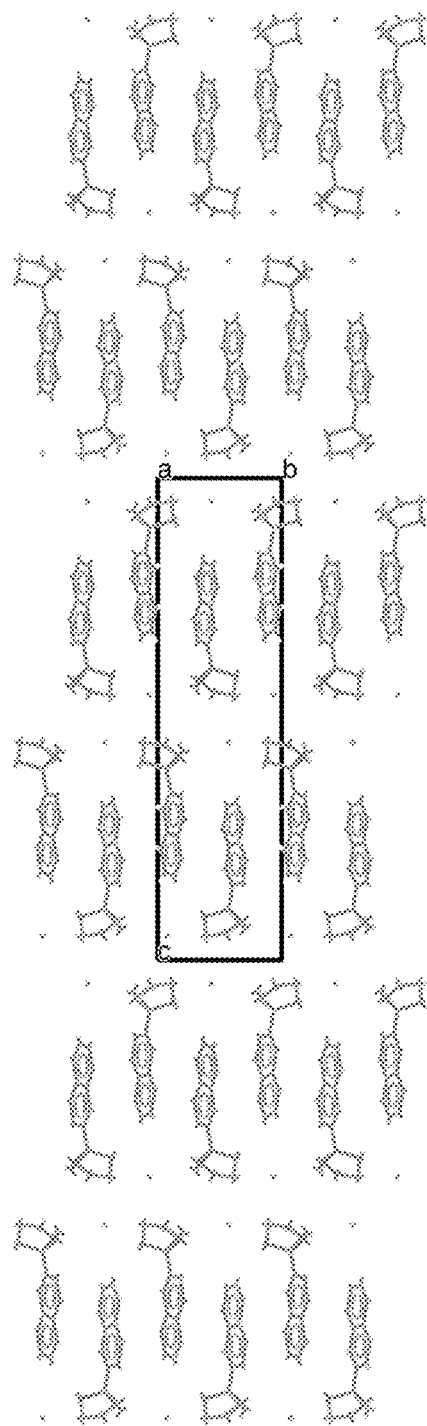
FIG. 25 depicts a packing diagram of Crystalline Form B viewed along the crystallographic a axis.
Figure 26:
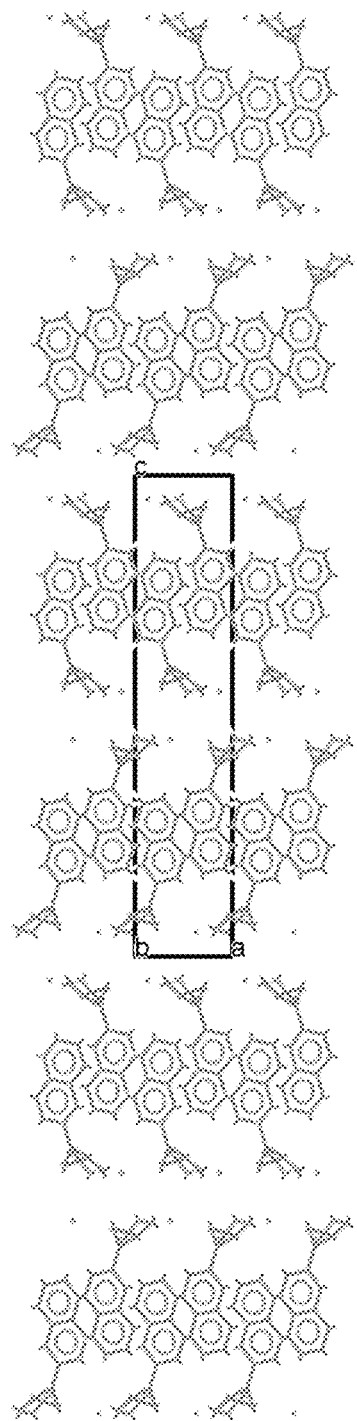
FIG. 26 depicts a packing diagram of Crystalline Form B viewed along the crystallographic b axis.
Figure 27:
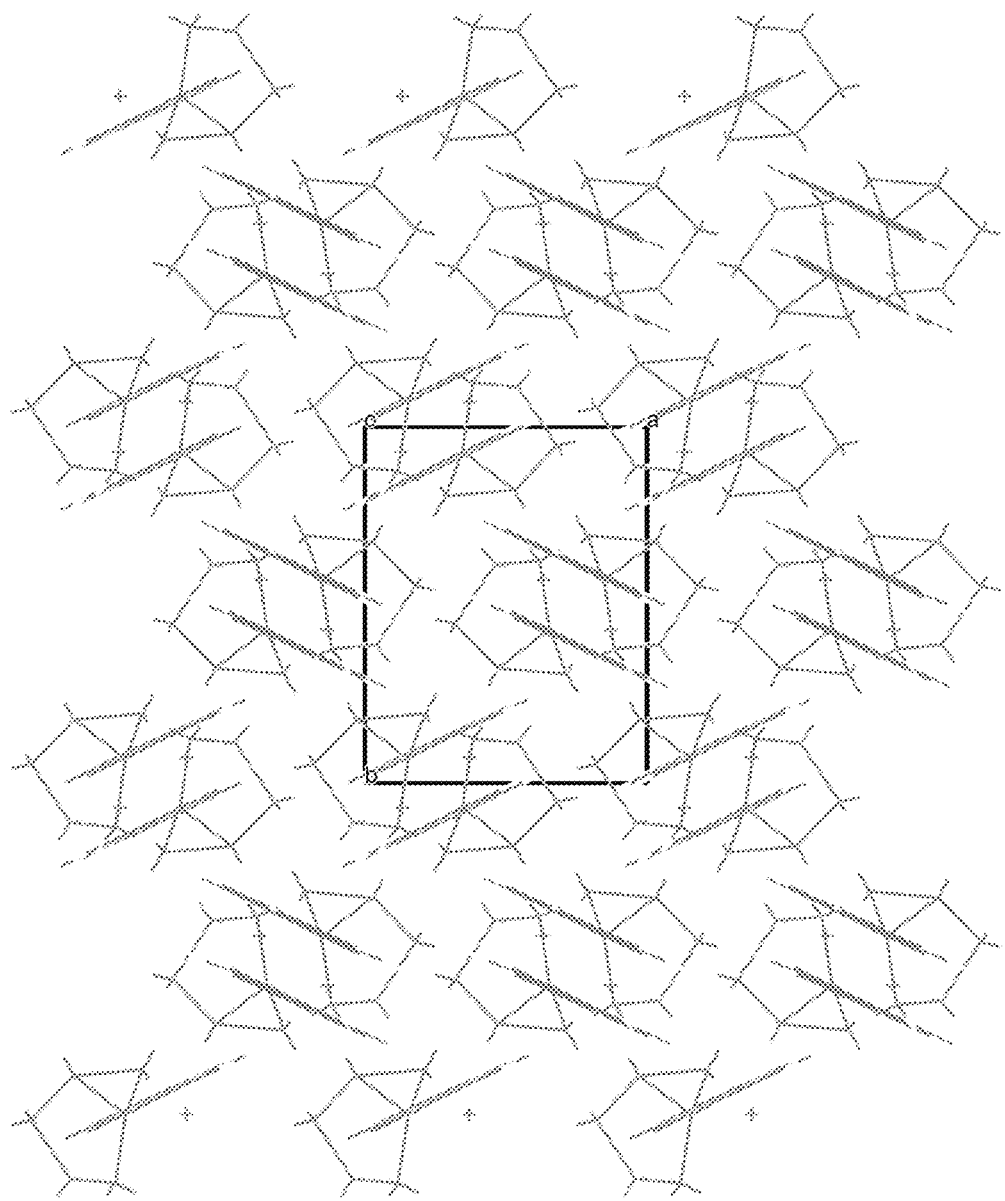
FIG. 27 depicts a packing diagram of Crystalline Form B viewed along the crystallographic c axis.
Figure 28:
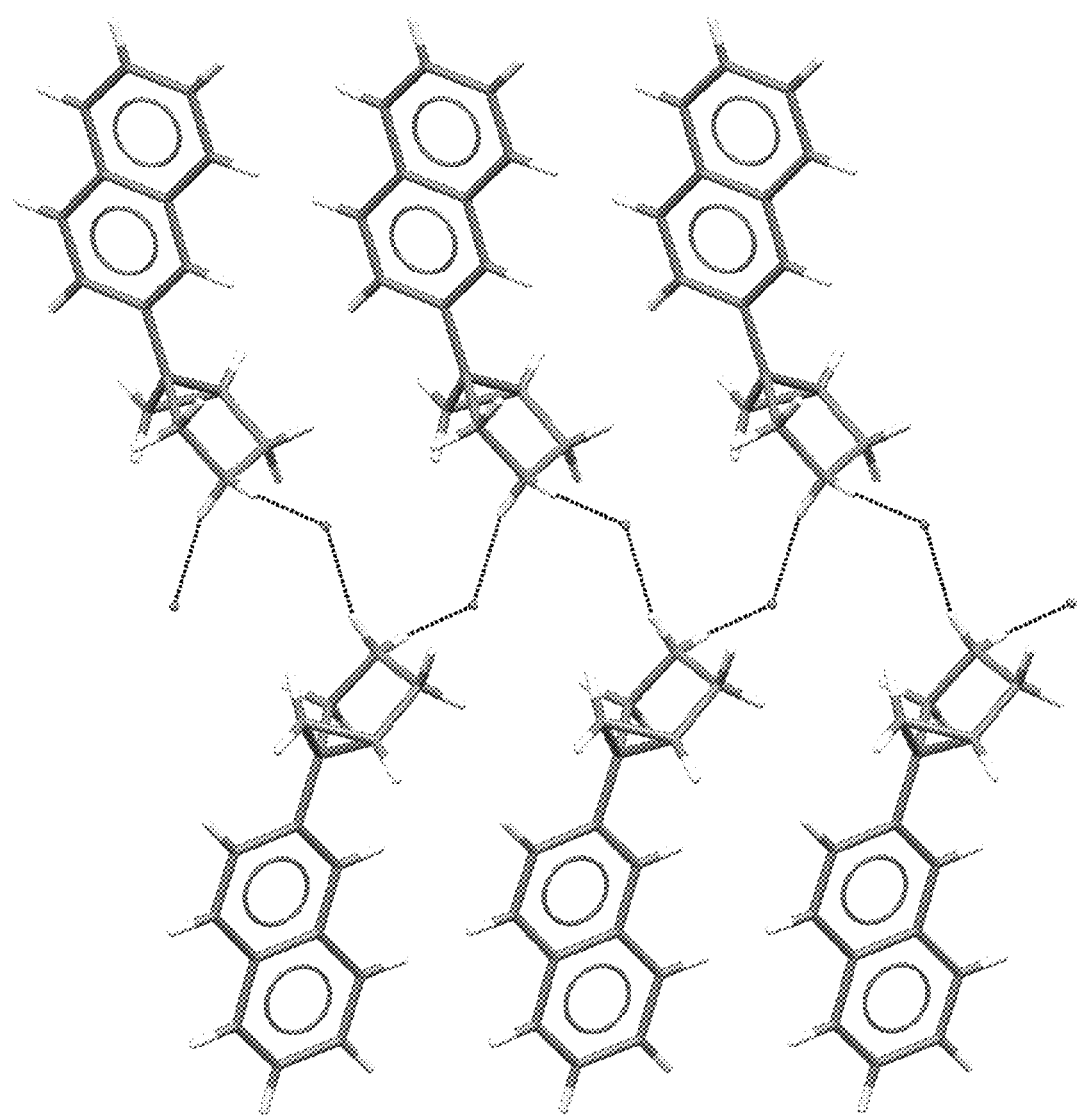
FIG. 28 depicts hydrogen bonding in the structure of Crystalline Form B.

Packing diagrams viewed along the a, b, and c crystallographic axes are shown in FIGS. 25-27, respectively. Hydrogen bonding occurs from the amine to the chloride, forming one-dimensional hydrogen bonded helical chains along the a axis, shown in FIG. 28.

Figure 29:
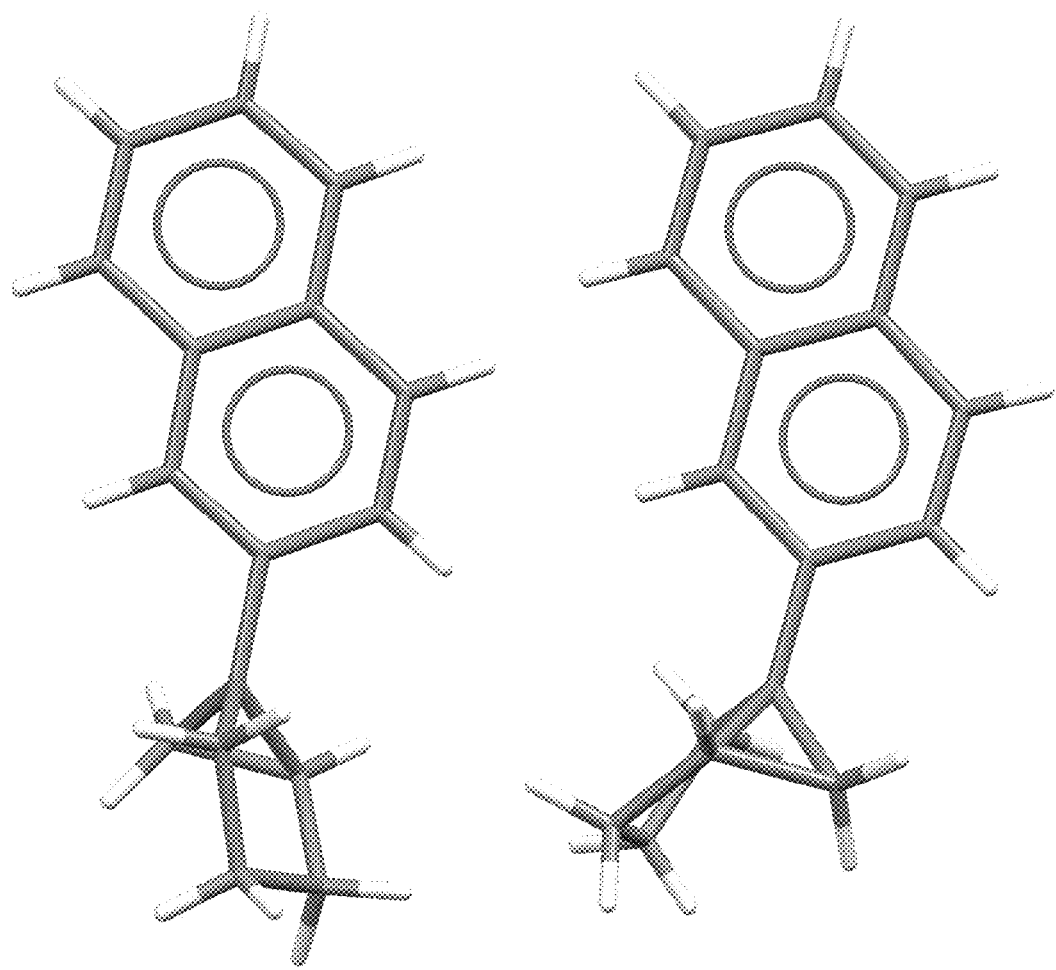
FIG. 29 depicts the molecular conformations of (1R,5S)-1-(naphthalen-2-yl)-3-azabicyclo[3.1.0]hexane in the structures of Crystalline Forms A and B (left: (1R,5S)-1-(naphthalen-2-yl)-3-azabicyclo[3.1.0]hexane in the structure of Crystalline Form A; right: (1R,5S)-1-(naphthalen-2-yl)-3-azabicyclo[3.1.0]hexane in the structure of Crystalline Form B).
Figure 30:
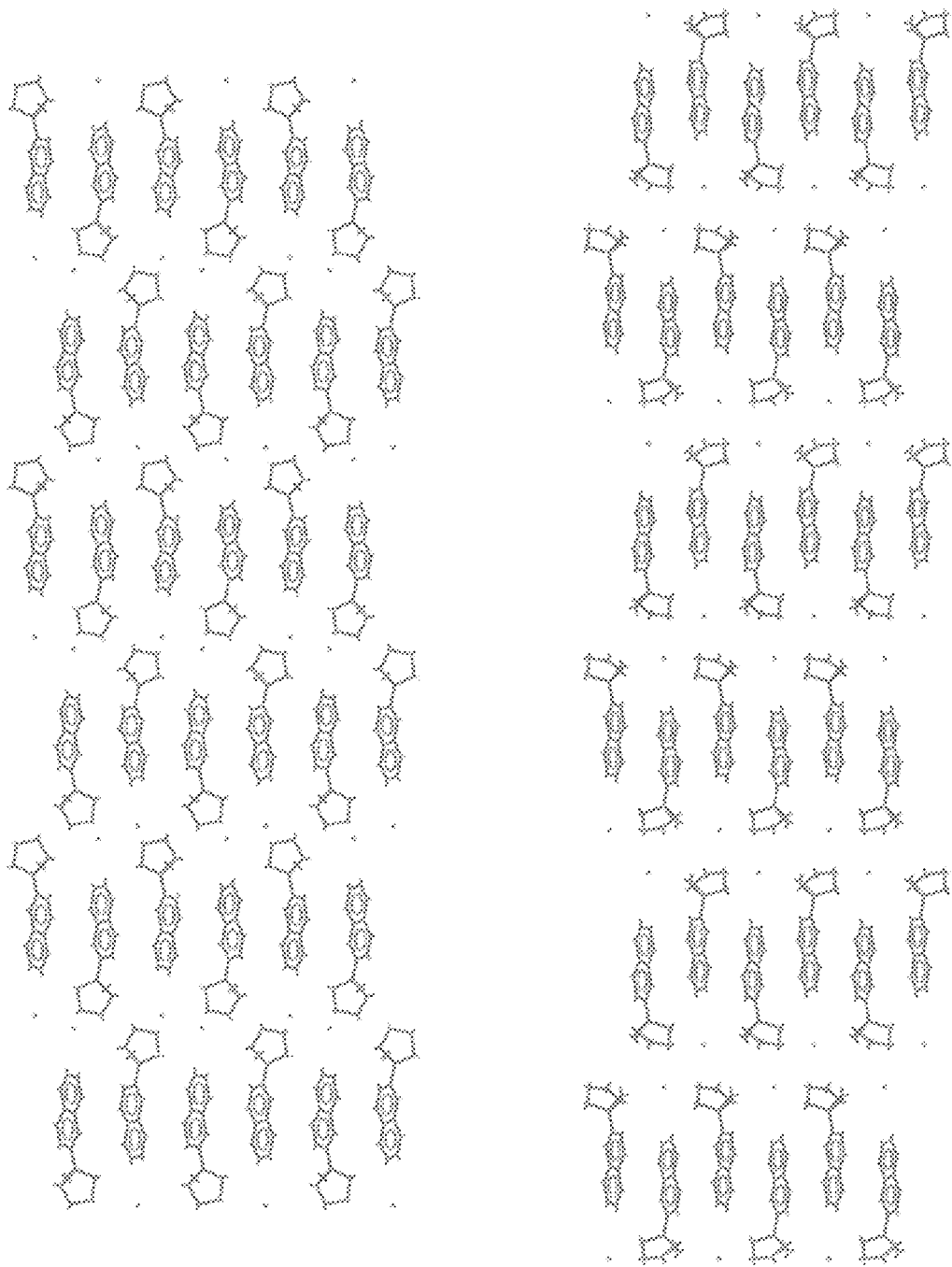
FIG. 30 depicts a packing diagram of Crystalline Forms A and B viewed along the crystallographic a axis (left: packing of Crystalline Form A; right: packing of Crystalline Form B).
Figure 31:
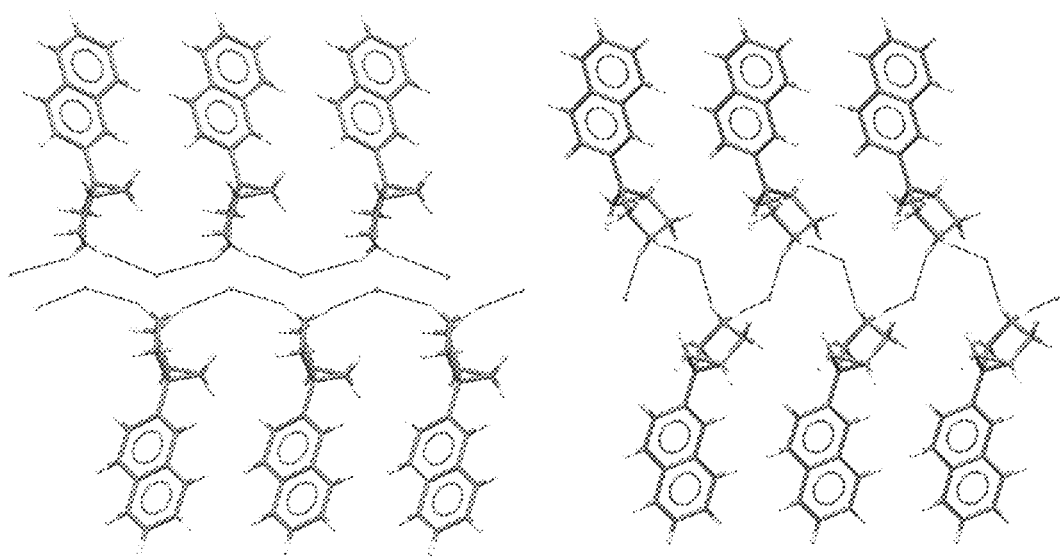
FIG. 31 depicts hydrogen bonding in the structures of Crystalline Forms A and B (left: hydrogen bonding in the structure of Crystalline Form A; right: hydrogen bonding in the structure of Form B).

The molecular conformation of the (1R,5S)-1-(naphthalen-2-yl)-3-azabicyclo[3.1.0]hexane molecules in the structure of Crystalline Form B is compared with the molecular conformation observed in the structure of Crystalline Form A in FIG. 29, and the packing of the two forms viewed along the a axis is compared in FIG. 30. The hydrogen bonding in the structures of Crystalline Forms A and B is shown in FIG. 31. Adjacent molecules are linked through chloride ions in the Crystalline Form A hydrogen bonding forming straight chains down the a axis. The amine groups of adjacent molecules are too far apart in the Crystalline Form B packing to be linked in a similar manner, and instead the hydrogen bonding in Crystalline Form B forms a helical chain.

The absolute structure can be determined through an analysis of anomalous X-ray scattering by the crystal. A refined parameter x, known as the Flack parameter (Flack, H. D.; Bernardinelli, G., *Acta Cryst.* 1999, A55, 908; Flack, H. D., Bernardinelli, G., *J. Appl. Cryst.* 2000, 33, 1143, Flack, H. D., *Acta Cryst.* 1983, A39, 876; Parsons, S.; Flack, H. D.; Wagner, T., *Acta Cryst.* 2013, B69, 249-259), encodes the relative abundance of the two components in an inversion twin. The structure contains a fraction 1−x of the model being refined, and x of its inverse. Provided that a low standard uncertainty is obtained, the Flack parameter should be close to 0 if the solved structure is correct, and close to 1 if the inverse model is correct. The measured Flack parameter for the structure of Crystalline Form B shown in FIG. 24 is 0.010 with a standard uncertainty of 0.010, which indicates strong inversion-distinguishing power. The compound is enantiopure and the absolute configuration can be assigned directly from the crystal structure.

Refinement of the Flack parameter (x) does not result in a quantitative statement about the absolute structure assignment. However, an approach applying Bayesian statistics to Bijvoet differences can provide a series of probabilities for different hypotheses of the absolute structure (Hooft, R. W. W.; Strayer, L. H.; and Spek, A. L., *J. Appl. Cryst.*, 2008, 41, 96-103 and Bijvoet, J. M.; Peerdeman, A. F.; van Bommel, A. J., *Nature*, 1951, 168, 271). This analysis provides a Flack equivalent (Hooft) parameter in addition to probabilities that the absolute structure is either correct, incorrect or a racemic twin. For the current data set the Flack equivalent (Hooft) parameter is determined to be −0.001(7), the probability that the structure is correct is 1.000, the probability that the structure is incorrect is 0.000 and the probability that the material is a racemic twin is 0.000.

This structure contains two chiral centers located at C2 and C3 (refer to FIG. 24), which bond in the S and R configuration, respectively.

Figure 32:
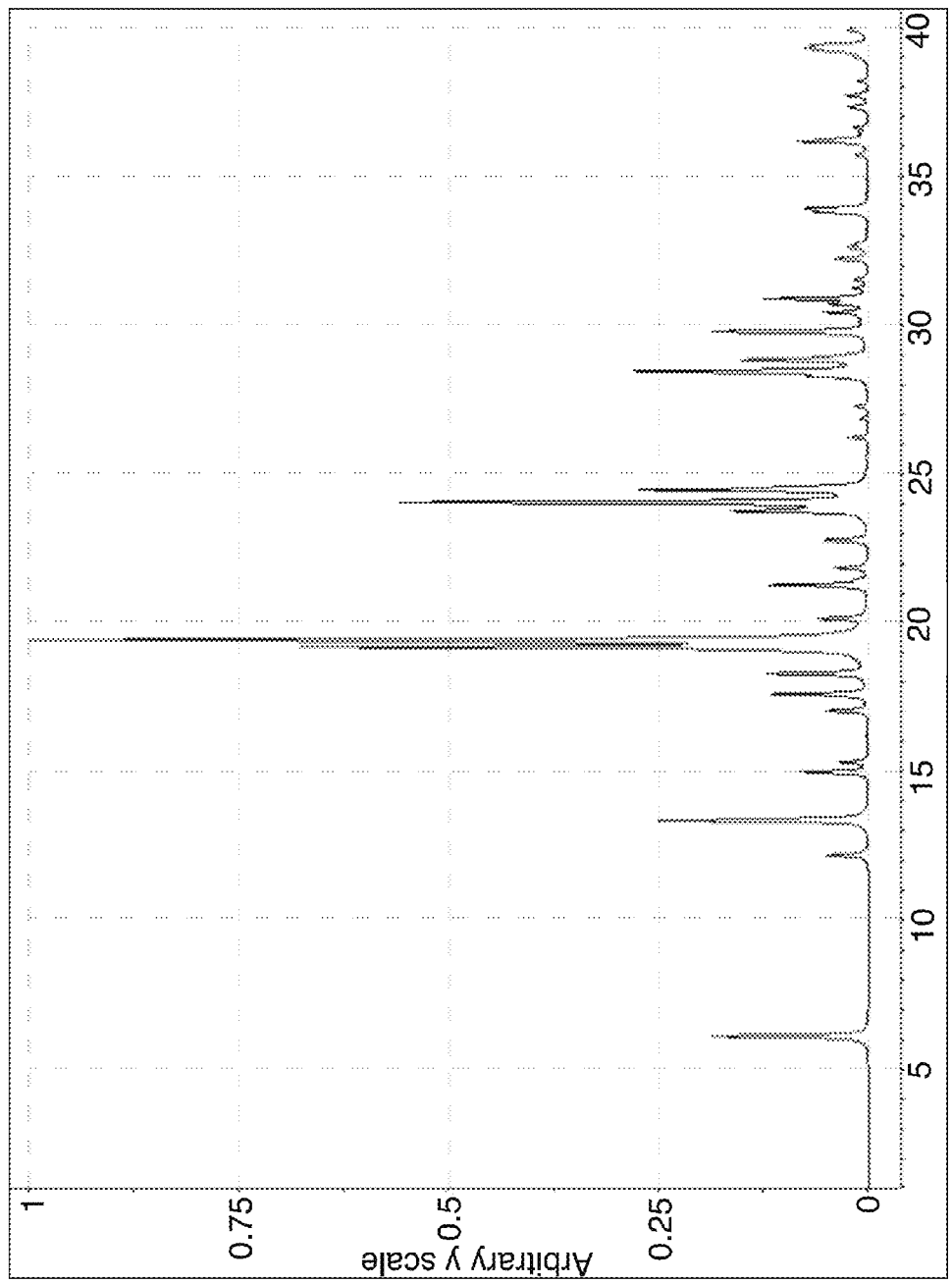
FIG. 32 depicts a calculated X-ray powder pattern of Crystalline Form B.

FIG. 32 shows a calculated XRPD pattern of Crystalline Form B, generated from the single crystal structure.

Figure 33:
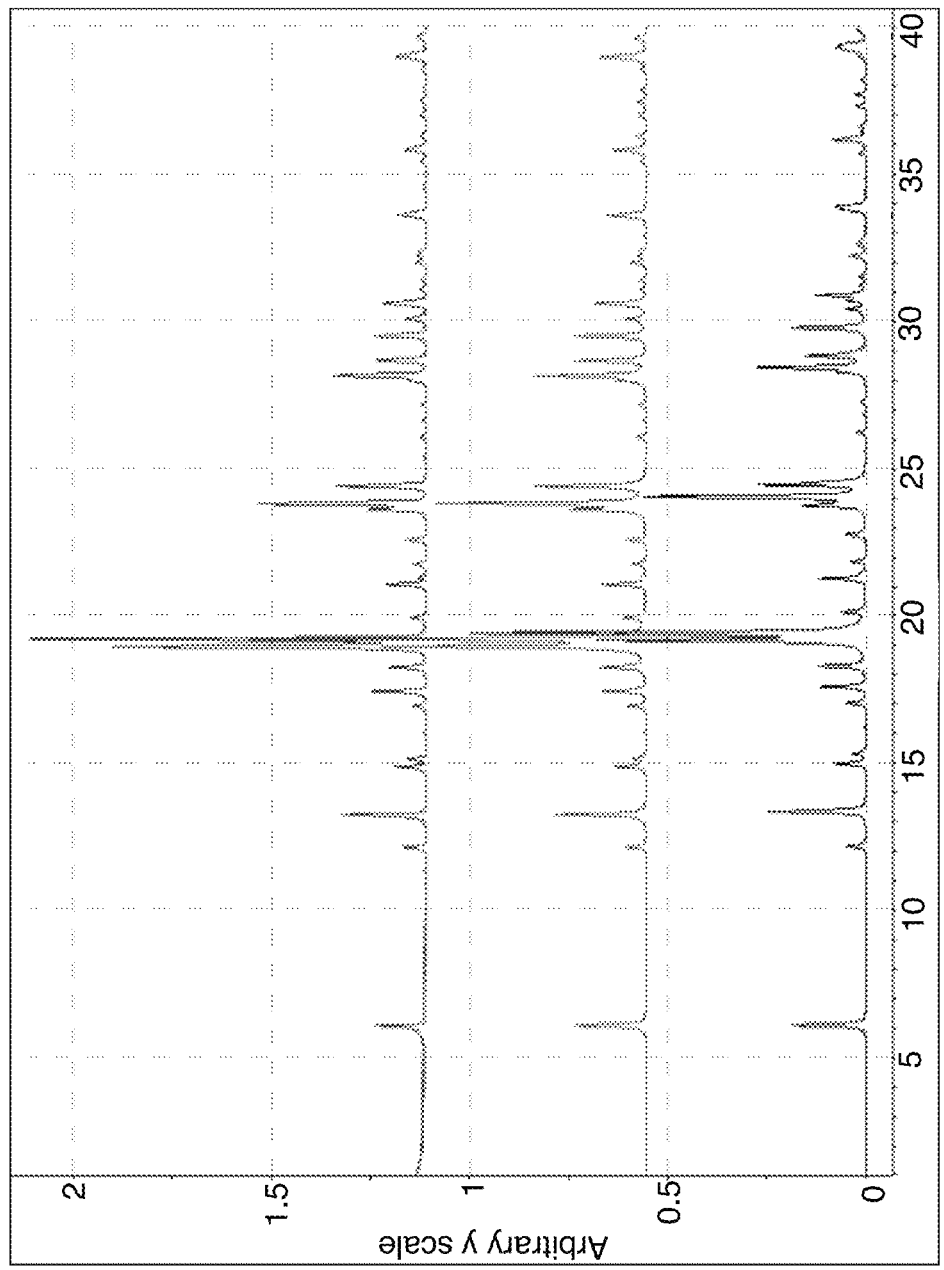
FIG. 33 depicts experimental and calculated XRPD patterns of Crystalline Form B (top: experimental XRPD pattern at room temperature; middle: calculated XRPD pattern adjusted to room temperature; bottom: calculated XRPD pattern at 100 K).

An experimental XRPD pattern of Crystalline Form B is shown in FIG. 33 (same as XPRD pattern in FIG. 40, Example 8), overlaid with the calculated pattern and a calculated pattern that has been adjusted to room temperature. All peaks in the experimental patterns are represented in the calculated XRPD pattern, indicating a single phase.

Differences in intensities between the calculated and experimental powder diffraction patterns often are due to preferred orientation. Preferred orientation is the tendency for crystals to align themselves with some degree of order. This preferred orientation of the sample can significantly affect peak intensities, but not peak positions, in the experimental powder diffraction pattern. Furthermore, some shift in peak position between the calculated and experimental powder diffraction patterns may be expected because the experimental powder pattern is collected at ambient temperature and the single crystal data are collected at 100 K. Low temperatures are used in single crystal analysis to improve the quality of the structure but can contract the crystal resulting in a change in the unit cell parameters, which is reflected in the calculated powder diffraction pattern. These shifts are particularly evident at high diffraction angles. The calculated XRPD pattern has been adjusted to room temperature using the unit cell obtained previously from XRPD indexing.

TABLE 15

Crystal Data and Data Collection Parameters for (1R,5S)-1-(naphthalen-2-yl)-3-azabicyclo[3.1.0]hexane hydrochloride Form B (Crystalline Form B)

| | |
|---|---|
| Empirical formula | $C_{15}H_{16}ClN$ |
| Formula weight | 245.74 |
| Temperature | 100(2) K |
| Wavelength | 1.54178 Å |
| Crystal system | Orthorhombic |

TABLE 15-continued

Crystal Data and Data Collection Parameters for (1R,5S)-1-(naphthalen-2-yl)-3-azabicyclo[3.1.0]hexane hydrochloride Form B (Crystalline Form B)

| | |
|---|---|
| Space group | $P2_12_12_1$ |
| Unit cell dimensions | a = 5.9055(2) Å   α = 90°. |
| | b = 7.4645(3) Å   β = 90°. |
| | c = 29.1139(13) Å   γ = 90°. |
| Volume | 1283.39(9) Å$^3$ |
| Z | 4 |
| Density (calculated) | 1.272 Mg/m$^3$ |
| Absorption coefficient | 2.422 mm$^{-1}$ |
| F(000) | 520 |
| Crystal size | 0.310 × 0.210 × 0.090 mm$^3$ |
| Theta range for data collection | 6.080 to 72.393°. |
| Index ranges | −7<=h<=7, −8<=k<=8, −35<=l<=35 |
| Reflections collected | 22958 |
| Independent reflections | 2415 [R(int) = 0.0495] |
| Completeness to theta = 67.679° | 98.5 % |
| Absorption correction | Semi-empirical from equivalents |
| Max. and min. transmission | 0.976 and 0.753 |
| Refinement method | Full-matrix least-squares on F$^2$ |
| Data/restraints/parameters | 2415/0/155 |
| Goodness-of-fit on F$^2$ | 1.150 |
| Final R indices [I > 2sigma(I)] | R1 = 0.0453, wR2 = 0.1224 |
| R indices (all data) | R1 = 0.0464, wR2 = 0.1240 |
| Absolute structure parameter | Flack parameter: 0.010(10) |
| | Hooft parameter: −0.001(7) |
| Extinction coefficient | 0.0055(8) |
| Largest diff. peak and hole | 0.318 and −0.313 e.Å$^{-3}$ |

Example 7—Preparation of Crystalline Form B 470.9 mg of Crystalline Form A from Example 5 above is mixed with 5 mL of water in a 20 mL glass vial. The slurry is stirred at ambient temperature for 16 days with a stir bar to allow conversion to occur. The solids are collected by vacuum filtration and briefly dried under nitrogen.

Example 8—Preparation of Crystalline Form B 1 g of the product from Example 16 below is stirred in 5 mL of Special Industrial 200 (ethanol denatured) over weekend at ambient temperature. The mixture is filtered and rinsed with 2 mL of Special Industrial 200 (ethanol denatured) and followed by isopropyl acetate (2×3 mL). Pull dry the solids over 2 hours and then dry at 40° C. over 6 hours to give 0.81 g of product.

Figure 40:
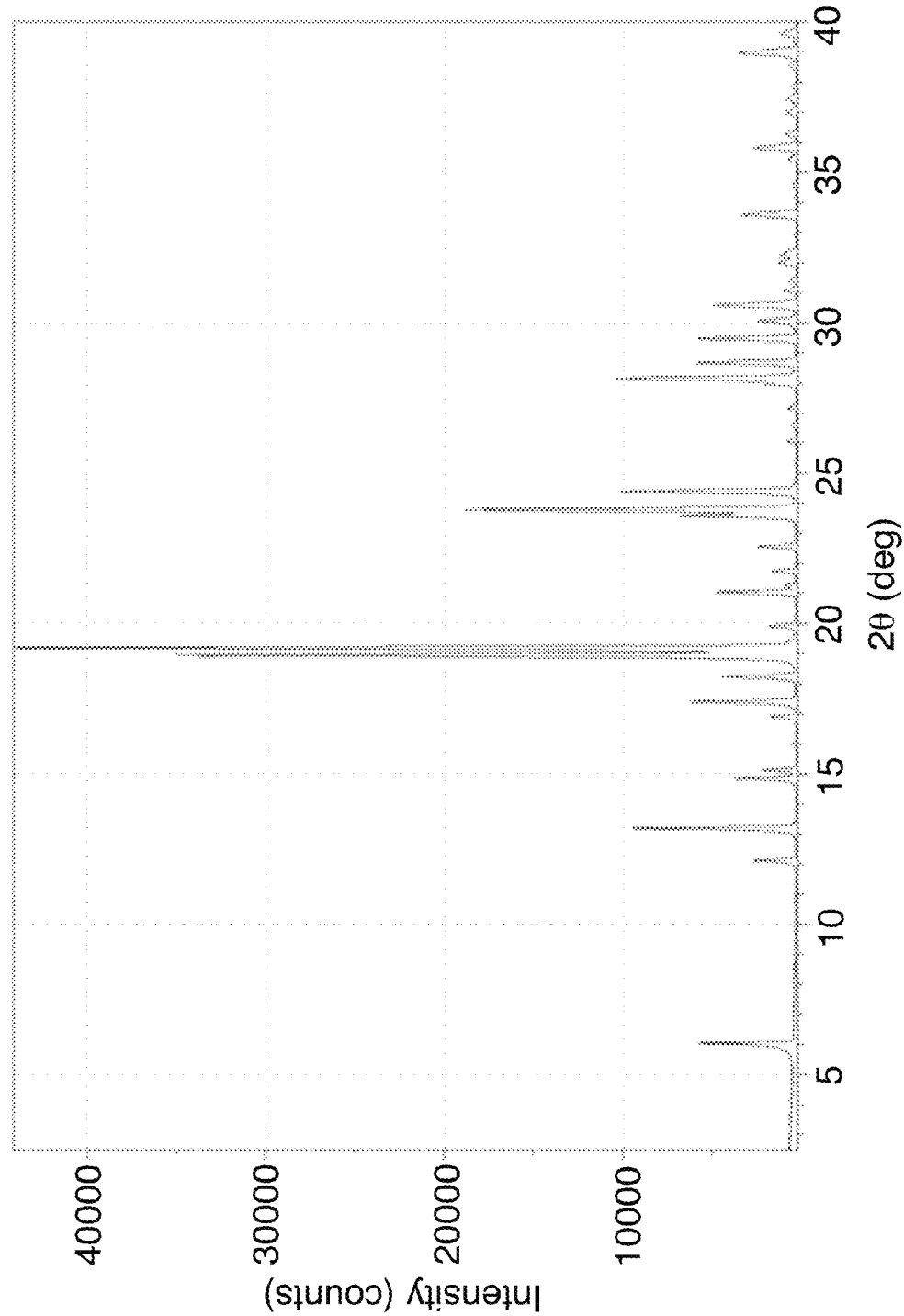
FIG. 40 depicts an XRPD pattern of Crystalline Form B.

An XRPD shows the product is Crystalline Form B (FIG. 40 and also shown as the top XRPD pattern in FIG. 33). The XRPD pattern is collected with a PANalytical X'Pert PRO MPD diffractometer using an incident beam of Cu radiation produced using an Optix long, fine-focus source. An elliptically graded multilayer mirror is used to focus Cu Kα X-rays through the specimen and onto the detector. Prior to the analysis, a silicon specimen (NIST SRM 640d) is analyzed to verify the observed position of the Si 111 peak is consistent with the NIST-certified position. A specimen of the sample is sandwiched between 3-μm-thick films and analyzed in transmission geometry. A beam-stop, short anti-scatter extension, and an anti-scatter knife edge are used to minimize the background generated by air. Soller slits for the incident and diffracted beams are used to minimize broadening from axial divergence. The diffraction pattern is collected using a scanning position-sensitive detector (X'Celerator) located 240 mm from the specimen and Data Collector software v. 2.2b. Data acquisition parameters are: Panalytical X-Pert Pro MPD PW3040 Pro, X-ray Tube: Cu (1.54059 Å), Voltage: 45 kV, Amperage: 40 mA, Scan Range: 1.01-39.98 °2θ, Step Size: 0.017 °2θ, Collection Time: 720 s, Scan Speed: 3.2°/min., Slit: DS: 1/2°, SS: null, Revolution Time: 1.0 s, Mode: Transmission.

Figure 41:
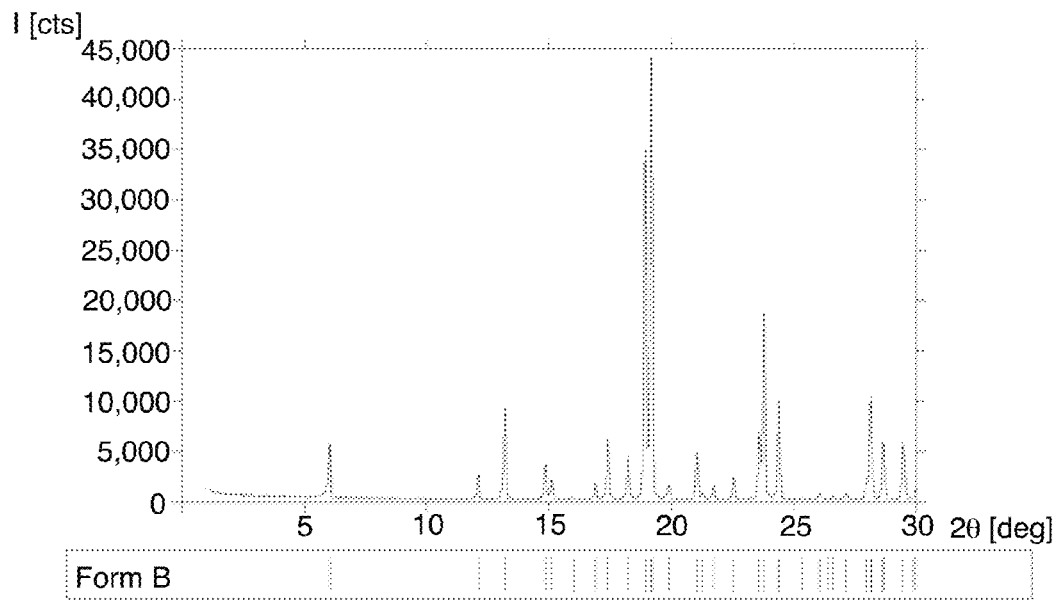
FIG. 41 depicts an indexing result for the XRPD pattern depicted in FIG. 40 collected with Cu Kα radiation.
Figure 42:
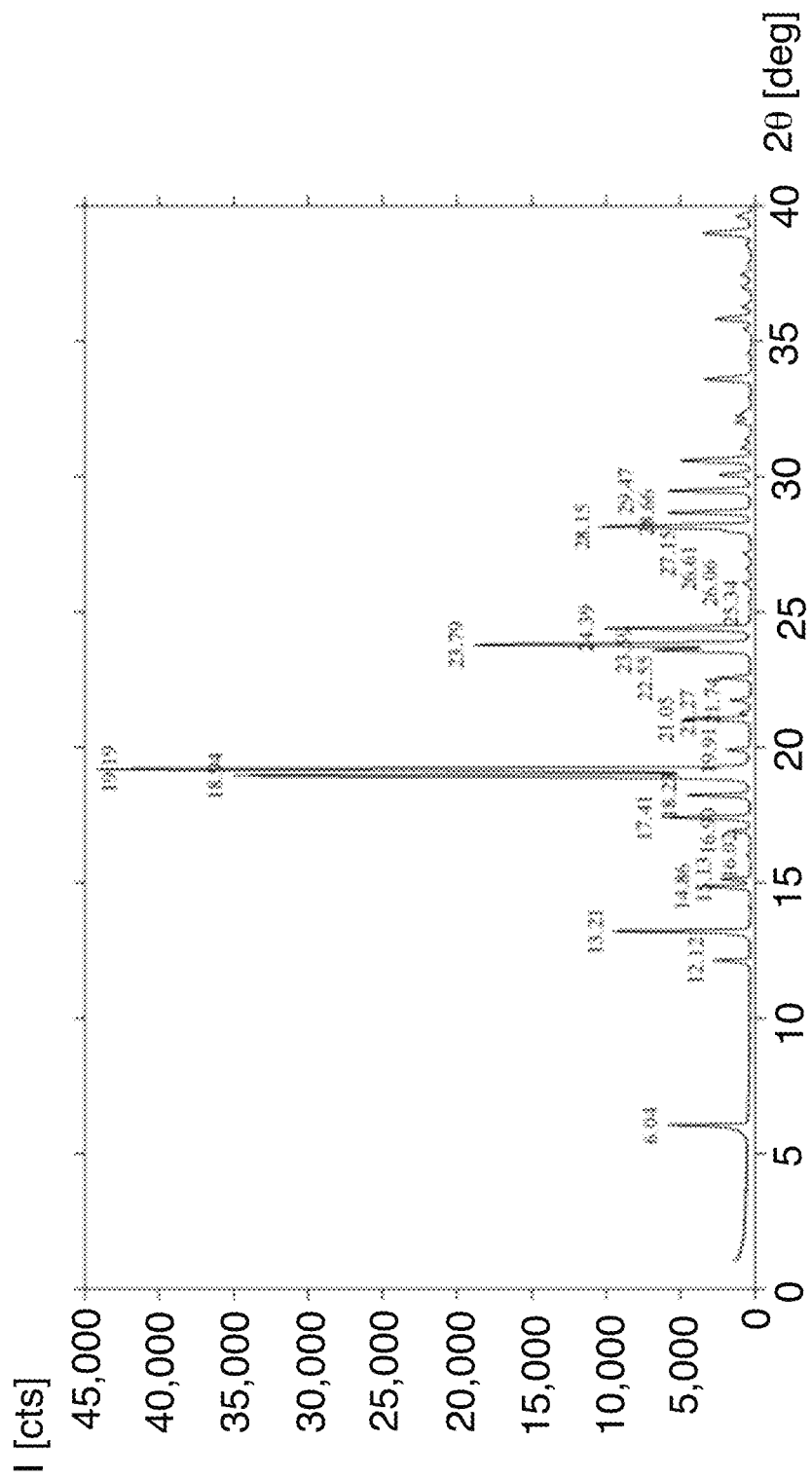
FIG. 42 depicts observed peaks for the XPRD pattern depicted in FIG. 40 collected with Cu Kα radiation.

One PANalytical pattern is analyzed for this material, and preferred orientation and particle statistic effects are assessed through comparison with additional XRPD patterns analyzed using alternate geometry in addition to a calculated XRPD pattern from single crystal analysis. An indexing result for the XRPD shown in FIG. 40 collected with Cu Kα radiation is shown in FIG. 41. The XRPD pattern is indexed using X'Pert High Score Plus 2.2a (2.2.1). Observed peaks are shown in FIG. 42 and listed in Table F in formula 1.109, representative peaks are listed in Table E in formula 1.102, and characteristic peaks are listed in Table D in formula 1.93.

Example 9—Crystalline Form C

A turbid solution containing 458.2 mg of Crystalline Form A from Example 5 and 40 mL of IPA is generated at elevated temperature. The hot solution is filtered with a 0.2-μm nylon filter into a clean vial and placed into a freezer. After two days, the solids are recovered by vacuum filtration and briefly dried under nitrogen. The solids are identified as a mixture of Crystalline Forms A and C. A slurry is generated with 42.2 mg of the mixture and 0.8 mL of a saturated DCM solution. (The saturated solution is generated with 65.4 mg of Crystalline Form A from Example 5 in 5 mL of DCM at ambient temperature. Excess solids are filtered from the solution the following day with a 0.2-μm nylon filter.) The slurry is stirred, 100 RPM, with an agate ball at 2° C. for 3 weeks to allow conversion to occur. Solids isolated from the resulting suspension through vacuum filtration are stored at a temperatures between −25 and −10° C.

Figure 43:
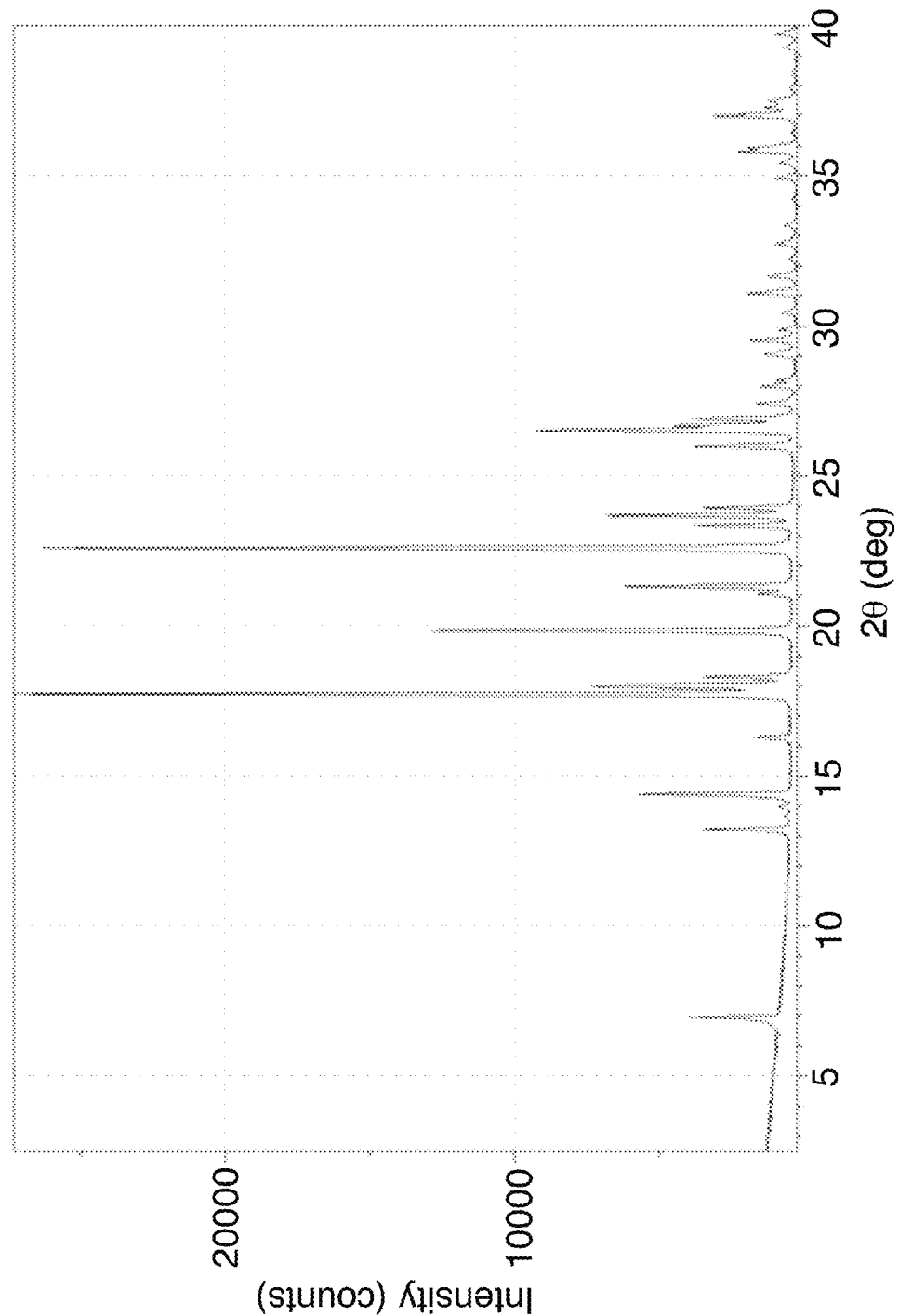
FIG. 43 depicts an XRPD pattern of Crystalline Form C.

An XRPD of the product is shown in FIG. 43. The XRPD pattern is collected with a PANalytical X'Pert PRO MPD diffractometer using an incident beam of Cu radiation produced using an Optix long, fine-focus source. An elliptically graded multilayer mirror is used to focus Cu Kα X-rays through the specimen and onto the detector. Prior to the analysis, a silicon specimen (NIST SRM 640d) is analyzed to verify the observed position of the Si 111 peak is consistent with the NIST-certified position. A specimen of the sample is sandwiched between 3-μm-thick films and analyzed in transmission geometry. A beam-stop, short anti-scatter extension, and an anti-scatter knife edge are used to minimize the background generated by air. Soller slits for the incident and diffracted beams are used to minimize broadening from axial divergence. The diffraction pattern is collected using a scanning position-sensitive detector (X'Celerator) located 240 mm from the specimen and Data Collector software v. 2.2b. Data acquisition parameters are: Panalytical X-Pert Pro MPD PW3040 Pro, X-ray Tube: Cu (1.54059 Å), Voltage: 45 kV, Amperage: 40 mA, Scan Range: 1.00-39.99 °2θ, Step Size: 0.017 °2θ, Collection Time: 720 s, Scan Speed: 3.2°/min., Slit: DS: 1/2°, SS: null, Revolution Time: 1.0 s, Mode: Transmission.

Figure 44:
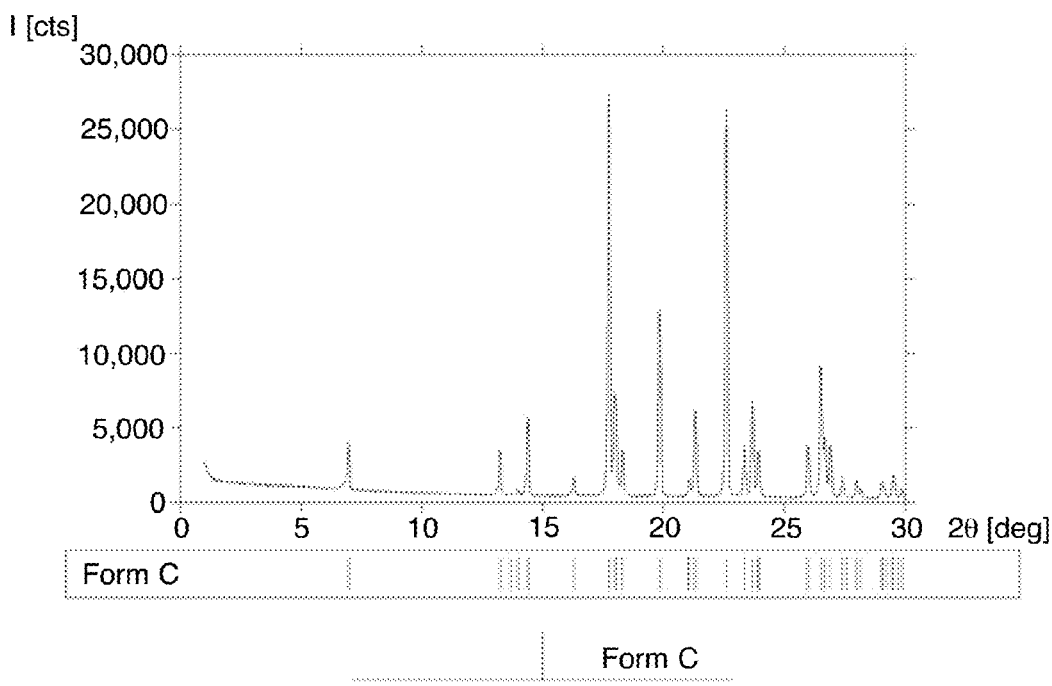
FIG. 44 depicts an indexing result for the XRPD pattern depicted in FIG. 43 collected with Cu Kα radiation.
Figure 45:
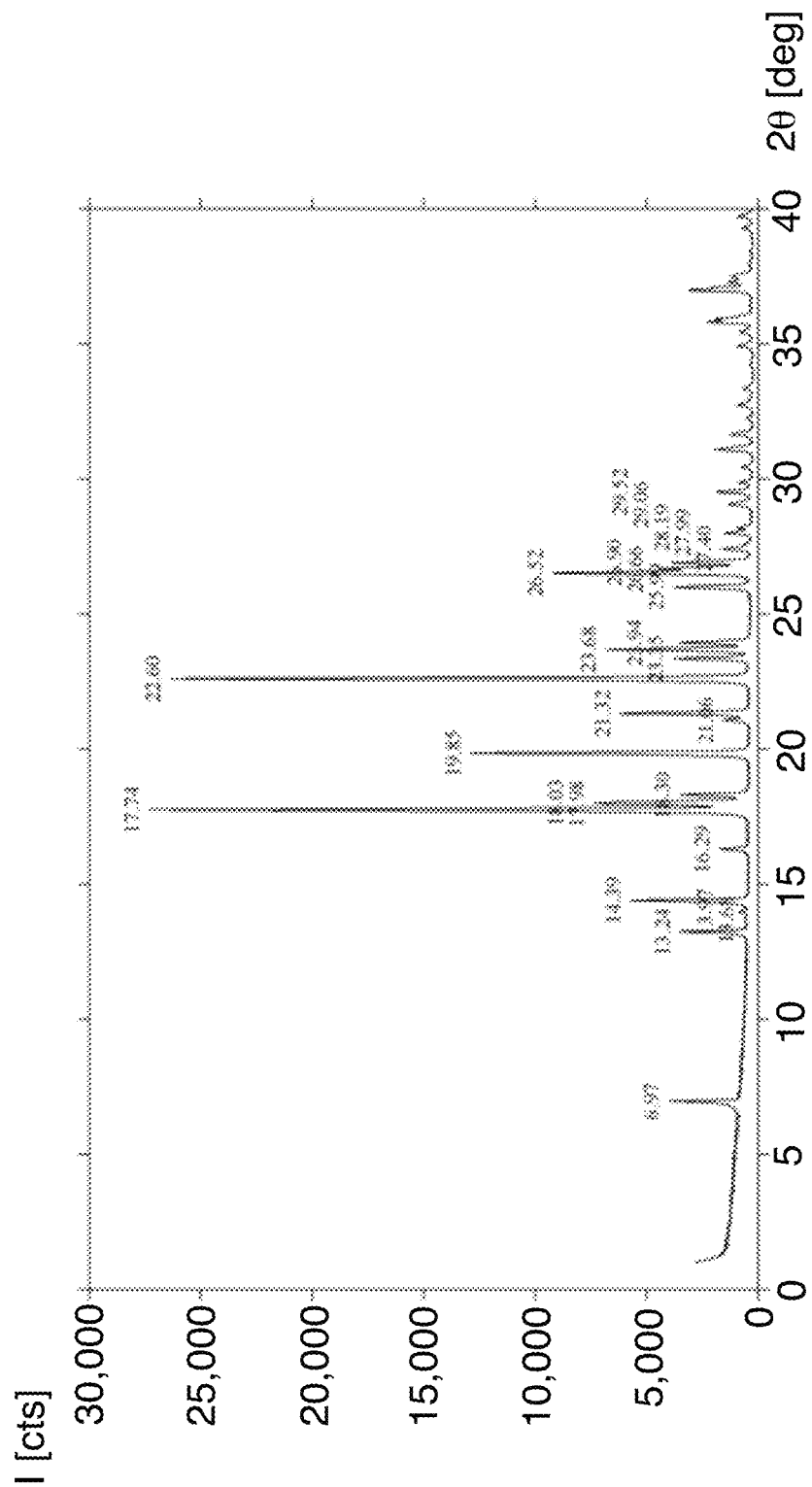
FIG. 45 depicts observed peaks for the XPRD pattern depicted in FIG. 43 collected with Cu Kα radiation.

One PANalytical pattern is analyzed for this material, and preferred orientation and particle statistic effects are assessed through comparison with additional XRPD patterns analyzed using alternate geometry. An indexing result for the XRPD pattern shown in FIG. 43 collected with Cu Kα radiation is shown in FIG. 44. The XRPD pattern is indexed using proprietary software (U.S. Pat. No. 8,576,985). Observed peaks are shown in FIG. 45 and listed in Table I in formula 1.183, representative peaks are listed in Table H in formula 1.176, and characteristic peaks are listed in Table G in formula 1.168.

Example 10—Interconversion Slurry Experiments

An Energy—Temperature Diagram is a semi-quantitative graphical solution of the Gibbs—Helmholtz equation, where the enthalpy (H) and free energy (G) isobars for each form are depicted as a function of temperature. The graph assumes that the free energy isobars intersect at most once and, second, that the enthalpy isobars of the polymorphs do not intersect. The melting point of a polymorph is defined as the temperature at which the free energy isobar of the polymorph intersects the free energy isobar of the liquid. The transition temperature is defined as the temperature at which the free energy isobar of one polymorph intersects the free energy isobar of the second. Thus, at $T_t$ both polymorphs have equal free energy, and consequently are in equilibrium with each other.

Figure 46:
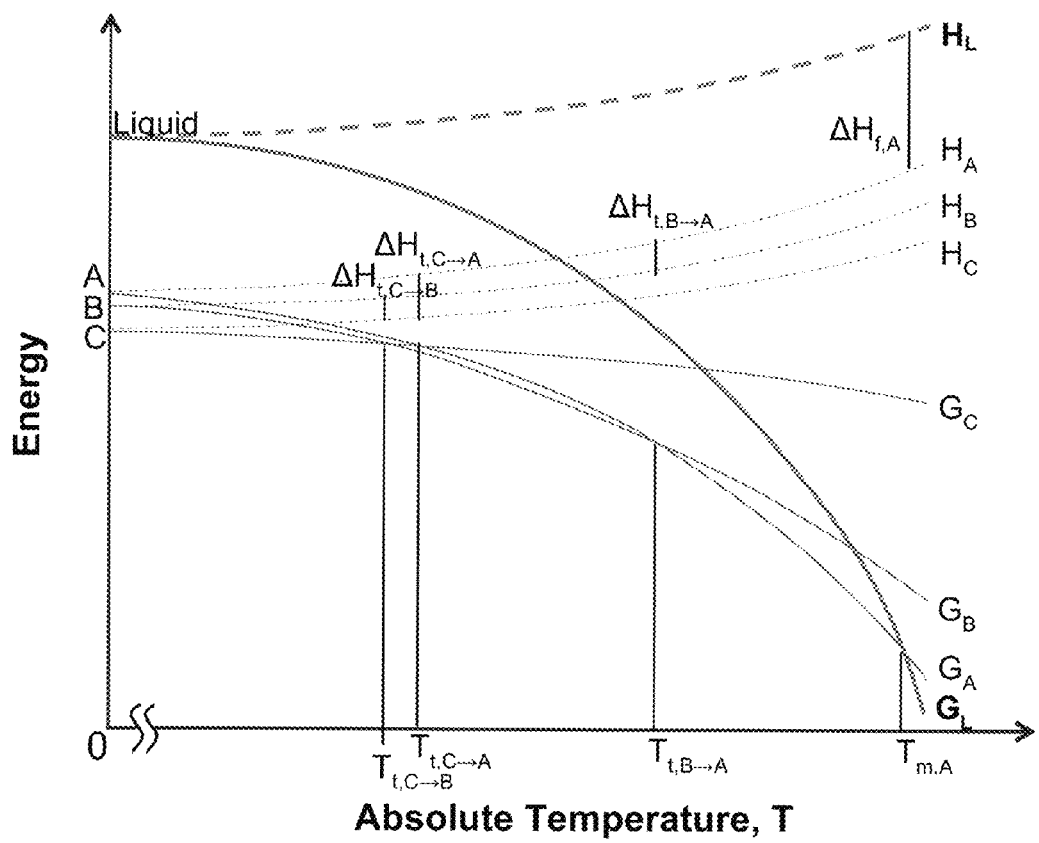
FIG. 46 depicts proposed energy—temperature plots for Crystalline Forms A, B, and C.

The proposed Energy—Temperature Diagram for Crystalline Forms A, B, and C is shown in FIG. 46. In the diagram, the enthalpy (H) and free energy (G) isobars for each form are depicted as a function of temperature (T). Subscripts A, B, C, and L refer to Crystalline Forms A, B, C, and liquid phase, respectively. Subscripts f, t, and m refer to fusion, transition point, and melting point, respectively. The graph assumes that the free energy isobars intersect at most once and, second, that the enthalpy isobars of the polymorphs do not intersect. The melting point of a polymorph is defined as the temperature at which the free energy isobar of the polymorph intersects the free energy isobar of the liquid. The transition temperature is defined as the temperature at which the free energy isobar of one polymorph intersects the free energy isobar of the second. Thus, at $T_t$ both polymorphic forms have equal free energy, and consequently are in equilibrium with each other. Crystalline Form C is the stable solid phase below $T_{t,C \rightarrow B}$ (because the free energy of Crystalline Form C is lower than that of Crystalline Form B), Crystalline Form B is the stable solid phase between $T_{t,C \rightarrow B}$ and and Crystalline Form A is the stable solid phase above $T_{t,B \rightarrow A}$. The low energy polymorph will have a lower fugacity, vapor pressure, thermodynamic activity, solubility, dissolution rate per unit surface area, and rate of reaction relative to the other polymorphs.

Interconversion experiments are performed to test the hypothetical thermodynamic relationship between materials illustrated by the Energy—Temperature Diagram above. Interconversion or competitive slurry experiments are a solution-mediated process that provides a pathway for the less soluble (more stable) crystal to grow at the expense of the more soluble crystal form (Bernstein, *J. Polymorphism in Molecular Crystals*. Clarendon Press, Oxford, 2006; Brittain, H. G., *Polymorphism in Pharmaceutical Solids*. Marcel Dekker, Inc., New York, 1999). Outside the formation of a solvate or degradation, the resulting more stable polymorph from an interconversion experiment is independent of the solvent used because the more thermodynamically stable polymorph has a lower energy and therefore lower solubility. The choice of solvent affects the kinetics of polymorph conversion and not the thermodynamic relationship between polymorphic forms (Gu, C. H., Young, V. Jr., Grant, D. J., *J. Pharm. Sci.* 2001, 90 (11), 1878-1890).

Binary interconversion slurry experiments between Crystalline Forms A, B, and C in different solvent systems at temperatures spanning approximately 2 through 67° C. are summarized in Table 16 below. Saturated solutions are generated and then added to mixtures composed of approximately equivalent quantities of two of the polymorphs. The samples are slurried from overnight to three weeks and the solids harvested and analyzed by XRPD. The results of the interconversion studies indicate that the relative thermodynamic stability of the enantiotropes Crystalline Forms A, B, and C are correctly depicted by the proposed Energy—Temperature Diagram. In addition, $T_{t,C \to B}$ is expected below 2° C. (is not determined), $T_{t,C \to A}$ will be between 2° C. and ambient temperature, and $T_{t,B \to A}$ will be between 37 and 54° C.

TABLE 16

Binary Interconversion Slurries between Crystalline Forms A, B, and C

| Crystalline Forms | Results | Temp[1] | Duration[1] | Solvent (v/v) |
|---|---|---|---|---|
| B + A | B | 2° C. | 3 weeks | DCM |
|  | B | 2° C. | 3 weeks | EtOH |
| B + C | B | 2° C. | 3 weeks | DCM |
|  | B | 2° C. | 3 weeks | EtOH |
| C + A | C | 2° C. | 3 weeks | DCM |
|  | C + A↓[2] | 2° C. | 3 weeks | EtOH |
| B + A | B | ambient | 2 weeks | DCM |
|  | B | ambient | 2 weeks | EtOH |
|  | B | ambient | 2 weeks | 10:1 ACN/H$_2$O |
| B + C | B | ambient | 2 weeks | DCM |
|  | B | ambient | 2 weeks | EtOH |
|  | B | ambient | 2 weeks | 10:1 ACN/H$_2$O |
| A + C | A | ambient | 2 weeks | DCM |
|  | A | ambient | 2 weeks | EtOH |
|  | B[3] | ambient | 2 weeks | 10:1 ACN/H$_2$O |
| B + A | B | 37° C. | 4 days | DCM |
| A + B | A | 54° C. | 3 days | EtOH |
| A + B | A + B↓[2] | 67° C. | overnight | EtOH |
|  | A | 67° C. | 4 days | EtOH |
| B + C | A[3] + B | 67° C. | overnight | EtOH |
| A + C | A | 67° C. | overnight | EtOH |

[1]Duration and temperatures are approximate.
[2]Downward arrow indicates the peak intensities of the associated crystalline phase have decreased relative to those of the starting mixture. The length of time of the experiment is not sufficient to reach equilibrium; nevertheless, conclusions of the predominant form can be made based on the resulting mixture.
[3]The solution-mediated interconversion process provides a pathway for the less soluble (more stable relative to the other) crystal to grow at the expense of the more soluble crystal form. However, when neither of the forms involved in the binary competitive slurry is the most thermodynamically stable form, the possibility of the most stable crystal to grow at the expense of the other two more soluble crystal forms can also result. This solvent-mediated polymorphic transformation is controlled by its nucleation rate, which is generally higher in a solvent giving higher solubility. In addition to the solubility, the strength of the solvent-solute interactions is also important. Degree of agitation and temperature also change the polymorphic transformation rate by influencing the crystallization kinetics of the more stable polymorph.

Crystalline Form B exhibits a lower apparent solubility than Crystalline Form A in both methanol and water (Table 17 below). Solution calorimetry (SolCal) analyses are also performed to determine the heats of solution in methanol at 25° C. and confirm the stable form at this temperature (see Example 15). Based on SolCal data, the dissolutions of both Crystalline Forms A and B in methanol are endothermic events with average heats of solution of 48.618 and 64.567 J/g, respectively, indicating that Crystalline Form B is more stable than Crystalline A at 25° C.

Experimental: Approximate Solubility

A weighed sample is treated with aliquots of the test solvent at room temperature. The mixture is sonicated between additions to facilitate dissolution. Complete dissolution of the test material is determined by visual inspection. Solubility is estimated based on the total solvent used to provide complete dissolution. The actual solubility may be greater than the value calculated because of the use of solvent aliquots that are too large or due to a slow rate of dissolution.

TABLE 17

Approximate Solubility of Crystalline Forms A and B

| Crystalline Form | Solvent | Solubility (mg/mL) |
|---|---|---|
| A | MeOH | 74 |
| B | MeOH | 63 |
| A | H$_2$O | 34[1] |
| B | H$_2$O | 21[2] |

[1]Nucleation observed after one day. A single crystal of Crystalline Form B is isolated.
[2]Nucleation of irregular fines with no birefringence observed after 7 days.

Example 11—Accelerated Stress Conditions

Crystalline Forms A, B, and C are exposed to accelerated stress conditions for two weeks (Table 18 below). Based on XRPD, Crystalline Forms A and B remain unchanged at 30° C./56% RH or 40° C./75% RH within the time frame evaluated. However, Crystalline Form C converts to a mixture of Crystalline Forms A and B within two weeks at 40° C./75% RH. Crystalline Form C is metastable at this condition. For Crystalline Form A, in the absence of seeds of the more stable polymorph, the critical free energy barrier for the nucleation of Crystalline Form B is not overcome in the solid state or in solvent mediated form conversion experiments within the time frame evaluated.

TABLE 18

Accelerated Stability Evaluation of Crystalline Form

| Crystalline Form | Condition | Time | Results (Crystalline Form) |
|---|---|---|---|
| A | source sample | — | A |
|  | subsample stored in freezer | T zero | — |
|  | 30° C./60% RH | 2 weeks | A |
|  | 40° C./75% RH | 2 weeks | A |
| B | source sample | — | B |
|  | subsample stored in freezer | T zero | — |
|  | 30° C./60% RH | 2 weeks | B |
|  | 40° C./75% RH | 2 weeks | B |
| C | source sample | — | C |
|  | subsample stored in freezer | T zero | — |
|  | 40° C./75% RH | 2 weeks | A + B |

$T_{t,B \to A}$ is between 37 and 54° C. A mixture of Forms A and B (combination of portions 1 and 2 from Example 17), completely converts to Form A upon exposure to 230° C. (Table 19 below).

Experimental: Relative Humidity Stress

The following relative humidity jars (saturated salt solutions are used to generate desired relative humidity) are utilized: 75% RH (NaCl) and 56% RH (NaBr) (Nyqvist, H., Int. J. Pharm. Tech. & Prod. Mfr. 1983, 4 (2), 47-48).

TABLE 19

Physical Stability of Mixture of Forms A and B

| Method[1] | Observation[2] | Results |
|---|---|---|
| expose to 230° C., moist pH paper held in head space above sample | sublimation is observed; no pH change is noted, suggesting no loss of HCl upon heating; fines and large blades, B | A |

[1]Time and temperature are approximate.
[2]B = birefringent when observed by polarized light microscopy
[3]Upward arrow indicates the peak intensities of the associated crystalline phase have increased relative to those of the starting mixture.

Example 12—Preparation of Crystalline Form B

Figure 48:
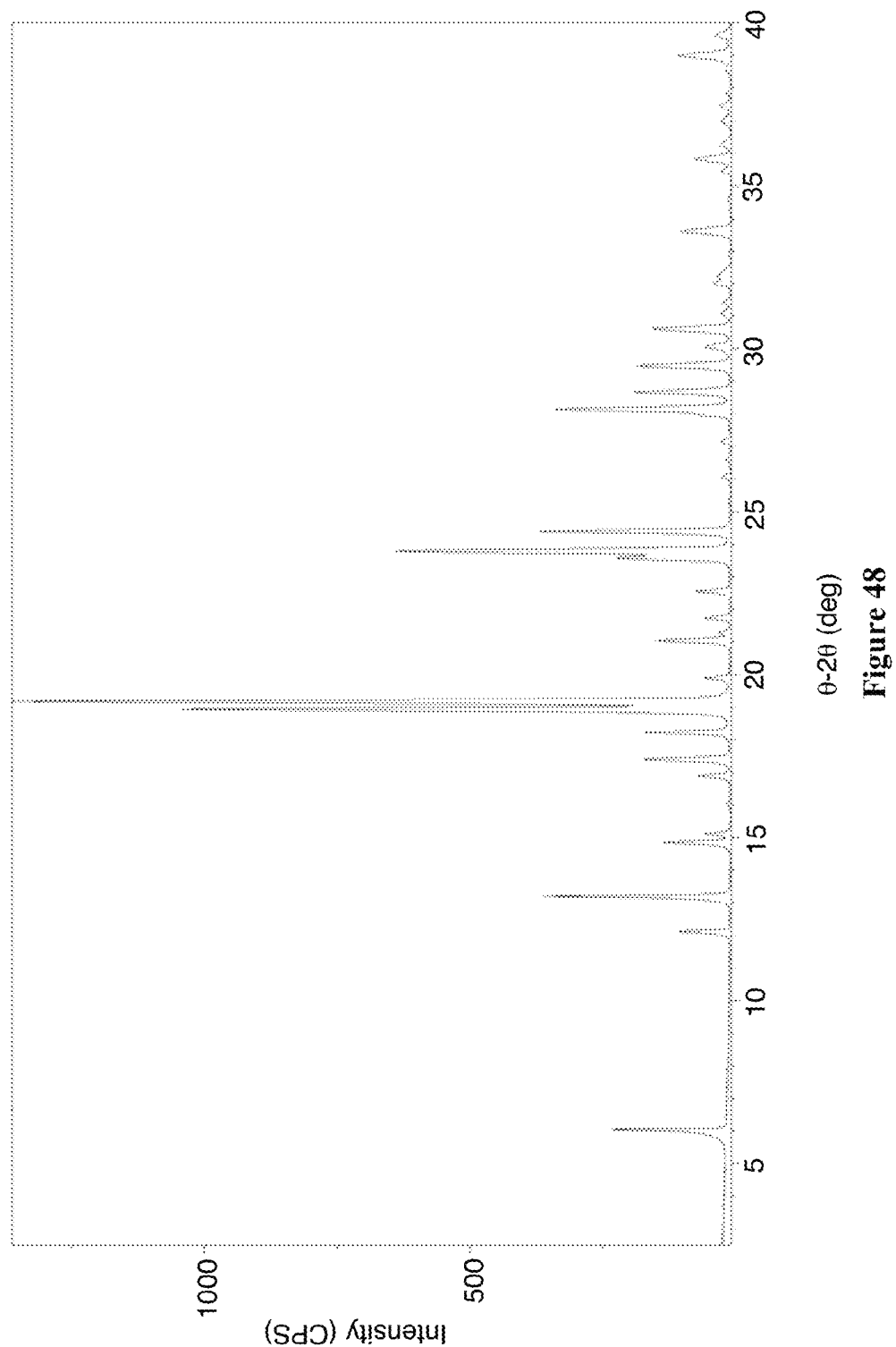
FIG. 48 depicts an XRPD pattern of Crystalline Form B.

A portion of Crystalline Form A from Example 5 above is slurried with water at ambient temperature for 16 days. Crystalline Form B is isolated. An XRPD of the product is in FIG. 48. The XRPD pattern is collected with a PANalytical X'Pert PRO MPD diffractometer using an incident beam of Cu radiation produced using an Optix long, fine-focus source. An elliptically graded multilayer mirror is used to focus Cu Kα X-rays through the specimen and onto the detector. Prior to the analysis, a silicon specimen (NIST SRM 640e) is analyzed to verify the observed position of the Si 111 peak is consistent with the NIST-certified position. A specimen of the sample is sandwiched between 3-µm-thick films and analyzed in transmission geometry. A beam-stop, short antiscatter extension, and an antiscatter knife edge are used to minimize the background generated by air. Soller slits for the incident and diffracted beams are used to minimize broadening from axial divergence. Diffraction patterns are collected using a scanning position-sensitive detector (X'Celerator) located 240 mm from the specimen and Data Collector software v. 2.2b. Data acquisition parameters are: Panalytical X-Pert Pro MPD PW3040 Pro, X-ray Tube: Cu (1.54059 Å), Voltage: 45 kV, Amperage: 40 mA, Scan Range: 1.00-39.99 °2θ, Step Size: 0.017 °2θ, Collection Time: 716 s, Scan Speed: 3.3°/min., Slit: DS: 1/2°, SS: null, Revolution Time: 1.0 s, Mode: Transmission.

Figure 49:
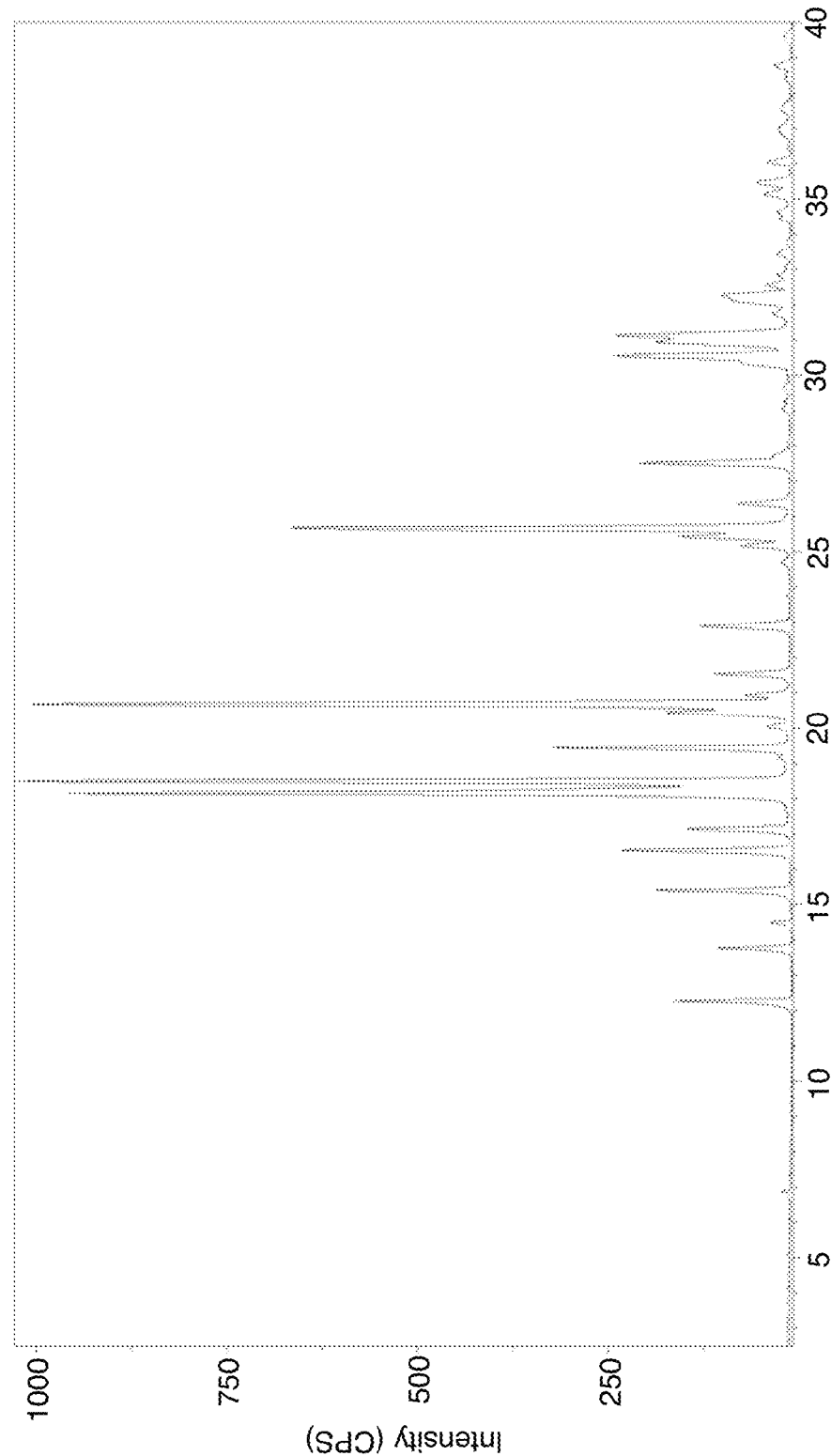
FIG. 49 depicts an XRPD pattern of a mixture of Crystalline Form A and a minor quantity of Crystalline Form B.

Example 13—XRPD of Mixture of Crystalline Form A and Minor Quantity of Crystalline Form B An XRPD pattern of a mixture of Crystalline Form A and a minor quantity of Crystalline Form B product is in FIG. 49 (Example 17 for synthesis). The XRPD pattern is collected with a PANalytical X'Pert PRO MPD diffractometer using an incident beam of Cu radiation produced using an Optix long, fine-focus source. An elliptically graded multilayer mirror is used to focus Cu Kα X-rays through the specimen and onto the detector. Prior to the analysis, a silicon specimen (NIST SRM 640e) is analyzed to verify the observed position of the Si 111 peak is consistent with the NIST-certified position. A specimen of the sample is sandwiched between 3-µm-thick films and analyzed in transmission geometry. A beam-stop, short antiscatter extension, and an antiscatter knife edge are used to minimize the background generated by air. Soller slits for the incident and diffracted beams are used to minimize broadening from axial divergence. Diffraction patterns are collected using a scanning position-sensitive detector (X'Celerator) located 240 mm from the specimen and Data Collector software v. 2.2b. Data acquisition parameters are: Panalytical X-Pert Pro MPD PW3040 Pro, X-ray Tube: Cu (1.54059 Å), Voltage: 45 kV, Amperage: 40 mA, Scan Range: 1.00-39.99 °2θ, Step Size: 0.017 °2θ, Collection Time: 720 s, Scan Speed: 3.2°/min., Slit: DS: 1/2°, SS: null, Revolution Time: 1.0 s, Mode: Transmission.

Example 14—Solution Calorimetry (SolCal) Analyses of Crystalline Forms A and B

Solution calorimetry analysis for each form is measured in triplicate in methanol and the data are summarized in Table 21. For each test, two heats of solution are obtained—one calculated using a calibration preceding the sample analysis and one calculated using a calibration following the sample analysis. The mean values from the two calibrations are also provided in the table. Clear solutions are observed after each test.

The dissolutions of both Crystalline Forms A and B in methanol are endothermic events with average heats of solution are 48.618 and 64.567 J/g, respectively. The standard deviation for each set is 0.457 and 0.344 J/g, respectively.

Crystalline Form B has a higher heat of solution value than Form A, indicating Crystalline Form B is more stable than A at 25° C. The enthalpy of the transition calculated from the SolCal data from Form B to Form A is about 15.9 J/g. The difference in the heat of fusion in the solid-state transition in the DSC of Crystalline Form B is 15.9 J/g (see FIGS. 8 and 55), which is in good agreement with the SolCal results.

Solution calorimetry is performed using a Thermometric 2225 Precision Solution calorimeter, a semi-adiabatic calorimeter. Solution calorimeter System v.1.2 software is used. Samples are weighed into glass crushing ampoules and are sealed using silicone rubber plugs and hot wax. Experiments are carried out in 100 mL of methanol at 25° C. The measurement of the heats of solution of the samples is both preceded and followed by calibrations using an internal heater. The heats of solution are calculated using dynamic of calibration model.

TABLE 21

Heats of Solution of Crystalline Forms A and B in Methanol

| Sample | Replicate | $\Delta H_1$, J/g[a] | $\Delta H_2$, J/g[b] | $\Delta H_{mean}$, J/g | Observation[c] |
|---|---|---|---|---|---|
| Crystalline Form A | 1 (52.540 mg Crystalline Form A, stirrer 500 rpm) | 46.050 | 50.168 | 48.109 | clear solution |
| | 2 (55.427 mg Crystalline Form A, stirrer 500 rpm) | 48.293 | 49.217 | 48.755 | clear solution |
| | 3 (49.393 mg Crystalline Form A, stirrer 500 rpm) | 48.077 | 49.905 | 48.991 | clear solution |
| | average, J/g | | | 48.618 | — |
| | standard deviation | | | 0.457 | — |
| Crystalline Form B | 1 (56.730 mg Crystalline Form A, stirrer 500 rpm) | 64.004 | 64.985 | 64.495 | clear solution |
| | 2 (49.276 mg Crystalline Form A, stirrer 500 rpm) | 63.471 | 65.057 | 64.264 | clear solution |
| | 3 (51.723 mg Crystalline Form A, stirrer 500 rpm) | 64.461 | 65.421 | 64.941 | clear solution |
| | average, J/g | | | 64.567 | — |
| | standard deviation | | | 0.344 | — |

[a]Calculated using the calibration before breaking the sample vial.
[b]Calculated using the calibration after breaking the sample vial.
[c]Observations are made at the time when tests are completed.

Example 15—Hot Stage Microscopy (HSM) of Crystalline Form A from Example 1

Hot stage microscopy is performed using a Linkam hot stage (model FTIR 600) mounted on a Leica DM LP microscope. Samples are observed using a 20× objective (obj.). Samples are placed on a coverslip, and a second coverslip is then placed over the sample. Each sample is visually observed as the stage is heated. Images are captured using a SPOT Insight™ color digital camera with SPOT Software v. 4.5.9. The hot stage is calibrated using USP melting point standards.

By HSM of Crystalline Form A, between 182 and 239° C., the smallest particles evaporate and the resulting vapor recrystallizes into larger crystals. Condensation and melt are observed between 239 and 247° C.; the needles appear to melt last consistent with the multiple endotherms observed by DSC. Two preparations are utilized for the analysis. For the first, discoloration (decomposition) is observed after melt. For the second, rapid cooling results in recrystallization of the melt.

Example 16—Preparation of Mixture of Crystalline Forms A and B

Commercially available reagents are used as received unless otherwise noted. Reactions requiring inert atmospheres are run under nitrogen unless otherwise noted.

| Compound | MW (g/mol) | d (g/mL) | Equivalents | Amt/mol |
|---|---|---|---|---|
| Reaction | | | | |
| 2-naphthylacetonitrile | 167.21 | NA | 1.0 mol eq (SM) | 50 Kg/ 299.03 mol |
| (S)-(+)-epichlorohydrin | 92.52 | 3.12 | 1.12 mol eq | 31.0 Kg/ 334.9 mol |
| tetrahydrofuran | 72.11 | 0.889 | 5.0 ml/g SM | 250 L |
| 2M sodium bis(trimethylsilyl)amide in THF | 2.0M | 0.916 | 2 mol eq | 299 L/ 598.0 mol |
| borane-dimethylsulfide | 10.0M | 0.80 | 2.5 mol eq | 89.7 L/ 897.0 mol |
| Isolation | | | | |
| 2M HCl (aqueous) | 2M | NA | 11.5 ml/g SM | 650 L |
| isopropyl acetate | 102.13 | 0.872 | 4 mL/g SM | as required |
| water | 18.02 | 1.00 | 5 mL/g SM | as required |
| ammonia (aqueous) | NA | 0.889 | 2.0 mL/g SM | 100 L |
| methylene chloride | 60 | 1.325 | 4 × 5 mL/g SM | as required |
| 2-methyltetrahydrofuran | 86.13 | 0.86 | 12.6 mL/g SM | as required |
| para-toluenesulfonic acid monohydrate | 190.22 | NA | 0.953 mol eq. | 54.2 Kg/ 284.9 mol |

Steps 1 and 2

2-naphthylacetonitrile (50 Kg) is dissolved in THF (250 L), 32 kg of (S)-(+)-epichlorohydrin is added and the solution cooled to −10° C. A 2.0 M solution of sodium hexamethyldisilylazane in THF (299 L) is then added keeping the internal temperature below −10° C. This addition requires 14 hrs., 14 minutes to complete. The reaction mixture is then stirred an additional four hours at approximately −10° C., after which a sample of the reaction mixture is analyzed by HPLC. While keeping the internal temperature less than 0° C., borane dimethylsulfide (71 kg) is added over four hours and 33 minutes. After completion of the borane addition the reaction mixture is slowly heated to 60° C. to reduce the nitrile to the amine. During this heat-up, an exotherm is noted, which initiates at 45° C. After heating at 60° C. for 14 hours and 46 minutes, a sample of the reaction mixture is analyzed by HPLC.

The reaction mixture is then cooled to 24° C. and transferred to a solution of 2M HCl over 2 hours and 28 minutes and the reactor is rinsed with THF (22.3 Kg) and transferred to the HCl containing reaction mixture. The two phase mixture is heated to 45° C. to 55° C. and stirred for 1 hour 48 minutes at this temperature followed by cooling to 30° C. The pH of the quenched reaction mixture is measured and found to be 1. Reaction workup continues by addition of IPAc, stir, and separate the layers. Charge 1 M HCl solution to the organic layer, stir, separate the layers, and discard the organic layer. Aqueous ammonia is added to the combined aqueous layer and the pH measured which shows a pH of 9. Workup then continues by extraction with two extractions of the aqueous layer with IPAc. The combined organic extracts are then washed with 5% sodium chloride solution. The resulting organic layer is partially concentrated to azeotropically dry and co-evaporation with methylene chloride four times and followed by dilution with methylene chloride and transfer of the reaction mixture via in-line filter to clean, dry reactor and diluting with IPAc. p-Toluenesulfonic acid hydrate (54 Kg) is then added in portions to precipitate the desired product as its pTsOH salt and the reaction suspension is stirred over three hours at 10° C. to 15° C. and the product is isolated by filtration. The filter cake is washed with 2-methyltetrahydrofuran and followed by IPAc then pull dried over two hours. The crude product is purified by stirring with 2-methyltetrahydrofuran over 11 hours 36 minutes at 10° C. to 15° C. and the product is isolated by filtration. The filtered solid is washed with 2-methyltetrahydrofuran and then dried to a constant weight to give 73.8 Kg of the desired product as a white solid. Yield=73.8 Kg (62%). HPLC=96.8%.

Steps 3 and 4

| Compound | MW (g/mol) | d (g/mL) | Equivalents | Amt/mol |
|---|---|---|---|---|
| Reaction | | | | |
| 2-naphthylcyclopropylamine-tosylate salt | 399.51 | NA | 1.0 mol eq | 73.8 Kg/ 184.7 mol |
| 2-methyltetrahydrofuran | 86.13 | 0.86 | 10 mL/g SM | as required |
| isopropylacetate | 102.13 | 0.872 | as required | as required |
| thionyl chloride | 118.97 | 1.638 | 1.2 eq | 26.4 Kg/ 221.9 mol |
| sodium hydroxide, 50% aqueous | 40 | 1.548 | 11 mol eq | 165.3 Kg |
| Isolation | | | | |
| water | 18.02 | 1.00 | 10 mL/g SM | as required |
| magnesium sulfate | NA | NA | 0.5 g/g | 36.5 Kg |
| hydrogen chloride in isopropyl alcohol | 5.7M | NA | 1.0 mol eq | 33.6 L |
| Ethyl alcohol 200 (Special Industrial denatured) | 80.25 | 0.786 | 14 mL/g SM | as required |

The amine-pTsOH salt (73.8 Kg) obtained from step 2 above is suspended in 2-methyltetrahydrofuran (738 L) to give a slurry. Thionyl chloride (26.4 kg) is then added over three hours. Upon completion of the thionyl chloride addition, the reaction mixture is stirred three additional hours. Aqueous sodium hydroxide (5M, 10 mol equivalents) is added over three hours followed by two hours of additional stirring. The layers are allowed to settle and the pH of the aqueous layer is checked and found to be 9. Water (2 mL/g, SM) is added, the reaction mixture is stirred 15 more minutes at room temperature, and the layers are separated and the organic layer washed twice with water. The aqueous layers are combined and back extracted with 2-methyltetrahydrofuran and the initial organic layer and the back extract combined. These combined organic layers are washed with brine, dried over magnesium sulfate, and partially concentrated. After concentration, hydrogen chloride in IPA (1.0 mol equivalent of HCl in IPA) is added and stirred 2 hours to form the crude salt which is isolated by filtration, washed with 2-methyltetrahydrofuran and followed by IPAc and then pull dried over 2 hours under vacuum.

The crude product (82.6 Kg) obtained from above is dissolved in 14 volumes of hot ethanol (70° C.) and then filtered via an encapsulated carbon filter to improve the color. The dissolution vessel and the encapsulated carbon filter and transfer line are then rinsed with additional hot ethanol (70° C.) and the rinse combined with the filtrate. The combined filtrate and washes are partially concentrated in vacuo to approximately 5 total volumes (relative to crude product input) and then stirred over two hours at 0° C. The resulting solids are isolated by filtration, the filter cake washed with cooled (0° C. to 5° C.) ethanol and followed by IPAc and the washed solids then dried to give 33.6 Kg of the product as a slightly off-white solid. Yield=33.6 Kg (73% yield). Achiral HPLC=98%.

The material is then dried via cone drying. After drying, the material is sieved.

A portion of the material (14 Kg) is then dissolved in 15 volumes of hot ethanol (70° C.) and filtered via an encapsulated carbon filter to improve the color. The dissolution vessel and the encapsulated carbon filter and transfer line are then rinsed with additional hot ethanol (70° C.) and the rinse combined with the filtrate. The combined filtrate and washes are partially concentrated in vacuo to approximately 8 total volumes (relative to starting 14 Kg of (1R,5S)-1-(naphthalen-2-yl)-3-azabicyclo[3.1.0]hexane hydrochloride input) and then stirred over two hours at 18° C. The resulting solids are isolated by filtration, the filter cake washed with cooled (5° C. to 10° C.) ethanol and followed by IPAc and the washed solids then dried to give 9.4 Kg (67.1% of yield) of (1R,5S)-1-(naphthalen-2-yl)-3-azabicyclo[3.1.0]hexane hydrochloride as a white solid. Achiral HPLC=98%.

Figure 56:
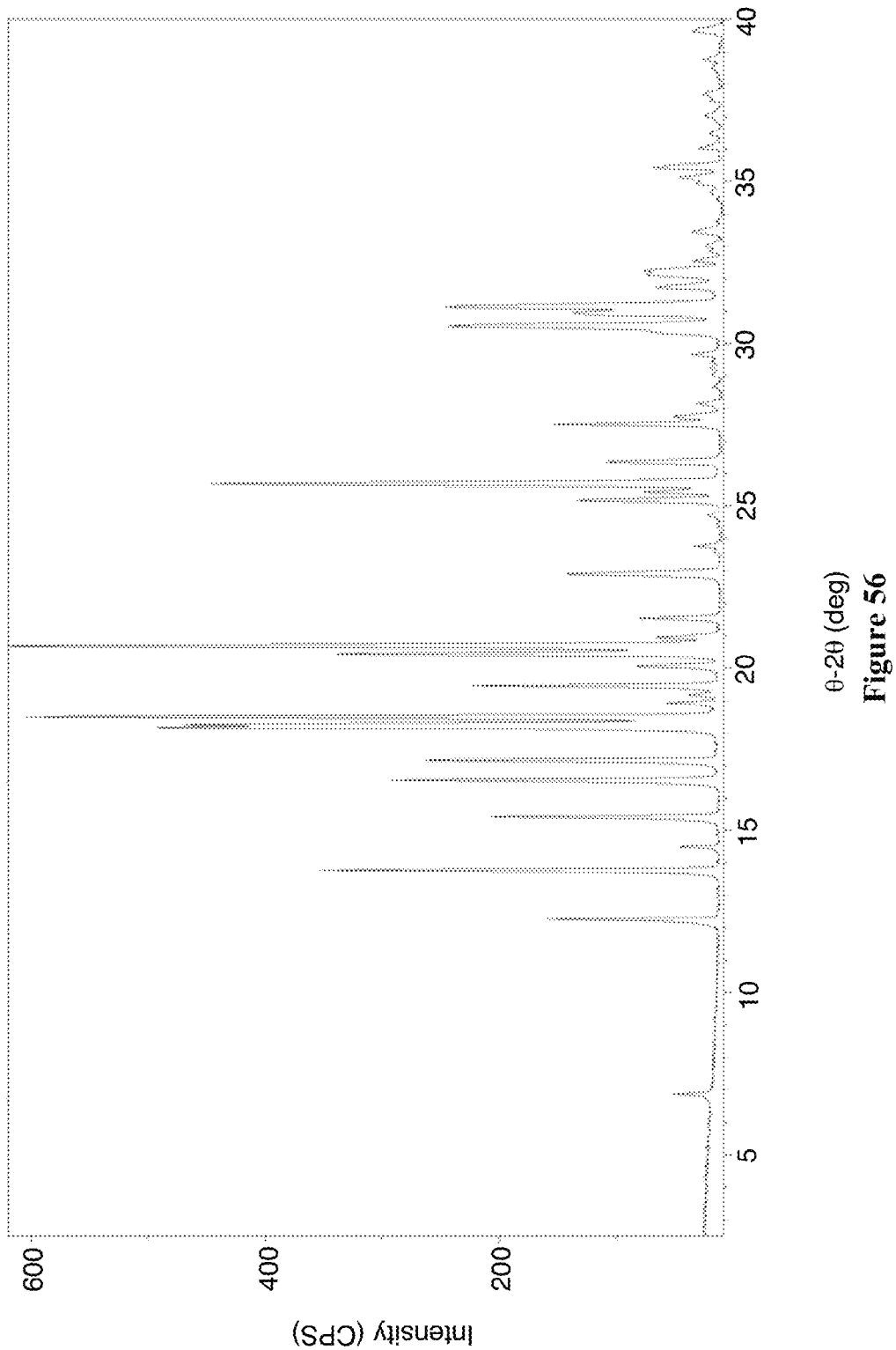
FIG. 56 depicts an XRPD pattern of a mixture of Crystalline Forms A and B.

An XRPD of the product is shown in FIG. 56. The XRPD is consistent with Crystalline Form A with evidence of lower intensity peaks at 18.9°, 19.2°, 23.6°, 23.8°, 28.2°, and 28.7° 2θ attributed to Crystalline Form B. The XRPD pattern is collected with a PANalytical X'Pert PRO MPD diffractometer using an incident beam of Cu radiation produced using an Optix long, fine-focus source. An elliptically graded multilayer mirror is used to focus Cu Kα X-rays through the specimen and onto the detector. Prior to the analysis, a silicon specimen (NIST SRM 640e) is analyzed to verify the observed position of the Si 111 peak is consistent with the NIST-certified position. A specimen of the sample is sandwiched between 3-μm-thick films and analyzed in transmission geometry. A beam-stop, short antiscatter extension, antiscatter knife edge, are used to minimize the background generated by air. Soller slits for the incident and diffracted beams are used to minimize broadening from axial divergence. Diffraction patterns are collected using a scanning position-sensitive detector (X'Celerator) located 240 mm from the specimen and Data Collector software v. 2.2b.

XRPD Data acquisition parameters are: Panalytical X-Pert Pro MPD PW3040 Pro, X-ray Tube: Cu (1.54059 Å), Voltage: 45 kV, Amperage: 40 mA, Scan Range: 1.00-39.99 °2θ, Step Size: 0.017 °2θ, Collection Time: 721 s, Scan Speed: 3.2°/min., Slit: DS: 1/2°, SS: null, Revolution Time: 1.0 s, Mode: Transmission.

Example 17—Preparation of Mixture of Crystalline Forms A and B

To a 2 L 3 neck round bottom flask with mechanical stirring, reflux condenser, nitrogen inlet, thermocouple, and heating mantle, is added 50 g of the product from Example 16 above and EtOH Special Industrial (750 mL, 15 vol). The mixture is heated to reflux (77° C.). Solids dissolve forming clear solution at 72° C. Loose charcoal slurry is added (5 g, 0.1 eq in 100 mL EtOH) and the mixture is stirred for 1 hour. Filter and rinse with hot EtOH (150 mL). Split filtrate into two equal portions.

Portion 1

Concentrate down to 10 vol (250 mL) at 50° C. Small amount of solids start to precipitate during concentration. Transfer to 500 mL 3 neck round bottom flask with mechanical stirring and allow to cool to room temp. Stir for 2 hours at room temp. Suspension forms. Filter and rinse with EtOH (50 mL, 2 vol) followed by IPAc (50 mL). Pull dry on filter. Yield=20.5 g (82%).

Portion 2

Concentrate down to 7 vol (175 mL) at 50° C. Small amount of solids start to precipitate during concentration. Transfer to 500 mL 3 neck round bottom flask with mechanical stirring and allow to cool to room temp. Stir for 2 hours at room temp. Suspension forms. Filter and rinse with EtOH (50 mL, 2 vol) followed by IPAc (50 mL). Pull dry on filter. Yield=19.8 g (79.2%).

Product from the two portions are combined and an XRPD pattern of the combined portions is in FIG. 49 (Example 13).

Example 18—Preparation of Crystalline Forms

Crystalline Form A from Example 5 is used to make the following crystalline forms.

| Solvent | Method[a] | Observation[b] | Results |
| --- | --- | --- | --- |
| IPA | 1. saturated solution, ambient<br>2. cooled in freezer | 1. —<br>2. fine irregular, B | A + C |
|  | 1. saturated solution, ambient<br>2. cooled in freezer | 1. —<br>2. fines, B | B + C |

[a]Time and temperature are approximate.
[b]B = birefringent when observed by polarized light microscopy.

The invention claimed is:

1. A process for making Crystalline Form A of (1R,5S)-1-(naphthalen-2-yl)-3-azabicyclo[3.1.0]hexane hydrochloride, wherein the process comprises seeding a solution or slurry of (1R,5S)-1-(naphthalen-2-yl)-3-azabicyclo[3.1.0]hexane hydrochloride with Crystalline Form A of (1R,5S)-1-(naphthalen-2-yl)-3-azabicyclo[3.1.0]hexane hydrochloride, wherein the Crystalline Form A exhibits an X-ray powder diffraction (XRPD) pattern comprising d-spacing (Å) values of 5.7, 5.4, 5.2, 4.8, 4.6, 4.3, 3.9, and 3.5.

2. The process of claim 1, wherein the solution or slurry is seeded while the temperature of the solution or slurry is above room temperature.

3. The process of claim 1, wherein the Crystalline Form A exhibits an X-ray powder diffraction (XRPD) pattern measured using an incident beam of Cu Kα radiation of wavelength 1.54059 Å substantially as shown in any figure selected from FIGS. 1, 35, 37, and 47.

4. The process of claim 2, wherein the Crystalline Form A exhibits an X-ray powder diffraction (XRPD) pattern measured using an incident beam of Cu Kα radiation of wavelength 1.54059 Å substantially as shown in any figure selected from FIGS. 1, 35, 37, and 47.

5. The process of claim 1 further comprising isolating the Crystalline Form A.

6. The process of claim 2 further comprising isolating the Crystalline Form A.

7. The process of claim 3 further comprising isolating the Crystalline Form A.

8. The process of claim 4 further comprising isolating the Crystalline Form A.

9. A process for making Crystalline Form A of (1R,5S)-1-(naphthalen-2-yl)-3-azabicyclo[3.1.0]hexane hydrochloride, wherein the process comprises dissolving (1R,5S)-1-(naphthalen-2-yl)-3-azabicyclo[3.1.0]hexane hydrochloride in ethanol with heating, optionally filtering, concentrating, seeding with Crystalline Form A of (1R,5S)-1-(naphthalen-2-yl)-3-azabicyclo[3.1.0]hexane hydrochloride before or after concentrating, and optionally filtering, wherein the Crystalline Form A exhibits an X-ray powder diffraction (XRPD) pattern comprising d-spacing (Å) values of 5.7, 5.4, 5.2, 4.8, 4.6, 4.3, 3.9, and 3.5.

10. The process of claim 9, wherein the Crystalline Form A exhibits an X-ray powder diffraction (XRPD) pattern measured using an incident beam of Cu Kα radiation of wavelength 1.54059 Å substantially as shown in any figure selected from FIGS. 1, 35, 37, and 47.

11. The process of claim 9 further comprising isolating the Crystalline Form A.

12. The process of claim 10 further comprising isolating the Crystalline Form A.

13. A process for making a pharmaceutical composition comprising Crystalline Form A of (1R,5S)-1-(naphthalen-2-yl)-3-azabicyclo[3.1.0]hexane hydrochloride, wherein the process comprises isolating Crystalline Form A of (1R,5S)-1-(naphthalen-2-yl)-3-azabicyclo[3.1.0]hexane hydrochloride and admixing the isolated Crystalline Form A with a pharmaceutically acceptable diluent or carrier, wherein the Crystalline Form A exhibits an X-ray powder diffraction (XRPD) pattern comprising d-spacing (Å) values of 5.7, 5.4, 5.2, 4.8, 4.6, 4.3, 3.9, and 3.5.

14. The process of claim 13, wherein the Crystalline Form A exhibits an X-ray powder diffraction (XRPD) pattern measured using an incident beam of Cu Kα radiation of wavelength 1.54059 Å substantially as shown in any figure selected from FIGS. 1, 35, 37, and 47.

\* \* \* \* \*

UNITED STATES PATENT AND TRADEMARK OFFICE
CERTIFICATE OF CORRECTION

PATENT NO.       : 9,856,217 B2
APPLICATION NO.  : 15/611580
DATED            : January 2, 2018
INVENTOR(S)      : Anthony Alexander McKinney et al.

It is certified that error appears in the above-identified patent and that said Letters Patent is hereby corrected as shown below:

Column 3, Lines 2, 36, 43, 50, 59, and 67; Column 4, Lines 8, 17, 25, 55, and 62; Column 5, Lines 14 and 35; Column 6, Line 18; Column 8, Lines 16, 22, and 62; Column 9, Lines 3 and 10; Column 10, Line 56; Column 17, Lines 7, 16, 29, 43, 54, and 65; Column 18, Lines 3 and 11; Column 25, Lines 10, 20, 32, 46, and 57; Column 26, Lines 1, 6, and 13; Column 28, Lines 33 and 40; Column 29, Lines 14, 21, and 63; Column 30, Line 3; Column 41, Lines 17, 22, and 27; Column 73, Line 59; and Column 77, Line 33, each occurrence of "XPRD" should read: -- XRPD --

Column 18, Line 14, and Column 26, Line 16, each occurrence of "e.g., Kα radiation," should read: -- e.g., Cu Kα radiation, --

Column 19, Lines 35-36, "2-theta value (°)" should read: -- 2 theta (°) value --

Column 24, Line 54; and Column 25, Line 44, each occurrence of "e.g., least fifteen peaks," should read: -- e.g., at least fifteen peaks, --

Column 33, Lines 34, 37, 40, and 45-46, each occurrence of "hydroxpropyl" should read: -- hydroxypropyl --

Column 34, Line 7, "less than 1%," should read: -- less than 1% w/w, --

Column 35, Line 33, ")" should read -- ); --

Column 40, Lines 7-8 and Lines 17-18, "pattern Crystalline Form" should read: -- pattern of Crystalline Form --

Column 42, Line 43, "0.1%" should read: -- 0.1 wt. % --

Column 44, Line 16, "Inhibitor™," should read: -- inhibitor (TRI) --

Column 46, Line 45, "at ambient in" should read: -- at ambient conditions in --

Signed and Sealed this
Seventeenth Day of July, 2018

Andrei Iancu
*Director of the United States Patent and Trademark Office*

CERTIFICATE OF CORRECTION (continued)

Column 47, Lines 41-42, "at ambient for" should read: -- at ambient conditions for --

Column 48, Line 3; Column 55, Line 18; Column 66, Line 41; and Column 68, Line 67, each occurrence of "TOC" should read: -- T0C --

Column 48, Line 24; Column 56, Line 53; and Column 75, Line 18, each occurrence of "20" should read: -- 2θ --

Column 48, Line 42, "Gobel" should read: -- Göbel --

Column 54, Line 5, "42 mL/g" should read: -- 1.42 mL/g --

Column 59, Line 12, "is shown FIG. 1." should read: -- is shown in FIG. 1. --

Column 61, Table 4, first entry on leftmost column, "C11" should read: -- Cl1 --

Column 61, the lines below Table 4, "The form of the anisotropic temperature factor is: $\exp[-2\pi h^2 a^{*2} U(1,1) + k^2 b^{*2} U(2,2) + l^2 c^{*2} U(3,3) + 2hka^*b^*U(1,2) + 2hla^*c^*U(1,3)+$" should read: -- The form of the anisotropic temperature factor is: $\exp[-2\pi h^2 a^{*2} U(1,1) + k^2 b^{*2} U(2,2) + l^2 c^{*2} U(3,3) + 2hka^*b^*U(1,2) + 2hla^*c^*U(1,3)+ 2klb^*c^*U(2,3)]$ where a*, b*, and c* are reciprocal lattice constants. --

Column 67, Lines 4-6, "For a solution placed in the freezer after cooling to room temperature with a lower concentration (7 mg/ml compared to 10 mg/mL) yield Form B." should read: -- A solution placed in the freezer after cooling to room temperature with a lower concentration (7 mg/mL compared to 10 mg/mL) yields Form B. --

Column 67, Line 10, "outcome" should read: -- outcomes --

Column 77, Line 17, "Strayer" should read: -- Straver --

Column 80, Line 3, "Gin" should read: -- G in --

Column 80, Line 41, "phase between $T_{t,C \to B}$ and and Crystalline Form A is the" should read: -- phase between $T_{t,C \to B}$ and $T_{t,B \to A}$, and Crystalline Form A is the --